(12) United States Patent
Hawthorne et al.

(10) Patent No.: US 11,065,345 B2
(45) Date of Patent: Jul. 20, 2021

(54) METHODS FOR ASSEMBLING SCAVENGING PARTICLES

(71) Applicant: NaNotics, LLC, Mill Valley, CA (US)

(72) Inventors: Louis Hawthorne, Mill Valley, CA (US); John Dodgson, London (GB)

(73) Assignee: NaNotics, LLC, Mill Valley, CA (US)

(*) Notice: Subject to any disclaimer, the term of this patent is extended or adjusted under 35 U.S.C. 154(b) by 0 days.

(21) Appl. No.: 16/476,049

(22) PCT Filed: Jan. 4, 2018

(86) PCT No.: PCT/US2018/012414
§ 371 (c)(1),
(2) Date: Jul. 3, 2019

(87) PCT Pub. No.: WO2018/129207
PCT Pub. Date: Jul. 12, 2018

(65) Prior Publication Data
US 2020/0179531 A1    Jun. 11, 2020

Related U.S. Application Data

(60) Provisional application No. 62/442,376, filed on Jan. 4, 2017, provisional application No. 62/442,327, filed on Jan. 4, 2017.

(51) Int. Cl.
*A61K 47/69* (2017.01)
*A61K 47/62* (2017.01)
*A61K 9/51* (2006.01)

(52) U.S. Cl.
CPC ........ *A61K 47/6929* (2017.08); *A61K 9/5115* (2013.01); *A61K 9/5153* (2013.01); *A61K 47/62* (2017.08); *A61K 47/6937* (2017.08)

(58) Field of Classification Search
CPC ............... A61K 47/6929; A61K 47/62; A61K 47/6937; A61K 47/6923; A61K 9/5115;
(Continued)

(56) References Cited

U.S. PATENT DOCUMENTS 7,727,528 B2    6/2010  Adcock
7,854,717 B1   12/2010  Lentz
(Continued)

FOREIGN PATENT DOCUMENTS

CN    101123990 A    2/2008
CN    106999550 A    8/2017
(Continued)

OTHER PUBLICATIONS

Fischer et al., "A TNF receptor 2 selective agonist rescues human neurons from oxidative stress-induced cell death," PLoS One, 6(11):e27621 (2011).
(Continued)

*Primary Examiner* — Carlos A Azpuru
(74) *Attorney, Agent, or Firm* — Foley Hoag LLP

(57) ABSTRACT

The disclosure provides, methods for preparing scavenging particles, as well as methods for attaching capture agents to the particles. The disclosure further provides compositions that bind to and inhibit the biological activity of soluble biomolecules, as well as pharmaceutical compositions thereof. The compositions may comprise a plurality of particles that specifically bind a target, such as a soluble biomolecule or a biomolecule on the surface of a pathogen, to inhibit the target (or pathogen) from interacting with other molecules or cells. Also provided herein are a number of applications (e.g., therapeutic applications) in which the compositions are useful.

15 Claims, 26 Drawing Sheets

Sponge impregnated w/TNF (yellow)

sTNF-Rs (brown) binding to TNF

CU of sTNF-Rs bound to TNF in sponge pores

(58) Field of Classification Search
CPC .... A61K 9/5153; A61K 9/0019; Y02A 50/30; B82Y 5/00; B82Y 30/00
See application file for complete search history.

(56) References Cited

U.S. PATENT DOCUMENTS

| | | | |
|---|---|---|---|
| 7,932,311 | B2 | 4/2011 | Aymonier et al. |
| 8,133,490 | B2 | 3/2012 | Lentz |
| 8,586,096 | B2 | 11/2013 | Katti et al. |
| 8,685,538 | B2 | 4/2014 | Torchilin et al. |
| 8,926,994 | B2 | 1/2015 | Serda et al. |
| 9,623,081 | B2 | 4/2017 | Hawthorne |
| 9,907,831 | B2 * | 3/2018 | Hawthorne .......... A61K 38/191 |
| 10,420,817 | B2 | 9/2019 | Hawthorne |
| 10,653,790 | B2 | 5/2020 | Dodgson et al. |
| 10,888,602 | B2 | 1/2021 | Hawthorne |
| 2004/0105821 | A1 | 6/2004 | Bernstein et al. |
| 2004/0166166 | A1 | 8/2004 | Matsunami et al. |
| 2004/0170626 | A1 | 9/2004 | Schuurman et al. |
| 2004/0265392 | A1 | 12/2004 | Tovar et al. |
| 2006/0199820 | A1 | 9/2006 | Bannen et al. |
| 2008/0075690 | A1 | 3/2008 | Howell |
| 2008/0277346 | A1 | 11/2008 | Kirkland et al. |
| 2012/0108787 | A1 | 5/2012 | Lue |
| 2012/0141797 | A1 | 6/2012 | Sherman et al. |
| 2012/0156135 | A1 | 6/2012 | Farokhzad et al. |
| 2013/0195972 | A1 | 8/2013 | Manku et al. |
| 2013/0196450 | A1 | 8/2013 | Van Hoonacker et al. |
| 2013/0337070 | A1 | 12/2013 | Brenneisen et al. |
| 2014/0010879 | A1 | 1/2014 | Shen et al. |
| 2014/0220133 | A1 | 8/2014 | Paciotti et al. |
| 2014/0235803 | A1 | 8/2014 | Jiang et al. |
| 2014/0296836 | A1 | 10/2014 | Shen et al. |
| 2014/0341975 | A1 | 11/2014 | Livneh |
| 2015/0112842 | A1 | 4/2015 | Sieger et al. |
| 2015/0231233 | A1 | 8/2015 | Lentz |
| 2017/0038382 | A1 | 2/2017 | Hawthorne |
| 2017/0056327 | A1 | 3/2017 | Mi et al. |
| 2018/0256747 | A1 | 9/2018 | Hawthorne et al. |
| 2020/0179531 | A1 | 6/2020 | Hawthorne et al. |

FOREIGN PATENT DOCUMENTS

| | | |
|---|---|---|
| CN | 107837389 A | 3/2018 |
| DE | 10144251 A1 | 3/2003 |
| EP | 1174129 A1 | 1/2002 |
| EP | 1949915 A2 | 7/2008 |
| WO | WO-01/37873 A2 | 5/2001 |
| WO | WO-2004/071641 A2 | 8/2004 |
| WO | WO-2005/107802 A2 | 11/2005 |
| WO | WO-2006/014646 A2 | 2/2006 |
| WO | WO-2006/086428 A2 | 8/2006 |
| WO | WO-2008/127515 A1 | 10/2008 |
| WO | WO-2009/030492 A2 | 3/2009 |
| WO | WO-2009061853 A2 | 5/2009 |
| WO | WO-2010/042555 A2 | 4/2010 |
| WO | WO-2012/163544 A1 | 12/2012 |
| WO | WO-2013/029278 A1 | 3/2013 |
| WO | WO-2013/052167 A2 | 4/2013 |
| WO | WO-2013/179143 A2 | 12/2013 |
| WO | WO-2014/041544 A1 | 3/2014 |
| WO | 2014/10984 * | 7/2014 |
| WO | WO-2014/109842 A2 | 7/2014 |
| WO | WO-2015/112842 A1 | 7/2015 |
| WO | 2016/054522 * | 4/2016 |
| WO | WO-2016/054522 A1 | 4/2016 |
| WO | 2016/054522 * | 7/2016 |
| WO | WO-2017/004159 A1 | 1/2017 |
| WO | WO-2017/019949 A1 | 2/2017 |
| WO | WO-2017/176762 A1 | 10/2017 |
| WO | WO-2018/129188 A1 | 7/2018 |
| WO | WO-2018/129207 A1 | 7/2018 |

OTHER PUBLICATIONS

Lentz et al., "Reduction of plasma levels of soluble tumor necrosis factor and interleukin-2 receptors by means of a novel immunoadsorption column," Ther Apher Dial, 12(6):491-499 (2008).
Lentz, "The role of therapeutic apheresis in the treatment of cancer: a review," Ther Apher, 3(1):40-49 (1999).
Richter et al., "Improved monovalent TNF receptor 1-selective inhibitor with novel heterodimerizing Fc," MABS, 11(4):653-665 (2019).
Rowe et al., "Novel TNF receptor-1 inhibitors identified as potential therapeutic candidates for traumatic brain injury," Journal of Neuroinflammation, 15:154 (2018).
Williams et al., "Paradoxical effects of a synthetic metalloproteinase inhibitor that blocks both P55 and P75 TNF receptor shedding and TNFα processing in RA synovial membrane cell cultures,"J Clin Invest, 97(12):2833-2841 (1996).
Mout et al., "Surface functionalization of nanoparticles for nanomedicine," Chem Soc Rev, 41(7):2539-2544 (2012).
Qhobosheane et al., "Biochemically functionalized silica nanoparticles," Analyst, 126:1274-1278 (2001).
Subbiah et al., "Nanoparticles: Functionalization and Multifunctional Applications in Biomedical Sciences," Current Medicinal Chemistry, 17:4559-4577 (2010).
Balamurugan et al., "Surface immobilization methods for aptamer diagnostic applications," Anal Bioanal Chem, 390: 1009-1021 (2008).
Boyer et al., "An Overview of protein-polymer particles," Soft Matter, 7: 1599-1614 (2011).
Costamagna et al., "Complexes of macrocycles with pendant arms as models for biological molecules," Coordination Chemistry Reviews, 196: 125-164 (2000).
De Wever et al., "Soluble cadherins as cancer biomarkers," Clin Exp Metastasis, 24: 685-697 (2007).
Hruby et al., "Design of Peptide and Peptidomimetic Ligands with Novel Pharmacological Activity Profiles," Annu Rev Pharmacol Toxicol, 53: 557-580 (2013).
Jiang et al., "Biomolecule-functionalized polymer brushes," Chem. Soc. Rev., 42: 3394-3426 (2013).
Kohga et al., "Anticancer Chemotherapy Inhibits MHC Class I-Related Chain A Ectodomain Shedding by Downregulating ADAM10 Expression in Hepatocellular Carcinoma," Cancer Res, 69: 8050-8057 (2009).
Pazos et al., "DNA Recognition by Synthetic Constructs," ChemBioChem, 12: 1958-1973 (2011).
Xing et al., "Immobilization of biomolecules on the surface of inorganic nanoparticles for biomedical applications," Sci. Technol. Adv. Mater., 11: 014101 (2010).
"Magnetic Nanoparticle Biospleen Device for Sepsis Therapy," Wyss Institute for Biology Inspired Engineering at Harvard, http://www.nanowerk.com/nanotechnology-news/newsid=37354.php (pp. 1-8) (2014).
Aderka et al., "Increased serum levels of soluble receptors for tumor necrosis factor in cancer patients," Cancer Res, 51(20): 5602-5607 (1991).
Bork, "Powers and Pitfalls in Sequence Analysis: The 70% Hurdle," Genome Research, 10:398-400 (2000).
Bowie et al., "Deciphering the Message in Protein Sequences: Tolerance to Amino Acid Substitutions," Science, 247:1306-1310 (1990).
Brown et al., "Tolerance of Single, but Not Multiple, Amino Acid Replacements in Antibody VH CDR2: a Means of Minimizing B Cell Wastage From Somatic Hypermutation?," J Immunol, 156(9):3285-3291 (1996).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J Cell Biol, 111:2129-2138 (1990).
Cauda et al., "Multiple core shell functionalized colloidal mesoporous silica nanoparticles," J American Chem Society, 131(32): 11361-11370 (2009).
Charych et al., "NKTR-214, an engineered cytokine with biased IL2 receptor binding, increased tumor exposure, and marked efficacy in mouse tumor models," Clin Cancer Res, 22(3):680-690 (2016).

(56) References Cited

OTHER PUBLICATIONS

Clark et al., "Discovery and Development of Janus Knase (JAK) Inhibitors for Inflammatory Diseases," J Med Chem, 57(12):5023-5038 (2014).
Douglas et al., "Self-assembly of DNA into nanoscale three-dimensional shapes," Nature, 459(7245):414-418 (2009).
Duffy et al., "The ADAMs: New Therapeutic Targets for Cancer?" Cancer Targeted Drug Delivery. Springer New York, 273-287 (2013).
Extended European Search Report for EP Application No. 15845555.0 dated Apr. 24, 2018.
Extended European Search Report for EP Application No. 16818651.8 dated Jan. 31, 2019.
Extended European Search Report issued by the European Patent Office in corresponding Application No. 15740254.6, dated Dec. 20, 2017.
Extended European Search Report received for EP Patent Application No. EP16831405.2, dated Feb. 5, 2019.
Giai et al. "Shedding of Tumor Necrosis Factor Receptor 1 Induced by Protein A Decreases Tumor Necrosis Factor Alpha Availability and Inflammation during Systemic *Staphylococcus aureus* Infection," Infection & Immunity, 81(11):4200 (2013).
Guido et al., "Virtual Screening and Its Integration with Modern Drug Design Technologies," Curr Med Chem, 15(1):37-46 (2008).
Holtan et al. "Cancer and Pregnancy: Parallels in Growth, Invasion, and Immune Modulation and Implications for Cancer Therapeutic Agents", Mayo Clinical Protocols, 84(11): 985-1000 (2009).
International Preliminary Report on Patentability for International Application No. PCT/US2017/025954 dated Oct. 9, 2018.
International Preliminary Report on Patentability for International Application No. PCT/US2018/012414 dated Jul. 9, 2019.
International Search Report and Written Opinion for International Application No. PCT/US2015/012653 dated Apr. 23, 2015.
International Search Report and Written Opinion for International Application No. PCT/US2015/053748 dated Dec. 28, 2015.
International Search Report and Written Opinion for International Application No. PCT/US2016/040022 dated Aug. 23, 2018.
International Search Report and Written Opinion for International Application No. PCT/US2016/044674 dated Oct. 13, 2016.
International Search Report and Written Opinion for International Application No. PCT/US2017/025954 dated Sep. 8, 2017.
International Search Report and Written Opinion for International Application No. PCT/US2018/012386, dated Mar. 28, 2018.
International Search Report and Written Opinion for International Application No. PCT/US2018/012414, dated Mar. 28, 2018.
Lazar et al., "Transforming Growth Factor alpha: Mutation of Aspartic Acid 47 and Leucine 48 Results in Different Biological Activities," Mol Cell Biol, 8:1247-1252 (1988).
Li et al., "PEGylated recombinant human tumor necrosis factor alpha: preparation and anti-tumor potency," Acta Pharmacol Sin, 22(6):549-555 (2001).
Liu et al., "Engineered interleukin-2 antagonists for the inhibition of regulatory T cells," J Immunother, 32(9):887-894 (2009).
Müllberg et al., "A Metalloprotease Inhibitor Blocks Shedding of the IL-6 Receptor and the p60 TNF Receptor," J Immunol, 155: 5198-5205 (1995).
Parker Annual Report (2014).
Partial Supplementary European Search Report issued by the European Patent Office in corresponding Application No. EP 15740254.6, dated Sep. 25, 2017.
Sheu et al., "A Novel Role of Metalloproteinase in Cancer-mediated Immunosuppression," Cancer Res, 61: 237-242 (2001).
Vajdos et al., "Comprehensive Functional Maps of the Antigen Binding Site of an Anti-ErbB2 Antibody Obtained with Shotgun Scanning Mutagenesis," J Mol Biol, 320(2):415-428 (2002).
Waldmann, "Anti-Tac (daclizumab, Zenapax) in the treatment of leukemia, autoimmune diseases, and in the prevention of allograft rejection: a 25-year personal odyssey," J Clin Immunol, 27(1):1-18 (2007).
Yang at al., "The use of polyethylene glycol☐modified interleukin☐2 (PEG☐IL☐2) in the treatment of patients with metastatic renal cell carcinoma and melanoma," Cancer, 76(4):687-694 (1995).
Yousef et al. "Systemic Attenuation of the TGF-β Pathway by a Single Drug Simultaneously Rejuvenates Hippocampal Neurogenesis and Myogenesis in the same old Mammal," Oncotarget, 6(14):11959 (2015).
U.S. Appl. No. 15/113,594, Published.
U.S. Appl. No. 14/873,847, Granted.
U.S. Appl. No. 15/450,769, Granted.
U.S. Appl. No. 15/909,820, Granted.
U.S. Appl. No. 16/534,428, Pending.
U.S. Appl. No. 15/738,954, Published.
U.S. Appl. No. 15/748,335, Published.

\* cited by examiner

A                                              B

METHODS FOR ASSEMBLING SCAVENGING PARTICLES

RELATED APPLICATIONS

This application is a national-stage application of International Application No. PCT/US2018/012414, filed Jan. 4, 2018, which claims the benefit of priority to U.S. Provisional Patent Application Ser. No. 62/442,376, filed Jan. 4, 2017, and U.S. Provisional Patent Application Ser. No. 62/442,327, filed Jan. 4, 2017. The entire contents of these applications are hereby incorporated herein by this reference in their entireties.

BACKGROUND

Dozens of anti-cancer therapies available clinically or under development involve stimulation of the immune system's ability either to recognize or destroy cancer, or both. Three of the most prominent are the anti-checkpoint inhibitors Yervoy® (ipilimumab) from Bristol-Myers Squibb, Keytruda® (pembrolizumab, formerly lambrolizumab) from Merck. However, these and other approaches involve net up-regulation of a subject's immune system, inducing potentially serious symptoms akin to autoimmune disorders and/or other significant side effects.

There is a need in the art for more effective pharmacological approaches for addressing cancer, particularly metastatic cancer, without disturbing a subject's capacity for avoiding auto-immunity. Among other things, the present disclosure provides methods and compositions based on alternative approaches for harnessing a subject's own immune system against cancer, including dis-inhibiting the tumor microenvironment, i.e., weakening the tumor's defensive system, versus stimulating immune cells.

SUMMARY

The disclosure provides, among other things, compositions that bind to and inhibit the biological activity of biomolecules, especially soluble molecules, as well as pharmaceutical compositions thereof. Also provided herein are a number of applications in which the compositions are useful. For example, compositions described herein are useful for inhibiting proliferation, growth, and/or survival of a cell, such as a cancer cell. Additionally, compositions described herein are useful for preventing and/or treating aging, metabolic disorders, and neurodegenerative diseases. In another example, compositions described herein can be useful to bind to and neutralize toxins (e.g., zootoxins, bacterial toxins, and/or plant toxins), viruses, or other foreign compounds in the circulation of a subject.

BRIEF DESCRIPTION OF THE DRAWINGS

In FIG. 5, each core subparticle and protecting subparticle is substantially spherical and approximately the same size; however, the subparticles within a particle may vary in shape and/or size. Additionally, the subparticles of FIG. 5 are shown as packing in a hexagonal pattern; however, the subparticles of a particle may pack with other geometries or they may pack randomly. The relative sizes of the subparticles, capture ligands, targets, and void space in FIG. 5 are not necessarily shown to scale. In particular, the length of the linkers connecting various subparticles may be adjusted to allow for more or less void space between the subparticles.

DETAILED DESCRIPTION

Figure 1:
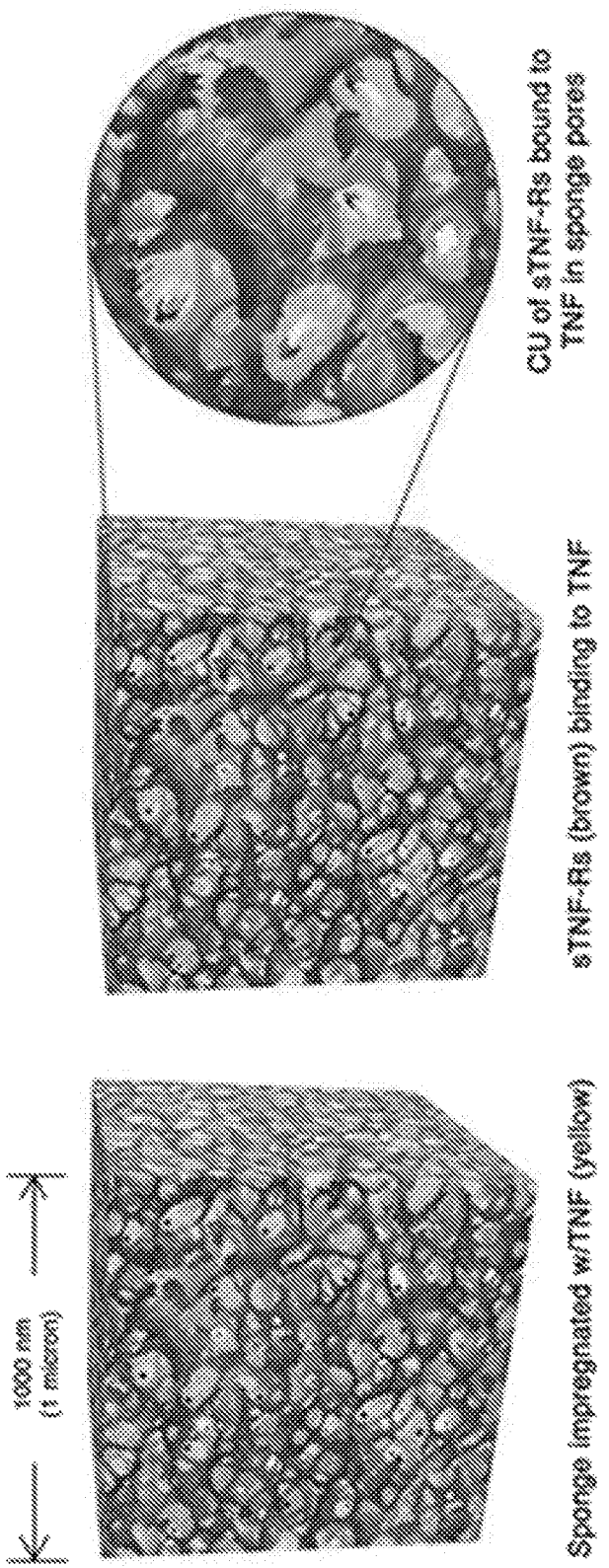
FIG. 1 depicts an exemplary embodiment of a particle that binds to soluble forms of TNF receptor (sTNF-R). The particle is approximately one cubic micron. The inner surfaces of the particle comprise an immobilized TNF agent, which is capable of binding to the sTNF-R target and sequestering (scavenging) it away from its natural ligands, thereby inhibiting interactions between the sTNF-R target and other proteins and cells. The inner surfaces of the particle define boundaries comprising void space.
Figure 2:
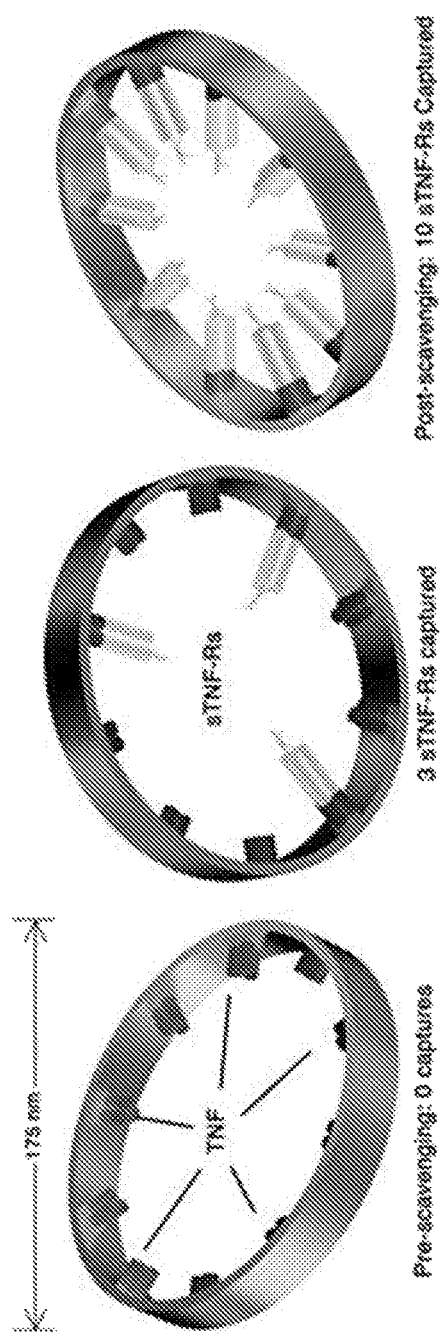
FIG. 2 depicts an exemplary embodiment of a particle comprising a TNF agent that binds to soluble forms of a TNF receptor (sTNF-R) target. The three particles shown in FIG. 2 are depicted as having bound 0, 3, or 10 molecules of the sTNF-R target. The ring-shaped particle has a diameter of approximately 175 nm, although the TNF agent and sTNF-R target are not shown to scale. The inner surfaces of the particle contain immobilized TNF agent, which is capable of binding to the sTNF-R target and sequestering (scavenging) it away from its natural ligands, thereby inhibiting interactions between the sTNF-R target and other proteins and cells. The interior of the ring-shaped particle comprises void space.
Figure 3:
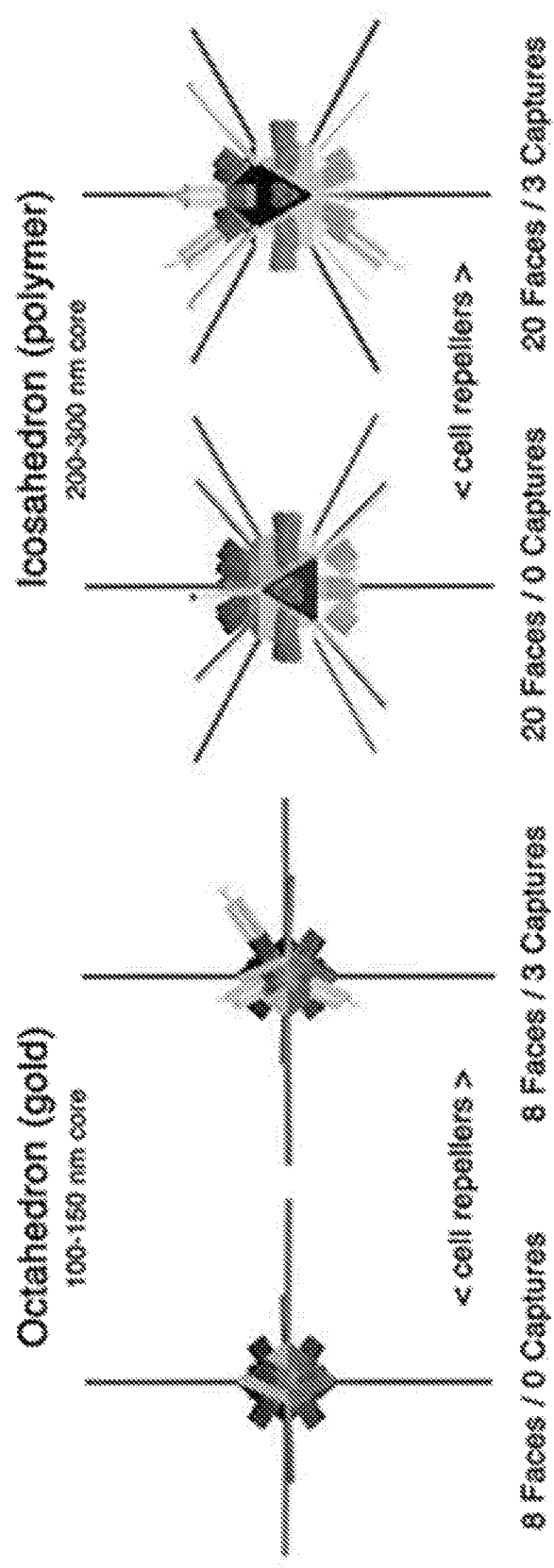
FIG. 3 depicts exemplary embodiments of particles comprising protrusions. The particle at the left of the figure is an octahedron with a core having a longest dimension of 100 to 150 nm. The particle at the right of the figure is an icosahedron with a core having a longest dimension of 200 to 300 nm. Each particle further comprises molecular protrusions pointing outward from the vertices of the core polyhedral structure. The particles are depicted as comprising an agent, shown in dark gray, and some particles are depicted as having bound a target (e.g., a biomolecule), shown in light gray and identified as 0 or 3 "captures." The protrusions serve as "cell repellers," which inhibit interactions between the target bound to the agent of the particle and cell surfaces. The representations of the particles, protrusions, agent, and bound target in FIG. 3 are not necessarily shown to scale.

The disclosure features compositions and methods for sequestering a soluble biomolecule away from its natural environment, e.g., to thereby inhibit the biological activity of the soluble biomolecule. For example, the disclosure provides a particle, or a plurality of particles, having a surface comprising an agent (e.g., immobilized on a surface of the particle) that selectively binds to a soluble biomolecule. Once the soluble biomolecule is bound by the agent, it is sequestered by the particle such that the soluble biomolecule has a reduced ability (e.g., substantially reduced ability or no ability) to interact with other natural binding partners of the soluble biomolecule. Thus, the soluble biomolecule becomes inert.

Various aspects of the disclosure relate to particles comprising reactive groups configured to link an agent to the particles. Thus, a particle may not comprise an agent, but the particle may nevertheless be capable of coupling to an agent.

Different agents may be attached to a particle based on the nature of the biomolecule to be scavenged.

In some aspects, the disclosure relates to a kit comprising particles and linkers. For example, linkers may be selected to react with an agent comprising a specific moiety to the particles. Thus, a single "universal scavenger" particle may be provided in a kit with a number of different linkers for linking a number of different types of agents to the particle (e.g., wherein different linkers are capable of linking different moieties to the same particle).

The reactive groups of a particle are preferably configured such that an agent linked to the particle has a higher selectivity for soluble forms of a target biomolecule than for membrane-bound or surface-bound forms of the biomolecule. For example, an agent that is not associated with a particle may bind soluble and membrane-associated forms of a biomolecule with a similar binding affinity (e.g., with a similar association constant $k_a$ and/or a similar equilibrium constant $K_D$). An agent linked either directly to a reactive group of a particle or indirectly to a reactive group of a particle (e.g., through a linker) may display higher binding affinity (e.g., higher $k_a$ and/or lower $K_D$) for soluble forms of a target biomolecule relative to membrane-associated forms of the same biomolecule.

In preferred embodiments, each reactive group of a plurality of reactive groups is configured on a particle such that an agent linked to a reactive group (either directly or indirectly, e.g., through a linker) has a lower binding affinity for membrane-associated forms of a target biomolecule than when the agent is not linked to a reactive group of the particle (e.g., and the agent is instead either free in solution or linked to an exposed surface). For example, a reactive group may be configured on a particle such that an agent linked to the reactive group (either directly or indirectly, e.g., through a linker) has a lower association constant $k_a$ for membrane-associated forms of a target biomolecule than when the agent is not linked to a reactive group of the particle. The $k_a$ of an agent that is linked to a particle ($k_{a,\ particle}$) may be less than the $k_a$ of the agent either free in solution or linked to an exposed surface ($k_{a,\ free}$) for membrane-bound forms of a target biomolecule by an order of 0.9, 0.8, 0.7, 0.6, 0.5, 0.4, 0.3, 0.2, 0.1, 0.05, 0.01, 0.005, or 0.001 (e.g., $k_{a,\ particle} \div k_{a,\ free} \leq 0.9$, 0.8, 0.7, 0.6, 0.5, 0.4, 0.3, 0.2, 0.1, 0.05, 0.01, 0.005, or 0.001 for agent and membrane-bound targets). Similarly, a reactive group may be configured on a particle such that an agent linked to the reactive group (either directly or indirectly, e.g., through a linker) has a higher equilibrium constant $K_D$ for membrane-associated forms of a target biomolecule than when the agent is not linked to a reactive group of the particle. The $K_D$ of an agent linked to a particle ($K_{D,\ particle}$) may be greater than the $K_D$ of the agent either free in solution or linked to an exposed surface ($K_{D,\ free}$) for membrane-bound forms of a target biomolecule by an order of 10%, 20%, 25%, 50%, 100%, 200%, 250%, 500%, 1000%, 5000%, 10,000%, 50,000%, or 100,000% (e.g., $K_{D,\ particle} \div K_{D,\ free} \geq 1.1$, 1.2, 1.25, 1.5, 2.0, 2.5, 3.5, 5.0, 10, 5, 100, 500, or 1000 for agent and membrane-bound targets).

In preferred embodiments, a particle is configured such that linking an agent to a reactive group of the particle essentially does not affect the binding affinity of the agent for soluble forms of a target biomolecule (e.g., relative to when the agent is not linked to a reactive group of the particle, and the agent is instead either free in solution or linked to an exposed surface). For example, a reactive group may be configured on a particle such that an agent linked to the reactive group (either directly or indirectly, e.g., through a linker) has about the same association constant $k_a$ for soluble forms of a target biomolecule relative to when the agent is not linked to a reactive group of the particle. The $k_a$ of an agent linked to a particle ($k_{a,\ particle}$) may be about the same as the $k_a$ of the agent either free in solution or linked to an exposed surface ($k_{a,\ free}$) for soluble forms of a target biomolecule (e.g., $k_{a,\ particle} \div k_{a,\ free}$ may be from 0.1 to 10, such as 0.2 to 5, 0.5 to 2, 0.8 to 1.2, or 0.9 to 1.1 for agent and soluble targets). Similarly, a reactive group may be configured on a particle such that an agent linked to the reactive group (either directly or indirectly, e.g., through a linker) has about the same equilibrium constant $K_D$ for soluble forms of a target biomolecule relative to when the agent is not linked to a reactive group of the particle. The $K_D$ of an agent linked to a particle ($K_{D,\ particle}$) may be about the same as the $K_D$ of the agent either free in solution or linked to an exposed surface ($K_{D,\ free}$) for soluble forms of a target biomolecule (e.g., $K_{D,\ particle} \div K_{D,\ free}$ may be from 0.1 to 10, such as 0.2 to 5, 0.5 to 2, 0.8 to 1.2, or 0.9 to 1.1 for agent and soluble targets).

Particles comprising a plurality of reactive groups may thus be linked to an agent (e.g., an antibody, Fab, scFv, or ligand of a cell-surface receptor) to engineer particles that selectively bind soluble forms of a target (e.g., an antigen and/or soluble form of a cell-surface receptor) but that do not appreciably bind membrane-bound forms of the target. Such particles may be utilized in vivo or in vitro, for example, to reduce the concentration of a soluble target in a fluid without exposing the agent to membrane-bound forms of the target.

I. Biomolecule

The soluble biomolecule is, generally, a first member of a specific binding pair. As used herein, a "binding partner," "specific binding partner," or a "member of a specific binding pair," generally comprises any member of a pair of binding members that bind to each other with substantial affinity and specificity. A pair of binding partners may bind to one another to the substantial exclusion of at least most or at least substantially all other components of a sample, and/or may have a dissociation constant of less than about $10^{-4}$, $10^{-5}$, $10^{-6}$, $10^{-7}$, or $10^{-8}$M, among others. A pair of binding partners may "fit" together in a predefined manner that relies on a plurality of atomic interactions to cooperatively increase specificity and affinity. Binding partners may be derived from biological systems (e.g., receptor-ligand interactions), chemical interactions, and/or by molecular imprinting technology, among others. Exemplary corresponding pairs of binding partners, also termed specific binding pairs, are presented in Table 1, with the designations "first" and "second" being arbitrary and interchangeable.

The term "biomolecule" as used herein, refers to any molecule that may exert an effect on a living organism. In some embodiments, the biomolecule is an atom, such as lithium or lead (e.g., the biomolecule may be a metal cation). In some embodiments, the biomolecule is not an atom or metal ion. For example, the biomolecule may be a molecule, such as an organic compound or inorganic compound. In some embodiments, the biomolecule is a drug, such as warfarin or dabigatran. The biomolecule may be a psychoactive drug, such as diacetylmorphine. The biomolecule may be a poison, toxin, or venom. The biomolecule may be an allergen. The biomolecule may be a carcinogen. The biomolecule may be the agent of a chemical weapon, such as a nerve agent. The biomolecule may be a molecule that is endogenous to the organism, such as a hormone, cytokine, neurotransmitter, soluble extracellular receptor, antibody, or soluble matrix protein. The biomolecule may be a peptide, polypeptide, protein, nucleic acid, carbohydrate, or sugar.

The biomolecule may comprise a peptide, polypeptide, protein, nucleic acid, carbohydrate, or sugar. The biomolecule may be a misfolded protein. The biomolecule may be an amyloid or the soluble precursor of an amyloid. "Polypeptide," "peptide," and "protein" are used interchangeably and mean any peptide-linked chain of amino acids, regardless of length or post-translational modification. The biomolecule may be a lipid, a steroid, or cholesterol. The biomolecule may comprise a lipid, a steroid, or cholesterol. The biomolecule may be a circulating, cell-free nucleic acid, such as a circulating, cell-free RNA. The biomolecule may be a micro RNA (miRNA).

The biomolecule may be a biomolecule that is secreted by a cell (e.g., a mammalian cell). The biomolecule may be an extracellular region of a membrane protein that is susceptible to cleavage into a soluble form. The biomolecule may be a cytosolic biomolecule. For example, the biomolecule may be a cytosolic biomolecule that is released in vivo following apoptosis, or a particle may be used in an in vitro method in which the cytosolic biomolecule is free in solution.

In certain preferred embodiments, the biomolecule is a soluble biomolecule. In certain preferred embodiments, the target is a soluble biomolecule. Nevertheless, a particle may target biomolecules that are not solutes in aqueous solution, and/or that do not interact with binding partners on a cell surface. For example, a particle may specifically bind a biomolecule that is associated with a protein aggregate, such as amyloid or a prion aggregate. Such particles may provide a therapeutic benefit by disassembling the aggregate (e.g., by shifting a thermodynamic equilibrium away from aggregated states) and/or by sequestering the aggregate (e.g., to inhibit further aggregation and/or to allow for clearance of the bound aggregate). Similarly, a particle may specifically bind to crystalline calcium or hydroxyapatite. Similarly, a particle may specifically bind to a biomolecule that is associated with a virus or cell, such as a bacterial, protozoan, fungal, or yeast cell, e.g., wherein the biomolecule is not a solute in aqueous solution, but the biomolecule is partitioned into a membrane, cell wall, or capsid. Thus, a particle may sequester a pathogenic virus or cell, thereby attenuating the pathogenicity of the virus or cell. A particle may specifically bind to a biomolecule that is associated with an extracellular vesicle, such as an ectosome, exosome, shedding vesicle, or apoptotic body. A particle may specifically bind to a low-density lipoprotein, e.g., to sequester low-density lipoprotein particles.

The biomolecule may be a ligand of a cell surface receptor. The ligand may be a naturally-occurring ligand or a synthetic ligand. The ligand may be a native ligand of the receptor (e.g., a ligand that is produced by a subject in vivo) or a non-native ligand (e.g., a ligand that is introduced into the subject, such as a virus or drug). The biomolecule may be a ligand for a cytosolic receptor or a nuclear receptor.

TABLE 1

Examples of specific binding pairs.

| First Binding Partner | Second Binding Partner |
| --- | --- |
| Cell Surface Receptor (e.g., TNF receptor) | Natural Ligand (e.g, TNFα) |
| Viral Coat or Envelope Protein (e.g, HIV-1 gp120) | Corresponding Cellular Receptor (e.g, CD4) |
| Botulinum Toxin | Synaptotagmin II Cell Surface Receptor |

TABLE 1-continued

Examples of specific binding pairs.

| First Binding Partner | Second Binding Partner |
| --- | --- |
| Soluble Receptor (e.g, soluble TNFR or soluble IL-2 receptor) | Natural Ligand (e.g, TNFα or IL-2) |

Tumor cells are known to protect themselves from host immune surveillance by shedding soluble forms of cytokine receptors, which soluble receptors bind to the cytokines produced by immune cells in the tumor microenvironment. For example, cancer cells shed soluble forms of TNF receptor and other cytokine receptors, such as IL-2 receptor and TRAIL receptor. These soluble receptors confer a growth advantage to cancer cells by relieving the cells of the pro-apoptotic effects of the TNFα, IL-2, and TRAIL. Karpatova et al. report the shedding of the 67 kD laminin receptor by human cancer cells, which may augment tumor invasion and metastasis (J Cell Biochem 60(2):226-234 (1996)). Thus, the particles described herein can be engineered for scavenging soluble forms of cell surface receptor proteins, e.g., for use in the treatment of cancer.

Accordingly, in some embodiments, the cell surface receptor protein is expressed by a cancer cell and/or the cell surface receptor protein is a protein shed by the cancer cell as a soluble form of the cell surface receptor protein. In some embodiments, the cell surface receptor protein, when activated, induces apoptosis (e.g., a death receptor). In some embodiments, the cell surface receptor protein is a tumor necrosis factor receptor (TNFR) protein (e.g., TNFR-1 or TNFR-2). In some embodiments, the cell surface receptor protein is a Fas receptor protein. In some embodiments, the cell surface receptor protein is a TNF-related apoptosis-inducing ligand receptor (TRAILR) protein, 4-1BB receptor protein, CD30 protein, EDA receptor protein, HVEM protein, lymphotoxin beta receptor protein, DR3 protein, or TWEAK receptor protein. In some embodiments, the cell surface receptor protein is an interleukin receptor protein, e.g., an IL-2 receptor protein. It is understood that in such embodiments, the target soluble biomolecule can be a soluble form of the cell surface receptor, e.g., shed from a cancer cell.

In some embodiments, the biomolecule is soluble Tim3 ("T-Cell Ig Mucin 3"). Soluble Tim3 (sTim3) has been implicated in autoimmune disease and cancer, and elevated sTim3 is associated with HIV infection. The association of Galectin 9 ("Gal9") and potentially other ligands with Tim3 in heterodimeric association with CEACAM1 leads to inhibition of T-cell responses, and co-blockade of Tim3 and CEACAM1 leads to anti-tumor immune response. Accordingly, the biomolecule may be sTim3 or a natural ligand for sTim3, such as Tim3L, or Gal9. A biomolecule may be a soluble isoform of CEACAM1. In this way, the particles may be adapted to scavenge sTim3 while not inhibiting interaction between Gal9 and membrane-bound Tim3 (mTim3). Similarly an agent may be sTim3, an antibody selective for sTim3 (or an antigen binding portion thereof), or a ligand for Tim3. An agent may be a natural ligand for CEACAM1 (such as Gal9 or variant thereof) or an antibody selective for either CEACAM1 or its soluble isoform. Any of the foregoing particles may be used, for example, in methods of treating cancer, methods of treating HIV infection, and methods of treating an autoimmune disease, such as graft-versus-host disease.

In some embodiments, the biomolecule may be Gal9 (Galectin 9). A particle may comprise an agent selective for Gal9, such as a natural ligand for Gal9, such as Tim3, or a variant thereof, or an antibody selective for Gal9. In this way, the particles may be adapted to scavenge Gal9 while not inhibiting interactions of membrane-bound Gal9 (mGal9) with membrane-bound Tim3 (mTim3). In some embodiments, the biomolecule may be a soluble isoform of CEACAM1 ("sCEACAM1"). An agent may be a natural ligand for sCEACAM1, such as Gal9, or a variant thereof, or an antibody selective for either CEACAM1 or a soluble isoform of CEACAM1.

In some embodiments, the biomolecule is soluble CTLA4. Soluble CTLA4 ("sCTLA4") has been implicated in cancer, and antibodies active against sCTLA4, but not against membrane bound CTLA4 ("mCTLA4"), are efficacious in animal models of cancer. In some embodiments, the biomolecule is sCTLA4. An agent may be a natural ligand for CTLA4, such as soluble B7-1 or soluble B7-2, or a variant thereof, or an antibody selective for CTLA4, such as ipilimumab or ticilimumab. In this way, particles may be adapted to scavenge sCTLA4 without inhibiting interaction between ligands and mCTLA4. Thus, sCTLA4 may be removed from the tumor microenvironment ("TME") and/or the circulation outside of the TME while leaving mCTLA4 free for interaction as part of a normal immune response. Particles that target sCTLA4 may be used, for example, in methods of treating with cancer.

Soluble PD-1 ("sPD1") is implicated in autoimmune diseases such as rheumatoid arthritis. Excess sPD1 may disturb the balance between PD1 and its ligands PD-L1 and PD-L2, leading to autoimmunity. Thus, the biomolecule may be sPD1. An agent may be a natural ligand for sPD1, such as PD-L1, PD-L2, or a variant thereof, or an antibody selective for PD1, such as a PD1 blockade drug, for example, nivolumab, pidilizumab, or pembrolizumab (Keytruda®). Thus, a particle may be adapted to scavenge sPD1 without inhibiting an interaction of PD-L1 or PD-L2 with membrane-bound PD1. Such particles may be used, for example, in methods of treating autoimmune diseases, such as arthritis.

LAG3 is a T-cell surface receptor that, when bound by its ligand, results in inhibition. Soluble forms of LAG3 ("sLAG3") correlate with autoimmunity, for example, in Type I diabetes and in other autoimmune diseases. The biomolecule may be sLAG3. An agent may be a natural ligand for sLAG3, or a variant thereof, or an antibody selective for sLAG3. Thus, a particle may adapted to scavenge sLAG3 without inhibiting interactions between ligands and membrane-bound LAG3. Such particles may be used, for example, in methods of treating an autoimmune disease, such as type I diabetes.

The biomolecule may be TNFα. The agent may comprise an anti-TNFα antibody, such as infliximab, adalimumab, cerolizumab, afelimomab, nerelimomab, ozoralizumab, or golimumab, or an the agent may comprise the antigen-binding portion of an anti-TNFα antibody. The agent may be etanercept. The agent may be a soluble receptor for TNFα (sTNF-R or a variant thereof). Particles targeting TNFα may be particularly useful for treating or preventing various autoimmune diseases, such as ankylosing spondylitis, Crohn's disease, hidradenitis suppurativa, psoriasis, plaque psoriasis, psoriatic arthritis, refractory asthma, juvenile idiopathic arthritis, ulcerative colitis, and rheumatoid arthritis. Particles targeting TNFα may also be useful for treating or preventing Alzheimer's disease, cardiovascular disease, type II diabetes, muscular dystrophy, and obesity, in addition to other diseases and conditions.

The biomolecule may be β2 microglobulin (B2M). The agent may be an anti-B2M antibody. Particles targeting B2M may be useful for treating or preventing memory loss, cognitive decline, peripheral arterial disease, dialysis-related amyloidosis, chronic lymphocytic leukaemia, multiple myeloma, and lymphoma, in addition to other diseases and conditions.

The biomolecule may be CCL2 (chemokine (C—C motif) ligand 2). The agent may be an anti-CCL2 antibody. Particles targeting CCL2 may be useful for treating or preventing Alzheimer's disease, atherosclerosis, ischemia (e.g., ischemic stroke), epilepsy, multiple sclerosis, psoriasis, rheumatoid arthritis, glomerulonephritis, and traumatic brain injury, in addition to other diseases and conditions.

The biomolecule may be CCL11 (C—C motif chemokine 11; eotaxin 1). The agent may be an anti-CCL11 antibody. Particles targeting CCL11 may be useful for treating or preventing memory loss and cognitive decline, in addition to other diseases and conditions.

The biomolecule may be CCL19. The agent may be an anti-CCL19 antibody. Particles targeting either CCL19 may be useful for treating or preventing aging and cognitive decline, in addition to other diseases and conditions.

The biomolecule may be interferon gamma (INFγ). The agent may comprise an anti-INFγ antibody, such as fontolizumab, or a soluble INFγ receptor (sINFγR). The biomolecule may be soluble INFγ receptor. The agent may comprise INFγ or an anti sINFγR antibody. Particles targeting interferon gamma may be particularly useful for treating or preventing autoimmune disease, such as Crohn's disease, rheumatoid arthritis, and psoriasis, in addition to other diseases and conditions.

The biomolecule may be clusterin (e.g., secretory clusterin, isoform 2). The agent may comprise an anti-clusterin antibody, or an antigen-binding portion thereof. Particles targeting clusterin may be useful for treating or preventing cancer (e.g., head and neck cancer, renal cell cancer, colorectal cancer, endometrial cancer, ovarian cancer, breast cancer, prostate cancer, pancreatic cancer, lung cancer, hepatocellular cancer, or melanoma), renal disease (e.g., nephropathic cystinosis), Fanconi syndrome, glomerulonephritis, atherosclerosis, and myocardial infarction, in addition to other diseases and conditions.

The biomolecule may be high mobility group box 1 (HMGB1). The agent may comprise an anti-HMGB1 antibody, or an antigen-binding portion thereof. The biomolecule may be a heat shock protein (e.g., HSP60, HSP70, HSP90). The agent may comprise an anti-HSP antibody, or an antigen-binding portion thereof. The biomolecule may be a peroxiredoxin (e.g., peroxiredoxin 1 or peroxiredoxin 2). The agent may comprise an anti-peroxiredoxin antibody, or an antigen-binding portion thereof.

The agent may be the extracellular portion of a scavenger receptor, such as a class A scavenger receptor (e.g., SCARA1 (Macrophage scavenger receptor 1; MSR1; CD204), SCARA2 (Macrophage receptor; MARCO), SCARA3, SCARA4 (COLEC12), SCARA5), class B scavenger receptor (e.g., SCARB1, SCARB2, SCARB3 (CD36)), CD68, mucin, or lectin-like oxidized LDL receptor-1 (LOX-1).

The biomolecule may be insulin-like growth factor 1 (IGF-1) or an insulin-like growth factor binding protein (e.g., IGFBP-1, IGFBP-2, IGFBP-3, IGFBP-4, IGFBP-5, IGFBP-6). The agent may be insulin-like growth factor 1 (IGF-1) or an insulin-like growth factor binding protein (e.g., IGFBP-1, IGFBP-2, IGFBP-3, IGFBP-4, IGFBP-5, IGFBP-6). The agent may be an antibody, or an antigen-binding portion thereof, that selectively binds insulin-like growth factor 1 (IGF-1) or an insulin-like growth factor binding protein (e.g., IGFBP-1, IGFBP-2, IGFBP-3, IGFBP-4, IGFBP-5, IGFBP-6).

The agent may be an antibody that selectively binds an extracellular epitope of CD63, CD9, or CD81. Particles targeting CD63, CD9, and/or CD81 may be particularly useful for scavenging extracellular vesicles, such as an ectosome, exosome, shedding vesicle, or apoptotic body. Particles that scavenge various extracellular vesicles may be particularly useful for treating or preventing cancer (e.g., cancers having a disease progression that correlates with the shedding of vesicles).

The biomolecule may be CXCL1, CXCL2, CXCL3, CXCL4, CXCL4L1, CXCL5, CXCL6, CXCL7, CXCL8, CXCL9, CXCL10, CXCL11, CXCL12, CXCL13, CXCL14, CXCL16, CXCL17, CCL1, CCL2, CCL3, CCL3L1, CCL3L3, CCL4, CCL4L1, CCL4L2, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, XCL1, XCL2, or CX3CL1 (see, e.g., Zlotnik, A. and Yoshie, O., Immunity, 36(5):705 (2012)). The agent may comprise an antibody (or an antigen-binding portion thereof) that specifically binds CXCL1, CXCL2, CXCL3, CXCL4, CXCL4L1, CXCL5, CXCL6, CXCL7, CXCL8, CXCL9, CXCL10, CXCL11, CXCL12, CXCL13, CXCL14, CXCL16, CXCL17, CCL1, CCL2, CCL3, CCL3L1, CCL3L3, CCL4, CCL4L1, CCL4L2, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, XCL1, XCL2, or CX3CL1.

The biomolecule may be interleukin 1, interleukin 1 alpha, interleukin 1 beta, interleukin 2, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, interleukin 16, interleukin 17, interleukin 18, interleukin 19, interleukin 20, interleukin 21, interleukin 22, interleukin 23, interleukin 24, interleukin 25, interleukin 26, interleukin 27, interleukin 28, interleukin 29, interleukin 30, interleukin 31, interleukin 32, interleukin 33, interleukin 35, or interleukin 36. The agent may comprise an antibody (or an antigen-binding portion thereof) that specifically binds interleukin 1, interleukin 1 alpha, interleukin 1 beta, interleukin 2, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, interleukin 16, interleukin 17, interleukin 18, interleukin 19, interleukin 20, interleukin 21, interleukin 22, interleukin 23, interleukin 24, interleukin 25, interleukin 26, interleukin 27, interleukin 28, interleukin 29, interleukin 30, interleukin 31, interleukin 32, interleukin 33, interleukin 35, or interleukin 36. The agent may comprise a soluble interleukin-2 receptor, soluble interleukin-3 receptor, soluble interleukin-4 receptor, soluble interleukin-5 receptor, soluble interleukin-6 receptor, soluble interleukin-7 receptor, soluble interleukin-9 receptor, soluble interleukin-10 receptor, soluble interleukin-11 receptor, soluble interleukin-12 receptor, soluble interleukin-13 receptor, soluble interleukin-15 receptor, soluble interleukin-20 receptor, soluble interleukin-21 receptor, soluble interleukin-22 receptor, soluble interleukin-23 receptor, soluble interleukin-27 receptor, or soluble interleukin-28 receptor. The agent may be soluble ST2, which binds interleukin 33.

The biomolecule may be a soluble interleukin-2 receptor, soluble interleukin-3 receptor, soluble interleukin-4 receptor, soluble interleukin-5 receptor, soluble interleukin-6 receptor, soluble interleukin-7 receptor, soluble interleukin-9 receptor, soluble interleukin-10 receptor, soluble interleukin-11 receptor, soluble interleukin-12 receptor, soluble interleukin-13 receptor, soluble interleukin-15 receptor, soluble interleukin-20 receptor, soluble interleukin-21 receptor, soluble interleukin-22 receptor, soluble interleukin-23 receptor, soluble interleukin-27 receptor, or soluble interleukin-28 receptor. The agent may comprise an antibody (or an antigen-binding portion thereof) that specifically binds soluble interleukin-2 receptor, soluble interleukin-3 receptor, soluble interleukin-4 receptor, soluble interleukin-5 receptor, soluble interleukin-6 receptor, soluble interleukin-7 receptor, soluble interleukin-9 receptor, soluble interleukin-10 receptor, soluble interleukin-11 receptor, soluble interleukin-12 receptor, soluble interleukin-13 receptor, soluble interleukin-15 receptor, soluble interleukin-20 receptor, soluble interleukin-21 receptor, soluble interleukin-22 receptor, soluble interleukin-23 receptor, soluble interleukin-27 receptor, or soluble interleukin-28 receptor. The agent may be interleukin 2, interleukin 3, interleukin 4, interleukin 5, interleukin 6, interleukin 7, interleukin 9, interleukin 10, interleukin 11, interleukin 12, interleukin 13, interleukin 15, interleukin 20, interleukin 21, interleukin 22, interleukin 23, interleukin 27, or interleukin 28.

The biomolecule may be epinephrine, norepinephrine, melatonin, serotonin, triiodothyronine, or thyroxine. The biomolecule may be a prostaglandin (e.g., prostacyclin I2 (PGI2), prostaglandin E2 (PGE2), prostaglandin F2α (PGF2α)), a leukotriene, prostacyclin, or thromboxane. The biomolecule may be testosterone, dehydroepiandrosterone (DHEA), androstenedione, dihydrotestosterone (DHT), aldosterone, estrone, estradiol, estriol, progesterone, cortisol, calcitriol, or calcidiol.

The biomolecule may be amylin, adiponectin, adrenocorticotropic hormone, angiotensinogen, angiotensin I, angiotensin II, antidiuretic hormone (vasopressin), apelin, atrial-natriuretic peptide, brain natriuretic peptide, calcitonin, chemerin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (somatomedin, e.g., IGF-I), leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (thyrotropin), thyrotropin-releasing hormone, or vasoactive intestinal peptide. The agent may comprise an antibody (or an antigen-binding portion thereof) that specifically binds amylin, adiponectin, adrenocorticotropic hormone, apelin, angiotensinogen, angiotensin I, angiotensin II, antidiuretic hormone (vasopressin), atrial-natriuretic peptide, brain natriuretic peptide, calcitonin, chemerin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (somatomedin, e.g., IGF-I), leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (thyrotropin), thyrotropin-releasing hormone, or vasoactive intestinal peptide.

The biomolecule may be vascular endothelial growth factor-A (VEGF-A). The agent may comprise an antibody that specifically binds VEGF-A, such as bevacizumab or brolucizumab, or an antigen-binding portion thereof, such as ranibizumab. For example, the agent may be aflibercept. Particles that target VEGF-A may be particularly useful for treating or preventing macular degeneration (e.g., wet macular degeneration), proliferative diabetic retinopathy, neovascular glaucoma, macular edema, cancer (e.g., colorectal cancer, lung cancer, prostate cancer, breast cancer, renal cancer, brain cancer), bronchial asthma, diabetes mellitus, ischemic cardiomyopathy, and myocardial ischemia, in addition to other conditions and diseases.

The biomolecule may be a soluble vascular endothelial growth factor receptor, such as soluble vascular endothelial growth factor receptor 1 (soluble VEGFR-1), soluble vascular endothelial growth factor receptor 2 (soluble VEGFR-2), or soluble vascular endothelial growth factor receptor 3 (soluble VEGFR-3). The agent may be an antibody, or antigen-binding portion thereof, that selectively binds a soluble VEGF receptor, such as alacizumab, icrucumab, or ramucirumab. The agent may be a ligand of a VEGF receptor, such as VEGF-A, VEGF-B, VEGF-C, VEGF-D, or placental growth factor (PGF). Particles targeting soluble VEGF receptors may be particularly useful for treating or preventing cancer, in addition to other disease and conditions.

The biomolecule may be a member of the epidermal growth factor family, such as epidermal growth factor (EGF), heparin-binding EGF-like growth factor (HB-EGF), transforming growth factor-α (TGF-α), amphiregulin (AR), epiregulin (EPR), epigen, betacellulin (BTC), neuregulin-1 (NRG1), neuregulin-2 (NRG2), neuregulin-3 (NRG3), or neuregulin-4 (NRG4). The agent may be an antibody, or antigen-binding portion thereof, that selectively binds EGF, HB-EGF, TGF-α, AR, EPR, epigen, BTC, NRG1, NRG2, NRG3, or NRG4. The agent may comprise a soluble EGF receptor, such as soluble EGF receptor, soluble HER2, or soluble HER3. Particles targeting members of the epidermal growth factor family may be particularly useful for treating or preventing cancer, in addition to other conditions and diseases.

The biomolecule may be a soluble epidermal growth factor receptor (EGF receptor), such as soluble EGF receptor, soluble human epidermal growth factor receptor 2 (soluble HER2) or soluble human epidermal growth factor receptor 3 (soluble HER3). The agent may be an antibody, or antigen-binding portion thereof, that selectively binds a soluble EGF receptor, such as cetuximab, futuximab, imgatuzumab, matuzumab, necitumumab, nimotuzumab, panitumumab, zalutumumab, duligotumab, patritumab, ertumaxomab, pertuzumab, or trastuzumab. The agent may be a ligand of an EGF receptor, such as an EGF family member as described above. Particles targeting soluble EGF receptors may be particularly useful for treating or preventing cancer, in addition to other disease and conditions.

The biomolecule may be an IgE antibody. The agent may comprise an anti-IgE antibody, such as omalizumab or talizumab, or an antigen-binding portion thereof. The agent may be the extracellular portion of FcεRI. Particles that target IgE antibodies may be particularly useful for treating chronic spontaneous urticarial and allergic asthma, in addition to other conditions and diseases.

The biomolecule may be proprotein convertase subtilisin/kexin type 9 (PCSK9). The agent may be an anti-PCSK9 antibody, such as alirocumab, lodelcizumab, ralpancizumab, or evolocumab, or an antigen-binding portion thereof. Particles targeting PCSK9 may be particularly useful for treating or preventing hypercholesterolemia, atherosclerosis, ischemia, and myocardial infarction, in addition to other conditions and diseases.

The biomolecule may be adrenomedullin, brain-derived neurtrophic factor, erythropoietin, fibroblast growth factor, hepatoma-derived growth factor, glucose-6-phosphate isomerase, keratinocyte growth factor, macrophage migration inhibitory factor, neurotrophin (nerve growth factor, brain-derived neurotrophic factor, neurotrophin-3, neurotrophin-4), platelet-derived growth factor, stem cell factor, thrombopoietin, T-cell growth factor, vascular endothelial growth factor (VEGF-A, VEGF-B, VEGF-C, VEGF-D, placental growth factor (PGF)), or renalase. The agent may comprise an antibody, or antigen-binding portion thereof, that selectively binds adrenomedullin, brain-derived neurtrophic factor, erythropoietin, fibroblast growth factor, hepatoma-derived growth factor, glucose-6-phosphate isomerase, keratinocyte growth factor, macrophage migration inhibitory factor, neurotrophin (nerve growth factor, brain-derived neurotrophic factor, neurotrophin-3, neurotrophin-4), platelet-derived growth factor, stem cell factor, thrombopoietin, T-cell growth factor, vascular endothelial growth factor (VEGF-A, VEGF-B, VEGF-C, VEGF-D, placental growth factor (PGF)), or renalase.

The biomolecule may be soluble tropomyosin receptor kinase B (soluble TrkB). The agent may be an anti-TrkB antibody, or an antigen-binding portion thereof. The biomolecule may be soluble tropomyosin receptor kinase A (soluble TrkA). The agent may be an anti-TrkA antibody, or an antigen-binding portion thereof. The agent may be brain-derived neurotrophic factor.

The biomolecule may be angiopoietin (e.g., angiopoietin 1, angiopoietin 2, angiopoietin 3, or angiopoietin 4) or an angiopoietin like protein (e.g., angiopoietin-like 1, angiopoietin-like 2, angiopoietin-like 3, angiopoietin-like 4, angiopoietin-like 5, angiopoietin-like 6, or angiopoietin-like 7). The agent may be an antibody that selectively binds to angiopoietin (e.g., angiopoietin 1, angiopoietin 2, angiopoietin 3, or angiopoietin 4) or an angiopoietin like protein (e.g., angiopoietin-like 1, angiopoietin-like 2, angiopoietin-like 3, angiopoietin-like 4, angiopoietin-like 5, angiopoietin-like 6, or angiopoietin-like 7).

The biomolecule may be a hedgehog protein (e.g., sonic hedgehog). The agent may be an antibody that selectively binds a hedgehog protein. Particles targeting hedgehog proteins may be particularly useful for treating or preventing cancer, such as pancreatic cancer, cerebellar cancer, and medulloblastomas, in addition to other conditions and diseases.

The biomolecule may be a soluble human leukocyte antigen (HLA) protein (e.g., soluble HLA-A, HLA-B, HLA-C, HLA-D, HLA-E, HLA-F, OR HLA-G (see, e.g., Bassani-Sternberg, M. et al., Proceedings National Academy Sciences USA 107(44):18769 (2010))). The agent may be an antibody that selectively binds a soluble human leukocyte antigen (HLA) protein. The agent may be a soluble killer cell immunoglobulin-like receptor. Particles that target a soluble HLA may be particularly useful for treating or preventing cancer, in addition to other diseases and conditions.

The biomolecule may be a soluble UL16-binding protein isoform (e.g., a soluble RAET1 (ULBP1; RAET1E2), soluble RAET1H (ULBP2), soluble RAET1N (ULBP3), soluble RAET1E (ULBP4), soluble RAET1G (ULBP5), or soluble RAET1L (ULBP6)). The agent may be an antibody that specifically binds a soluble UL16-binding protein isoform, or an antigen-binding portion thereof. The agent may be soluble NKG2D receptor (see, e.g., PCT Patent Application Publication No. WO 2006/024367, hereby incorporated by reference in its entirety).

The biomolecule may be soluble MIC-A or soluble MIC-B (see, e.g., Groh, V. et al., Nature 419(6908):734 (2002)). The agent may be an anti-MIC-A antibody or an anti-MIC-B antibody, or an antigen binding portion of either antibody. The agent may be soluble NKG2D receptor (see, e.g., PCT Patent Application Publication No. WO 2006/024367, hereby incorporated by reference in its entirety).

The agent may be a soluble natural cytotoxicity receptor (see, e.g., Jarahian, M. et al. PloS Pathogens 7(8): e1002195 (2011)).

The biomolecule may be soluble C-type lectin domain family 2 member D (soluble CLEC2D; soluble Lectin Like Transcript-1 (LLT1)) (see, e.g., Chalan, P. et al., PloS One 10(7): e0132436 (2015)). The agent may be an antibody that selectively binds soluble LLT1. Particles that target a soluble LLT1 may be particularly useful for treating or preventing autoimmune diseases, such as rheumatoid arthritis, in addition to other diseases and conditions.

The biomolecule may be soluble CD16 (see, e.g., Hoover, R. G., J Clinical Investigation 95:241 (1995)). The agent may be an antibody that selectively binds a soluble CD16. Particles that target soluble CD16 may be particularly useful for treating or preventing cancer, in addition to other diseases and conditions.

The biomolecule may be plasminogen activator inhibitor-1 (PAI-1), plasminogen activator inhibitor-1 (PAI-2), tissue plasminogen activator, urokinase, plasminogen, thrombin, or α2-macroglobulin. The agent may be an antibody that selectively binds plasminogen activator inhibitor-1 (PAI-1), plasminogen activator inhibitor-1 (PAI-2), tissue plasminogen activator, urokinase, plasminogen, thrombin, or α2-macroglobulin.

The biomolecule may be Factor XII, Factor XIIa, Factor XI, Factor XIa, Factor IX, Factor IXa, Factor X, Factor Xa, Factor VII, Factor VIIa, Factor XIII, Factor XIIIa, Factor V, prothrombin, thrombin, von Willebrand factor, thromboxane A2, fibrinogen, or fibrin. The agent may be an antibody that selectively binds to Factor XII, Factor XIIa, Factor XI, Factor XIa, Factor IX, Factor IXa, Factor X, Factor Xa, Factor VII, Factor VIIa, Factor XIII, Factor XIIIa, Factor V, prothrombin, thrombin, von Willebrand factor, thromboxane A2, fibrinogen, or fibrin.

The biomolecule may be a serpin (e.g., α1-antitrypsin, antitrypsin-related protein, α1-antichymotrypsin, kallistatin, protein C inhibitor, transcortin, thyroxine-binding globulin, angiotensinogen, centerin (GCET1), protein Z-related protease inhibitor, vaspin, antithrombin, heparin cofactor II, plasminogen activator inhibitor 1, glia derived nexin (protease nexin I), pigment epithelium derived factor, α2-antiplasmin, complement 1-inhibitor, neuroserpin, plasminogen activator inhibitor, 2SERPINA1, or SERPINA2). The agent may comprise an antibody that selectively binds a serpin, or an antigen-binding portion thereof.

The biomolecule may be soluble ST2. The agent may be interleukin 33 or an antibody that specifically binds soluble ST2 (or a fragment thereof). Particles that target soluble ST2 may be particularly useful for treating or preventing heart disease, myocardial infarction, acute coronary syndrome, and heart failure, in addition to other disease and conditions.

The biomolecule may be myostatin (growth differentiation factor 8 (GDF-8)). The agent may be an anti-myostatin antibody, such as stamulumab or trevogrumab. The agent may be an activin receptor or a myostatin-binding portion thereof, e.g., the agent may be soluble activin type IIB receptor. Particles targeting myostatin may be particularly useful for treating muscular dystrophy, cachexia, sarcopenia, and various forms of muscle loss (such as zero-gravity muscle loss), in addition to other diseases and conditions.

The biomolecule may be ghrelin. The agent may be an anti-ghrelin antibody. Particles targeting ghrelin may be particularly useful for treating or preventing obesity, Prader-Willi syndrome, addiction, alcoholism, and leptin resistance (e.g., genetic leptin resistance).

The biomolecule may be sLR11 (soluble SORL1; soluble SORLA; soluble SORLA1). The agent may be an anti-sLR11 antibody. Particles targeting sLR11 may be particularly useful for treating or preventing obesity, in addition to other diseases and conditions.

The biomolecule may be TGF-β (transforming growth factor beta, e.g., TGF-β1, TGF-β2, or TGF-β3). The agent may be an anti-TGF-β antibody, such as fresolimumab, lerdelimumab, or metelimumab. The agent may comprise the TGF-β binding domain of a TGF-β receptor. The agent may be LTBP1 (latent-transforming growth factor beta-binding protein 1), 14-3-3-protein epsilon (tyrosine 3-monooxygenase/tryptophan 5-monooxygenase activation protein, epsilon; YWHAE), or eukaryotic translation initiation factor 3 subunit I (EIF3I), each of which binds to TGF-β. Particles targeting TGF-β may be particularly useful for treating or preventing scleroderma, idiopathic pulmonary fibrosis, renal disease, focal segmental glomerulosclerosis, keratoconus, Marfan syndrome, Alzheimer's disease, cognitive decline, traumatic brain injury, muscle wasting, and cancer (e.g., kidney cancer and melanoma), in addition to other diseases and conditions.

The biomolecule may be Wnt (e.g., Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, or Wnt16). The agent may be an anti-Wnt antibody. Particles targeting Wnt may be particularly useful for treating or preventing obesity, type II diabetes, atherosclerosis, calcific aortic valve stenosis, heart attack, heart failure, stroke, and cancer (e.g., breast cancer, colorectal cancer, esophageal cancer, melanoma, prostate cancer, lung cancer, non-small cell lung cancer, mesothelioma, sarcoma, glioblastoma, or ovarian cancer), in addition to other diseases and conditions.

The biomolecule may be a soluble Notch ligand (e.g., soluble Jagged1, soluble Jagged2, soluble Delta-like ligand 1 (DLL1), soluble Delta-like ligand 3 (DLL3), and Delta-like ligand 4 (DLL4)). The agent may be an anti-Notch ligand antibody, such as demcizumab or enoticumab, or a soluble Notch receptor (e.g., soluble NOTCH1, NOTCH2, NOTCH3, or NOTCH4) or a variant thereof. Particles targeting soluble Notch ligands may be particularly useful for treating or preventing atherosclerosis, calcific aortic valve stenosis, heart attack, heart failure, stroke, and cancer (e.g., breast cancer, pancreatic cancer renal cell carcinoma, non-small cell lung cancer, and solid tumors), in addition to other diseases and conditions.

The biomolecule may be a soluble Notch receptor (e.g., soluble NOTCH1, NOTCH2, NOTCH3, or NOTCH4). The agent may be an anti-Notch receptor antibody, such as tarextumab or brontictuzumab, or a soluble Notch ligand. Particles targeting soluble Notch receptors may be particularly useful for treating or preventing atherosclerosis, calcific aortic valve stenosis, heart attack, heart failure, stroke, and cancer (e.g., breast cancer, pancreatic cancer renal cell carcinoma, non-small cell lung cancer, and solid tumors), in addition to other diseases and conditions.

The target may be hydroxyapatite or calcium (e.g., crystalline calcium). The agent may be a chelating agent such as ethylene diamine tetraacetic acid (EDTA), diethylene triamine pentaacetic acid (DTPA), sodium thiosulfate (STS), inositol hexaphosphate, or citric acid. Particles targeting hydroxyapatite or calcium may be particularly useful for treating or preventing atherosclerosis, calcific aortic valve stenosis, and calcific tendinitis, in addition to other diseases and conditions.

In some embodiments, the biomolecule is an autoantibody. An autoantibody is an antibody produced by a subject that specifically binds an antigen produced by the subject. Autoantibodies are associated with many different disease states, including lupus. Additionally, the induction of new autoantibodies may be associated with a therapeutic intervention, e.g., resulting in drug-induced lupus. Thus, a composition comprising a plurality of particles comprising an agent that selectively binds one or more autoantibodies may be used, for example, in a method of treating or preventing lupus (e.g., drug-induced lupus). The biomolecule may be, for example, a double-stranded DNA autoantibody or an anti-nuclear autoantibody.

A particle that targets an autoantibody may comprise an agent that is the antigen of the autoantibody.

The biomolecule may be an anti-β adrenoceptor autoantibody or an anti-M2 muscarinic receptor autoantibody, e.g., for preventing or treating idiopathic dilated cardiomyopathy. In particular, a particle that targets an anti-β adrenoceptor autoantibody or an anti-M2 muscarinic receptor autoantibody may be administered to a subject with Chagas' disease, which correlates with the induction of such autoantibodies (see, e.g., Herda, L. R. et al., Br J Pharmacol 166(3)847 (2012)). The biomolecule may be an anti-alpha-1-adrenergic receptor autoantibody, e.g., for treating or preventing hypertension (see, e.g., Luther, H. P. et al., Hypertension 29(2): 678 (1997)). The biomolecule may be an anti-muscarinic type 3 receptor autoantibody, e.g., for use in treating or preventing Sjögren's syndrome (see, e.g., Lee, B. H. et al., PloS One 8(1):e53113 (2013)).

Autoantibodies against hormones and cytokines may buffer the concentration of hormones and cytokines, for example by reversibly binding to them to control the concentration of free, active species. Deviations from healthy autoantibody levels may contribute to diseases arising from loss of cytokine or hormonal homeostasis. For example, anti-IFNγ autoantibodies may induce disseminated non-tuberculosis mycobacterial infections, anti-IL-17 autoantibodies are associated with the development of chronic mucosal candidiasis, and anti-IL-6 autoantibodies are associated with severe staphylococcal or streptococcal infections. Autoantibodies to the hunger hormone ghrelin may mediate the effective concentration of ghrelin available to bind to ghrelin receptor GHSR1.

In some embodiments, the biomolecule is an autoantibody. For example, the autoantibody may be an anti-IFNγ, anti-IL-17, anti-IL-6, or anti-ghrelin autoantibody. In some embodiments, the agent is the natural ligand of an autoantibody (e.g., an antigen targeted by the autoantibody). For example, the agent may be IFNγ, IL-17, IL-6, or ghrelin. In some embodiments, the invention relates to a method of treating a patient with a disease of dysregulation of a cytokine, such as an autoimmune disease. In some embodiments, the invention relates to a method of treating a patient with metabolic disorder, such as obesity.

Activin binding to activin type IIB receptor ActRIIB leads to muscle wasting in models of cachexia. Excessive activin levels in serum are associated with muscle wasting and fibrosis in models of cachexia, which may be reversed by antibodies that block activin A and B/ActRIIB signalling, and elevated activin levels are found in serum of cancer patients. Sarcopenia is a progressive condition of loss of muscle mass in aging and has also been associated with excessive activin signalling. The biomolecule may thus be activin (e.g., activin A or activin B). The agent may be a natural ligand for an activin, such as an activin receptor protein such as ActRIIB or a variant thereof, or an antibody against an activin. The agent may be myostatin. In some embodiments, the invention relates to a method of treating a patient a muscle-wasting disease, such as cachexia or sarcopenia.

A skilled artisan will also appreciate that the particles described herein are also useful for scavenging a wider variety of targets whose biological activity may be, e.g., undesirable. For example, the particles can be engineered to bind to components of viral capsids or envelopes to thereby sequester virus from the blood of a subject. The particles may be, in some embodiments, engineered to bind and sequester toxins (e.g., bacterial toxins, plant toxins, and zootoxins, such as one or more components of snake venom) in the circulation of a subject. In some embodiments, the particles can be engineered to bind to and sequester small molecules (e.g., psychoactive drugs or small molecular toxins) from the circulation of a subject. In such embodiments, the particles can be useful to remove toxins from the body, e.g., following a snake or insect bite. In some embodiments, the particles can be used for treating, preventing, delaying the onset, or reducing the severity of, anaphylactic shock in a subject (e.g., by scavenging the antigen giving rise to the anaphylactic immune response).

In some embodiments, the target is associated with a virus, e.g., a viral structural protein (such as a viral capsid or viral envelope protein) that is bound by the agent. In such embodiments, the particles are useful as anti-viral therapies, e.g., for a subject infected with a virus or at risk of being infected with a virus. A virus may be an enveloped or non-enveloped virus.

In some embodiments, the soluble biomolecule is a small molecule or macromolecule. In some embodiments, the longest dimension of the soluble biomolecule is no greater than 600 nm (e.g., less than 550, 500, 450, 400, 350, 300, 250, 200, 150, 100, 50, or 25 nm). For example, the biomolecule may have a molecular radius of about 1 Å to about 1 μm, such as about 1 Å to about 100 nm, about 1 Å to about 20 nm, about 1 nm to about 1 μm, about 1 nm to about 100 nm, or about 1 nm to about 20 nm. The biomolecule may have a molecular weight of about 3 amu to about $10^7$ amu, such as about 100 amu to about $10^7$ amu, about 3 amu to about $10^6$ amu, about 3 amu to about $10^5$ amu, about 100 amu to about $10^6$ amu, or about 400 amu to about $10^6$ amu. The biomolecule may have a molecular weight of about $10^5$ amu to about $10^7$ amu.

The terms "specific binding," "specifically binds," "selective binding," "selectively binds," and like grammatical terms, as used herein, refer to two molecules forming a complex that is relatively stable under physiologic conditions. Typically, binding is considered specific when the association constant ($k_a$) is higher than $10^6$ M$^{-1}$s$^{-1}$. Thus, a first member of a specific binding pair can specifically bind to the second member of the binding pair with a $k_a$ of at least (or greater than) $10^6$ M$^{-1}$s$^{-1}$ (e.g., at least or greater than $10^7$, $10^8$, $10^9$, $10^{10}$, $10^{11}$, $10^{12}$, $10^{13}$, $10^{14}$, or $10^{15}$M$^{-1}$s$^{-1}$ or higher). In some embodiments, a selective interaction has a dissociation constant ($k_d$) of less than or equal to $10^{-3}$ s$^{-1}$ (e.g., $8\times10^{-4}$, $5\times10^{-4}$, $2\times10^{-4}$, $10^{-4}$, or $10^{-5}$ s$^{-1}$).

Specific binding does not refer to an interaction that is primarily driven by a non-specific electrostatic interaction or a non-specific hydrophobic interaction, which may have a favorable association constant. For example, nucleic acids, which are negatively charged, may bind to a cationic particle with a favorable association constant, independent of a specific interaction, and such binding is not "specific binding" as defined herein. Similarly, a lipid may bind to a hydrophobic particle with a favorable association constant, independent of a specific interaction, and such binding is not "specific binding" as defined herein.

In some embodiments, the biomolecule and the particle have the same charge at physiological pH (~7.4). For example, the biomolecule may have a negative charge and the particle may have a negative charge or the biomolecule may have a positive charge and the particle may have a positive charge. In some embodiments, the biomolecule and the particle have opposite charges at physiological pH. For example, the biomolecule may have a positive charge and the particle may have a negative charge or the biomolecule may have a negative charge and the particle may have a positive charge. In some embodiments, the biomolecule has a neutral charge at physiological pH and/or the particle has a neutral charge at physiological pH.

The biomolecule may have an isoelectric point of about 0 to about 14. Nucleic acids have an isoelectric point of about 4 to about 7, and thus, the biomolecule may have an isoelectric point of about 4 to about 7. Proteins generally have an isoelectric point of about 4 to about 10, and thus, the biomolecule may have an isoelectric point of about 4 to about 10. Nevertheless, unmodified peptides and proteins may have isoelectric points ranging from about 2.5 (based on aspartate; pI~2.8) to about 11 (based on arginine; pI~11), although proteins with isoelectric points falling outside of this range are known. Accordingly, the biomolecule may have an isoelectric point ranging from about 2.5 to about 11. Secreted proteins and the soluble, extracellular portions of membrane proteins typically have a slight negative charge at physiological pH, and thus, the biomolecule may have an isoelectric point of about 4 to about 7, such as about 4 to about 6. The biomolecule may have an isoelectric point of about 0 to about 4, about 2 to about 6, about 4 to about 8, about 6 to about 10, about 8 to about 12, or about 10 to about 14. The biomolecule may have an isoelectric point of about 0 to about 2, about 1 to about 3, about 2 to about 4, about 3 to about 5, about 4 to about 6, about 4 to about 6, about 5 to about 7, about 6 to about 8, about 7 to about 9, about 8 to about 10, about 9 to about 11, about 10 to about 12, about 11 to about 13, or about 12 to about 14.

In some embodiments, a selective interaction has a $K_D$ of less than $10^{-8}$, $10^{-9}$, $10^{-10}$, $10^{-11}$, or $10^{-12}$ M. The equilibrium constant $K_D$ is the ratio of the kinetic rate constants—$k_d/k_a$. In some embodiments, a selective interaction has a $K_D$ of less than $1\times10^{-9}$M.

As used herein, the term "interaction," when referring to an interaction between two molecules, refers to the physical contact (e.g., binding) of the molecules with one another. Generally, such an interaction results in an activity (which produces a biological effect) of one or both of said molecules. To inhibit such an interaction results in the disruption of the activity of one or more molecules involved in the interaction.

As used herein, the term "inhibiting" and grammatical equivalents thereof refer to a decrease, limiting, and/or blocking of a particular action, function, or interaction. In one embodiment, the term refers to reducing the level of a given output or parameter to a quantity (e.g., the background level of the interaction between two members of a specific binding pair) which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The invention does not require, and is not limited to, methods that wholly eliminate the output or parameter. Substantial inhibition can be, e.g., at least 50% (e.g., 55, 60, 65, 70, 75, 80, 85, 90, or 95% or greater) inhibition of an interaction between two biomolecules (e.g., the first and second members of a binding pair).

Methods for detecting an interaction or measuring the affinity of one biomolecule for another are known in the art. For example, the binding of two biomolecules can be detected and/or quantified using a variety of techniques such as, but not limited to, BioLayer Interferometry (BLI), Western blot, dot blot, surface plasmon resonance method (SPR), enzyme-linked immunosorbent assay (ELISA), AlphaScreen® or AlphaLISA® assays, or mass spectrometry based methods.

In some embodiments, binding can be assayed using any SPR-based assays known in the art for characterizing the kinetic parameters of the interaction of two biomolecules. Any SPR instrument commercially available including, but not limited to, BIAcore Instruments (Biacore AB; Uppsala, Sweden); 1Asys instruments (Affinity Sensors; Franklin, Mass.); IBIS system (Windsor Scientific Limited; Berks, UK), SPR-CELLIA systems (Nippon Laser and Electronics Lab; Hokkaido, Japan), and SPR Detector Spreeta (Texas Instruments; Dallas, Tex.) can be used in the methods described herein. (See, e.g., Mullett et al., *Methods* 22:77-91(2000); Dong et al., *Reviews in Mol Biotech* 82:303-323 (2002); Fivash et al., *Curr Opin Biotechnol* 9:97-101(1998); and Rich et al., *Curr Opin Biotechnol* 11:54-61(2000)).

In some embodiments, biomolecular interactions between two biomolecules can be assayed using BLI on an Octet (ForteBio Inc.). BLI is a label-free optical analytical technique that senses binding between a ligand that is immobilized on a biosensor tip and an analyte in solution by measuring the change in the thickness of the protein layer on the biosensor tip in real-time.

In some embodiments, AlphaScreen (PerkinElmer) assays can be used to characterize binding of two biomolecules. The acronym ALPHA stands for Amplified Luminescent Proximity Homogeneous Assay. AlphaScreen is a bead-based proximity assay that senses binding between molecules attached to donor and acceptor beads by measuring the signal produced by energy transfer between the donor and acceptor beads. (See, e.g., Eglen et al., *Curr Chem Genomics* 1:2-10(2008)).

In some embodiments, AlphaLISA® (PerkinElmer) assays can be used to characterize binding of two biomolecules. AlphaLISA is modified from the AlphaScreen assay described above to include europium-containing acceptor beads and functions as an alternative to traditional ELISA assays. (See, e.g., Eglen et al., *Curr Chem Genomics* 1:2-10(2008)).

A variety of immunoassay techniques, including competitive and non-competitive immunoassays, can be used. The term "immunoassay" encompasses techniques including, without limitation, flow cytometry, FACS, enzyme immunoassays (EIA), such as enzyme multiplied immunoassay technique (EMIT), enzyme-linked immunosorbent assay (ELISA), IgM antibody capture ELISA (MAC ELISA), and microparticle enzyme immunoassay (MEIA), furthermore capillary electrophoresis immunoassays (CEIA), radio-immunoassays (RIA), immunoradiometric assays (IRMA), fluorescence polarization immunoassays (FPIA), and chemiluminescence assays (CL). If desired, such immunoassays can be automated. Immunoassays can also be used in conjunction with laser induced fluorescence. Liposome immunoassays, such as flow-injection liposome immunoassays and liposome immunosensors, are also suitable for use in the present invention. In addition, nephelometry assays, in which, for example, the formation of biomolecular complexes results in increased light scatter that is converted to a peak rate signal as a function of the marker concentration, are suitable for use in the methods of the present invention. In a preferred embodiment of the present invention, the incubation products are detected by ELISA, RIA, fluoro immunoassay (FIA) or soluble particle immune assay (SPIA).

In some embodiments, binding of two biomolecules can be assayed using thermodenaturation methods involving differential scanning fluorimetry (DSF) and differential static light scattering (DSLS).

In some embodiments, binding of two biomolecules can be assayed using a mass spectrometry based method such as, but not limited to, an affinity selection coupled to mass spectrometry (AS-MS) platform. This is a label-free method where the protein and test compound are incubated, unbound molecules are washed away and protein-ligand complexes are analyzed by MS for ligand identification following a decomplexation step.

In some embodiments, binding of two biomolecules can be quantitated using, for example, detectably labeled proteins such as radiolabeled (e.g., $^{32}P$, $^{35}S$, $^{14}C$ or $^3H$), fluorescently labeled (e.g., FITC), or enzymatically labeled biomolecule, by immunoassay, or by chromatographic detection.

In some embodiments, the present invention contemplates the use of fluorescence polarization assays and fluorescence resonance energy transfer (FRET) assays in measuring, either directly or indirectly, the degree of interaction between two biomolecules.

II. Particles

As used herein, the term "particle" refers to a small mass that can comprise any material, such as alumina, metal (e.g., gold or platinum), glass, silica, latex, plastic, agarose, polyacrylamide, methacrylate or any polymeric material, and be of any size and shape. In some embodiments, the particle or particles comprise silicon. (See, e.g., International Patent Application Publication Nos. WO 2013/011764, WO 2013/029278, and WO 2014/151381, and U.S. Patent Application Publication No. 2014/0271886, the disclosures of each of which are incorporated by reference in their entirety). In some embodiments, the particles comprise or consist of starch (see, e.g., International Patent Application Publication No. WO 2010/084088). In some embodiments, the particle or particles are composed of nucleic acid (e.g., naturally-occurring or non-naturally occurring nucleic acid). Methods for making such nucleic acid-based microscopic structures are known in the art and are described in, e.g., Douglas et al., *Nucl Acids Res* 37(15):5001-5006 (2009); Douglas et al., *Nature* 459(7245):414-428 (2009); Voigt et al., *Nat Nanotechnol* 5(3):200-203 (2010); and Endo et al., *Curr Protoc Nucleic Acid Chem* Chapter 12(Unit 12.8) (2011).

In preferred embodiments, the particle is insoluble in aqueous solution (e.g., the particle may be insoluble in water, blood serum, blood plasma, extracellular fluid, and/or interstitial fluid). For example, a particle may be separated from aqueous solution by centrifuging a solution comprising the particle, e.g., at speeds that are sufficient to separate the cells of a cell suspension from the aqueous solution of the cell suspension. Nevertheless, a particle may readily exist as a suspension in aqueous solution, e.g., mild shaking or vortexing of a plurality of particles in aqueous solution is sufficient to suspend the particles in the solution. In some embodiments, the particle is not a hydrogel. In some embodiments, the particle does not comprise a hydrogel. In some embodiments, the particle does not comprise a polymer.

A particle is preferably large enough to bind to more than one biomolecule and inhibit the interaction of more than one bound biomolecule with a binding partner. For example, a particle may be about 50 nm to about 10 μm. A particle may be 1 μm to 5 μm in size, 1.2 μm to 4 μm, 1.5 μm to 4 μm, or 2 μm to 4 μm.

Particles with sizes less than 300 nm, such as less than 200 nm or less than 150 nm, are preferred for applications in which the particles are intended to enter and/or exit the vasculature of a subject, such as particles that may be administered by subcutaneous injection. Nevertheless, larger particles are similarly well-suited for subcutaneous injection for methods in which the particles are not intended to enter the vasculature. Particles with sizes of about 1 μm to about 5 μm are preferable for applications in which the particles are intended to circulate within the vasculature of a subject, e.g., following intravenous administration. Particles with sizes greater than 5 μm may be preferable for applications in which the particles are intended to reside at the site in which they are implanted, such as within or adjacent to a tumor; however, particles smaller than 5 μm may also be suitable for implantation. Particles of any size may be utilized for in vitro applications.

Also featured herein are collections of particles. In some embodiments, the plurality of particles has a narrow or broad polydispersity. As used herein, "polydispersity" refers to the range of sizes of particles within a particular particle population. That is, an extremely polydisperse population might involve particles having a mean size of, say, 1 μm with individual particles ranging from 0.1 to 4 μm. In some embodiments, a "narrow polydispersity" is preferred. That is, given a particular mean particle size, it is presently preferred that individual particles in the population differ by no more than ±20%, preferably no more than ±15%, and most preferably at present no more than ±10% from the mean particle size. More specifically, a particle population preferably has a mean particle size of about 0.5 to about 2 μm, more preferably at present from about 0.8 to about 1.5 μm. Thus, if a mean particle size of 1 μm is selected, individual particles in the population would most preferably be within the range of from about 0.8 to about 1.2 μm. In some embodiments, the particle population has a mean particle size of about 0.3 to about 1 μm, e.g., about 0.4 to about 0.9, about 0.5 to about 0.9, about 0.4 to about 0.8, about 0.5 to about 0.7, about 0.3 to about 0.9, or about 0.3 to about 0.7 μm. In some embodiments, the particle population has a mean particle size of about 1 μm to about 10 μm, e.g., about 1.1 μm to about 4.8, about 1.2 μm to about 4.6, about 1.4 µm to about 4.4, about 1.6 µm to about 4.2, about 1.8 µm to about 4.0, or about 2.0 µm to about 3.8 µm.

In some embodiments, the disclosure features a collection or plurality of particles having a defined mean particle size. As used herein, "mean particle size" is arrived at by measuring the size of individual particles and then dividing by the total number of particles. The determination of mean particle size is well known in the art. Typically, the longest average dimension of the particles is no greater than 4 µm. In some embodiments, the longest average dimension of the particles is no greater than 3.9 (e.g., no greater than 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, or 1)µm. In some embodiments, the longest average dimension of the particles is no greater than 2.5 µm, 2 µm, 1.5 µm, or 1.25 µm. In some embodiments, the longest average dimension of the particles is at least 1 µm, but no greater than 4 µm. In some embodiments, the longest average dimension of the particles is at least 1 µm, but no greater than 2 µm. In some embodiments, the longest average dimension of the particles is at least 1 µm, but no greater than 1.5 µm. In some embodiments, the longest average dimension of the particles is at least 0.5 µm (e.g., at least 0.6, 0.7, 0.8, 0.9, 1, 1.1, 1.2, 1.3, 1.4, or 1.5 µm), but no greater than 4 µm (e.g., no greater than 3.9 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, or 1.6 µm).

In some embodiments, the particles are nanoparticles. In some embodiments, the longest average dimension of the particles is no greater than 900 nm (e.g., 850, 800, 750, 700, 650, 600, 550, 500, 450, 400, 450, 400, 350, 300, 250, 200, or 150 nm). In some embodiments, a particle is shaped and sized to circulate in the blood or vasculature (e.g., arteries, veins, and capillaries) of a subject (e.g., a human subject). Exemplary particle designs are set forth in FIGS. 1 to 6.

In some embodiments, the longest dimension of the particle is about 50 nm to about 5 µm, such as about 100 nm to about 4.5 µm, about 200 nm to about 4 µm, about 300 nm to about 3.5 µm, about 300 nm to about µm, or about 400 nm to about 3 µm. In some embodiments, the shortest dimension of the particle is at least about 300 nm, such as about 300 nm to about 4 µm or about 400 nm to about 3 µm.

In some embodiments, a plurality of the particles are polyhedral, e.g., cubic. In some embodiments, a plurality of the particles are spherical. In some embodiments, any of the particles described herein can be porous. Such porous particles comprise an outer surface and inner surfaces of the pores of the particle. The agent can be, e.g., immobilized on the inner surfaces. In some embodiments, a plurality of pores have a cross-sectional dimension of at least 50 nm. In some embodiments, a plurality of pores have a cross-sectional dimension of at least 100 nm. Porous nanoparticles have been described in, e.g., U.S. Patent Application Publication Nos. 20140199352, 20080277346, and 20040105821, the disclosures of each of which are incorporated by reference in their entirety. Spherical particles are described in, e.g., U.S. Pat. Nos. 8,778,830 and 8,586,096, each of which is hereby incorporated by reference.

In some embodiments, spherical particles can further comprise two intersecting ridges extending from the spherical surface of the particle, wherein the longest dimension of each of the structures is no greater than 4 µm (e.g., no greater than 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, or 1 µm), and wherein the ridges are sized and oriented: (i) to inhibit the agent immobilized on the surface of the spherical particle from binding to, or activating, a cell surface receptor protein and/or (ii) when the soluble biomolecule is bound to the agent, to inhibit the interaction of the soluble biomolecule and a second member of a specific binding pair of which the soluble biomolecule is the first member.

In some embodiments, a plurality of particles are toroidal. In such embodiments, the agent can be immobilized on an inner circumferential surface of the particle (e.g., around the hole—see FIG. 2). In some embodiments, the diameter of the particle is no greater than 4 μm (e.g., 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, or 1 μm). In some embodiments, the diameter of the particle is no greater than 900 nm (e.g., 850, 800, 750, 700, 650, 600, 550, 500, 450, 400, 350, 300, 200, or 150 nm).

In some embodiments, the particles described herein are dendritic. Such particles are described in, e.g., Du et al., *Small* 11(4):392-413 (2015); Siegwart, D. J. et al., Proceedings National Academy Sciences USA 108(32):12996 (2011); U.S. Pat. Nos. 5,814,272 and 7,932,311; and U.S. Patent Application Publication No. 20040166166, the disclosures of each of which are hereby incorporated by reference herein. As elaborated on below, in some embodiments the geometry of the dendritic particles is such that the agent immobilized on the inner surface of the particle has a reduced, or substantially reduced, ability to interact with a biomolecule on the surface of a cell and/or the soluble biomolecule bound to the particle by virtue of the agent has a reduced, or substantially reduced, ability to interact with its cognate ligand (the second member of the specific binding pair).

In some embodiments, a plurality of particles are polyhedral, e.g., octahedral or icosahedral (see, e.g., FIG. 3), whether regular or irregular. The particles may comprise at least one protrusion from at least one of their vertices (see, e.g., FIG. 3). The particles may comprise more than one (e.g., 2, 3, 4, 5, 6, 7, or 8 or more) protrusion from their vertices. Such protrusions can be, e.g., sized and/or oriented: (i) to inhibit the agent immobilized on the surface of the spherical particle from binding to, or activating, a cell surface receptor protein and/or (ii) when the soluble biomolecule is bound to the agent, to inhibit the interaction of the soluble biomolecule and a second member of a specific binding pair of which the soluble biomolecule is the first member.

A particle may comprise void space, referred to as a "void" or "voids" herein. A void is the space in a particle that is filled by a fluid (e.g., a liquid, which may comprise a biomolecule, or a gas, such as when a particle is dried) or by empty space (e.g., when a particle is in a vacuum, such as after lyophilization). The void volume of a particle may include, for example, the pore volume of a particle and/or the volume of the interior of a hollow core/shell particle, the lumen of a tube, torus, or ring.

In some embodiments, a particle is configured such that blood plasma may freely enter and/or exit the void space of the particle, e.g., when the particle is located in the vasculature of a subject. In some embodiments, a particle is configured such that blood serum may freely enter and/or exit the void space of the particle, e.g., when the particle is located in the vasculature of a subject. In preferred embodiments, a particle is configured such that blood cells cannot enter the void space of the particle. In some embodiments, a particle is configured such that platelets cannot enter the void space of the particle. Nevertheless, a particle may allow for a platelet to enter its void space, e.g., when the particle is configured for use in vitro or when the particle is configured to bind a virus, bacterium, protist, fungal or yeast cell, or other large target, such as a target sized from about 100 nm to about 2 µm.

In some embodiments, a particle is configured such that extracellular fluid may freely enter and/or exit the void space of the particle. In some embodiments, a particle is configured such that interstitial fluid may freely enter and/or exit the void space of the particle. In some embodiments, a particle is configured such that cerebrospinal fluid may freely enter and/or exit the void space of the particle.

The volume of the void space in a particle is preferentially large enough to accommodate more than one biomolecule, e.g., the total void volume of a particle is preferentially large enough to accommodate each biomolecule that is bound to the particle. Nevertheless, a void may be smaller than the total volume of each bound biomolecule so long as the particle is capable of inhibiting interactions between each bound biomolecule and the second members of the binding pairs that include each biomolecule. For example, a particle may need only sequester a binding site of a biomolecule to inhibit interactions between the biomolecule and a second member of a binding pair, and such a particle may contain a void volume that accommodates the binding site of each biomolecule but that allows for other portions of one or more biomolecules to project outward from the void space.

In some embodiments, a particle may comprise about 5% to about 95% void space. A particle comprising protrusions may comprise little or no void space, e.g., because the protrusions may inhibit interactions between bound biomolecule and a second member of a binding pair. A particle comprising a tube may comprise a large amount of void space, e.g., because a tube may comprise a large internal volume relative to the thickness of the walls of the tube. Nevertheless, the void volume of particles with similar geometries may comprise varying amounts of void volume, e.g., tubes comprising walls of the same thickness may vary substantially in void volume percentage depending on tube diameter.

A particle may comprise 0% to about 40% void space, about 20% to about 60% void space, about 40% to about 80% void space, or about 60% to 100% void space. A particle may comprise 0% to about 20% void space, about 10% to about 30% void space, about 20% to about 40% void space, about 30% to about 50% void space, about 40% to about 60% void space, about 50% to about 70% void space, about 60% to about 80% void space, about 70% to about 90% void space, or about 80% to 100% void space. A particle may comprise 0% to about 10% void space, about 5% to about 15% void space, about 10% to about 20% void space, about 15% to about 25% void space, about 10% to about 20% void space, about 15% to about 25% void space, about 10% to about 20% void space, about 15% to about 25% void space, about 10% to about 20% void space, about 15% to about 25% void space, about 20% to about 30% void space, about 25% to about 35% void space, about 30% to about 40% void space, about 35% to about 45% void space, about 40% to about 50% void space, about 45% to about 55% void space, about 50% to about 60% void space, about 55% to about 65% void space, about 60% to about 70% void space, about 65% to about 75% void space, about 70% to about 80% void space, about 75% to about 85% void space, about 80% to about 90% void space, about 85% to about 95% void space, or about 90% to 100% void space.

The particle may comprise a neutral charge at physiological pH (e.g., ~7.4). The particle may comprise a slightly negative or slightly positive charge at physiological pH. The surface of a particle (e.g., outer surface) may comprise a slightly negative or slightly positive charge at physiological pH. In preferred embodiments, the surface of a particle (e.g., outer surface) comprises a slightly negative or neutral charge at physiological pH. The isoelectric point of the particle may be about 5 to about 9, preferably about 6 to about 8. Particles comprising a nucleic acid may have an isoelectric point of about 4 to about 7. In some embodiments, the isoelectric point of the particle is less than 7.4, i.e., such that the particle has a net negative charge at physiological pH. For example, the isoelectric point of the particle may be about 6.0 to about 7.4, such as about 6.4 to about 7.4. A particle comprising a net negative charge at physiological pH is less likely to interact with eukaryotic cells (e.g., mammalian cells) because eukaryotic cells generally comprise cell membranes with a net negative charge. A particle preferably does not comprise sufficient charge (and/or charge density) to engage in non-specific interactions with other charged molecules.

III. Particles Comprising Pores

In some embodiments, the material used to make the particles (e.g., silicon) may have a porosity of about 40% to about 95%, such as about 60% to about 80%. Porosity, as used herein, is a measure of the void spaces in a material, and is a fraction of the volume of voids over the total volume of the material. In certain embodiments, the carrier material has a porosity of at least about 10%, at least about 20%, at least about 30%, at least about 40%, at least about 50%, at least about 60%, at least about 70%, at least about 80%, or even at least about 90%. In particular embodiments, the porosity is greater than about 40%, such as greater than about 50%, greater than about 60%, or even greater than about 70%.

In certain embodiments, the agent is distributed to a pore depth from the surface of the material of at least about 0.005 µm, at least 0.05 µm, at least about 0.1 µm, at least about 0.2 µm, at least about 0.3 µm, at least about 0.4 µm, at least about 0.5 µm, at least about 0.6 µm, or at least about 0.7 µm. In certain embodiments, the agent is distributed in the pores of the carrier material substantially uniformly.

The agent may be loaded into the particle to a depth which is measured as a ratio to the total width of the particle. In certain embodiments, the agent is distributed to a depth of at least about 10% into the particle, to at least about 20% into the particle, at least about 30% into the particle, at least about 40% into the particle, at least about 50% into the particle, or at least about 60% into the particle.

Methods for immobilizing an agent on a porous particle are known, including methods for both immobilizing an agent to a first surface of a particle and immobilizing a different molecule (e.g., coating) to a second surface of the particle (see, e.g., Cauda, V. et al., J. Am. Chem. Soc. 131(32):11361-11370 (2009) and Guan, B. et al., Langmuir, 27(1):328-334 (2011), each of which is hereby incorporated by reference in its entirety). Further, such methods are generally applicable for the manufacture of any of the particles described herein.

The pore size may be preselected to the dimensional characteristics of the agent and target biomolecule to control the release of the biomolecule. Typically, pore sizes that are too small preclude loading of the agent and/or binding of the biomolecule. For example, the average pore diameter for a material may be selected from larger pores, e.g., 15 nm to 40 nm, for high molecular weight molecules, e.g., 200,000-500,000 amu, and smaller pores, e.g., 2 nm to 10 nm, for molecules of a lower molecular weight, e.g., 10,000-50,0000 amu. For instance, average pore sizes of about 6 nm in diameter may be suitable for molecules of molecular weight around 14,000 to 15,000 amu such as about 14,700 amu. Average pore sizes of about 10 nm in diameter may be selected for molecules of molecular weight around 45,000 to 50,000 amu such as about 48,000 amu. Average pore sizes of about 25-30 nm in diameter may be selected for molecules of molecular weight around 150,000 nm.

The pore size may be preselected to be adapted to the molecular radii of the agent or biomolecule. For instance, average pore sizes of about 25 nm to about 40 nm in diameter may be suitable for molecules with a largest molecular radius from about 6 nm to about 8 nm. Molecular radii may be calculated by any suitable method such as by using the physical dimensions of the molecule based on the X-ray crystallography data or using the hydrodynamic radius which represents the solution state size of the molecule. As the solution state calculation is dependent upon the nature of the solution in which the calculation is made, it may be preferable for some measurements to use the physical dimensions of the molecule based on the X-ray crystallography data. As used herein the largest molecular radius reflects half of the largest dimension of the therapeutic agent.

In certain embodiments, the average pore diameter is selected to limit the aggregation of molecules, e.g., proteins, within a pore. It would be advantageous to prevent biomolecules such as proteins from aggregating in a carrier material as this is believed to impede the controlled release of molecules into a biological system. Therefore, a pore that, due to the relationship between its size and the size of a biomolecule, allows, for example, only one biomolecule to enter the pore at any one time, will be preferable to a pore that allows multiple biomolecules to enter the pore together and aggregate within the pore. In certain embodiments, multiple biomolecules may be loaded into a pore, but due to the depth of the pore, the proteins distributed throughout this depth of the pore will aggregate to a lesser extent.

IV. Particles Comprising at Least One Tube

In some embodiments, the particle comprises at least one tube. In preferred embodiments, the at least one tube comprises one open end or two open ends.

The term "tube" refers to a three-dimensional shape having a length along an axis (e.g., a one-dimensional axis in Cartesian space) and an internal cavity, lumen, void, or reservoir along the length of the shape. In some embodiments, perpendicular cross sections along the axis of the tube have a substantially identical shape and/or size. The term "cross section," as used in relation to a tube, refers to a two-dimensional cross section that is perpendicular to the axis of the tube. A larger structure may comprise a tube. For example, a syringe comprises a tube, but the tube does not comprise the syringe plunger. A particle or other article may comprise more than one tube. For example, a syringe may comprise two tubes corresponding to the syringe needle and the syringe barrel, or to parallel barrels of a double syringe (e.g., used for epoxy compositions).

A tube may have a diameter, which is the average length of the line segments that are perpendicular to the axis of the tube, wherein each line segment is bounded by two points on the outer surface of the tube. A tube may have a width and height, wherein the width of the tube is the longest line segment defined by two points on the outer surface of the tube that is perpendicular to the axis of the tube, and the height of the tube is the line segment defined by two points on the outer surface of the tube that is perpendicular to both the axis of the tube and the line segment defining the width of the tube.

A tube may have an internal diameter, which is the average length of the line segments that are perpendicular to the axis of the tube, wherein each line segment is bounded by two points on the inner surface of the tube. A tube may have an internal width and internal height, wherein the internal width of the tube is the longest line segment defined by two points on the outer surface of the tube that is perpendicular to the axis of the tube, and the internal height of the tube is the line segment defined by two points on the outer surface of the tube that is perpendicular to both the axis of the tube and the line segment defining the width of the tube.

A tube may be substantially cylindrical. The tube may have a substantially circular cross section. The cross section of the tube may be an ellipsoid, such as a circle.

The cross section of the tube may be a polygon, such as a regular polygon. The cross section of the tube may be a triangle, such as an equilateral triangle. The cross section of the tube may be a quadrilateral, such as a regular quadrilateral, a rectangle, or a square. The cross section of the tube may be a pentagon, such as a regular pentagon. The cross section of the tube may be a hexagon, such as a regular hexagon. A tube may be a triangular tube, square tube, pentagonal tube, hexagonal tube, heptagonal tube, or octahedral tube.

The length of a tube may be about 5 nm to about 5 µm, such as about 5 nm to about 4 µm, about 5 nm to about 3 µm, about 5 nm to about 2 µm, or about 5 nm to about 1 µm. The length of a tube may be about 50 nm to about 5 µm, such as about 50 nm to about 4 µm, about 50 nm to about 3 µm, about 50 nm to about 2 µm, or about 50 nm to about 1 µm. The length of a tube may be about 100 nm to about 5 µm, such as about 100 nm to about 4 µm, about 100 nm to about 3 µm, about 100 nm to about 2 µm, or about 100 nm to about 1 µm. The length of a tube may be about 300 nm to about 5 µm, such as about 300 nm to about 4 µm, about 300 nm to about 3 µm, about 300 nm to about 2 µm, or about 300 nm to about 1 µm. The length of a tube may be about 500 nm to about 5 µm, such as about 500 nm to about 4 µm, about 500 nm to about 3 µm, about 500 nm to about 2 µm, or about 500 nm to about 1 µm.

The diameter, width, and/or height of a tube may be about 5 nm to about 5 µm, such as about 5 nm to about 4 µm, about 5 nm to about 3 µm, about 5 nm to about 2 µm, about 5 nm to about 1 µm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, or about 5 nm to about 100 nm. The diameter, width, and/or height of a tube may be about 50 nm to about 5 µm, such as about 50 nm to about 4 µm, about 50 nm to about 3 µm, about 50 nm to about 2 µm, about 50 nm to about 1 µm, about 50 nm to about 900 nm, about 50 nm to about 800 nm, about 50 nm to about 700 nm, about 50 nm to about 600 nm, about 50 nm to about 500 nm, about 50 nm to about 400 nm, about 50 nm to about 300 nm, about 50 nm to about 200 nm, or about 50 nm to about 100 nm.

The internal diameter, internal width, and/or internal height of a tube are preferentially large enough to accommodate both the agent and the biomolecule. The internal diameter, internal width, and/or internal height of a tube are preferentially small enough to inhibit a cell from entering the interior of the tube (e.g., a nucleated eukaryotic cell, such as a nucleated human cell or a diploid human cell). The internal diameter, internal width, and/or internal height of a tube may be about 5 nm to about 4 µm, such as about 5 nm to about 3 µm, about 5 nm to about 2 µm, about 5 nm to about 1 µm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, or about 5 nm to about 100 nm. The internal diameter, internal width, and/or internal height of a tube may be about 20 nm to about 4 µm, such as about 20 nm to about 3 µm, about 20 nm to about 2 µm, about 20 nm to about 1 µm, about 20 nm to about 900 nm, about 20 nm to about 800 nm, about 20 nm to about 700 nm, about 20 nm to about 600 nm, about 20 nm to about 500 nm, about 20 nm to about 400 nm, about 20 nm to about 300 nm, about 20 nm to about 200 nm, or about 20 nm to about 100 nm. The internal diameter, internal width, and/or internal height of a tube may be about 40 nm to about 4 µm, such as about 40 nm to about 3 µm, about 40 nm to about 2 µm, about 40 nm to about 1 µm, about 40 nm to about 900 nm, about 40 nm to about 800 nm, about 40 nm to about 700 nm, about 40 nm to about 600 nm, about 40 nm to about 500 nm, about 40 nm to about 400 nm, about 40 nm to about 300 nm, about 40 nm to about 200 nm, or about 40 nm to about 100 nm.

In certain preferred embodiments, the particle comprises a plurality of tubes. Each tube of the plurality of tubes may be substantially parallel. In some embodiments, at least two tubes of the plurality of tubes are not parallel. In some embodiments, none of the tubes of the plurality of tubes are parallel. The tubes may be arranged in a configuration other than parallel to distribute the openings to the tubes over different faces of the particle or to allow the particle to tumble in flow (e.g., laminar flow or turbulent flow).

A plurality of tubes may be arranged in a lattice or bundle.

A plurality of tubes may be arranged in a polyhedron, such as a regular polyhedron. The plurality of tubes may be arranged in a tetrahedron, such as a regular tetrahedron. The plurality of tubes may be arranged in a hexahedron, such as a cuboid, rectangular cuboid, or cube. The plurality of tubes may be arranged in an octahedron, such as a regular octahedron. The plurality of tubes may be arranged in a dodecahedron, such as a regular dodecahedron. The plurality of tubes may be arranged in an icosahedron, such as a regular icosahedron. In some embodiments, each edge of the polyhedron is defined by a single tube. In some embodiments, less than each edge of the polyhedron is defined by a single tube (e.g., when each of the tubes are substantially parallel).

A plurality of tubes may be arranged in a pyramid, such as a triangular pyramid, rhombic pyramid, rectangular pyramid, square pyramid, pentagonal pyramid, hexagonal pyramid, heptagonal pyramid, or octagonal pyramid. The plurality of tubes may be arranged in a right pyramid or an oblique pyramid. In some embodiments, each edge of the pyramid is defined by a single tube. In some embodiments, less than each edge of the pyramid is defined by a single tube (e.g., when each of the tubes are substantially parallel).

A plurality of tubes may be arranged in a prism, such as a triangular prism, rectangular prism, square prism, pentagonal prism, hexagonal prism, heptagonal prism, or octagonal prism. The plurality of tubes may be arranged in a right prism, an oblique prism, or a truncated prism. In some embodiments, each edge of the prism is defined by a single tube. In some embodiments, less than each edge of the prism is defined by a single tube (e.g., when each of the tubes are substantially parallel).

A plurality of tubes may be arranged in a configuration that has a length, width, and height, wherein no single dimension is more than 5 times larger than any other dimension. For example, the plurality of tubes may be arranged in a configuration wherein no single dimension is more than 4 times larger than any other dimension or no single dimension is more than 3 times larger than any other dimension. Such configurations are favorable, for example, for intravenous administration of a particle because oblong particles may not flow as well in a patient's bloodstream.

A plurality of tubes may be arranged in a configuration that has a length and diameter, wherein the length of the configuration is not more than 5 times its diameter. For the plurality of tubes may be arranged in a configuration wherein the length of the configuration is not more than 4 times its diameter or the length of the configuration is not more than 3 times its diameter. Such configurations are favorable, for example, for intravenous administration of the particle because oblong particles may not flow as well in a patient's bloodstream.

A particle may comprise 1 to 500 tubes, such as 1 to 100 tubes. A particle may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 330, 31, 32, 33, 34, 35, 36, 37, 38, 39, 40, 41, 42, 43, 44, 45, 46, 47, 48, 49, 50, 51, 52, 53, 54, 55, 56, 57, 58, 59, 50, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 tubes.

A plurality of tubes may comprise 1 to 500 tubes, such as 1 to 100 tubes. A plurality of tubes may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 330, 31, 32, 33, 34, 35, 36, 37, 38, 39, 40, 41, 42, 43, 44, 45, 46, 47, 48, 49, 50, 51, 52, 53, 54, 55, 56, 57, 58, 59, 50, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 tubes.

Each tube of the plurality of tubes may have the same length, or different tubes of the plurality of tubes may have different lengths. The average length of a tube may be about 5 nm to about 5 µm, such as about 5 nm to about 4 µm, about 5 nm to about 3 µm, about 5 nm to about 2 µm, or about 5 nm to about 1 µm. The average length of a tube may be about 50 nm to about 5 µm, such as about 50 nm to about 4 µm, about 50 nm to about 3 µm, about 50 nm to about 2 µm, or about 50 nm to about 1 µm. The average length of a tube may be about 100 nm to about 5 µm, such as about 100 nm to about 4 µm, about 100 nm to about 3 µm, about 100 nm to about 2 µm, or about 100 nm to about 1 µm. The average length of a tube may be about 300 nm to about 5 µm, such as about 300 nm to about 4 µm, about 300 nm to about 3 µm, about 300 nm to about 2 µm, or about 300 nm to about 1 µm. The average length of a tube may be about 500 nm to about 5 µm, such as about 500 nm to about 4 µm, about 500 nm to about 3 µm, about 500 nm to about 2 µm, or about 500 nm to about 1 µm.

Each tube of the plurality of tubes may have the same diameter, width, and/or height, or different tubes of the plurality of tubes may have different diameters, widths, and/or heights. The average diameter, width, and/or height of a tube may be about 5 nm to about 5 µm, such as about 5 nm to about 4 µm, about 5 nm to about 3 µm, about 5 nm to about 2 µm, about 5 nm to about 1 µm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, or about 5 nm to about 100 nm. The average diameter, width, and/or height of a tube may be about 50 nm to about 5 µm, such as about 50 nm to about 4 µm, about 50 nm to about 3 µm, about 50 nm to about 2 µm, about 50 nm to about 1 µm, about 50 nm to about 900 nm, about 50 nm to about 800 nm, about 50 nm to about 700 nm, about 50 nm to about 600 nm, about 50 nm to about 500 nm, about 50 nm to about 400 nm, about 50 nm to about 300 nm, about 50 nm to about 200 nm, or about 50 nm to about 100 nm.

Each tube of the plurality of tubes may have the same internal diameter, internal width, and/or internal height, or different tubes of the plurality of tubes may have different internal diameters, widths, and/or heights. The average internal diameter, internal width, and/or internal height of a tube may be about 5 nm to about 4 µm, such as about 5 nm to about 3 µm, about 5 nm to about 2 µm, about 5 nm to about 1 µm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, or about 5 nm to about 100 nm. The average internal diameter, internal width, and/or internal height of a tube may be about 20 nm to about 4 µm, such as about 20 nm to about 3 µm, about 20 nm to about 2 µm, about 20 nm to about 1 µm, about 20 nm to about 900 nm, about 20 nm to about 800 nm, about 20 nm to about 700 nm, about 20 nm to about 600 nm, about 20 nm to about 500 nm, about 20 nm to about 400 nm, about 20 nm to about 300 nm, about 20 nm to about 200 nm, or about 20 nm to about 100 nm. The average internal diameter, internal width, and/or internal height of a tube may be about 40 nm to about 4 µm, such as about 40 nm to about 3 µm, about 40 nm to about 2 µm, about 40 nm to about 1 µm, about 40 nm to about 900 nm, about 40 nm to about 800 nm, about 40 nm to about 700 nm, about 40 nm to about 600 nm, about 40 nm to about 500 nm, about 40 nm to about 400 nm, about 40 nm to about 300 nm, about 40 nm to about 200 nm, or about 40 nm to about 100 nm.

A tube may comprise, for example, a polymer. The polymer may be a naturally-occurring polymer or a synthetic polymer. The polymer may be, for example, a nucleic acid (e.g., DNA) or protein.

III(A). Particles Comprising Agent on Inner and Outer Surfaces

In some embodiments, the particle comprises an interior or inner surface and an exterior surface or outer surface and the agent is immobilized on the interior surface and the outer surface, the total amount of agent on the interior surface being greater than the total amount of agent on the outer surface.

In some such embodiments the particle comprises pores, and comprises an outer surface, and inner surfaces of the pores of the particle, wherein the agent is immobilized on the inner surfaces of the pores and also on the outer surface of the particle, the total amount of agent on the inner surfaces being greater than the total amount of agent on the outer surface.

In other such embodiments the particle comprises a core particle and a plurality of subparticles, such as protecting subparticles, bound to the core particle, and the interior surface comprises regions of the surface of the core particle not occupied by the subparticles. In some embodiments the interior may comprise regions of the surface of the subparticles not oriented outwards from the particle, such as for example the surface of the side of the subparticles facing the core particle, such as the surface of the hemisphere oriented towards the core particle in the case that the subparticle is spherical.

The amount of agent on the interior or inner surfaces may be substantially 100%, or over 99%, over 98%, over 97%, over 95%, over 90%, over 85%, over 80%, or over 50% of the total amount of agent immobilized on all of the surfaces of the particle. In some embodiments the agent on the outer surface may be able to bind to or activate a biomolecule on the surface of a cell, such as a cell surface receptor, but the agent on the inner surfaces is not. In this way, on the whole, the agent immobilized on the particle is inhibited from binding to or activating a biomolecule on a cell surface, i.e., the agent has a higher selectivity for soluble forms of a target biomolecule than for membrane-bound or surface-bound forms of the biomolecule.

In some embodiments a particle, such as a porous particle, the inner surface has an area that is greater than the area of the outer surface by a factor of 2, 5, 10, 15, 20, 30, 40, 50, 100 or over 100 times. In this way, even though the agent is immobilized on both the inner and the outer surfaces, the majority of the agent is immobilized on an inner surface. In some embodiments, a method of fabricating a particle comprises functionalizing both the inner and the outer surfaces of a particle, such as a porous particle, with a reactive group that will react with a functional group on the agent, and contacting the particle with a solution comprising the agent, thereby causing the agent to be immobilized on the functionalized surface. In this way, a particle is readily fabricated with the majority of the capture agent on the inner surface.

V. Particles Comprising a DNA Scaffold

In some embodiments, the particle comprises a DNA scaffold, e.g., the particle may comprise a DNA origami scaffold (see, e.g., U.S. Pat. Nos. 8,554,489 and 7,842,793; U.S. Patent Application Publication Nos. 2013/0224859 and 2010/0216978; and PCT Patent Application Publication No. 2014/170898, each of which is hereby incorporated by reference).

The particle may comprise a DNA scaffold, and the DNA scaffold may comprise at least one tube or a plurality of tubes as described herein. For example, the DNA scaffold may comprise at least one substantially hexagonal tube (see, e.g., U.S. Patent Application Publication No. 2013/0224859, hereby incorporated by reference).

The DNA scaffold may comprise a honeycomb or lattice, such as a hexagonal lattice or a square lattice (see, e.g., U.S. Pat. No. 8,554,489, hereby incorporated by reference).

In some embodiments, the particle comprises a DNA scaffold, and the DNA scaffold does not comprise a tube. For example, the DNA scaffold may comprise a three-dimensional shape, such as a polyhedron, and the agent may be immobilized in the interior surface of the shape.

The DNA scaffold may comprise a polyhedron, such as a regular polyhedron. The DNA scaffold may comprise a tetrahedron, such as a regular tetrahedron. The DNA scaffold may comprise a hexahedron, such as a cuboid, rectangular cuboid, or cube. The DNA scaffold may comprise an octahedron, such as a regular octahedron. The DNA scaffold may comprise a dodecahedron, such as a regular dodecahedron. The DNA scaffold may comprise an icosahedron, such as a regular icosahedron.

The DNA scaffold may comprise a pyramid, such as a triangular pyramid, rhombic pyramid, rectangular pyramid, square pyramid, pentagonal pyramid, hexagonal pyramid, heptagonal pyramid, or octagonal pyramid. The DNA scaffold may comprise a right pyramid or an oblique pyramid.

The DNA scaffold may comprise a prism, such as a triangular prism, rectangular prism, square prism, pentagonal prism, hexagonal prism, heptagonal prism, or octagonal prism. The DNA scaffold may comprise a right prism, an oblique prism, or a truncated prism.

The DNA scaffold may comprise a length, width, and height, wherein no single dimension is more than 5 times larger than any other dimension. For example, no single dimension may be more than 4 times larger than any other dimension or no single dimension may be more than 3 times larger than any other dimension. Such configurations are favorable, for example, for intravenous administration of the particle because oblong particles may not flow as well in a patient's bloodstream.

In some embodiments, the agent is immobilized on the DNA scaffold. In some embodiments, the agent is bound to a nucleic acid comprising a nucleotide sequence that is complementary to a nucleotide sequence on the DNA scaffold, i.e., the nucleotide sequence has at least about 95%, 96%, 97%, 98%, 99%, or 100% sequence identity with the reverse complement of the nucleotide sequence of the DNA scaffold. Thus, the agent may be immobilized on a surface of the particle by hybridizing the nucleic acid to the DNA scaffold.

VI. Particles Comprising a Shield

A particle may comprise a core subparticle and a shield, e.g., wherein the shield inhibits biomolecules bound to the core subparticle from interacting with molecules on the surface of a cell. The shield may comprise a plurality of shield components. The core subparticle may comprise silica. For example, the core subparticle may comprise a silica surface. The core subparticle may comprise gold, silicon, or a polymer. For example, the core subparticle may comprise a gold, silicon, or polymer surface.

A particle comprising an inner core subparticle and having a shield comprising a plurality of shield components attached to the core subparticle may comprise a core subparticle comprising a silica surface, such as a solid silica subparticle, a porous silica subparticle, or a silica nanoshell having a non-silica interior. The core subparticle may comprise a non-silica core material, such as silicon or gold, coated with silica. The shield components may be in the form of shield subparticles that are smaller than the core subparticle, such as nanospheres, and may comprise silica or a different material, such as gold or a polymer. The material of the surface of the core subparticle and of the shield components may be selected to be different to allow different coupling chemistry to be used to couple further components or species to the surfaces. The core subparticle may comprise a surface moiety having a reactive group, and the shield components may comprise a functional group capable of reaction with the reactive group to form a covalent bond between the surface of the core subparticles and the surface of the shield components or subparticles, as described herein.

An agent may be provided on the surface of the core subparticle but to a lesser extent, or preferably not at all, on the surface of the shield components. For example, an agent may be attached to the surface of a silica core subparticle by a bond (e.g., an ionic, covalent, or electrostatic interaction) that forms preferentially (or exclusively) with the silica core subparticle and not with the shield subparticles, e.g., having a gold surface instead of a silica surface.

In some embodiments, such a particle may comprise a silica core, such as a substantially spherical silica core, and a shield comprising a plurality of gold nanoparticles on the surface of the silica core, the gold nanoparticles having a cross-sectional dimension smaller than a cross-sectional dimension of the core, such as the diameter of the core. The gold nanoparticles may be substantially spherical. The core subparticle may be solid and non-porous or may have a porous surface. Formation of the silica core and of gold nanoparticles on the core may be achieved, for example, as described in U.S. Pat. No. 6,344,272, Sadtler and Wei, Chem. Comm. 1604-5 (2002); Meuhlig et al., ACS Nano, 5(8):6586-6592 (2011) (each of which is hereby incorporated by reference herein in its entirety). For example, gold nanoparticles may be adsorbed onto an amine-coated silica core by means of electrostatic attraction, or may be linked to a silica core having thiol groups conjugated to the silica surface that then bond to the gold surface of the gold nanoparticles.

A linker group may be provided between the silica of a core subparticle comprising silica and thiol groups for attaching a shield component to the core subparticle. The linker may have a length selected to set a maximum distance between a silica surface and a thiol group (or, when the thiol is attached to a gold surface, between the silica surface and the gold surface). In this way, the distance between the surface of the silica subparticle and the gold subparticle can be varied over a range of distances, potentially allowing a greater number of linkages (e.g., because more gold subparticles can be packed at a greater distance from the core silica subparticle), and/or strengthen the association between the silica and gold subparticles (e.g., because at shorter distances, more linkages from the surface of the silica subparticle may be able to interact with the same gold subparticle, reinforcing the association). A linker may comprise an alkylene chain whose length can be selected to vary the distance between the surface of the core subparticle and a shield subparticle.

The core subparticle may have a cross-sectional dimension, such as the diameter of a spherical or cylindrical subparticle, of 50 nm to 4 $\mu$m, such as 50 nm to 200 nm, 100 nm to 500 nm, 200 nm to 1 $\mu$m, or 500 nm to 4 $\mu$m.

Particles may be assembled from a range of core subparticle diameters and shield subparticle diameters. The available surface area of the core subparticle for scavenging of a biomolecule may depend on the diameter of the shield subparticles and the effective height above the surface of the core subparticle needed for binding of the target/agent complex to the surface, including the effective extent above the surface of any linker between the surface and the capture agent.

The number of agents that may be bound to a core subparticle may be calculated based on the surface area of the subparticle. Analogously, the number of target biomolecules that may be bound to the core subparticle may be calculated in a similar fashion. Such calculations may be confirmed, for example, by in vitro studies of protein binding, and may be used to predict the dose of particles that may be needed to scavenge a selected number of target biomolecules (or, in some embodiments, the effective dose of particles or of a formulation containing them for removing a number or reducing a concentration of target biomolecules from a system such as an in vitro system or from the circulation of a patient in treatment of disease).

A particle may comprise an available surface area for the capture of a target of 0.01 $\mu m^2$ to 50 $\mu m^2$, such as 0.01 $\mu m^2$ to 0.1 $\mu m^2$, 0.05 $\mu m^2$ to 0.5 $\mu m^2$, 0.1 $\mu m^2$ to 1.0 $\mu m^2$, 0.5 $\mu m^2$ to 5 $\mu m^2$, 1.0 $\mu m^2$ to 10 $\mu m^2$, 5 $\mu m^2$ to 25 $\mu m^2$, or 10 $\mu m^2$ to 50 $\mu m^2$. For a selected loading of agent per unit area of a core subparticle surface, a maximum dose of particles may be established as suitable to scavenge a desired quantity of target biomolecules based on the core and shield subparticle diameters.

A cross-sectional dimension, such as the diameter, of the shield subparticle may be a multiple of a cross-sectional dimension, such as the diameter, of the core particle. The multiple may be, for example, 0.01 to 0.5, such as 0.02 to 0.2, such as 0.05 to 0.1.

For effective access of a target biomolecule to an agent, the target must be able to diffuse between the shield components to reach the agent on the surface of the core subparticle. For example, targets of less than 100 kDa (e.g., sTNF-R1/2) have sizes that may readily diffuse between shielding spheres that are 40 nm in diameter or greater. For smaller shielding spheres, the effective pore length between the spheres is short, and thus shielding spheres that are smaller than 40 nm are similarly unlikely to impede diffusion.

VII. Particles Comprising Subparticles

In some embodiments, a particle may comprise a core subparticle and a plurality of protecting subparticles. The particle may comprise a shield and the shield may comprise the plurality of protecting subparticles. The agent may be immobilized on a surface of a core subparticle, e.g., wherein the surface of a core subparticle is an inner surface. The plurality of protecting subparticles may be configured to inhibit an interaction of a biomolecule with a second member of a specific binding pair, e.g., when the biomolecule is bound to the particle. The plurality of protecting subparticles may be configured to inhibit an interaction between a biomolecule and a cell, such as a mammalian cell, e.g., when the biomolecule is bound to the particle.

The protecting subparticles may define an outer surface. In preferred embodiments, the agent is not immobilized on the surface of the protecting subparticles.

A core subparticle is preferably large enough to bind to more than one molecule of an agent. For example, a core subparticle may be about 20 nm to about 4 μm in size, such as about 50 nm to about 2 μm in size. A core subparticle may be about 100 nm to about 1000 nm, about 100 nm to about 800 nm, about 100 nm to about 600 nm, about 100 nm to about 400 nm, about 100 nm to about 200 nm, about 200 nm to about 1000 nm, about 200 nm to about 800 nm, about 200 nm to about 600 nm, about 200 nm to about 400 nm, about 400 nm to about 1000 nm, about 400 nm to about 800 nm, about 400 nm to about 600 nm, about 600 nm to about 1000 nm, or about 600 nm to about 800 nm in size. A core subparticle may be about 100 nm to about 4 μm, 100 nm to about 3 μm, 100 nm to about 2 μm, about 200 nm to about 4 μm, 200 nm to about 3 μm, 200 nm to about 2 μm, about 400 nm to about 4 μm, 400 nm to about 3 μm, 400 nm to about 2 μm, about 600 nm to about 4 μm, 600 nm to about 3 μm, 600 nm to about 2 μm, about 800 nm to about 4 μm, 800 nm to about 3 μm, or 800 nm to about 2 μm in size.

A core subparticle may comprise metal, gold, alumina, glass, silica, silicon, starch, agarose, latex, plastic, polyacrylamide, methacrylate, a polymer, or a nucleic acid. In some embodiments, a core subparticle comprises silicon, such as porous silicon.

A core subparticle may be any shape (e.g., cubic, pyramidal, conic, spherical, cylindrical, disk, tetrahedral, hexahedral, octahedral, dodecahedral, or icosahedral) or a core subparticle may lack a defined shape.

A particle may comprise 1 core subparticle. For example, the core subparticle may be a particle of U.S. Pat. No. 7,368,295 or 8,920,625 (each of which is hereby incorporated by reference in its entirety), which is further bound to a plurality of protecting subparticles.

Figure 4:
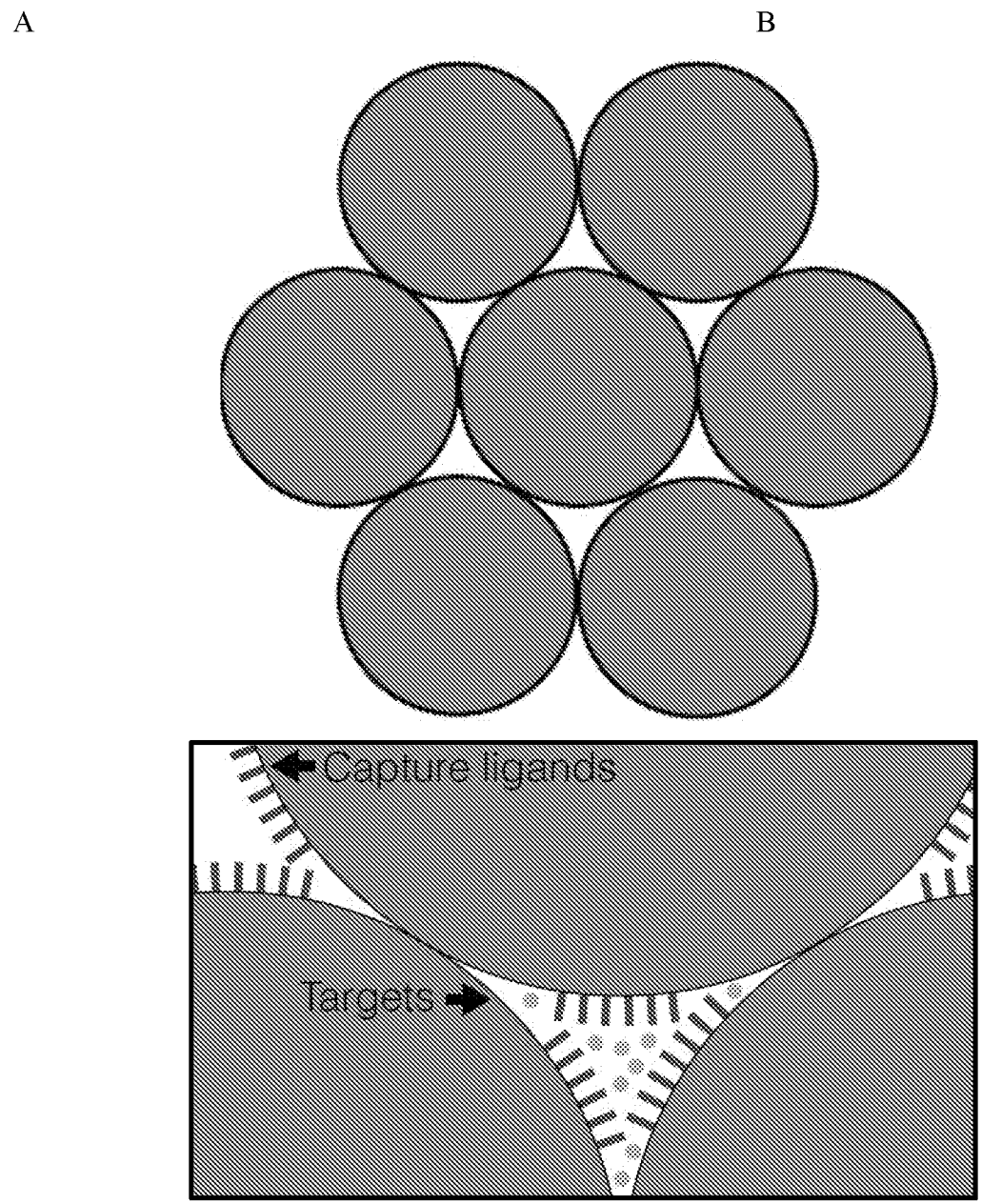
FIG. 4 consists of two panels, labeled panels (A) and (B). Panel (A) depicts the packing of subparticles within a particle comprising core subparticles and protecting subparticles, wherein each subparticle is substantially spherical and approximately the same size. Nevertheless, a particle may comprise subparticles of varying shapes and/or sizes. Additionally, the subparticles are shown as packing in a hexagonal pattern; however, subparticles may pack randomly or with other geometries. Panel (B) depicts (i) "capture ligands" (i.e., agent), which are immobilized on the surface of core subparticles, (ii) targets (e.g., biomolecules) specifically bound to the agent, and (iii) targets within the fluid-filled void space of the particle. Panel (B) does not depict protecting subparticles. The relative sizes of the subparticles, capture ligands, targets, and void space in FIG. 4 are not necessarily shown to scale.
Figure 5:
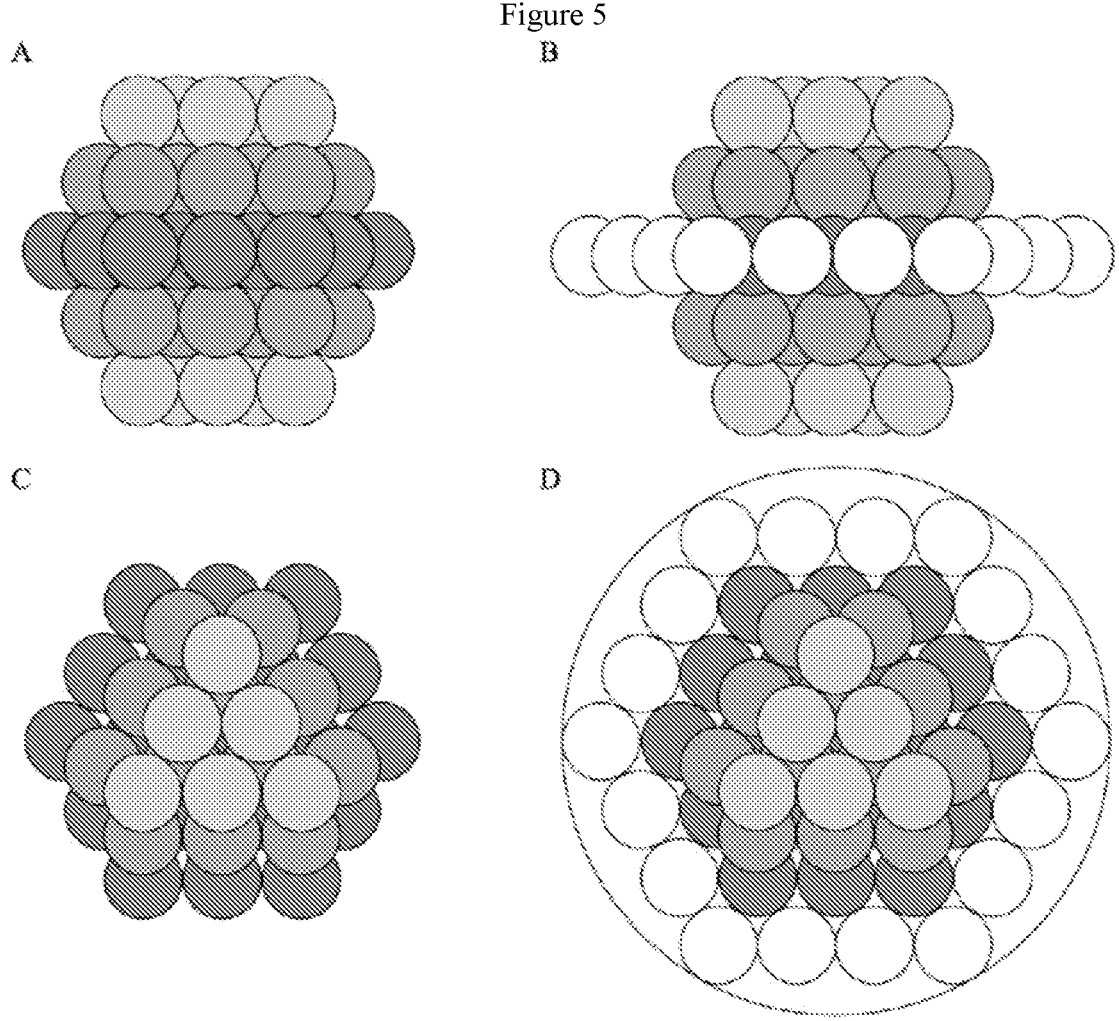
FIG. 5 consists of four panels, labeled panels (A), (B), (C), and (D). Each panel depicts subparticles of a particle, in which core subparticles are shown in gray and protecting subparticles are shown in white. Each particle comprises 55 core subparticles. Panels (A) and (B) depict views of the particle that are orthogonal to the views depicted in panels (C) and (D). Panels (A) and (C) depict the core subparticles only, and panels (B) and (D) depict the core subparticles and a number of protecting subparticles. A completed particle comprising core subparticles and protecting subparticles is preferably covered by at least one layer of protecting subparticles, which is not shown in its entirety in any panel.

A particle may comprise a plurality of core subparticles, such as 2 to 300 core subparticles, 2 to 200 core subparticles, 2 to 150 core subparticles, 2 to 100 core subparticles, 2 to 80 core subparticles, or 2 to 42 core subparticles (see, e.g., FIGS. 4 and 5). In embodiments in which a particle comprises a plurality of core subparticles, each of the core subparticles are preferentially substantially spherical. A particle comprising a plurality of spherical core subparticles allows for voids, thereby allowing the diffusion of soluble biomolecules through the interior of the particle. Nevertheless, core subparticles of various other shapes may allow for voids. A particle comprising a plurality of core subparticles may comprise core subparticles of varying shapes and sizes.

A particle may comprise 1 to about $10^6$ core subparticles, 1 to about $10^5$ core subparticles, 1 to about $10^4$ core subparticles, 1 to about 1000 core subparticles, 1 to about 100 core subparticles, or 1 to about 10 core subparticles. A particle may comprise 2 to about $10^6$ core subparticles, 2 to about $10^5$ core subparticles, 2 to about $10^4$ core subparticles, 2 to about 1000 core subparticles, 2 to about 100 core subparticles, or 2 to about 10 core subparticles. A particle may comprise about 10 to about $10^6$ core subparticles, about 10 to about $10^5$ core subparticles, about 10 to about $10^4$ core subparticles, about 10 to about 1000 core subparticles, or about 10 to about 100 core subparticles.

The core subparticles of a plurality of core subparticles may be connected by linkers (e.g., covalent linkers). For example, each core subparticle of a plurality of core subparticles may be connected to another core subparticle by a linker.

A core subparticle may comprise pores, i.e., a core subparticle may be porous.

A protecting subparticle may comprise metal, gold, alumina, glass, silica, silicon, starch, agarose, latex, plastic, polyacrylamide, methacrylate, a polymer, or a nucleic acid. Some protecting subparticles are preferentially tethered to core subparticles by a linker, such as a covalent linker. Nevertheless, the protecting subparticles may be associated with one or more core subparticles without any covalent attachment. The protecting subparticles may be tethered to other protecting subparticles by linkers, such as by covalent linkers. For example, the protecting subparticles may form a web or net around the core subparticles, thereby sequestering the core subparticles within the particle.

In some embodiments, each protecting subparticle of the plurality of protecting subparticles are tethered to a core subparticle by a linker, such as a covalent linker. In some embodiments, some protecting subparticles of the plurality of protecting subparticles are tethered to a core subparticle, and each protecting subparticle of the plurality that is not directly tethered to a core subparticle is tethered to a protecting subparticle, i.e., such that each protecting subparticle of the plurality is either directly or indirectly tethered to a core subparticle. Thus, a particle may comprise a single layer of protecting subparticles (e.g., wherein substantially all of the protecting subparticles are directly tethered to one or more core subparticle(s)) or a particle may comprise more than one layer of protecting subparticles (e.g., wherein a substantial portion of the protecting subparticles are indirectly tethered to one or more core subparticle(s) through direct linkages with other protecting subparticles).

In some embodiments, a particle comprises a first layer of protecting subparticles comprising a first material and a second layer of protecting subparticles comprising a second material. For example, the first material may comprise silica or silicon and the second material may comprise gold. A particle may be assembled, for example, by linking the subparticles of the first layer of subparticles to one or more core subparticles and then linking the subparticles of the second layer of subparticles to the first layer of subparticles. The subparticles of the second layer may comprise a similar surface as the core subparticle(s), e.g., thereby allowing the subparticles of the first layer to link to both the core subparticle(s) and the subparticles of the second layer using similar chemistries.

A particle may be assembled using a layer-by-layer method. For example, a particle may be formed by first linking a plurality of core subparticles. The plurality of core subparticles may be substantially homogenous, e.g., such that a linking molecule may crosslink the core subparticles. The plurality of subparticles may comprise at least two types of subparticles, e.g., with different shapes, sizes, and/or surfaces that allow for a desired feature, such as voids, within the particle. After linking the plurality of core subparticles, a plurality of protecting subparticles may be linked to the plurality of core subparticles. After linking the plurality of protecting subparticles to the core subparticles, a second plurality of protecting subparticles may be linked to the plurality of protecting subparticles. Nevertheless, a particle may be assembled in many different ways, and many different layer-by-layer strategies may be employed depending on the desired properties of the particle and the desired chemistries utilized to link the subparticles.

Methods for crosslinking subparticles are known, including methods for crosslinking subparticles that comprise antibodies for use in vivo (see, e.g., Cheng, K. et al., ACS Appl Mater Interfaces 2(9):2489-2495 (2010), hereby incorporated by reference in its entirety). Such methods may be adapted to produce a particle as described herein, for example, by simply altering the relative sizes of the subparticles.

A protecting subparticle may be about 10 nm to about 4 μm in size, such as about 10 nm to about 1 μm in size, or about 20 nm to about 500 nm in size. A protecting subparticle may be about 10 nm to about 200 nm, 10 nm to about 100 nm, about 10 nm to about 80 nm, about 10 nm to about 60 nm, about 10 nm to about 40 nm, about 10 nm to about 20 nm, 20 nm to about 200 nm, about 20 nm to about 100 nm, about 20 nm to about 80 nm, about 20 nm to about 60 nm, about 20 nm to about 40 nm, 30 nm to about 200 nm, about 40 nm to about 100 nm, about 40 nm to about 80 nm, about 40 nm to about 60 nm, 60 nm to about 200 nm, about 60 nm to about 100 nm, or about 60 nm to about 80 nm in size. A protecting subparticle may be about 100 nm to about 1000 nm, about 100 nm to about 800 nm, about 100 nm to about 600 nm, about 100 nm to about 400 nm, about 100 nm to about 200 nm, about 200 nm to about 1000 nm, about 200 nm to about 800 nm, about 200 nm to about 600 nm, about 200 nm to about 400 nm, about 400 nm to about 1000 nm, about 400 nm to about 800 nm, about 400 nm to about 600 nm, about 600 nm to about 1000 nm, or about 600 nm to about 800 nm in size. A protecting subparticle may be about 100 nm to about 4 μm, about 100 nm to about 3 μm, about 100 nm to about 2 μm, about 200 nm to about 4 μm, about 200 nm to about 3 μm, about 200 nm to about 2 μm, about 400 nm to about 4 μm, about 400 nm to about 3 μm, about 400 nm to about 2 μm, about 600 nm to about 4 μm, about 600 nm to about 3 μm, about 600 nm to about 2 μm, about 800 nm to about 4 μm, about 800 nm to about 3 or about 800 nm to about 2 μm in size.

A particle may comprise 1 to about $10^6$ protecting subparticles, about 4 to about $10^6$ protecting subparticles, about 10 to about $10^6$ protecting subparticles, 1 to about $10^5$ protecting subparticles, about 4 to about $10^5$ protecting subparticles, about 10 to about $10^5$ protecting subparticles, 1 to about $10^4$ protecting subparticles, about 4 to about $10^4$ protecting subparticles, about 10 to about $10^4$ protecting subparticles, 1 to about 1000 protecting subparticles, about 4 to about 1000 protecting subparticles, about 10 to about 1000 protecting subparticles, 1 to about 100 protecting subparticles, about 4 to about 100 protecting subparticles, or about 10 to about 100 protecting subparticles.

A core subparticle and a protecting subparticle may or may not have similar or identical shapes, sizes, and compositions. Nevertheless, a core subparticle varies from a protecting subparticle because (1) agent may be immobilized on a core subparticle whereas agent is preferentially not immobilized on a protecting subparticle, and (2) core subparticles are preferentially located in the interior of a particle whereas protecting subparticles may exist on the outer surface of a particle.

VII(A) Particles Comprising a Nucleic Acid Scaffold

In some aspects, the present invention provides particles comprising a core subparticle, a scaffold comprising a nucleic acid such as a DNA or RNA, and an agent. 3D nanostructures comprising a scaffold formed from nucleic acids, such as DNA or RNA (see Li et al Nano Today (2015) 10, 631-655), are known in the art, such as formed by the method of DNA origami as described above. Herein, such structures will be referred to as DNA scaffolds. According to these aspects, the DNA scaffold acts as a protecting subparticle. The DNA scaffold may be shaped and linked to the core subparticle so as to define a protected surface. The protected surface includes surface areas on the core subparticle and on the DNA scaffold where bound agents are inhibited from coming into contact with, or binding to, a biomolecule on a cell surface. In some embodiments, the agent is bound to the protected surface. The DNA scaffold may be configured to have a base, a height and a width, and may be configured to be immobilized preferentially onto the surface of the core subparticle on its base. The DNA scaffold may comprise a base region that links to the surface of the core subparticle, and a protruding region that protrudes from the surface of the core subparticle. The DNA scaffold may also comprise an overhanging region that overhangs an area of the core subparticle. The dimensions of the DNA scaffold (e.g., height, base area, overhanging area) may be selected such that an agent immobilized on the surface of the core subparticle or on the DNA scaffold is inhibited from coming into contact with, or binding to, a biomolecule on a cell surface. For instance, when the cell is in contact with the end of a protruding region of the DNA scaffold, the cell may not be able to deform sufficiently to bring the cell surface in contact with the agents on or near the DNA scaffold. In some embodiments, an overhanging region of a DNA scaffold may block a cell from approaching the surface of the DNA scaffold or the core subparticle. In other embodiments, the DNA scaffold is shaped to form an interior volume, which is inaccessible to cells. These different strategies may be employed separately or in combination depending on the types of cell the agent is desired to be sequestered from. For instance, B cells are known to actively explore surfaces and may require a more restrictive structure, such as a DNA scaffold comprising an overhang or an interior volume, as opposed to a simple protrusion. According to these embodiments, the surface area (whether on the core subparticle or on the DNA scaffold itself) that the DNA scaffold protects (whether by a protrusion, overhang, or included void) is a protected surface. Thus, in some embodiments, the present disclosure provides particles comprising a core subparticle, a DNA scaffold, and a protected surface.

The protecting DNA scaffold subparticles may be selectively functionalized on the lower surface of their base so as to attach preferentially to the surface of the core subparticle in the correct orientation. The DNA scaffold may be in the form of a rectilinear 3D shape such as a nano-brick (see for example Ke at al. DNA brick crystals with prescribed depths *Nature Chemistry* 6, 994-1002, 2014) or may have a shape comprising a base and a protrusion extending outwards from the base. In some embodiments, the base comprises two tubes oriented at an angle to each other. In some embodiments, the base comprises the ends of one or more tubes, in which case the tubes are supported on the surface by their ends. See for example Pelligrotti et al, Nano Letters 2016 16 (10), 6222-6230, FIG. 1, Iinuma et al., *Science* 2014: Vol. 344, Issue 6179, pp. 65-69, FIG. 1; Endo et al, Angew. Chem. Int. Ed. 53, 7484-7490 (2014). The lower surface of the base may be functionalized with a first binding partner or a first reactive group, a second binding partner or reactive group being provided on the surface of the core subparticle. In this way when the DNA origami protecting subparticle is mixed with the core particles, the protecting subparticle is immobilized in the correct orientation. The number of protecting subparticles on the surface of a core subparticle may be controlled by the reaction conditions and concentration of particles. In some embodiments, the surface of the core particle may be patterned according to techniques known to those of skill in the art to provide areas of surface on which a protecting subparticle may preferentially become immobilized as well as areas on which immobilization is inhibited, so as to control the number and distribution of protecting subparticles on the core particle.

In some embodiments it is advantageous for a protecting subparticle to occupy a smaller area of the surface of the core subparticle, in order to leave the surface free for immobilisation of capture agent, while having structural stability on its base to resist stresses, for example in processing or handling the particles in use. In some embodiments a protecting subparticle has a first and a second planar portions joined at a common edge with an angle between them, such as a right angle, the planar portions being functionalized on their lower narrow edge so as to bond to the surface at that edge. In this way the protecting subparticle stands on the narrow edge, and the two portions at an angle acts to stabilize each other against a tendency for the planar portions to tilt or fold down against the surface. The planar portions then comprise a protruding region that can block cell access to the surface of the core subparticle, or to regions of the DNA scaffold itself. For example, a subparticle may have a cross section in the shape of a letter H, T, L, X or Z when viewed from above when in situ on the surface, the portions of the form acting to stabilize the shape of the subparticle against folding. Such configurations have the advantage of inhibiting a cell from contacting the surface, while occupying a relatively small portion of the surface. In some embodiments, a subparticle is shaped such that, when a plurality of subparticles are bound stacked in proximity to each other, for example so as to tessellate over a surface, the subparticles maintain free vertical surfaces. Such forms are advantageous to maintain available vertical surface area if the subparticles are deposited on the surface of the core subparticle in close proximity to one another. Examples of such forms include a circle or ovoid, X, Y, a pound or hash shape: #. Other examples will be described below.

In some embodiments, the protecting subparticle comprises a body and two or more protrusions from the body, the protrusions having end surfaces functionalized to bind to the surface of the core particle. Such protecting subparticles may be immobilized on the surface in the form of a bridge or overhanging region, and may be configured so that one or more agents may be immobilized on the surface under the bridge or overhanging region. Agents may also be immobilized on the underside of the bridge or overhanging region itself. Access to the agent by soluble biomolecules may then be under the sides of the bridge, while the agent is protected from contact with or binding to the biomolecule when on the surface of a cell. A particle may comprise a plurality of such bridge protecting particles, and they may be provided at a mean separation such that most, or substantially all, agents bound on the surface in regions between adjacent protecting subparticles are inhibited from contacting the target biomolecule when on a cell surface.

In some embodiments, a plurality of agents is bound to the surface of the core subparticle, and the portion of the area of the core subparticle that is protected surface is greater than 50%, greater than 60%, greater than 70%, greater than 80%, or greater than 90%.

In some embodiments, a plurality of agents are bound to the core subparticle and the DNA scaffold. In such embodiments, the portion of the plurality of agents that is bound to a protected surface is greater than 50%, greater than 60%, greater than 70%, or greater than 80%. Preferably, the portion of the plurality of agents that is bound to a protected surface is greater than 90%, greater than 95%, greater than 99%, or 100%. In some embodiments, substantially all of the plurality of agents is bound to a protected surface.

In some embodiments, a plurality of DNA scaffolds are bound to the core subparticle, a plurality of agents is bound to the DNA scaffolds, and no or substantially no agent is bound to the core subparticle.

When two adjacent subparticles are closely spaced, cell contact with the region of the surface of the core particle between them is inhibited. When two adjacent subparticles are spaced farther apart, such inhibition is reduced owing to the deformability of the cell membrane. The distances at which these effects are observed depend on the morphology of the subparticles, for example on their height above the surface. Accordingly, in some embodiments the subparticles are provided such that an average separation between them is in the range of 0.5-10 times their average height above the surface, preferably 1-5 times. A protecting subparticle may have a height above its base, and for example a height above the surface when provided on the surface, in the range 10 nm to 200 nm, such as in the range 10-50 nm, 20-100 nm, or 50-200 nm. In some embodiments the protecting subparticle has a height above its base in the range 40 to 80 nm.

A DNA scaffold may comprise a single strand scaffold DNA and a plurality of linkers, as known in the art of DNA origami. The scaffold DNA may be for example a DNA strand from phage M13. See for example Kick et al., Nano Lett., 2015, 15 (7), pp 4672-4676. The subparticle scaffold may be adapted to be made from a single M13 strand, or a plurality of M13 strands linked together, in order to form a larger DNA scaffold. In a typical embodiment, an M13 strand may be used to form a tubular structure. The height and cross-sectional dimension (such as a diameter) of the tubular structure may be selected according to the length of the DNA scaffold strand(s). Typically, as the height of a structure is increased, the cross-sectional dimension will decrease. If a single M13 strand is used, a tubular structure may have a height of around 40 nm and a cross-sectional dimension (such as a diameter) of around 40 nm, or may have a height of around 67 nm and a cross-sectional dimension of around 25 nm. A tubular structure may have a height in the range around 35 nm to 70 nm, and a cross-sectional dimension in the range 20 nm to 45 nm. A tubular structure may have a height and a cross-sectional dimension smaller than this range by designing the M13 strand to be folded and configured in an appropriate way, for example so as to have thicker walls, or by truncation of the strand. A scaffold strand may be selected from another organism, or designed and fabricated, to have a selected length and/or base configuration to provide a DNA scaffold that is larger or smaller in one or more dimensions, and/or to use fewer distinct linkers (see Niekamp et al, Nucleic Acids Research, 2016 1-6 doi: 10.1093/nar/gkw208).

The subparticles may be attached to the surface using methods known in the art for DNA origami. Examples are given below.

VII(B) Particles Comprising Assemblies of DNA Scaffolds

In some embodiments a particle comprises a plurality of subparticles, each comprising a DNA scaffold, bonded together so as to define an internal space, such as a void. In some embodiments such a particle is porous, the pores being defined by surfaces of the subparticles forming part of the particle. The particle may further comprise one or more agents within the space. According to these embodiments, the particle is configured such that an agent within the internal space is inhibited from coming into contact with a biomolecule on the surface of a cell. Thus, the agent is inhibited from, for example, binding to or activating the biomolecule.

In some embodiments a particle comprises a first subparticle that comprises a binding site for an agent, and further comprises a second subparticle bound to the first subparticle, wherein the second subparticle is configured to prevent a biomolecule on the surface of a cell from interacting with an agent bound at the binding site. In a further embodiment, the particle further comprises an agent bound to the binding site. According to these embodiments, the agents on the surface are protected from interacting with a biomolecule on the surface of a cell. In some embodiments, the second subparticle comprises a second binding site for an agent, and the first particle is configured to prevent a biomolecule on the surface of a cell from interacting with an agent bound at the second binding site. In these embodiments, both the first and second subparticles both provide a binding site for an agent and provide protection for an agent bound at the binding site on the other particle. The second subparticle may comprise a DNA scaffold, and may be substantially identical to the first subparticle. The first and second subparticles may be configured to bond together at selected binding positions on the first and the second subparticles, so that the configuration of the assembled particle so formed is predictable and controlled. See for example Ke et al, cited above, for assemblies of DNA nanoparticles assembled in this way. In some embodiments, the particle comprising DNA subparticles provides one or more interior spaces or voids, into which a cell membrane has no access, and hence the agent within the interior spaces or voids is shielded from interaction with a biomolecule such as a receptor molecule on the cell surface.

The particle may be assembled from subparticles by methods known to those of skill in the art. In some embodiments, the subparticles are assembled into the particle by a layer-by-layer method, or as a linear stack. In some embodiments, the subparticles are assembled in a 2D or 3D pattern to form a particle comprising internal spaces and openings between those inward spaces and the external medium, to allow inward access by soluble biomolecules. In some embodiments the particle further comprises binding sites for agents on an external surface of the particle and protrusions from the external surface that are configured to shield the binding sites on the external surfaces. In further embodiments, the particle comprises agents bound to the binding sites on the external surfaces.

The way that the particle is assembled from DNA subparticles may be controlled by providing specific binding partners at selected binding sites on each particle, for example as described by Ke et al. A particle may comprise between 2 and 1000 subparticles, such as 2 to 100, 10 to 200, or 50 to 500 subparticles. An assembled particle may have a maximum external dimension in the range 50 nm to 5 µm, such as in the range 100 nm to 2.0 µm, or in the range 100 nm to 200 nm, or in the range 500 nm to 1.5 µm. An assembled particle may comprise a single type of subparticle, or more than one type. A type of subparticle may have a shape, a binding partner, or a set of binding sites of capture agent, that is different from other types of subparticle. For example, a first type of subparticle may comprise binding sites for capture agent and a second type of subparticle may comprise no binding sites for capture agent. An assembled particle may comprise the first type in its interior and the second type around its exterior to act as a shield.

In some embodiments, the present disclosure provides a method of assembling a particle comprising providing a plurality of subparticles comprising an interior surface, immobilizing an agent on the interior surface, and assembling the subparticles into the particle. In some embodiments, the agent is first immobilized on the interior surface, then the subparticles are assembled. In some embodiments, the subparticles are first assembled, then the agent is immobilized on the interior surface.

VII(C) Particles Comprising Active Subparticles

In some embodiments, a core subparticle has one or more active subparticles bound to the core particle, wherein an active subparticle is configured to scavenge, e.g. to sequester, a soluble biomolecule away from its natural environment. The active subparticle is thus capable of inhibiting the biological activity of the soluble biomolecule, such that the soluble biomolecule has a reduced ability to interact with other natural binding partners of the soluble biomolecule. According to these embodiments, the active subparticle comprises an agent selected to bind the soluble biomolecule and the agent is oriented on the subparticle such that it is sterically inhibited from binding the biomolecule when present on the surface of a cell.

A core subparticle may be inert in the sense that it may have no scavenging capability and may function as a carrier particle for the active subparticles. However, while inert in the sense of lacking a scavenging capability, the core subparticle may still have other functionalities as described elsewhere herein. In some embodiments, all or substantially all of the active subparticles are configured to scavenge a soluble biomolecule. In some embodiments the active subparticles comprise a first group of subparticles configured to scavenge a first biomolecule and a second group of subparticles configured to scavenge a second biomolecule, different from the first. The active subparticles may be smaller than the core subparticle. A subparticle may have a maximum characteristic dimension, such as a diameter, a width or a length, equal to or less than a maximum characteristic dimension of the core particle. For example, a subparticle may have a maximum characteristic dimension in the range 0.001 to 1 times a maximum characteristic dimension of the core particle. A core particle may have a shape, such as being substantially spherical, oblate, a tube, a rod, a substantially flat particle, a disc, or another shape as described herein. A subparticle may have the same shape as the core particle, or a different shape, such as being spherical, a tube, a rod, a substantially flat particle, a disc, or another shape as described herein, the subparticle being further configured to have a surface, such that an agent bound onto the surface is oriented on the surface such that it is sterically inhibited from binding a binding partner of the agent when the binding partner is present on the surface of a cell. In some embodiments the surface is provided within a recess (e.g., a concavity or a void) within the subparticle, the agent being disposed within the recess. In some embodiments the subparticle comprises one or more protrusions, wherein the said surface is protected from interactions with the surface of a cell by the one or more protrusions.

A core particle may be substantially spherical, or may be in the form of a disc, or may have a polygonal shape, and may have a largest cross-sectional dimension, such as a diameter, in the range 50 nm to 5 μm, such as in the range 50 nm-500 nm, 100 nm-1 um. An active subparticle may be disposed on the surface of the core particle. An active subparticle may have a characteristic dimension, for example measured parallel to or tangential to the surface of the core particle, in the range 10 nm-1 μm, such as 10-100 nm, 20-200 nm, 30-300 nm, or 50-500 nm. An active subparticle may have a characteristic dimension, such as a cross-sectional dimension, selected according to the number and types of capture agents or binding sites on its surface, such as within an interior space. An active subparticle may comprise between 1 and 10 binding sites and/or agent, between 1 and 100, or between 100 and more than 1000 sites and/or agent. A typical subparticle comprising 1-5 binding sites may have a characteristic dimension in the range 20 to 60 nm. A subparticle comprising 1 or 2 binding sites may have a characteristic dimension in the range 10-30 nm. A particle may comprise between 1 and 100,000 active subparticles, such as 1-100, 10-1000, 50-5000, or 100-10000 subparticles. In typical embodiments, a particle comprises between 100 and 10,000 subparticles, such as 500 to 5000 subparticles.

According to such embodiments, a particle comprising a core particle and active subparticles may be configured to remain in the circulation of a subject, while individually the active subparticles are in a size range such that they would tend to extravasate if separated from the core particle. In this way the particle is configured to support the subparticles and to retain them against a tendency to extravasate.

VII(D) Active Subparticles Comprising a DNA Scaffold

In some embodiments, a subparticle may comprise a DNA scaffold as described herein. The DNA scaffold may be configured to attach to the surface of the core particle in a preferred (e.g., predefined) orientation, such as being attached by a specific face or edge, thereby presenting other edges as outward-facing from the assembled particle. A DNA scaffold may comprise a three-dimensional shape defining an interior volume and comprising an interior surface and the agent may be immobilized in the interior volume and/or on the interior surface of the shape. The shape may have a single opening, such as a single ended tube or cup, an open box, blind pore, recess, concavity, or void, or more than one opening such as a double ended tube, a through pore or an interior void space having more than one opening to it. The agent may be immobilized on the interior surface of a pore, tube or other interior space within the DNA scaffold. In some embodiments such a particle is porous, having a porous surface, the pores being defined by the interior surfaces of the subparticles attached to the surface of the core particle.

In some embodiments, a subparticle comprising a DNA scaffold comprises an internal space and a binding site for an agent on an interior surface within the internal space. In some embodiments, a subparticle comprises an agent within the internal space. In some embodiments, a particle comprises a plurality of subparticles, each comprising a DNA scaffold comprising an internal space. For example, a particle may comprise a plurality of subparticles in the form of a tube, some or all of the subparticles comprising a binding site for an agent, or an agent bound to a binding site, the site being provided on the internal surface of the tube. The subparticles may have an external surface, and may be bonded to further subparticles such that the external surface of a first subparticle is bonded to an external surface of a further subparticle, for example by linker chemistry as described herein. In this way a particle may comprise an assembly of subparticles coupled together, the assembly having a characteristic dimension, such as a cross-sectional dimension, larger than that of each subparticle. In some embodiments, the characteristic or cross-sectional dimension is in the range 50 nm to 5 μm, such as in the range 100 nm to 2.0 μm, or in the range 100 nm to 200 nm, or in the range 500 nm to 1.5 um. In this way, the invention provides a particle comprising a plurality of subparticles coupled together, the subparticles comprising a DNA scaffold having an internal volume and an internal surface, and an agent immobilized on the internal surface. Such a particle is advantageous in certain applications in that it is sized to remain in circulation in a subject, rather than to extravasate, though each subparticle, if presented individually, would be small enough to tend to extravasate. For example, particles in a size range 100 nm to 200 nm tend to extravasate preferentially into tumours (see e.g. Blanco et al. Nature Biotechnology 33(9) 2015 p. 941-951). Particles in the size range 500 nm to 1.5 um may remain in circulation without accumulating in capillaries, for example in the lungs.

In some embodiments, the openings in the DNA scaffolds may have a maximum size of 10-300 nm. In some embodiments, the maximum size of the opening is 10-60 nm, or 20-40 nm. In some embodiments, the maximum size of the opening is 30-300 nm, 30-150 nm, or 30-100 nm.

In this way, in preferred embodiments, each active subparticle is independently capable of scavenging a soluble biomolecule through binding of the biomolecule to the agent, while inhibiting contact of the agent with a biomolecule on the surface of a cell. The active subparticles are disposed on the surface of a core particle to act as a carrier, so as to create a particle that is larger than the individual subparticles, and to limit the tendency of the small subparticles to extravasate. The active subparticles may be configured optimally for scavenging, while the core particle and the overall size and shape of the assembled particle may be configured optimally to remain in circulation, to travel closer to the center of a blood vessel (as is known for approximately spherical particles) or closer to an edge of a blood vessel (as is known for oblate or discoidal particles).

Cup-like DNA origami NP might be formed for example using methods derived from those of Zhao et al. Nanocaged enzymes with enhanced catalytic activity and increased stability against protease digestion, Nature Communications, doi: 10/1038/ncomms10619, 10 Feb. 2016; see FIG. 1 and supplementary information; an open cup might be formed analogously to one part of the closed container described by Zhao et al. DNA scaffolds having an interior volume are also disclosed by Ke at al., Nature Chemistry 6, 994-1002, 2014, and Linko et al., Chem. Commun., 2015, 51, 5351.

VII(E) Types of Core Subparticle

In some embodiments, the core subparticle may comprise an inorganic material such as silica, a glass, or a metal, or may be a subparticle as described elsewhere herein. A core subparticle may have a silica surface and may be a silica bead or silica shell, such as a silica nanosphere. In some embodiments, the core subparticle has a core that differs from the material of its external surface, such as a core that does not consist of silica. For instance, the core may comprise silicon (the silica might be a native oxide or a thin shell on the core), a magnetic material such as an oxide of iron, a metal such as gold, a radioactive material to allow tracing of the core subparticle. The core subparticle may be formed from a polymer with surface functionalization to bind to the subparticles. The core subparticle may be spherical, or elongated, such as rod-shaped. The core subparticle may be solid, or may be shell particle with a hollow core, and might have contents within it, such as a drug or a reagent. The core subparticle may be formed from a nucleic acid scaffold, and may have a shape to provide binding locations for a plurality of active subparticles each comprising a nucleic acid scaffold, such as planar facets, or shaped surfaces to interface with a matching shaped surface on the active subparticles. A core subparticle may have a largest cross-sectional dimension that is smaller than the largest cross-sectional dimension of the active subparticles, that is about the same, or smaller. In this way, the size of the core subparticle may be selected so as to select the overall size of the particle and the number of active subparticles that it comprises.

VII(F) DNA Scaffold Attachment Methods

The subparticles may be attached to the surface of the core subparticle using methods known in the art for DNA origami, such as, for example, linking a first member of an oligonucleotide binding pair to the lower surface of the subparticle and a second member of the oligonucleotide binding pair to the surface of the core subparticle. A first oligonucleotide binding partner may be introduced to the DNA origami scaffold in the form of an oligonucleotide linker having the first binding partner sequence at one end. For example, the second oligonucleotide may be coupled to a surface using the Solulink™ process; see Shaw et al. Purification of Functionalized DNA Origami Nanostructures, *ACS Nano*, 2015, 9 (5), pp 4968-4975. Functionalization of the surface of a core particle, such as a silica surface, with the counterpart Solulink™ ligand is standard in the art. The oligonucleotide may be immobilized to the surface by coupling the two Solulink ligands. Other linker chemistry between oligonucleotides and solid surfaces are known in the art.

DNA can be attached to silica surfaces following treatment of the surfaces with APTES to provide a positively charged surface—see, e.g., Sarveswaran et al., Adhesion of DNA nanostructures and DNA origami to lithographically patterned self-assembled monolayers on Si[100], Proc. SPIE 7637, Alternative Lithographic Technologies II, 76370M (Apr. 1, 2010); doi:10.1117/12.848392. DNA structures adsorb and adhere on silica surfaces also in the presence of Mg2+, which reverses the net negative charge of the silica surface—see, e.g., Albrecht, B. et al., Adsorption studies of DNA origami on silicon dioxide, in Proceedings of the 21st Micromechanics and Micro systems Europe Workshop, Enschede, The Netherlands, Sep. 26-29, 2010; Abelmann, L, et al. Eds.; University of Twente, Transducers Science and Technology: Enschede, The Netherlands; pp 153-156.

The subparticles may be attached to the core subparticle by linkers—examples of linkers are disclosed herein. For DNA origami subparticles, one or more attachment points may be provided on the DNA structure which can be used to anchor a linker or one member of a binding pair, the other member being provided on the core subparticle. Specific methods to attach of planar DNA origami structures to solid supports are disclosed in US2015/0298090, which discloses use of a binding pair, in which one half of the pair is provided on a surface of the DNA structure and the other half on the support, bonding between the two resulting in attachment of the DNA structure. Examples of binding pairs are biotin/avidin and complementary DNA strands. US2016/0102344 also discloses use of complementary DNA strands to immobilise a planar DNA origami structure. In typical embodiments, it is not necessary for the binding pair member to be patterned on the surface of the core subparticle, as is disclosed in these references; rather, the binding pair member can be provided over the whole of the surface of the core subparticle, or in portions of it. Subparticles may then associate with and be attached to the surface stochastically.

VII(G) Particles Configured to Scavenge Exosomes or Vesicles

In some embodiments a particle is configured to scavenge an exosome or a vesicle from a liquid environment, such that a biomolecule on or within the exosome or vesicle is inhibited from interacting with a binding partner of the biomolecule in solution or on a cell membrane. Exosomes and vesicles are known to be produced in disease conditions such as cancer and to be involved in signaling that may promote the course of disease. See for example Yu et al, Oncotarget, Vol. 6, No. 35 p. 37151-37168. Exosomes have a typical dimension, such as a diameter, in the range 30-150 nm and vesicles have a typical dimension in the range 150 nm to 1 μm (see Yu et al, above). An exosome may comprise a biomolecule that is a binding partner for a signaling molecule that is involved in promotion or inhibition of a disease state. For example, TNFR molecules are known to be present in the serum of human subjects on the surface of exosomes (see Hawari et al. PNAS 2004 vol. 101 no. 5 1297-1302, Zhang et al., Biochem Biophys Res Commun. 2008 Feb. 8; 366(2): 579-584) and these may bind to membrane-bound TNF alpha on immune cells, such as natural killer (NK) cells, to inhibit NK cell attack on diseased target cells, such as in cancer. Further, exosomes and vesicles are known to carry a variety of cytokines that may promote cancer, such as metastatic cancer (see for example Hoshino et al. Nature 527, 329-335 2015), and scavenging of such exosomes or vesicles may be advantageous to inhibit the progress of disease. Herein the term exosome will be used for both exosomes and vesicles, and the embodiments described are intended to relate to scavenging of both exosomes and vesicles, with dimensions of the features of the embodiments described for exosomes being selected to allow scavenging of vesicles.

Accordingly, in some embodiments the regions of protected surface are configured to allow binding of an exosome adjacent to the region. In some embodiments an internal space or void is configured to allow binding of an exosome within the space or void. In some embodiments a recess or pore extending from the surface of a particle is configured to allow an exosome to enter the recess or pore and to bind within the recess or pore. In some embodiments a subparticle is spaced apart from a second subparticle on the surface of a core subparticle to allow an exosome to bind to the surface between the subparticles. In some embodiments a subparticle comprises a first and a second planar portion spaced apart to allow an exosome to bind to the subparticle between the first and second planar portions. In some embodiments, a first subparticle and a second subparticle are bound together to create a space to allow an exosome to bind within the space.

Binding of an exosome means for example that a biomolecule on the surface of the exosome binds to an agent provided on the surface of a particle. The agent may be provided bound to a region of protected surface, bound to a surface within an internal space or void, bound to a surface within a recess or pore, on a surface of a core subparticle adjacent to a protecting subparticle, or on a surface of an active subparticle. An agent may be selected to bind a biomolecule found predominantly or specifically on the surface of exosomes, such as CD9, CD63, CD81 or CD82 (see for example Yu et al., op cit). A particle may comprise a first agent and a second agent, where the second agent differs from the first, each of the first and second agents being selected to bind a biomolecule on the surface of an exosome. For example, a first agent may bind a receptor molecule such as TNFR1/2 and a second agent may bind a second protein typically associated with the membrane of an exosome, such as CD9, CD63, CD81 or CD82. The particle may be configured such that an exosome may contact a first region and a second region of the surface of the particle, wherein the second region is at an angle with respect to the first, such as an angle between 0 and 90 degrees. For example, a first region may be the surface of a core subparticle and a second region may be on the surface of a subparticle provided on the surface of the core subparticle; a first region may be the base and the second region may be a sidewall of an active subparticle. A first agent may be provided on the first region and a second agent may be provided on the second region. In this way, an exosome may bind both to the first and the second regions, so that it is retained attached to the surface of the particle, so being scavenged from the liquid environment.

Typically a particle configured to scavenge exosomes has a characteristic dimension, such as a minimum dimension, of a capture environment to receive the exosome, such as a minimum dimension of a protected surface, of the cross-section of an internal space or void, of the cross-section of a recess or pore, of the distance between a first and second protecting subparticles, or of an internal dimension of an active subparticle, sufficient to receive the exosome, such as in the range 30 nm-1 µm, typically in the range 30 nm to 300 nm, more typically in the range 30 nm-120 nm. The internal dimension may be selected to scavenge exosomes in a selected size range, such as for example in the size range 30-50 nm to scavenge exosomes comprising TNFR1/2 according to Hawari et al (op cit). A particle may be configured to scavenge a selected type of exosome, and may have a characteristic dimension selected in the size range to capture the said type, and one or more capture agents selected to bind to a biomolecule on the surface of the said type. For example, a particle configured to capture exosomes comprising TNFR1/2 may have a characteristic dimension in the range 30-50 nm and also an agent to bind to TNFR1/2, such a TNF alpha, a variant or mutein of TNF alpha, or an antibody to TNFR1/2.

Particles comprising a DNA scaffold are suited for use in scavenging exosomes as the DNA scaffold may be configured precisely to provide a suitably dimensioned capture space for the exosome. For example, a DNA scaffold may be configured as a tube, a cup, a recess, a pore, or a shape comprising two or more spaced apart planar portions, having a configuration and characteristic dimensions selected to receive and to capture an exosome. The embodiments below include examples suited for scavenging exosomes.

In some embodiments, the surface of a particle may comprise both protected and non-protected surface, such as for example a non-protected surface on the surface of a core subparticle and a protected surface on a region of the surface of an active subparticle. In some embodiments, a first capture agent selective for a biomolecule that may be present on the surface of a cell, such as a receptor molecule, may be provided on the protected surface, and a second capture agent, selective for a biomolecule that may be present preferentially or specifically on the surface of an exosome, may be provided on the non-selective surface. In this way, a particle may be configured to scavenge an exosome, while the agent on the surface of the particle is inhibited from binding to, or activating, a biomolecule such as a receptor on the surface of a cell. In some embodiments, such inhibition may be total, and in some embodiments, such inhibition may be partial, such that a beneficial balance is achieved of therapeutic effect through scavenging versus side effects through binding of a proportion of the capture agent on the particle to a cell surface receptor.

VII(H) Description of Embodiments

Referring to FIG. 20, particle 10 comprises a core particle 12 and a plurality of active subparticles 14 disposed on the surface 20 of the particle. Subparticle 14 comprises a cup- or open ended box-shaped structure 16 having an interior surface and an agent 18 disposed on the interior surface within the cup, such as on the base of the cup, such that the agent is inhibited from interaction with a binding partner on the surface of a cell. The subparticles may be disposed randomly on the surface 20 or may be disposed in an array, which may be regular, imperfect or patchy on the surface, as indicated at 22. The core particle 12 may act as a carrier for the subparticles 14, allowing the subparticles to circulate within the circulation of a subject without extravasation. The subparticles are preferably oriented on the surface with the opening of the cup facing outwards. The subparticles may be coupled to the surface of the core particle by an adsorption process, such a physisorption. The subparticles may be bound to the surface 20 by a binding partner or a linker chemistry provided preferentially or only on the base of the cup, on the external side of the cup, opposite to the interior surface. In this way in this embodiment the core particle may be substantially covered with active subparticles, each oriented outwards to provide ready access for a soluble biomolecule to the agent within the subparticles.

Particle 10 may be assembled from a plurality of subparticles 14, each comprising a binding site on an interior surface; a core particle 12 having a surface 20; and a plurality of agents 18 by a method comprising: immobilizing the plurality of agents 18 on the binding sites of the plurality of subparticles 14; and binding the plurality of subparticles 14 to the surface 20. In one embodiment, the agents may be immobilized on the binding sites before the subparticles are bound to the surface. In another embodiment, the subparticles are bound to the surface before the agents are immobilized on the binding sites.

The subparticles are dimensioned to allow the target biomolecule to enter the subparticle and bind to the agents on the interior surface. The subparticles may be dimensioned to allow a soluble biomolecule, such as a soluble receptor molecule to enter and to bind, such as having a cross-sectional dimension of the cup in the range 10-60 nm, or in the range 20-40 nm. The subparticles comprise 1 or 2 binding sites, and may have a cross-sectional dimension, such as the opening to the interior space inside the cup, in the range 10-20 nm, and a depth in the range 10-20 nm. The subparticles may comprise further binding sites, and may have larger dimensions accordingly. The skilled person may select a dimension based on the number and configuration of the binding sites and/or agents, in order to reduce or avoid steric hindrance of access by target to an agent within the interior space. The subparticles may be dimensioned to allow an exosome to enter and to bind to agent on the interior surface, such as having a cross-sectional dimension of the cup in the range 40-300 nm, or in the range 40-150 nm, or 50-100 nm. In this way the particle may be configured to scavenge a target biomolecule when present in a liquid on a surface of an exosome. A particle may comprise a first group and a second group of active subparticles, each group comprising a different agent and/or having a different configuration, such as a different shape or a different cross-sectional dimension. In this way, the particle 10 may be configured to scavenge both a first target biomolecule and a second target biomolecule, in some embodiments wherein the second target biomolecule is present on the surface of an exosome.

Figure 21:
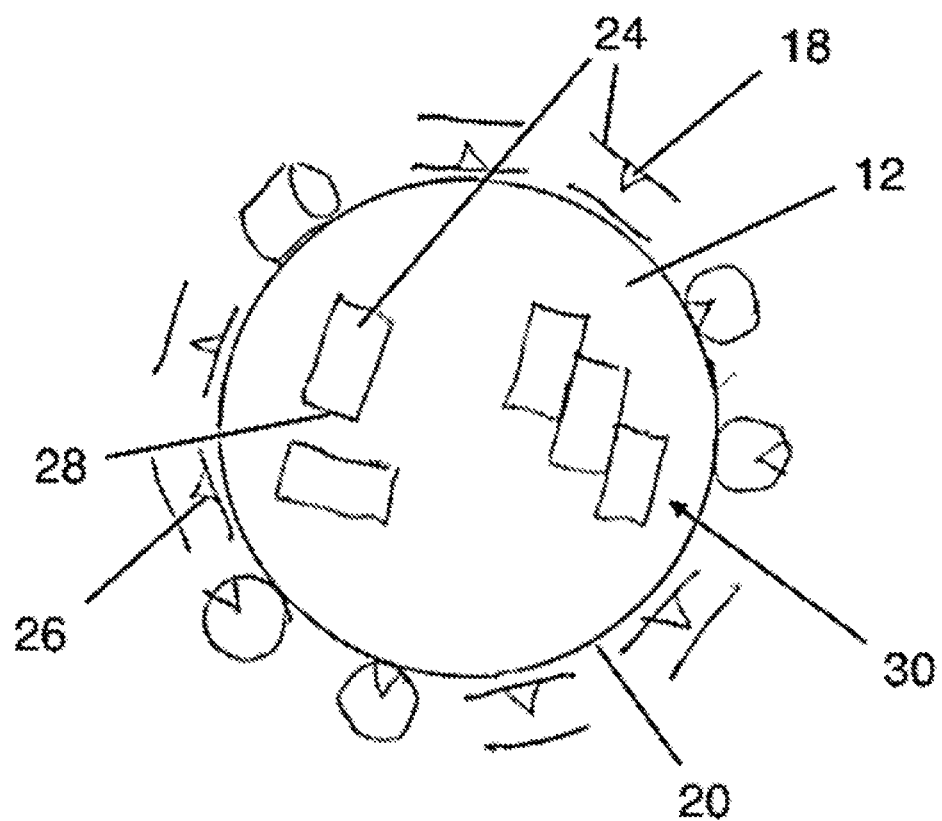
FIG. 21 depicts an exemplary arrangement of a core particle bound to a plurality of tube-shaped active subparticles.

Referring to FIG. 21, particle 10 comprises a core particle 12 and a plurality of tubular active subparticles 24 disposed on the surface 20 of the particle, each subparticle comprising an agent 18 provided on the interior surface of the subparticle. The subparticles are bound to the core particle by a binding partner or a linker chemistry provided preferentially (such as solely) on the exterior surface of the tubular structure of the subparticle. As shown in FIG. 21, the subparticles may be disposed on the core particle in a random or semi-random orientation, or may be disposed in a regular or aligned orientation as shown at 30. As shown at 26, the orientation of the agent within the subparticle may be random, or it may be selected in some embodiments. Each subparticle comprises at least one opening through which a biomolecule may pass to reach the agent on the interior surface. As shown at 28, the opening may be facing a further subparticle and, if in close proximity, may be occluded by the further subparticle. In some embodiments, a regular or semi-random arrangement of subparticles on the surface 20 is used to provide access to the openings into the subparticles. In some embodiments, a random arrangement of subparticles on the surface 20 is used and the number of particles adhering to the surface is controlled (e.g., by stoichiometry) so as to probabilistically limit the number of partially or completely occluded openings.

In some embodiments the subparticles may be porous. A subparticle may comprise a porous material or structure as described herein, such a porous silicon or silica, with the agent disposed preferentially or wholly within the pores of the subparticle. In some embodiments, the core particles are also porous.

Figure 22:
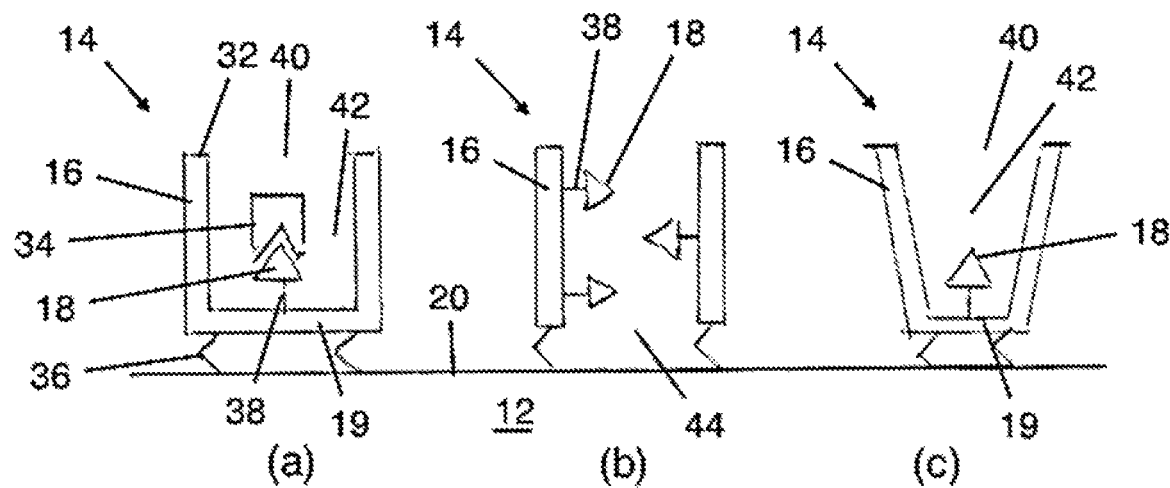
FIG. 22 depicts exemplary arrangements of active subparticles of various shapes on the surface of a core subparticle.

Referring to FIG. 22, three arrangements of subparticles 14 on a surface 20 of a core particle 12 are shown. At (a), a cup-shaped subparticle is shown comprising a structure 16 and an agent 18 mounted within the structure 16. The soluble biomolecule, being a binding partner for the agent 18, is shown as 34. The subparticle comprises an interior void volume 42 and an opening 40 to the void volume. The agent 18 is immobilized on the interior, protected surface of the subparticle by a linker 38. The structure 16 is sized such that when a cell contacts the upper surface 32 the biomolecules present on the surface of the cell, do not reach the agent 18. The sizing may take into account that the cell may deform such that a portion of the cell membrane, on which the biomolecule 34 is present, may pass some ways through the opening 40, a surface biomolecule 34 still being unable to reach the agent 18. The sizing may also take into account that it is only necessary to restrict certain biomarkers (which may be present only on certain cell types) from access to agent 18. As is known in the art, different cell types present different biomarkers on their surface, and different cell types also have different propensities to deform around obstacles such as structure 16 or surface 32. The person of skill in the art will be able to account for these factors in selecting, e.g., the appropriate depth and width of, e.g., structure 16 for a certain application involving a certain agent. For example, upper surface 32 may be a distance from base 19 of the subparticle in the range 5 nm to 200 nm, such as 10 nm to 50 nm. The subparticle may comprise a plurality of agents 18, some or all of which are disposed within the interior volume 42 so as to be inhibited from interacting with the biomolecule 34 when present on the surface of a cell. In some embodiments, a proportion of the agent is so inhibited, such as in the range 10-100%, such as 95%, 90%, 80%, 70% or 50% of the agent, while the remainder is provided close enough to the opening 40 than in some cases, an agent may interact with a biomolecule present on the surface of a cell, but at least a proportion of the agent will not. The proportion of agent that is protected is selected to be sufficient that a therapeutically effective particle is created.

The subparticle is immobilized on the surface by a linker 36, the linker being bonded to the exterior of base 19 and to surface 20. A linker may comprise a first reactive group provided on the base of the subparticle and a second reactive group provided on the surface 20, the two functional groups being reacted to form the linker. Examples of linker chemistry and such reactive groups are given herein.

In FIG. 22(b), a tubular subparticle 14 comprises a plurality of capture agents 18 disposed on the interior surface within the interior volume of the tube 16 by linkers 38 on the interior surface. The tube is attached to the surface 20 by linkers preferentially (such as solely) provided on the lower rim of the tube, surrounding the lower opening 44. For example, a first binding partner or reactive group may be provided on one rim of a tubular structure 16, and the second binding partner or reactive group may be provided on the surface 20. Subparticle 14 will then tend to immobilize on the surface in the orientation shown. This orientation is advantageous in practice as the upper openings of the tubes are aligned and pointing outwards, so reducing the tendency to occlusion of the openings that arises if tubes are disposed on the surface 20 on their sides, as shown in FIG. 21 at 28.

In FIG. 22(c), a cup-shaped subparticle is shown, having a taper from the opening 40 to the base 19.

In each of the embodiments described herein the subparticle may be dimensioned according to the type of target to be scavenged, for example a soluble biomolecule or a biomolecule on the surface of an exosome.

Figure 23:
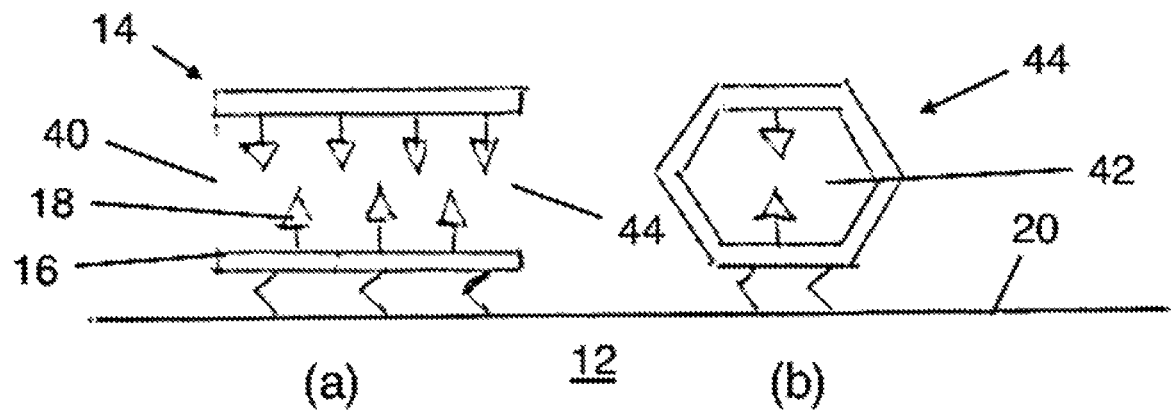
FIG. 23 depicts exemplary arrangements of active subparticles of various shapes on the surface of a core subparticle.

Referring to FIG. 23, a tubular subparticle comprising a tubular structure 16 is immobilised on the surface 20 by linkers as before. However, in this embodiment, the linkers are attached to the exterior surface of the structure 16. The agent 18 is attached to the interior surface. The subparticle has openings 40, 44 at each end of the tube to allow access of the biomolecule to the interior. As shown in FIG. 23(b) the structure 16 may have a polygonal cross-section, such as a triangular, square, pentagonal, hexagonal (as depicted), heptagonal, octagonal, or higher polygonal.

The subparticles may be formed from example from a DNA scaffold, as described further below. A hexagonal tubular structure as shown in FIG. 23(b) is an advantageous structure for fabrication using DNA origami as described herein. It will be apparent that in some embodiments the structure of FIGS. 23(a) and (b) may be attached to the surface 20 in a vertical orientation as shown in FIG. 22(b).

Figure 24:
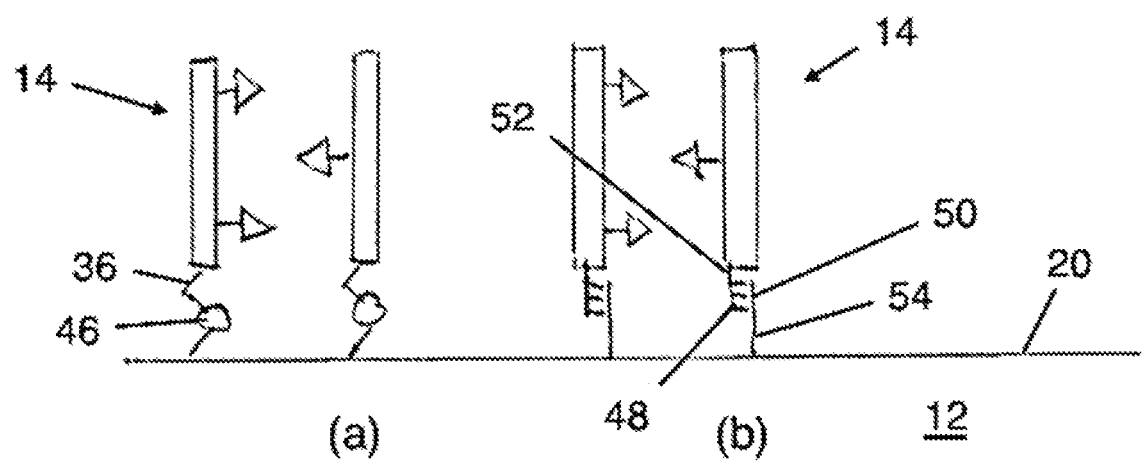
FIG. 24 depicts exemplary arrangements of active subparticles of various shapes on the surface of a core subparticle.

Referring to FIG. 24(a), a tubular subparticle is attached to the core particle by a linker 36 comprising a linker group or coupling group 46. The group 46 may be formed from reaction of a first and second reactive groups. For example, group 46 may be formed from a reaction between an amine and a carboxylic acid group, or from a reaction between a maleimide and a thiol group, or from reactions involving other linker chemistry as described herein. Referring to FIG. 24(b) a tubular subparticle is attached to the surface by a first and a second binding partners comprising oligonucleotides. Here oligonucleotide 48 is attached by linker 52 to the subparticle and oligonucleotide 54 is attached by linker 54 to surface 20 of the core particle. Linker 52 might itself comprise a nucleic acid such as DNA, for example attached to a DNA origami tubular structure 16. Examples of complementary oligonucleotides used for linking DNA subcomponent to a further component are a chain of thymine and a chain of adenine residues (see for example in Gerdon A E et al., Controlled Delivery of DNA Origami on Patterned Surfaces, Small 2009, 5, No. 17, 1942-1946). Other examples of binding pairs are biotin/avidin and antibody/antigen pairs.

Figure 25:
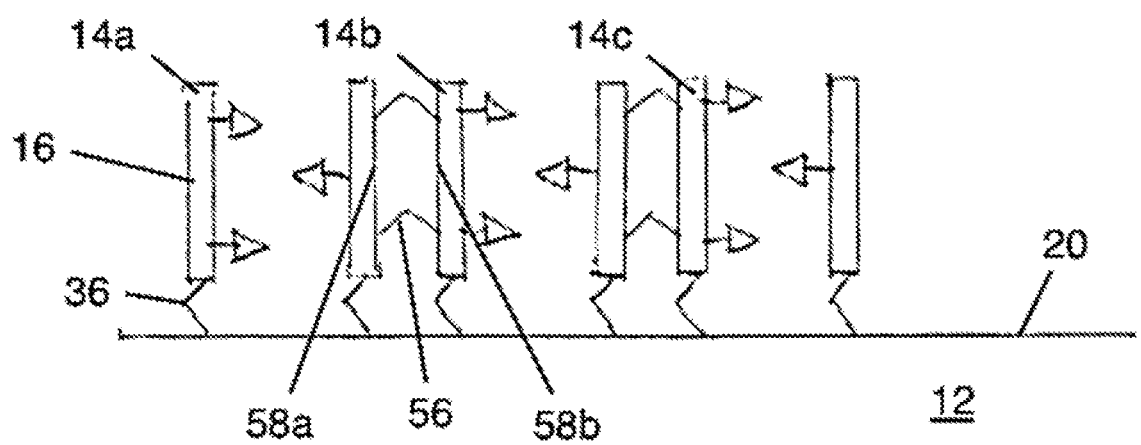
FIG. 25 depicts exemplary arrangements of linked active subparticles of various shapes on the surface of a core subparticle.

Referring to FIG. 25, a plurality of subparticles 14a, b, c each comprising a structure 16 having an agent on its interior surface may be bonded to the surface 20 of core particle 12 by linkers 36 and also to each other by further linkers 56 attached to the exterior surfaces 58a and 58b of the structures. The linkers 56 may comprise the same linker chemistry as linkers 36 or different chemistry. For example, linkers 36 may comprise a first pair of complementary oligonucleotides, and linkers 56 may comprise a second pair of complementary oligonucleotides, all four being different from one another, such that the structures 16 do not bind to the surface 20 by their exterior surfaces. Alternatively, linkers 36 may comprise a first pair of complementary reactive groups and linkers 56 may comprise a second pair of complementary reactive groups, such that the linker chemistry is orthogonal (i.e., the first pair of reactive groups do not react with to an appreciable extent with the second pair of reactive groups, and vice versa).

Figure 26A:
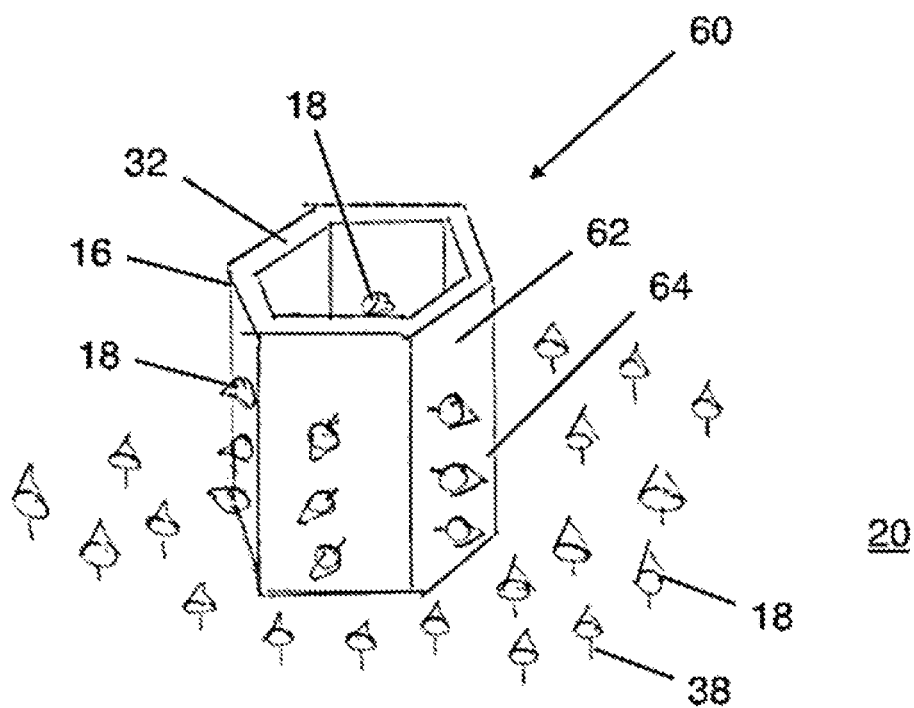
FIG. 26A depicts an exemplary arrangement of binding sites on an active subparticle.
Figure 26B:
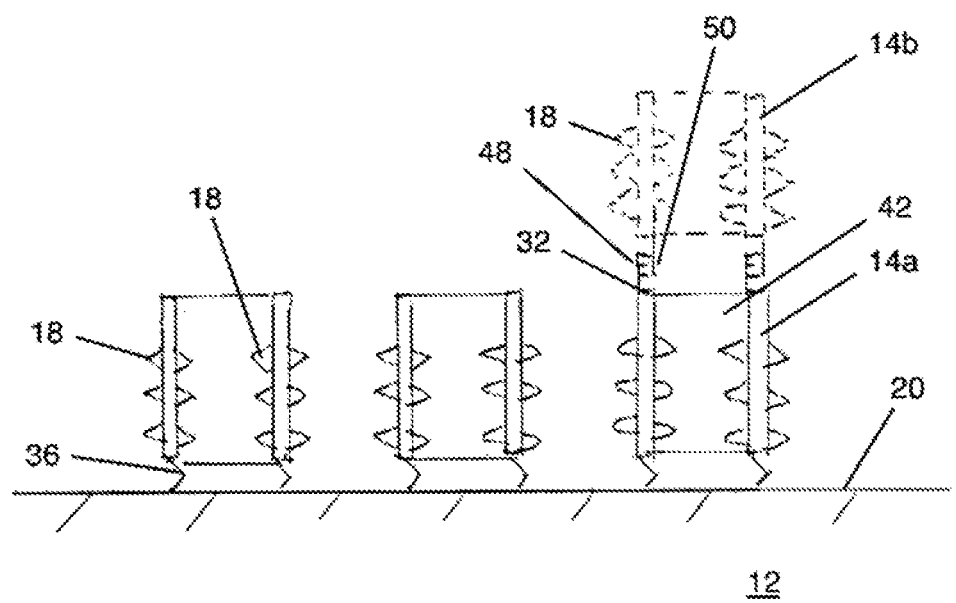
FIG. 26B depicts exemplary arrangements of the subparticles in relation to one another on the surface of a core subparticle.

Referring to FIGS. 26A and 26B, subparticle 60 comprises a tubular DNA scaffold 16, having for example a circular or polygonal cross-section (shown here as hexagonal), and may be immobilized by its base on the surface 20 of a core particle by linkers 36. One or more surfaces of subparticle 60 may comprise agent 18. In some embodiments, an interior, protected surface of subparticle 60 comprises agent 18. In some embodiments, an exterior surface of subparticle 60 comprises agent 18. In some embodiments, both the exterior and interior surfaces of subparticle 60 comprise agent 18. The subparticle may be configured to comprise binding sites for the agent or for a linker 38 configured to immobilize the agent on the surface of the subparticle. The binding sites may be positioned uniformly over the surface, or may be provided at selected locations. As shown in FIG. 26A, the binding sites, and the agent, may be provided in a first region 64 of the surface of the subparticle, and not in a second region 62. By forming a protrusion above the surface 20, subparticle 60 inhibits contact of a cell surface with exterior surfaces 62, 64 of the subparticle, so providing a protected surface on the surface of the subparticle. A region such as region 62 of the surface closer to the upper surface 32 of the scaffold may offer less inhibition, as a cell membrane may deform to allow contact with that region of the surface. Accordingly, provision of binding sites and agents may be limited to region 64. The protrusion of the subparticle above the surface also inhibits cell contact with a region of the surface surrounding the subparticle, so providing a region of protected surface on the surface 20 of the core subparticle, and so in some embodiments agent may be provided in a region of protected surface on the surface 20 also. A particle as a whole may comprise subparticles such as that depicted in FIG. 26A having an average spacing apart in the range 0.5 to 5× the height of the subparticles. The number and or concentration of subparticles in a mixture from which subparticles are immobilized onto the surface may be selected to achieve such a surface coverage. In this way a region of protected surface is provided adjacent to or between the subparticles.

As shown in FIG. 26B, in some embodiments the subparticles may be stacked, with a second subparticle, 14b, being immobilized on an upper surface of the first subparticle 14a, such as the upper surface 32 of the first subparticle. Linking strategies disclosed elsewhere herein may be used to link the subparticles. For example, complementary nucleic acid linking groups 48 and 50 may be provided on surface 32 and one end of the second layer subparticle 14b, so as to preferentially locate 14b on top of 14a. In this way the interior space 42 and interior surface area of the subparticles is extended, and the effective surface area for immobilization of agent may be increased greatly over the area of surface 20. Additionally, in some embodiments, the increased height of the stacked subparticles above the surface 20 results in an increased region of protected surface on the surface 20.

Figure 27A:
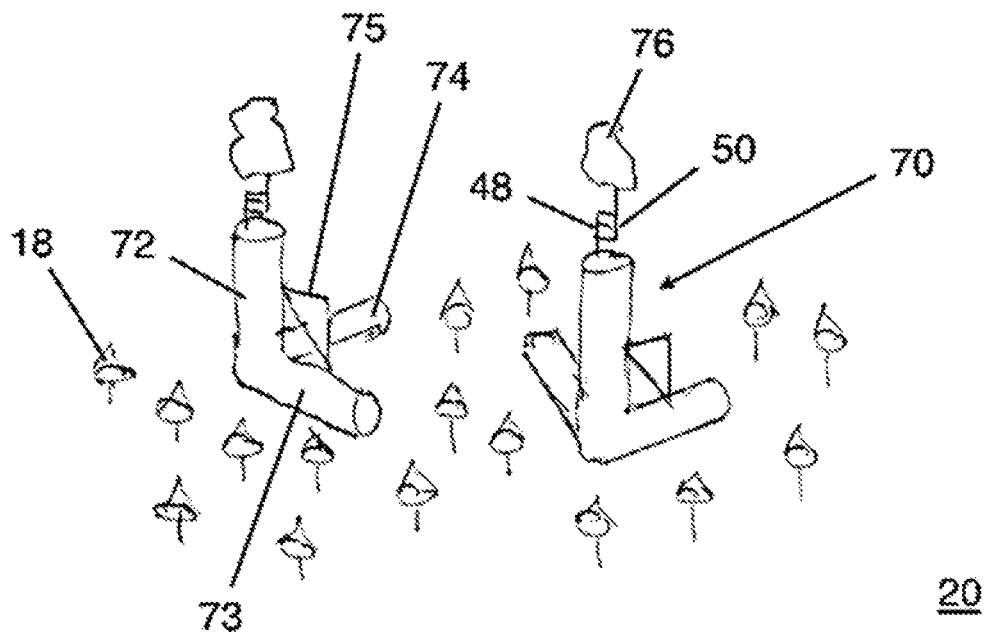
FIG. 27A depicts an exemplary active subparticle, and an exemplary arrangement of binding sites thereon.
Figure 27B:
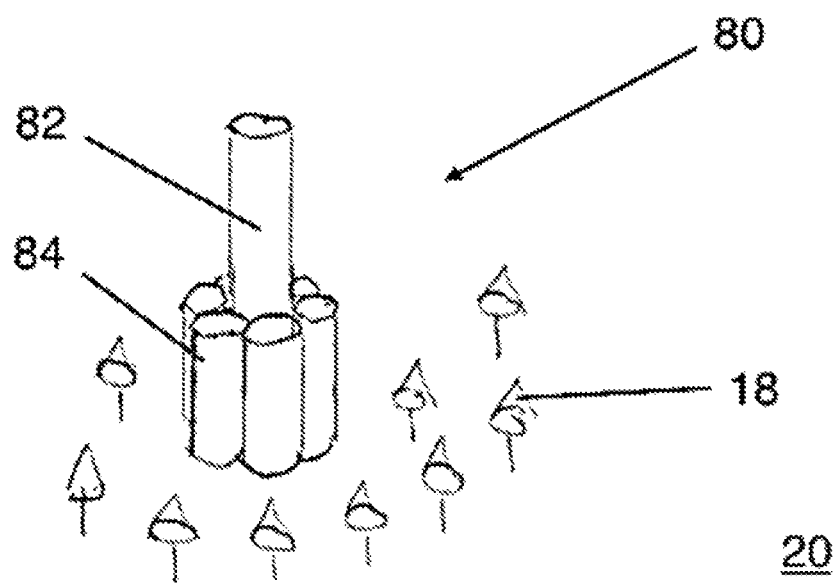
FIG. 27B depicts an exemplary subparticle disposed on the surface of a core subparticle.

Referring to FIG. 27A, subparticle 70 comprises first, second and third arms 72, 73, 74 and a supporting structure 75, as disclosed by Iinuma et al., Science 2014: Vol. 344, Issue 6179, pp. 65-69, FIG. 1. Such a structure may be immobilized on surface 20 by linker chemistry provided on arms 73 and 74. Arm 72 then acts as a protrusion to inhibit contact between a cell membrane and agent 18 provided on the surface 20, so as to provide a region of protected surface on the surface 20. Referring to FIG. 27B, a subparticle 80 comprises a pillar structure comprising a linked plurality of DNA origami tubes, as disclosed by Pellegrotti et al, Nano Letters 2016 16 (10), 6222-6230, FIG. 1, in which the surrounding tubular structures 84 are bonded to the central structure 82, so acting to stabilizer and support the central structure, which acts to inhibit cell contact with the surrounding surface 20.

Such subparticles 70 may be active subparticles in some embodiments. For example, agents may be provided on one or more arms, such as at least on the upright arm 72. An embodiment configured to scavenge an exosome comprises an agent on arm 72 selected to bind to a biomolecule on the surface of the exosome. Further agent on arms 73 or 74, or on the surface 20, may also be selected to bind to the same or a different biomolecule on the surface of the exosome.

Figure 28A:
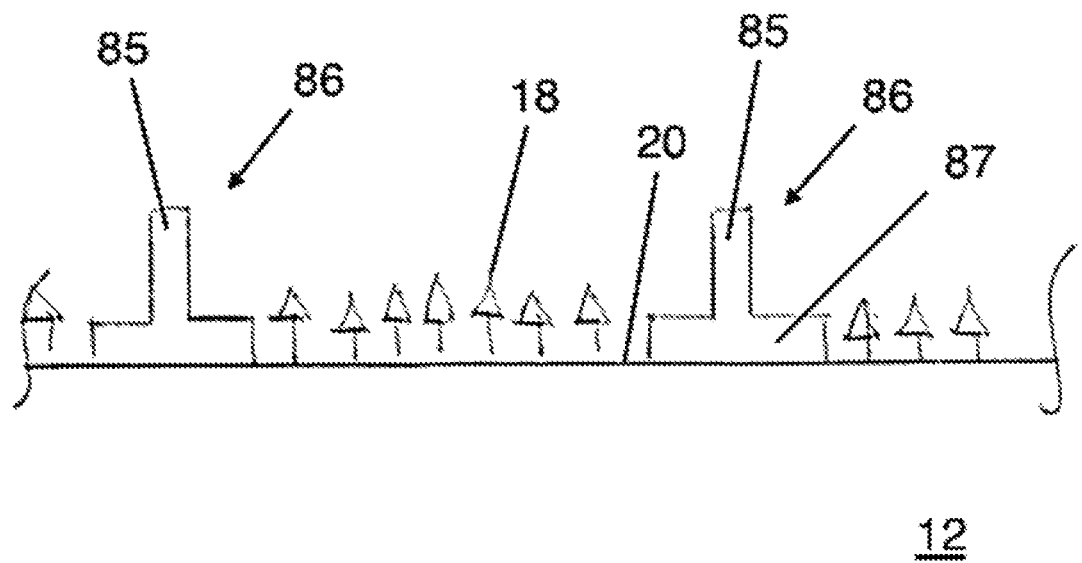
FIGS. 28A and 28B depicts an exemplary arrangement of a core subparticle bound to a plurality of protrusions.
Figure 28B:
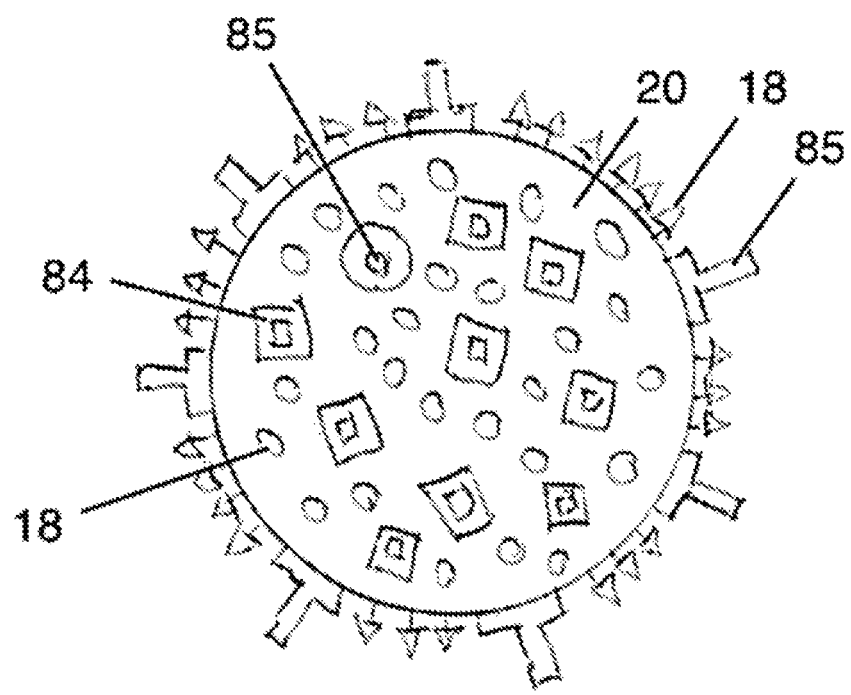

Referring to FIGS. 28A and 28B, particle 12 comprises a plurality of capture agents 18 on its surface 20 and a plurality of protrusions 85, the protrusions being dimensioned and spaced apart on the surface such that at least a proportion of the agents 18 are inhibited from coming into contact with and/or binding to a biomolecule on a cell surface in contact with the protrusions 85. In some embodiments the protrusions have a height above the surface in the range 10 nm to 200 nm, such as 40 nm to 80 nm. The protrusions may be spaced apart such that all, or substantially all, of the agents are inhibited from interacting with the biomolecule when present on the surface of a cell. The protrusions may be spaced apart such that a therapeutically acceptable proportion of the capture agents are inhibited from contacting the biomolecule on the surface of the cell.

In some embodiments the protrusions comprise subparticle 86, comprising a DNA scaffold, for example as shown in FIG. 27A or 27B, 29, 30, or 31, for example comprising a base portion 87 to support protruding portion 85. The protrusion and base portion may have any suitable shape, as required to support the protrusion and to remain anchored on the surface, for example having circular or rectilinear shape. The subparticle may be immobilized on the surface 20 as described before, for example by linker chemistry provided on the lower surface of the subparticle. The spacing apart of the protrusions may be an average spacing, for example as determined for an ensemble of particles by the reaction conditions between the core particles and the subparticles. It will be understood that the configuration of DNA scaffold-based subparticles, that provide protrusions from the surface 20 and hence act as protecting-subparticles, is not limited to those shown, and other designs may be used as known to those of skill in the art—for example the columnar DNA origami described by Endo et al, Angew. Chem. Int. Ed. 53, 7484-7490 (2014), or the elongated brick-like forms described by Ke at al. Nature Chemistry 6, 994-1002, 2014, may be immobilized in an upright configuration by providing linker chemistry on the surface to be linked to the surface 20.

The active subparticles in the embodiments in FIGS. 20 to 26B may comprise further moieties in addition to the agent 18. For example a moiety may be provided on a surface of the DNA scaffold 16. It is an advantage of DNA origami technology that the binding location for a moiety may be precisely defined by the provision of a mounting linker for the moiety that hybridizes to a specific sequence within the scaffold DNA, and the position of that sequence is known from the design process of the scaffold.

For example, referring to FIG. 27A, a moiety 76 may be immobilized on the upper end of the protrusion, arm 72. Such a moiety may be a protein, for example CD47, that may inhibit digestion by macrophages, or a recognition protein that promotes uptake by macrophages. Such a moiety may be selected to reduce immune recognition, for example to prolong life of the assembled particle in circulation, such as a polymer such as PEG or PLGA. The moiety may be linked by any of the strategies described here, for example by a pair of complementary nucleotide chains 48, 50, one chain (48) being linked with the DNA scaffold, such as having a second end that hybridizes to a sequence within it.

The protecting subparticles may have agent immobilized on an exterior surface such that the agent is not inhibited from contact with a biomolecule on a cell surface while the subparticle is separate from the core particle, but the core particle and the subparticle together act to inhibit contact of the agent on the subparticle with a biomolecule on the cell surface. In this way subparticles may increase the effective surface area for capture, and the amount of capture agent provided on a particle, above the surface area of the core particle 12. The bonding of protecting or active subparticles to the core subparticle may additionally create regions on protected surface on the surface of one or both of the core subparticle and the protecting or active subparticles.

Referring to FIG. 26A, agent on surface 64 would not be inhibited from such contact if particle 60 were not attached to surface 20. Further, referring to FIGS. 29 and 31, in some embodiments a subparticle may comprise two or more substantially planar portions joined at an angle, such as a right angle. In some embodiments, a particle comprises a core particle having a surface 20 and a plurality of subparticles immobilized on the surface such that at least one planar portion is raised at an angle to the surface. Preferably the two planar portions are mounted on the surface on their edges, so as to provide an upper edge 32 at a height above the surface 20. Agent 18 may be provided on the surface 20 and on the surfaces 64 of the subparticle. Optionally, a region 62 of the surface may be left without agent to reduce or avoid the chance of contact between agent in region 62 with a biomolecule on a cell surface.

Figure 29:
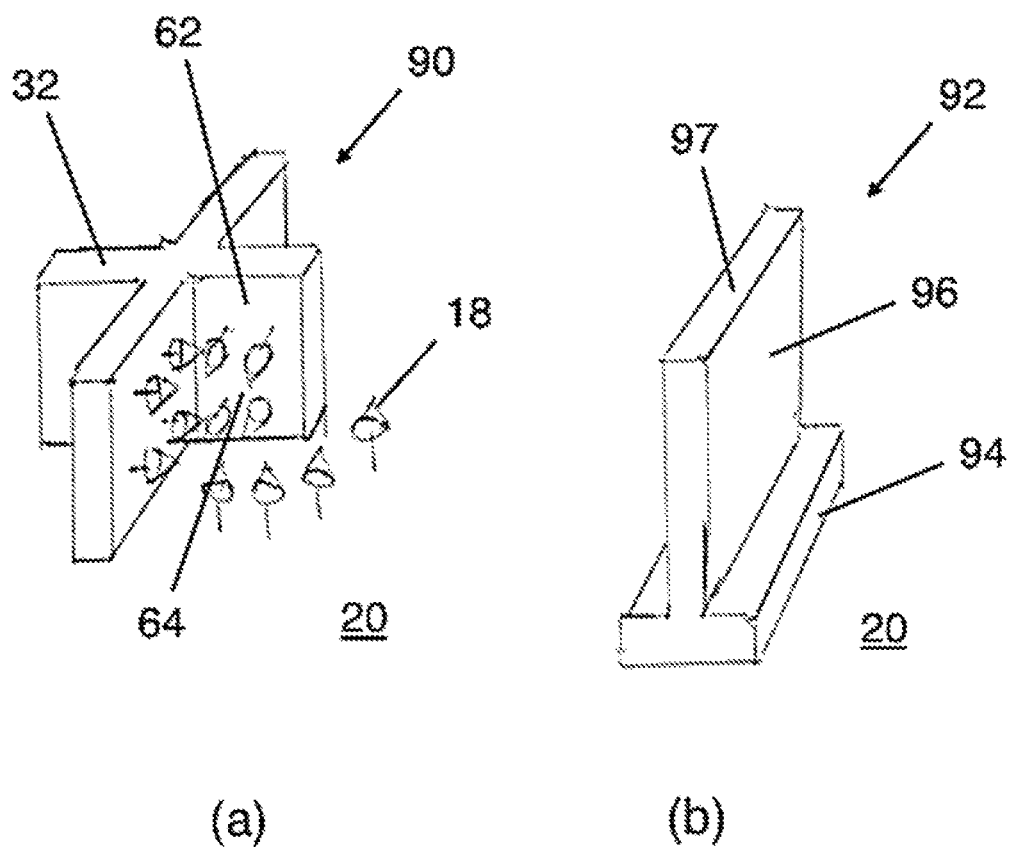
FIG. 29 depicts two exemplary subparticles.
Figure 30:
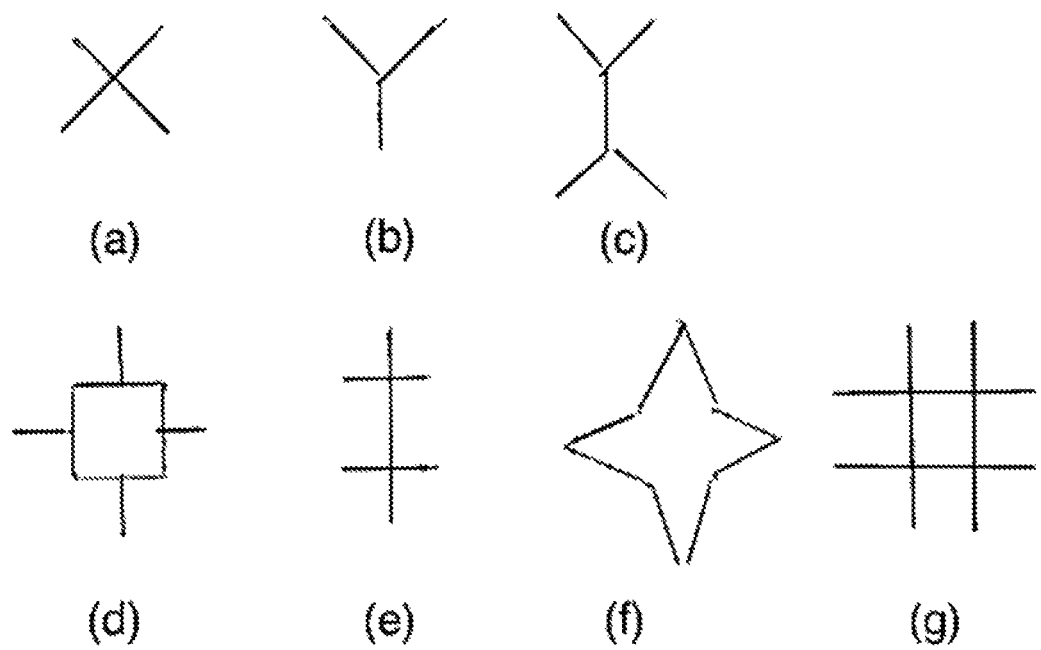
FIG. 30 depicts exemplary shapes of subparticles, or parts thereof.
Figure 31:
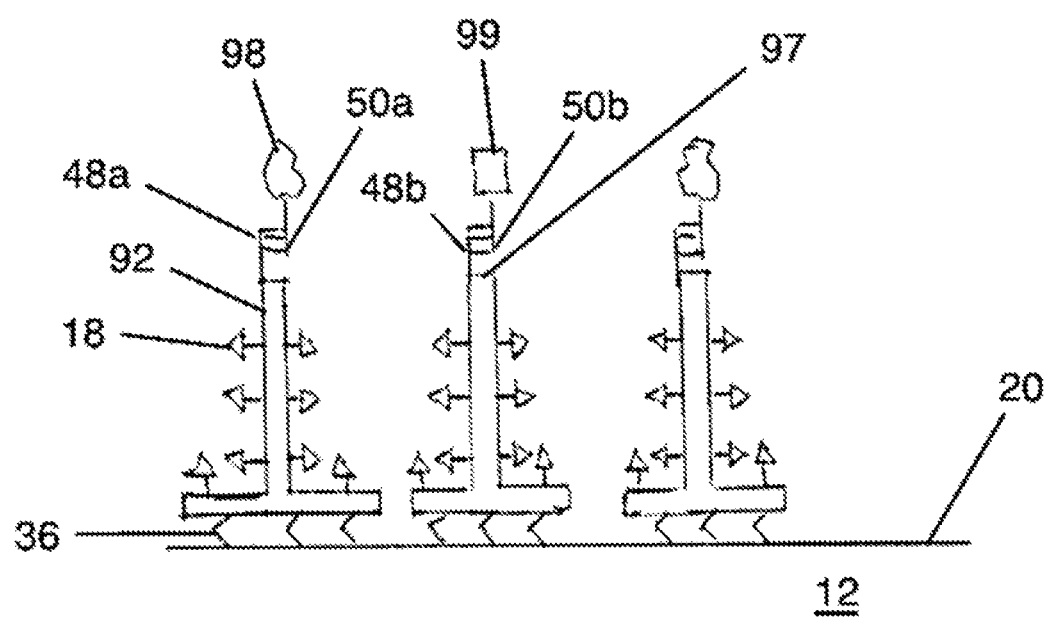
FIG. 31 depicts an exemplary arrangement of binding sites on an active subparticle.
Figure 32:
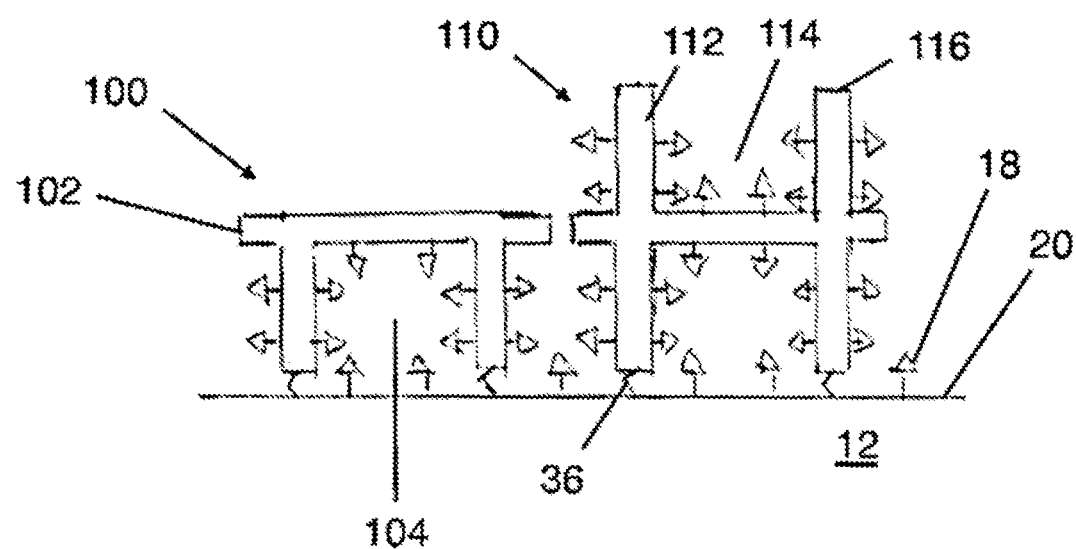
FIG. 32 depicts an exemplary configuration of subparticles.
Figure 33:
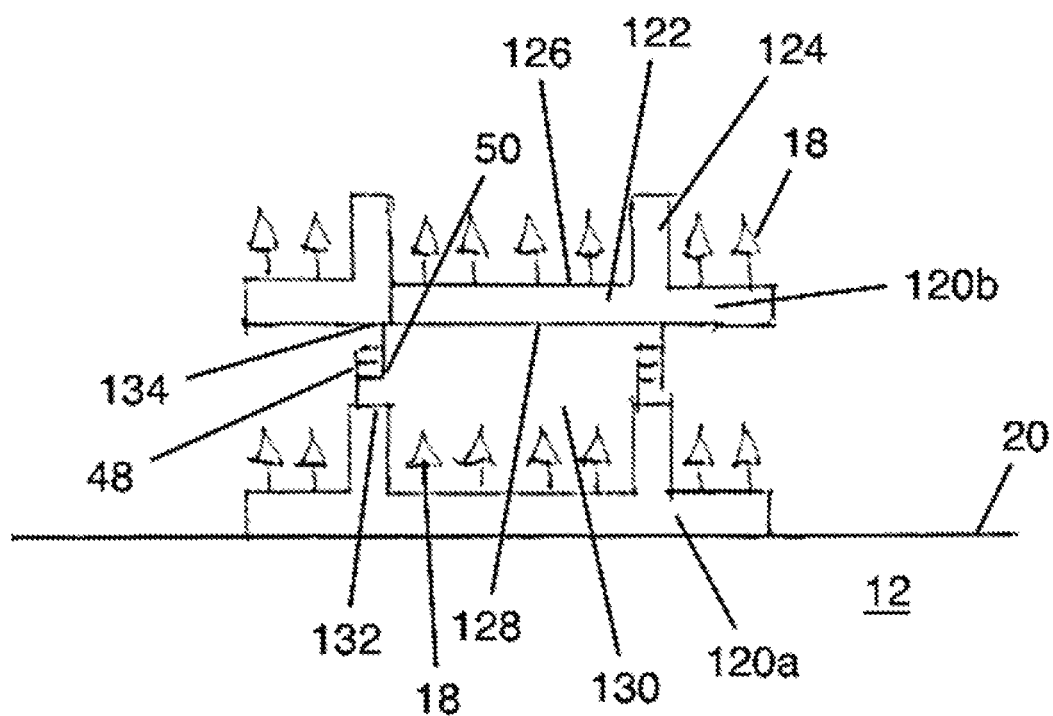
FIG. 33 depicts an exemplary configuration of subparticles.

An X-shaped subparticle 90 as in FIG. 29(*a*) is advantageous as it is stable and provides a large area of surface 64 for a small area of contact with the surface 20. Referring to FIG. 29(*b*) and FIG. 31, a particle may comprise an inverted T shaped subparticle 92 comprising a base 94 and protruding wall 96. This structure has the advantage that the base 94 prevents the faces of the walls 96 from coming into contact when the subparticles are disposed on the surface 20, as shown in FIG. 31. Further moieties 98, 99 may be provided on a selected location on the DNA scaffold 48*a* or 48*b*, for example on the upper edges 97 of the subparticles.

Such subparticles 90 and 92 may form part of particles configured to scavenge an exosome. The X-shaped subparticle 90 may be dimensioned such that an exosome may be received into a capture space between the arms of the X and an agent on the surface 64 may be selected to bind to a biomolecule on the surface of the exosome. Further agent on the surface 20 may also be selected to bind to the same or a different biomolecule on the surface of the exosome. Further subparticles as shown in FIG. 30 may be dimensioned to receive an exosome into a capture space defined between the planar portions of the subparticle. The inverted T-shaped subparticle 92 may have an agent on the surface 96 selected to bind to a biomolecule on the surface of the exosome. Further agent on the surface 20 may also be selected to bind to the same or a different biomolecule on the surface of the exosome.

Referring to FIG. 30, examples are shown of shapes of DNA scaffolds to form part of a subparticle, seen in plan view. The DNA scaffold may be formed from planar portions arranged to form the shape, as shown in FIG. 29 for a X shape in plan. The shapes are examples of shapes that do not stack exactly when in contact. Thus, when a portion of such a subparticle contacts a neighboring subparticle of the same shape, at least a portion of the surface area of both shapes is free of contact. By contrast, a Z shape may nest with other Z shapes such that all sides of each Z in the center of a cluster of Z shapes are in contact with further sides. Each of shapes (a) to (g) will provide free surface area when clustered. An advantageous shape is a hash or pound shape (g) which provides free surface area in at least its center when stacked with some of the outer projections parallel to, and next to, those of a neighboring subparticle.

Referring to FIG. 32, subparticles may have a configuration such as 100 or such as 110, in which the particle contacts the surface 20 of the core particle along an edge, so supporting one or more planar portions 102 of the subparticle. This 'bridge' configuration is advantageous to allow agent 18 to be immobilized on the surface 20 as well as on the surfaces of the subparticles. Subparticle 110 is equivalent to shape (e) in FIG. 30, mounted on two edges, and is advantageous in that it does not stack exactly—spaces 104 and 114 are preserved if a second such shape is immobilized alongside it.

Referring to FIG. 33, a particle comprises a core particle 12 and a plurality of subparticles 120*a* and 120*b* comprising a DNA scaffold, the subparticles comprising a capture agent 18 and being configured to stack to provide a space 130 between them, such that agent provided within the space so formed is inhibited from contacting a biomolecule on the surface of a cell. In this embodiment a subparticle comprises a base portion 122 and a support portion 124 that protrudes from the base. The support portion is typically dimensioned to allow the space 130 to permit indiffusion of soluble biomolecule into the space to bind to the agent. The second layer subparticle 120b may be bound to the first layer subparticle 120a by methods disclosed herein or known to those of skill in the art, for example by nucleotide linkers, shown diagrammatically as 48 and 50, one linker being provided on the upper surface 132 of the support portions and the other at a selected location 134 on the base 128 of the subparticle, at which it is to bind to the support portion—see for example Ke et al. In this embodiment, agent 18 may be provided on the surface 126 between the support portions and/or on the lower surface 128. It will be apparent that more than two layers may be immobilized, or that the subparticles so layered may have a range of shapes. For example, two layers of subparticles such as 110 in FIG. 13 may be layered with appropriate functionalization of the edges 116.

Figure 34A:
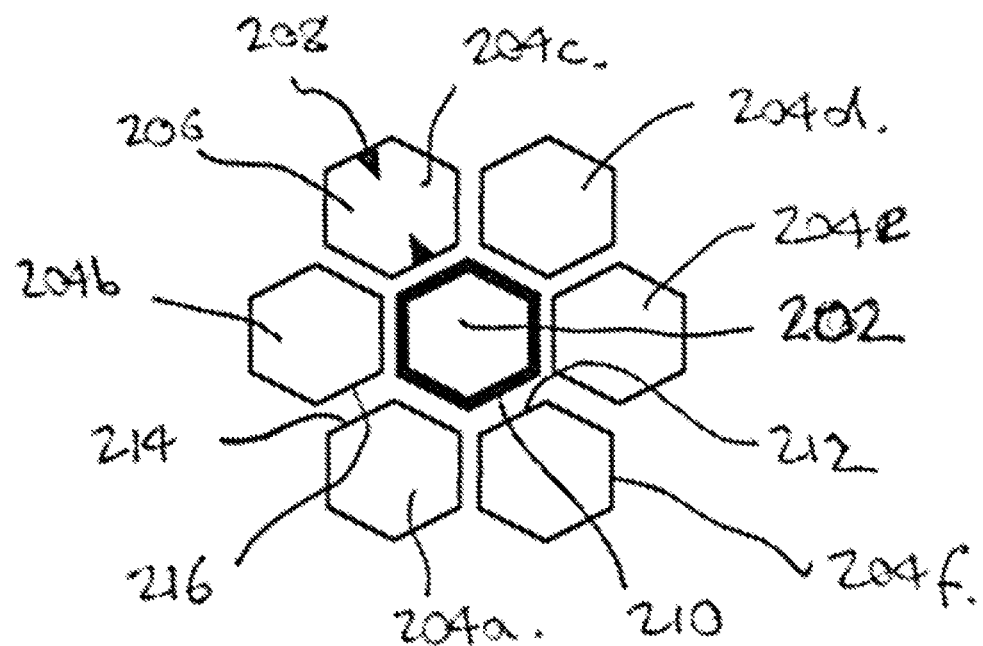
FIG. 34 depicts an exemplary DNA-based configuration of subparticles
Figure 34B:
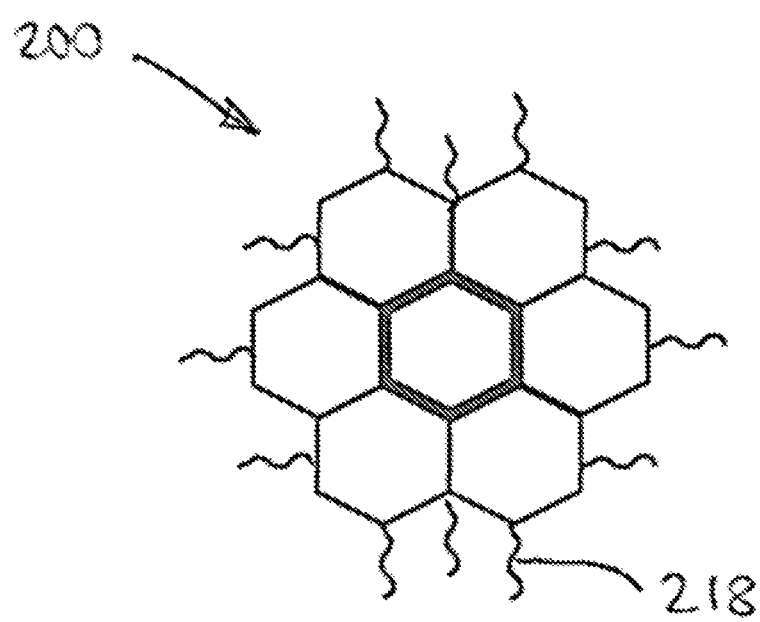

Referring to FIGS. 34A and 34B, a particle 200 comprises a core subparticle 202 and a plurality of subparticles 204 attached to the core particle. Six subparticles are shown attached to the core particle, and each subparticle is a hexagonal tube having an interior space 206 open at the ends, but it will be understood that the core subparticle and attached subparticles may have different shapes and the core may have a different number of subparticles attached to it. One or more, or all, subparticles comprise a capture agent 208 immobilized inside the interior space, or a reactive group at which a capture agent may be immobilized. The core particle may also comprise an open interior space and may comprise a capture agent or reactive group within the interior space.

Examples of hexagonal tubular DNA origami structures that may form part of such an embodiment are shown in Praetorius et al., Nature, 2017, 552 p. 84-87, which is hereby incorporated by reference in its entirety. A person of skill in the art will appreciate that the structures of Praetorius et al. may be constructed to have a large range of dimensions. Those specifically exemplified in Praetorius have an external dimension across the faces of the hexagon of around 20 nm, and a length of around 20 nm. In certain embodiments of the particles disclosed herein, a DNA origami particle may have dimensions as described in section IV herein, Particles comprising at least one tube. In certain embodiments, the internal cross-sectional dimension of the tubular subparticles may be in the range 5-50 nm, such as in the range 10-20 nm, to allow space for a capture agent to be immobilized on the interior wall and for a target to diffuse readily into the tube and, in some embodiments, past a first capture agent to reach a second capture agent located further down the interior of the subparticle.

The outer surfaces 212 of the core particle comprise first reactive groups, such as first DNA strands, to which second reactive groups reactive with the first reactive groups, such as second DNA strands complementary to the first, may bond to couple the subparticles to the core particle. An assembled particle is shown in plan view in FIG. 34B, in which the subparticles are bonded to the core and a coating 218 is coupled to the outer surface of the particle.

VIII. Substantially 2-Dimensional Particles

Figure 6:
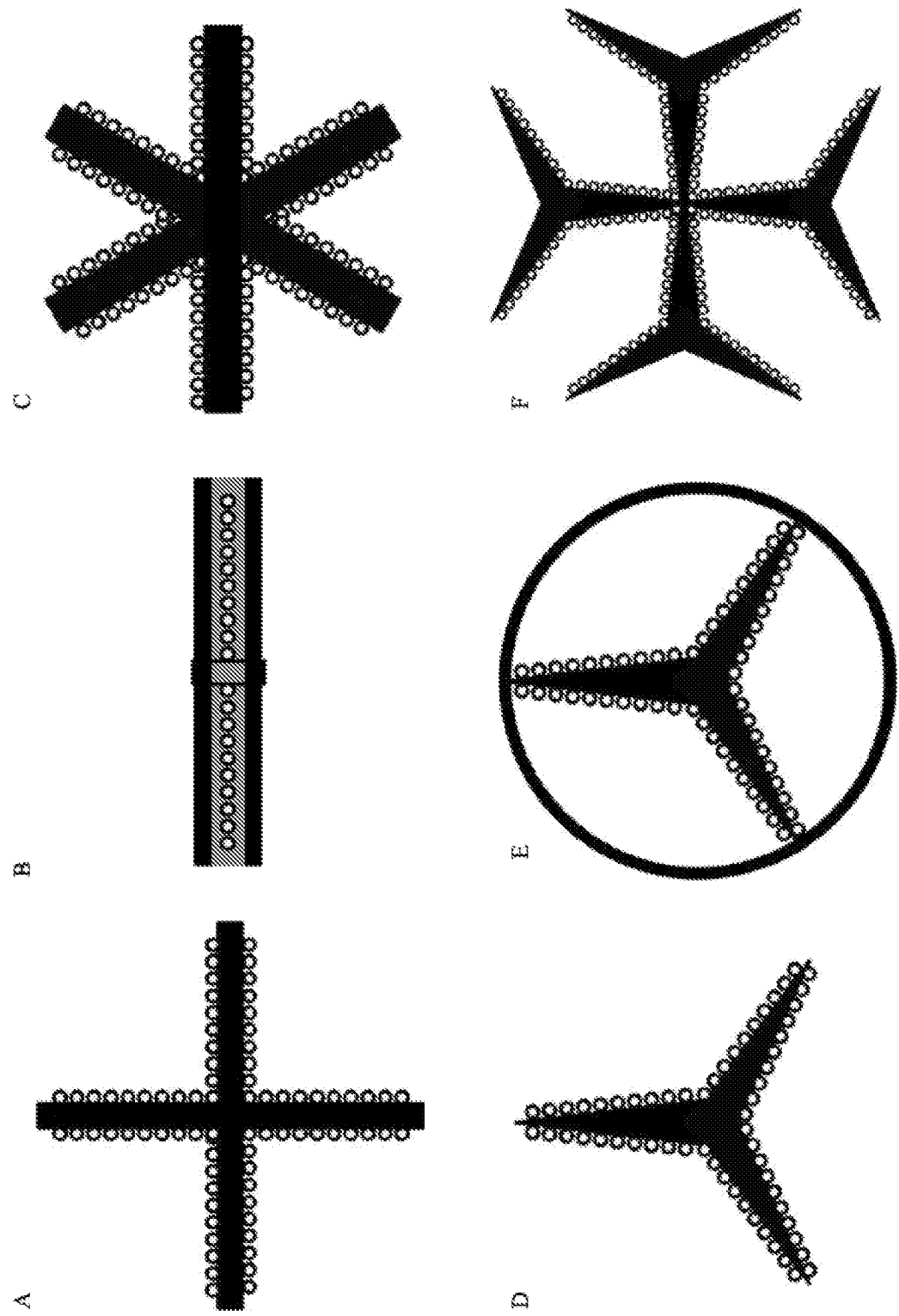
FIG. 6 consists of 6 panels, labeled panels (A), (B), (C), (D), (E), and (F). Each panel depicts a view of a substantially 2-dimensional particle. In each panel, circles depict agent that is immobilized on the surface of the particle. Substantially 2-dimensional particles may comprise "void space," e.g., between the arms of a cross or star. Panel (A) depicts a "top-view" of a particle comprising a cross shape, and panel (B) depicts an orthogonal, "side-view" of the same, cross-shaped particle. The "cross shape" of panel (A) is the "substantially 2-dimensional shape," and the orthogonal, "side-view" is the third dimension, which does not contain the 2-dimensional shape. The "side-view" shows that a substantially 2-dimensional particle may comprise different surfaces, i.e., an "interior surface," on which the agent is immobilized (black), and an "exterior surface" (i.e., "outer surface"), which is substantially free of agent (gray). The different surfaces may comprise different materials, e.g., the particle may be lamellar, or the different surfaces may be prepared, for example, by masking one surface while the other surface is crosslinked to an agent or a coating molecule. Depending on the size of the particle and the nature of the agent and target, a cross shape will inhibit interactions between a bound target (e.g., biomolecule) and other proteins or cells to varying extents. The geometry of a particle may be adjusted, for example, to further inhibit such interactions. Panel (C) depicts a particle comprising a 6-pointed star geometry, which may inhibit interactions between bound target and other proteins or cells to a greater extent than the cross-shaped particle of panel (A). Panel (D) depicts a 3-pointed star, which may only minimally inhibit interactions between bound target and other proteins or cells. Nevertheless, particles comprising a 3-pointed star geometry may be modified to inhibit interactions between bound target and other proteins or cells to a greater extent. For example, panel (E) depicts a particle comprising a 3-pointed star geometry in which a material that is substantially free of agent encircles the particle, and panel (F) depicts a particle comprising a 3-pointed star geometry (i.e., comprising four 3-pointed stars) having outer surfaces that are substantially free of agent.

A particle may be a 2-dimensional shape. For example, a particle may be a circle, ring, cross, fishbone, ellipse, triangle, square, pentagon, hexagon, heptagon, octagon, or star. A particle may be a star and the star may be a concave hexagon, concave octagon, concave decagon, or concave dodecagon. The shape may be a regular shape or an irregular shape. Examples of substantially 2-dimensional particles are shown in FIG. 6.

In some embodiments, a particle comprises a first side, a second side, and an edge. The first side and second side may be substantially the same shape. The first side and second side may comprise a length and a width. The edge may define a height, which is the distance between the first side and the second side. The width and length may be at least 4 times larger than the height, such as 4 to 1000 times larger, 6 to 100 times larger, 8 to 75 times larger, or 10 to 50 times larger than the height. The width and/or length may be 0.2 times to about 20 times larger than the height.

An edge may comprise one or more concave or re-entrant portions. The agent may be bound to the concave or re-entrant portions of the edge. A re-entrant portion is one in which the perimeter of the particle comprises two adjacent perimeter portions at an exterior angle between them of greater than 270 degrees, such as either side of the points of a star. In this way, the capture agent may be shielded from contact with the membrane of a cell in contact with the particle.

In some embodiments, the first side and/or second side are substantially planar. In some embodiments, the first side and/or second side comprise a concave or re-entrant portion.

In some embodiments, the particle is in the form of a substantially flat star, e.g., with re-entrant portions between the points. A star may have 3, 4, 5, 6, 7, 8, 9, 10, 11, 12, 13, 14, 15, 16, or more points. The particle may comprise regular sides or irregular sides.

In some embodiments, the particle is in the form of a cross or fishbone shape, e.g., comprising a backbone with arms extending on each side outwards from the backbone to define re-entrant surface portions between the arms. The arms of a cross or fishbone may further comprise lateral projections.

The re-entrant edges between the points of the star or the arms of the cross or fishbone preferably extend a distance from the line joining the points such that a cell membrane cannot deform between the points so as to come into contact with the edges. For example, the number of points and the angle between them may determine the depth of the re-entrant edge portions between the points.

Particles suitable for use in the invention may be formed by nanofabrication, for example by nanoprinting or nanomoulding. For example, particles may be produced by the PRINT ("Particle Replication In Non-wetting Templates") process (see, e.g., International patent application WO2007/024323; Perry, J. L. et al., Acc Chem Res. 44(10):990-998 (2011), each of which is hereby incorporated by reference). Particles may be produced by photolithography using known methods.

In some embodiments, an agent may be immobilized on the edge of a particle and not immobilized, or immobilized to a lesser extent, on the first and second sides of a particle.

In some embodiments a desirable surface area per particle is in the range 0.2 to 25 $\mu m^2$. The areas of the shielded edge portions of particles able to be fabricated by nanomoulding are therefore in a desirable range.

IX. Agent

In some embodiments, the agent immobilized on the surface of a particle is a small molecule, a macrocycle compound, a polypeptide, a peptidomimetic compound, an aptamer, a nucleic acid, or a nucleic acid analog. "Small molecule" as used herein, is meant to refer to an agent, which has a molecular weight of less than about 6 kDa and most preferably less than about 2.5 kDa. Many pharmaceutical companies have extensive libraries of chemical and/or biological mixtures comprising arrays of small molecules, often fungal, bacterial, or algal extracts, which can be screened with any of the assays of the application. This application contemplates using, among other things, small chemical libraries, peptide libraries, or collections of natural products. Tan et al. described a library with over two million synthetic compounds that is compatible with miniaturized cell-based assays (*J Am Chem Soc* 120:8565-8566(1998)).

Peptidomimetics can be compounds in which at least a portion of a subject polypeptide is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a non-peptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of humans or animals. It should be noted that peptidomimetics may or may not have similar two-dimensional chemical structures, but share common three-dimensional structural features and geometry. Each peptidomimetic may further have one or more unique additional binding elements.

Aptamers are short oligonucleotide sequences that can be used to recognize and specifically bind almost any molecule, including cell surface proteins. The systematic evolution of ligands by exponential enrichment (SELEX) process is powerful and can be used to readily identify such aptamers. Aptamers can be made for a wide range of proteins of importance for therapy and diagnostics, such as growth factors and cell surface antigens. These oligonucleotides bind their targets with similar affinities and specificities as antibodies do (see, e.g., Ulrich (2006) *Handb Exp Pharmacol* 173:305-326).

The agent may be an antibody, or an antigen-binding portion thereof (i.e., an antibody fragment), wherein the antibody, or antigen-binding portion thereof, specifically binds to a target (e.g., a soluble biomolecule). The agent may comprise an antibody, or an antigen-binding portion thereof, wherein the antibody, or antigen-binding portion thereof, specifically binds to a target (e.g., a soluble biomolecule). The term "antibody" refers to whole antibodies including antibodies of different isotypes, such as IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

The term "antibody fragment," "biomolecule-binding fragment," "antigen-binding portion of an antibody" and similar terms refer to a fragment of an antibody that retains the ability to bind to a target antigen. Such fragments include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein (see, e.g., Todorovska et al., *J Immunol Methods* 248(1):47-66 (2001); Hudson and Kortt *J Immunol Methods* 231(1):177-189 (1999); Poljak *Structure* 2(12): 1121-1123 (1994); Rondon and Marasco *Annual Review of Microbiology* 51:257-283 (1997), the disclosures of each of which are incorporated herein by reference in their entirety). Bispecific antibodies (including DVD-Ig antibodies) are also embraced by the term "antibody." Bispecific antibodies are monoclonal, preferably human or humanized, antibodies that have binding specificities for at least two different antigens.

As used in herein, the term "antibody" also includes, e.g., single domain antibodies such as camelized single domain antibodies. See, e.g., Muyldermans et al., *Trends Biochem Sci* 26:230-235(2001); Nuttall et al., *Curr Pharm Biotech* 1:253-263(2000); Reichmann et al., *J Immunol Meth* 231: 25-38(1999); PCT application publication nos. WO 94/04678 and WO 94/25591; and U.S. Pat. Nos. 6,005,079, 6,015,695, and 7,794,981, all of which are incorporated herein by reference in their entireties. In some embodiments, the disclosure provides single domain antibodies comprising two VH domains with modifications such that single domain antibodies are formed.

In some embodiments, the agent is a non-antibody, scaffold protein. These proteins are, generally, obtained through combinatorial chemistry-based adaptation of pre-existing ligand- or antigen-binding proteins. For example, the binding site of human transferrin for human transferrin receptor can be modified using combinatorial chemistry to create a diverse library of transferrin variants, some of which have acquired affinity for different antigens (see Ali et al., *J Biol Chem* 274:24066-24073(1999)). The portion of human transferrin not involved with binding the receptor remains unchanged and serves as a scaffold, like framework regions of antibodies, to present the variant binding sites. The libraries are then screened, as an antibody library is, against a target antigen of interest to identify those variants having optimal selectivity and affinity for the target antigen. Non-antibody scaffold proteins, while similar in function to antibodies, are touted as having a number of advantages as compared to antibodies, which advantages include, among other things, enhanced solubility and tissue penetration, less costly manufacture, and ease of conjugation to other molecules of interest (see Hey et al., *TRENDS Biotechnol* 23(10):514-522(2005)).

One of skill in the art would appreciate that the scaffold portion of the non-antibody scaffold protein can include, e.g., all or part of: the Z domain of *S. aureus* protein A, human transferrin, human tenth fibronectin type III domain, kunitz domain of a human trypsin inhibitor, human CTLA-4, an ankyrin repeat protein, a human lipocalin, human crystallin, human ubiquitin, or a trypsin inhibitor from *E. elaterium* (see Hey et al., *TRENDS Biotechnol* 23(10): 514-522 (2005)).

In some embodiments, the agent is a natural ligand of a target biomolecule. For example, the agent can be a cytokine. As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epidermal keratinocytes and B-lymphocytes. Lymphokines are generally referred to as being produced by lymphocyte cells. Examples of cytokines include, but are not limited to, Interleukin-1 (IL-1), Interleukin-2 (IL-2), Interleukin-6 (IL-6), Interleukin-8 (IL-8), Tumor Necrosis Factor-alpha (TNFα), and Tumor Necrosis Factor beta (TNFβ).

In some embodiments, the agent is a tumor necrosis factor (TNF) family ligand, e.g., the TNF family ligand is selected from TNFα, TNFβ, Fas ligand, lymphotoxin, lymphotoxin alpha, lymphotoxin beta, 4-1BB Ligand, CD30 Ligand, EDA-A1, LIGHT (TNFSF14), TNF-like ligand 1A (TL1A), TNF-related weak inducer of apoptosis (TWEAK), and TNF-related apoptosis-inducing ligand (TRAIL). The agent may be CD40 Ligand, CD27 Ligand, OX40 Ligand, B-cell activating factor (BAFF; TNFSF13B; BLYS), ectodysplasin A (EDA), activation-inducible TNFR family receptor ligand (AITRL), vascular endothelial growth inhibitor (VEGI), a proliferation-inducing ligand (APRIL), or receptor activator of nuclear factor kappa-B ligand (RANKL). In some embodiments, the target is TNFα, TNFβ, Fas ligand, lymphotoxin, lymphotoxin alpha, lymphotoxin beta, 4-1BB Ligand, CD30 Ligand, EDA-A1, LIGHT, TL1A, TWEAK, TRAIL, CD40 Ligand, CD27 Ligand, OX40 Ligand, B-cell activating factor (BAFF; TNFSF13B; BLYS), ectodysplasin A (EDA), activation-inducible TNFR family receptor ligand (AITRL), vascular endothelial growth inhibitor (VEGI), a proliferation-inducing ligand (APRIL), or receptor activator of nuclear factor kappa-B ligand (RANKL).

In some embodiments, the agent is a viral protein, or a portion thereof, which specifically binds to a target (e.g., a soluble form of a membrane protein). In some embodiments, the agent is vTNF, which is a protein capable of specifically-binding TNF that is not encoded by the genome of an organism comprising TNF and TNF receptors. vTNF includes TNF-binding proteins from viruses, such as poxvirus (e.g., Yatapoxvirus, such as Yaba-like disease virus, Tanapox virus, and Yaba monkey tumor virus; Cowpox virus; Myxoma virus; and Mousepox virus) and retrovirus (e.g., Simian foamy virus). For example, vTNF may be Crm B, Crm C, Crm D, or Crm E of the Cowpox virus, M-T2 of the Myxoma virus, S-T2 of the Simian foamy virus, vCD30 of the Cowpox virus, or TPV2L of the Tanapox virus. In some embodiments, the agent is the E6 or E7 of the human papilloma virus, which binds TNFR1, or TRAILR2 ortholog, CAR1 of the Avian sarcoma leukosis virus, which binds to TNFRs.

In some embodiments, the agent is a variant of a natural ligand for a target biomolecule, e.g., a variant interleukin polypeptide, such as variant IL-2 or variant TNFα. Variants, in accordance with some embodiments of the invention, can contain one or more amino acid substitutions, deletions, or insertions. The substitutions can be conservative or non-conservative. As used herein, the term "conservative substitution" refers to the replacement of an amino acid present in the native sequence in a given polypeptide with a naturally or non-naturally occurring amino acid having similar steric properties. Where the side-chain of the native amino acid to be replaced is either polar or hydrophobic, the conservative substitution should be with a naturally occurring amino acid or a non-naturally occurring amino acid that is also polar or hydrophobic, and, optionally, with the same or similar steric properties as the side-chain of the replaced amino acid. Conservative substitutions typically include substitutions within the following groups: glycine and alanine; valine, isoleucine, and leucine; aspartic acid and glutamic acid; asparagine, glutamine, serine, and threonine; lysine, histidine, and arginine; and phenylalanine and tyrosine. One letter amino acid abbreviations are as follows: alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W); tyrosine (Y); and valine (V). Variants also include fragments of the full-length, wild-type natural ligands as well as fragments comprising one or more amino acid substitutions, insertions, or deletions relative to the wild-type, full-length natural ligand from which the fragment was derived.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted.

In some embodiments, a variant polypeptide comprises at least two (e.g., at least three, four, five, six, seven, eight, nine, 10, 15, 20, 25, 30, 35, 40, 45, 50, 55, 60, 65, 70, 75, 80, 85, 90, 95, 100, or more than 100) amino acid substitutions, deletions, or insertions, relative to the wild-type, full-length polypeptide from which it was derived. In some embodiments, a variant polypeptide comprises no more than 150 (e.g., no more than 145, 140, 135, 130, 125, 120, 115, 110, 105, 100, 95, 90, 85, 80, 75, 70, 65, 60, 55, 50, 45, 40, 35, 30, 25, 24, 23, 22, 21, 20, 19, 18, 17, 16, 15, 14, 13, 12, 11, 10, 9, 8, 7, 6, 5, 4, 3, or 2) amino acid substitutions, deletions, or insertions, relative to the wild-type, full-length polypeptide from which it was derived.

In some embodiments, a variant polypeptide (e.g., a variant IL-2 or TNFα polypeptide) retains at least 10 (e.g., at least 15, 20, 25, 30, 35, 40, 45, 50, 55, 60, 65, 70, 75, 80, 85, 90, 95, or 100) % of the ability of the wild-type, full-length polypeptide from which it was derived to bind to the target biomolecule (e.g., the member of the specific binding pair of which the wild-type, full-length polypeptide is a member). In some embodiments, the variant polypeptide will have a greater affinity for the target biomolecule than the wild-type, full-length polypeptide from which the variant was derived. For example, in some embodiments, the variant polypeptide has two (three, four, five, 10, 20, 30, 40, 50, 100, 200, 500, or even 1000) times greater affinity for the target biomolecule than does the wild-type, full-length polypeptide from which the variant polypeptide was derived. Methods for detecting or measuring the interaction between two proteins are known in the art and described above.

In some embodiments, the wild-type, full-length natural ligand modulates the activity of a cell surface receptor. Accordingly, variants of the natural ligands can have enhanced or reduced ability to modulate the activity of the receptor, relative to the activity of the wild-type natural ligand. For example, in some embodiments, a variant polypeptide has less than 90 (e.g., 85, 80, 75, 70, 65, 60, 55, 50, 45, 40, 35, 30, 25, 20, 15, 10, or less than 5) % of the ability of the full-length, wild-type polypeptide from which the variant was derived to activate a cell surface receptor protein. In some embodiments, the variant polypeptide does not activate the receptor to which it binds.

Such exemplary variant polypeptides are known in the art. For example, International Patent Application Publication No. WO 2012/085891 describes TNF family ligand variants having reduced ability to trimerize, and thus a reduced ability to activate TNF family receptors (see also U.S. Patent Application Publication No. U.S. 2014/0096274, hereby incorporated by reference). Yet the variant TNF ligands retain the ability to bind to TNF family receptors. Suitable methods for comparing activity between variant and wild-type natural ligands are known in the art.

In some embodiments, the soluble biomolecule is a ligand for a cell surface receptor, e.g., a cytokine or chemokine (e.g., MCP-1/CCL2, CCL5, CCL11, CCL12, or CCL19), such as any of those known in the art or described herein. In some embodiments, the ligand is a tumor necrosis factor (TNF) family ligand or a variant thereof. In some embodiments, the TNF family ligand is TNFα or a variant thereof. In some embodiments, the TNF family ligand is Fas ligand, lymphotoxin, lymphotoxin alpha, lymphotoxin beta, 4-1BB Ligand, CD30 Ligand, EDA-A1, LIGHT, TL1A, TWEAK, TNFβ, TRAIL, or a variant of any of the foregoing. In some embodiments, the ligand is a TGFβ superfamily ligand or variant thereof, e.g., activin A, activin B, anti-müllerian hormone, growth differentiation factor (e.g., GDF1 or GDF11), a bone morphogenic protein (BMP), inhibin (e.g., inhibin alpha, inhibin beta), lefty, persephin, nodal, neurturin, TGFβ1, TGFβ2, TGFβ3, or myostatin. In some embodiments, the ligand is hormone (e.g., a peptide hormone), such as ghrelin.

In some embodiments, the soluble biomolecule is haptoglobin or beta-2 microglobulin.

In some embodiments, the soluble biomolecule is one identified in Table 2.

TABLE 2

Exemplary Soluble Biomolecules and/or Agents

| First Member of Specific Binding Pair (Soluble Biomolecule or Agent) | Gene Abbrev. | Molecule Class | Associated Disease State | Second member of Specific Binding Pair |
|---|---|---|---|---|
| Tumor Necrosis Factor alpha | TNF | Cytokine | AD, obesity, Type II Diabetes (T2D), Alzheimer's | sTNF-R |
| Soluble Interleukin-2 receptor | IL2RA | Decoy | Cancer | IL-2, daclizumab, basiliximab, inolimomab |
| Ghrelin | GHRL | Hormone | Obesity | Ghrelin receptor (GHSR1); anti-ghrelin autoantibodies |
| Soluble Tumor Necrosis Factor receptor-1 | TNFRSF1A | Decoy | Cancer | rTNF |
| Soluble Tumor Necrosis Factor receptor-2 | TNFRSF1B | Decoy | Cancer | rTNF |
| Transforming Growth Factor beta1 | LTBP1 | Growth Factor | Muscle Degeneration, dis-Differentiation | |
| C-C motif ligand 11, aka: eosinophil chemotactic protein, eotaxin-1 | CCL11 | Cytokine | Decreased Neurogenesis and Cognition | |
| Interleukin-2 | IL2 | Cytokine | AD | sIL-2R, briakinumab |
| Interleukin-6 | IL6 | Cytokine | AD | sIL-6R, olokizumab, sarilumab, siltuximab |
| Interleukin-8 | CXCL8 | Cytokine | AD | IL-8R |
| Interleukin-1A | IL1A | Cytokine | AD | sIL-1RA |
| Interleukin-1B | IL1B | Cytokine | Inflammation, diabetes | canakinumab, gevokizumab |
| C-X-C motif chemokine 10 | CXCL10 | Chemokine | Immune activation | CXCR3, eldelumab |
| Growth Differentiation Factor 8, aka: Myostatin | MSTN | Growth Factor | Sarcopenia | Activin receptor (ActRIIB) |
| Decoy receptor-3 | FAS | Decoy | Cancer | FAS-L |
| Soluble death receptor-4 | TNFRSF10A | Decoy | Cancer | TRAIL-R1 |
| Soluble death receptor-5 | TNFRSF10B | Decoy | Cancer | TRAIL-R2, drozitumab |
| Fas ligand | FASLG | Cytokine | AD | sDcR3 |
| TNF-related apoptosis inducing ligand | TNFSF10 | Cytokine | AD, T2D | sDR4/5 |
| Chemokine (C-X-C Motif) Ligand 1 (Melanoma Growth Stimulating Activity, Alpha) | CXCL1 | Chemokine | Senescence/ Cancer | |
| Amyloid beta | APP | Fragment | Alzheimer's | anti-amyloid beta antibodies, e.g., aducanumab |
| β2 microglobulin | B2M | Protein | Aging | |
| TNF-related weak inducer of apoptosis | TNFSF12 | Cytokine | TBD | sDR3 |
| Matrix Metallopeptidase 1 (Interstitial Collagenase) | MMP1 | Protease | Senescence/ Cancer | |
| Matrix Metallopeptidase 2 (Gelatinase A, 72 kDa Gelatinase, 72 kDa Type IV Collagenase) | MMP2 | Protease | OA/Cancer | |

TABLE 2-continued

Exemplary Soluble Biomolecules and/or Agents

| First Member of Specific Binding Pair (Soluble Biomolecule or Agent) | Gene Abbrev. | Molecule Class | Associated Disease State | Second member of Specific Binding Pair |
|---|---|---|---|---|
| Matrix Metallopeptidase 3 (Stromelysin 1, Progelatinase) | MMP3 | Protease | Senescence/Cancer | |
| Matrix Metallopeptidase 9 (Gelatinase B, 92 kDa Gelatinase, 92 kDa Type IV Collagenase) | MMP9 | Protease | OA/Cancer | |
| Matrix Metallopeptidase 10 (Stromelysin 2) | MMP10 | Protease | Senescence/Cancer | |
| Matrix Metallopeptidase 12 (Macrophage Elastase) | MMP12 | Protease | Senescence/Cancer | |
| Indoleamine 2,3-dioxygenase | IDO1 | Enzyme | Cancer | |
| Neurogenic locus notch homolog protein 1 | NOTCH1 | Cytokine' | Stem cell dysfunction | |
| Neurogenic locus notch homolog protein 2 | NOTCH2 | Cytokine | Stem cell dysfunction | |
| Neurogenic locus notch homolog protein 3 | NOTCH3 | Cytokine | Stem cell dysfunction | |
| Neurogenic locus notch homolog protein 4 | NOTCH4 | Cytokine | Stem cell dysfunction | |
| Interleukin-5 | IL5 | Cytokine | AD | Mepolizumab, reslizumab |
| Soluble Interleukin-5 receptor | IL5RA | Decoy | Cancer | IL-5 |
| Soluble interleukin-6 receptor | IL6R | Decoy | Cancer | IL-6, tocilizumab |
| Soluble interleukin-8 receptor | CXCR1 | Decoy | Cancer | IL-8 |
| Soluble interleukin-1A receptor | IL1R1 | Decoy | Cancer | IL-1A |
| C-Reactive Protein | CRP | Protein | Marker of inflammation | |
| Haptoglobin | HP | Protein | | |
| Fibrinogen Alpha Chain | FGA | Protein | Heart disease | |
| Soluble death receptor-3 | TNFRSF25 | Decoy | | TWEAK |
| CD47 | CD47 | Protein | Cancer | thrombospondin-1; signal-regulatory protein alpha (SIRPα) |

"AD" refers to autoimmune disorders and/or inflammatory disorders.
"OA" refers to osteoarthritis.

In some embodiments, an agent may bind (e.g., specifically bind) to a biomolecule selected from TNFα, TNFβ, a soluble TNF receptor, soluble TNFR-1, soluble TNFR-2, lymphotoxin, lymphotoxin alpha, lymphotoxin beta, 4-1BB Ligand, CD30 Ligand, EDA-A1, LIGHT, TL1A, TWEAK, TRAIL, soluble TRAIL receptor, IL-1, soluble IL-1 receptor, IL-1A, soluble IL-1A receptor, IL-1B, soluble IL-1B receptor, IL-2, soluble IL-2 receptor, IL-5, soluble IL-5 receptor, IL-6, soluble IL-6 receptor, IL-8, IL-10, soluble IL-10 receptor, CXCL1, CXCL8, CXCL9, CXCL10, CX3CL1, FAS ligand, soluble death receptor-3, soluble death receptor-4, soluble death receptor-5, TNF-related weak inducer of apoptosis, MMP1, MMP2, MMP3, MMP9, MMP10, MMP12, CD28, a soluble member of the B7 family, soluble CD80/B7-1, soluble CD86/B7-2, soluble CTLA4, soluble PD-L1, soluble PD-1, soluble Tim3, Tim3L, galectin 3, galectin 9, soluble CEACAM1, soluble LAG3, TGF-β, TGF-β1, TGF-β2, TGF-β3, anti-müllerian hormone, artemin, glial cell-derived neurotrophic factor (GDNF), a bone morphogenic protein (e.g., BMP2, BMP3, BMP3B, BMP4, BMP5, BMP6, BMP7, BMP8A, BMP8B, BMP10, BMP 11, BMP 12, BMP13, BMP15), a growth differentiation factor (e.g., GDF1, GDF2, GDF3, GDF3A, GDF5, GDF6, GDF7, GDF8, GDF9, GDF10, GDF11, GDF15), inhibin alpha, inhibin beta (e.g., inhibin beta A, B, C, E), lefty, nodal, neurturin, persephin, myostatin, ghrelin, sLR11, CCL2, CCL5, CCL11, CCL12, CCL19, interferon alpha, interferon beta, interferon gamma, clusterin, VEGF-A, granulocyte colony-stimulating factor (G-CSF), granulocyte-macrophage colony-stimulating factor (GM-CSF), prostaglandin E2, hepatocyte growth factor, nerve growth factor, sclerostin, complement C5, angiopoietin 2, angiopoietin 3, PCSK9, amyloid beta, activin, activin A, activin B, β2 microglobulin, soluble NOTCH1, soluble NOTCH2, soluble NOTCH3, soluble NOTCH4, soluble Jagged1, soluble Jagged2, soluble DLL1, soluble DLL3, soluble DLL4, haptoglobin, fibrinogen alpha chain, corticotropin releasing factor, corticotropin releasing factor type 1, corticotropin releasing factor type 2, urocortin 1, urocortin 2, urocortin 3, CD47, an anti-interferon γ autoantibody, an anti-interleukin 6 autoantibody, an anti-interleukin 17 autoantibody, an anti-ghrelin autoantibody, wnt, indoleamine 2,3-dioxygenase, C-reactive protein, HIV-1 gp120, endotoxin, ricin toxin, epsilon toxin of *Clostridium perfringens, Staphylococcus* enterotoxin B, and botulinum toxin.

In some embodiments, the agent may comprise an antibody (or an antigen-binding portion thereof) that specifically binds to TNFα, TNFβ, a soluble TNF receptor, soluble TNFR-1, soluble TNFR-2, lymphotoxin, lymphotoxin alpha, lymphotoxin beta, 4-1BB Ligand, CD30 Ligand, EDA-A1, LIGHT, TL1A, TWEAK, TRAIL, soluble TRAIL receptor, IL-1, soluble IL-1 receptor, IL-1A, soluble IL-1A receptor, IL-1B, soluble IL-1B receptor, IL-2, soluble IL-2 receptor, IL-5, soluble IL-5 receptor, IL-6, soluble IL-6 receptor, IL-8, IL-10, soluble IL-10 receptor, CXCL1, CXCL8, CXCL9, CXCL10, CX3CL1, FAS ligand, soluble death receptor-3, soluble death receptor-4, soluble death receptor-5, TNF-related weak inducer of apoptosis, MMP1, MMP2, MMP3, MMP9, MMP10, MMP12, CD28, a soluble member of the B7 family, soluble CD80/B7-1, soluble CD86/B7-2, soluble CTLA4, soluble PD-L1, soluble PD-1, soluble Tim3, Tim3L, galectin 3, galectin 9, soluble CEACAM1, soluble LAG3, TGF-β, TGF-β1, TGF-β2, TGF-β3, anti-müllerian hormone, artemin, glial cell-derived neurotrophic factor (GDNF), a bone morphogenic protein (e.g., BMP2, BMP3, BMP3B, BMP4, BMP5, BMP6, BMP7, BMP8A, BMP8B, BMP10, BMP 11, BMP 12, BMP13, BMP15), a growth differentiation factor (e.g., GDF1, GDF2, GDF3, GDF3A, GDF5, GDF6, GDF7, GDF8, GDF9, GDF10, GDF11, GDF15), inhibin alpha, inhibin beta (e.g., inhibin beta A, B, C, E), lefty, nodal, neurturin, persephin, myostatin, ghrelin, sLR11, CCL2, CCL5, CCL11, CCL12, CCL19, interferon alpha, interferon beta, interferon gamma, clusterin, VEGF-A, granulocyte colony-stimulating factor (G-CSF), granulocyte-macrophage colony-stimulating factor (GM-CSF), prostaglandin E2, hepatocyte growth factor, nerve growth factor, sclerostin, complement C5, angiopoietin 2, angiopoietin 3, PCSK9, amyloid beta, activin, activin A, activin B, (β2 microglobulin, soluble NOTCH1, soluble NOTCH2, soluble NOTCH3, soluble NOTCH4, soluble Jagged1, soluble Jagged2, soluble DLL1, soluble DLL3, soluble DLL4, haptoglobin, fibrinogen alpha chain, corticotropin releasing factor, corticotropin releasing factor type 1, corticotropin releasing factor type 2, urocortin 1, urocortin 2, urocortin 3, CD47, an anti-interferon γ autoantibody, an anti-interleukin 6 autoantibody, an anti-interleukin 17 autoantibody, an anti-ghrelin autoantibody, wnt, indoleamine 2,3-dioxygenase, C-reactive protein, HIV-1 gp120, endotoxin, ricin toxin, epsilon toxin of *Clostridium perfringens, Staphylococcus* enterotoxin B, or botulinum toxin.

The agent may comprise ipilimumab, pembrolizumab, nivolumab, infliximab, adalimumab, certolizumab (e.g., certolizumab pegol), golimumab, etanercept, stamulumab, fresolimumab, metelimumab, demcizumab, tarextumab, brontictuzumab, mepolizumab, urelumab, canakinumab, daclizumab, belimumab, denosumab, eculizumab, tocilizumab, atlizumab, ustekinumab, palivizumab, aducanumab, bevacizumab, brolucizumab, ranibizumab, aflibercept, actoxumab, elsilimomab, siltuximab, afelimomab, nerelimomab, ozoralizumab, pateclizumab, sirukumab, omalizumab, aducanumab, bapineuzumab, crenezumab, gantenerumab, ponezumab, solanezumab, dapirolizumab, ruplizumab, toralizumab, enoticumab, alacizumab, cetuximab, futuximab, icrucumab, imgatuzumab, matuzumab, necitumumab, nimotuzumab, panitumumab, ramucirumab, zalutumumab, duligotumab, patritumab, ertumaxomab, pertuzumab, trastuzumab, alirocumab, anrukinzumab, diridavumab, drozitumab, dupilumab, dusigitumab, eculizumab, edobacomab, efungumab, eldelumab, enoblituzumab, enokizumab, evinacumab, evolocumab, exbivirumab, exbivirumab, fasinumab, felvizumab, fezakinumab, ficlatuzumab, firivumab, fletikumab, foralumab, foravirumab, fulranumab, faliximab, ganitumab, gevokizumab, fuselkumab, idarucizumab, imalumab, inolimomab, iratumumab, ixekizumab, lampalizumab, lebrikizumab, lenzilumab, lerdelimumab, lexatumumab, libivirumab, ligelizumab, lodelcizumab, lulizumab, mapatumumab, motavizumab, namilumab, nebacumab, nesvacumab, obiltoxaximab, olokizumab, orticumab, pagibaximab, palivizumab, panobacumab, pascolizumab, perakizumab, pidilizumab, pexelizumab, pritoxaximab, quilizumab, radretumab, rafivirumab, ralpancizumab, raxibacumab, regavirumab, reslizumab, rilotumumab, romosozumab, rontalizumab, sarilumab, secukinumab, setoxaximab, sevirumab, sifalimumab, siltuximab, suvizumab, tabalumab, tacatuzumab, talizumab, tanezumab, tefibazumab, TGN1412, tildrakizumab, tigatuzumab, TNX-650, tosatoxumab, tralokinumab, tremelimumab, trevogrumab, tuvirumab, urtoxazumab, vantictumab, vanucizumab, or an antigen binding portion of any one of the foregoing.

In some embodiments, the agent comprises TNFα, TNFβ, a soluble TNF receptor, soluble TNFR-1, soluble TNFR-2, vTNF, lymphotoxin, lymphotoxin alpha, lymphotoxin beta, 4-1BB Ligand, CD30 Ligand, EDA-A1, LIGHT, TL1A, TWEAK, TRAIL, soluble TRAIL receptor, IL-1, soluble IL-1 receptor, IL-1A, soluble IL-1A receptor, IL-1B, soluble IL-1B receptor, IL-2, soluble IL-2 receptor, IL-5, soluble IL-5 receptor, IL-6, soluble IL-6 receptor, IL-8, IL-10, soluble IL-10 receptor, CXCL1, CXCL8, CXCL9, CXCL10, CX3CL1, FAS ligand, soluble death receptor-3, soluble death receptor-4, soluble death receptor-5, TNF-related weak inducer of apoptosis, MMP1, MMP2, MMP3, MMP9, MMP10, MMP12, CD28, a soluble member of the B7 family, soluble CD80/B7-1, soluble CD86/B7-2, soluble CTLA4, soluble PD-L1, soluble PD-1, soluble Tim3, Tim3L, galectin 3, galectin 9, soluble CEACAM1, soluble LAG3, TGF-β, TGF-β1, TGF-β2, TGF-β3, sLR11, CCL2, CCL5, CCL11, CCL12, CCL19, activin, activin A, activin B, soluble NOTCH1, soluble NOTCH2, soluble NOTCH3, soluble NOTCH4, soluble Jagged1, soluble Jagged2, soluble DLL1, soluble DLL3, soluble DLL4, or haptoglobin.

In some embodiments, each particle comprises a plurality of agents. The plurality of agents may comprise 10 to about $10^9$ copies of the agent, such as about $10^3$ to about $10^7$ copies of the agent or about $10^4$ to about $10^6$ copies of the agent.

X. Methods for Producing an Antibody

As noted above, in some embodiments the agents immobilized on the surface of the particle or particles is an antibody or antigen-binding fragment thereof. Antibodies may be elicited by methods known in the art. For example, a mammal, such as a mouse, a hamster or rabbit, may be immunized with an immunogenic form of a biomolecule (e.g., a soluble TNFR, a toxin, or a viral protein). Alternatively, immunization may occur by using a nucleic acid, which in vivo expresses a biomolecule (e.g., a soluble protein) giving rise to the immunogenic response observed. Techniques for conferring immunogenicity on a protein or peptide include conjugation to carriers or other techniques well known in the art. For instance, a peptidyl portion of a polypeptide of the invention may be administered in the presence of adjuvant. The progress of immunization may be monitored by the detection of antibody titers in plasma or serum. Standard ELISA or other immunoassays may be used with the immunogen as antigen to assess the concentrations of antibodies.

Following immunization, antisera reactive with a polypeptide of the invention may be obtained and, if desired, polyclonal antibodies isolated from the serum. To produce monoclonal antibodies, antibody producing cells (lymphocytes) may be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), as the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with the polypeptides of the invention and the monoclonal antibodies isolated.

XI. Immobilizing an Agent on a Particle

An agent may be immobilized on a surface of a particle by a covalent bond or a non-covalent bond, such as by ionic bond, hydrogen bond, hydrophobic bond, coordination, adhesive, or physical absorption or interaction A particle may comprise a reactive group, e.g., for immobilizing an agent. The particle may comprise about 10 to about $10^9$ reactive groups, such as about $10^2$ to about $10^8$ reactive groups, about $10^3$ to about $10^7$ reactive groups, or about $10^4$ to about $10^6$ reactive groups. A particle may comprise a plurality of reactive groups. For example, the plurality of reactive groups may comprise about 10 to about $10^9$ reactive groups, such as about $10^2$ to about $10^8$ reactive groups, about $10^3$ to about $10^7$ reactive groups, or about $10^4$ to about $10^6$ reactive groups.

Methods for adding reactive groups to various different types of particles are known (see, e.g., Xu, Z. et al. J Nanoparticle Research 17:56 (2015); Yu, M. K. et al. Theranostics 2(1):3 (2012); Sanz, V. et al. J Nanoparticle Research 14:917 (2012); Jokerst, J. V. et al. Nanomedicine 6(4):715 (2011); Guan, B. et al. Langmuir 27(1):328 (2011); Cheng, K. et al. ACS Applied Materials & Interfaces 2(9):2489 (2010); Godin, B. et al. J Biomed Mater Res A 94(4):1236 (2010); Cauda, V. et al. J. Am. Chem. Sco. 131(32):11361 (2009); Kecht, J. et al. Chemistry of Materials 20(23):7207 (2008); Boisselier, E. et al. Chemical Communications 30(44):5788 (2008); Sun, X.-L. et al. Bioconjugate Chemistry 17(1):52 (2006), each of which is hereby incorporated by reference in its entirety).

Figure 7:
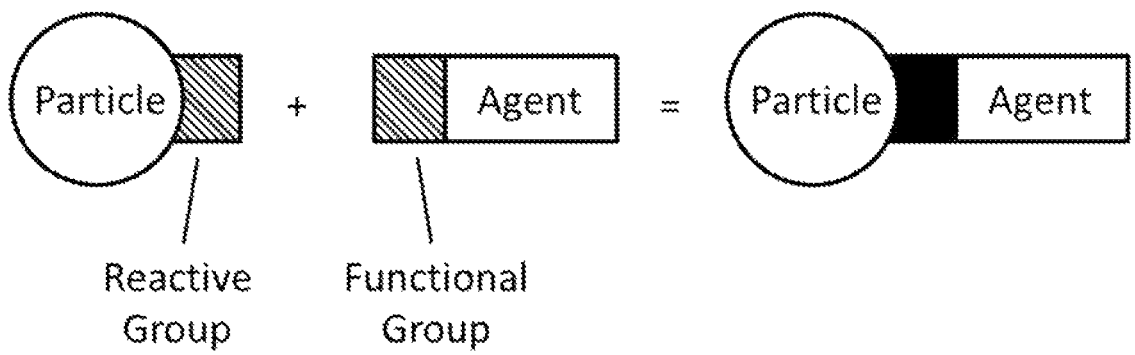
FIG. 7 depicts a particle comprising a reactive group and an agent comprising a functional group. Combining the particle and agent may thus form a covalent or non-covalent bond between the reactive group and functional group, depending on the nature of each group.

Each reactive group may selectively react with a predetermined functional group. In some embodiments, a reactive group can form a bond with an agent, as described herein, which may comprise (e.g., by coupling via a linker) a functional group capable of reacting, preferably selectively reacting, with the reactive groups (FIG. 7). In some embodiments, an agent, as described herein, can form a bond with a reactive group. In some embodiments, each reactive group of the plurality of reactive groups can form a bond with an agent, as described herein. In some embodiments, each agent of a plurality of agents can form a bond with a reactive group. The bond may be a covalent bond or a non-covalent bond. Examples of non-covalent bonds include the base pairing of complementary nucleotides in a nucleotide sequence (e.g., when the reactive group comprises a nucleic acid) inclusion complexes (e.g., between a cyclodextrin ring and a non-polar moiety), and biotin complexes (e.g., with avidin, streptavidin, neutravidin, and monomeric forms of the foregoing). A particle may comprise a plurality of agents (which may be the same or different) coupled to the particle through the reactive groups, e.g., wherein each agent is linked, directly or indirectly, to a reactive group.

In some aspects, the invention relates to a method of making a particle as described herein, comprising incubating an unloaded particle (e.g., a particle comprising one or more reactive groups) with an agent of the invention (e.g., coupled, if necessary, to a functional group capable of reacting with the reactive groups), thereby forming a bond between the particle (e.g., a reactive group of the particle) and the agent. In some embodiments, the method comprises incubating an unloaded particle (e.g., a particle comprising a plurality of reactive groups) with a plurality of agents, which may be the same or different, thereby forming bonds between the particle (e.g., a population of reactive groups of the particle) and a population of agents.

A particle may comprise a linker, e.g., for linking an agent to a reactive group. The particle may comprise about 10 to about $10^9$ linkers, such as about $10^2$ to about $10^8$ linkers, about $10^3$ to about $10^7$ linkers, or about $10^4$ to about $10^6$ linkers. A particle may comprise a plurality of linkers. For example, the plurality of linkers may comprise about 10 to about $10^9$ linkers, such as about $10^2$ to about $10^8$ linkers, about $10^3$ to about $10^7$ linkers, or about $10^4$ to about $10^6$ linkers.

In some embodiments, a reactive group and/or agent of the invention can form a bond with a linker. In some embodiments, a linker can form a bond with a reactive group and/or agent. In some embodiments, each reactive group of the plurality of reactive groups can form a bond with a linker. In some embodiments, each agent of the plurality of agents can form a bond with a linker. In some embodiments, each linker of the plurality of linkers can form a bond with a reactive group. In some embodiments, each linker of the plurality of linkers can form a bond with an agent. The bond may be a covalent bond or a non-covalent bond. In some embodiments, the particle comprises a linker. The linker may be bound to a reactive group. In some embodiments, a particle comprises a plurality of linkers. For example, a particle may comprise a plurality of reactive groups and a plurality of linkers, e.g., wherein each linker of the plurality of linkers is bound to a reactive group of the plurality of reactive groups. A particle may comprise a plurality or reactive groups, a plurality of linkers, and a plurality of agents, e.g., wherein each agent is bound to a linker and/or each linker is bound to a reactive group.

A linker may comprise a functional group. In some embodiments, a reactive group and/or agent of the invention can form a bond with a functional group. In some embodiments, a functional group can form a bond with a reactive group, e.g., to form an amide or ester when a carboxylate and amine or alcohol react, or an amine or thioether when an amine or thiol reacts with a maleimide or other Michael acceptor. In some embodiments, each reactive group of the plurality of reactive groups can form a bond with a functional group. In some embodiments, each functional group of the plurality of functional groups can form a bond with a reactive group. The bond may be a covalent bond or a non-covalent bond. In some embodiments, the particle comprises a functional group. The functional group may be bound to a reactive group, e.g., presenting as an amide, ester, amine, thioether, or other product of the reaction of a functional group and a reactive group. In some embodiments, a particle comprises a plurality of functional groups. For example, a particle may comprise a plurality of reactive groups and a plurality of functional groups, e.g., wherein each functional group of the plurality of functional groups is bound to a reactive group of the plurality of reactive groups, e.g., presenting as an amide, ester, amine, thioether, or other product of the reaction of a functional group and a reactive group. A particle may comprise a plurality of reactive groups, a plurality of functional groups, and a plurality of agents, e.g., wherein each agent is bound to a functional group and/or each functional group is bound to a reactive group. Of course, it is not necessary that each reactive group of the particle be coupled to a functional group/agent, so long as a plurality of these reactive groups are coupled to functional groups/agents to impart the desired functionality to the particle.

A linker may comprise a first functional group and a second functional group. The first functional group may be capable of selectively reacting with an agent bearing a predetermined moiety capable of reacting with the first functional group. The second functional group may be capable of selectively reacting with the reactive groups of the particles. The first functional group and/or the second functional group may be, for example, an alkene, alkyl halide, alkyne, amine, aryl azide, aryl halides, azide, carbodiimide, carboxyl, diene, dienophile, glyoxal, haloacyl, imidoester, isocyanide, maleimide, N-hydroxysuccinimidyl (NHS) ester, phosphine, tetrazine, thiol, or nucleic acid.

A linker may be, for example, succinimidyl 4-(N-maleimidomethyl)cyclohexane-1-carboxylate (SMCC), sulfosuccinimidyl 4-(N-maleimidomethyl)cyclohexane-1-carboxylate (sulfo-SMCC), poly(ethylene glycol) (N-hydroxysuccinimide 5-pentanoate) ether N'-(3-maleimidopropionyl)aminoethane (NHS-PEG-MAL), succinimidyl 3-(2-pyridyldithio)propionate) (SPDP), or succinimidyl iodoacetate (SIA) (see, e.g., Yu, M. K. et al. Theranostics 2(1):3 (2012)).

A linker may comprise a first functional group and a second functional group, wherein either the first functional group is an amine and the second functional group is a carboxylic acid, or the first functional group is a carboxylic acid and the second functional group is an amine. A particle may comprise a plurality of functional groups, wherein the functional groups are primary amine groups.

The particle may be a silica particle, or a particle comprising a silica surface (e.g., a silicon particle having an oxidized surface or a particle having a non-silica core and a silica outer layer). The particle may comprise a gold surface (e.g., the particle may be a gold particle or have a gold surface coating a core comprising a different material). The particle may comprise a polymer surface (e.g., the particle may be a polymer particle or have a polymer surface coating a core comprising a different material). A surface of a coated particle may be a continuous surface (e.g., covering substantially all of a surface of a particle), or a discontinuous surface (e.g., covering a portion or portions of a surface of a particle).

Each reactive group of the particle may be the gold, which may bind, for example, a thiol functional group. A linker or agent may therefore comprise a thiol. In some embodiments, a linker comprises a thiol (e.g., wherein the thiol is a functional group) and a carboxylic acid. A particle may comprise an amine reactive group (e.g., a plurality of amine reactive groups). For example, a particle may be a silica particle or comprise a silica surface, and the particle may comprise a plurality of reactive groups, wherein each reactive group of the plurality of reactive groups is an amine. A particle may be a polymer particle or comprise a polymer surface, and the particle may comprise a plurality of reactive groups, wherein each reactive group of the plurality of reactive groups is an amine.

A reactive group may comprise an aromatic hydrazine (e.g., 6-hydrazino-nicotinic acid) and a functional group may comprise an aromatic aldehyde (e.g., 4-formylbenzoate), or a reactive group may comprise an aromatic aldehyde (e.g., 4-formylbenzoate) and a functional group may comprise an aromatic hydrazine (e.g., 6-hydrazino-nicotinic acid), for example, thereby allowing the reactive group to bind the functional group in the presence of aniline (see, e.g., U.S. 2014/0302001, hereby incorporated by reference in its entirety, and http://www.solulink.com/solulink-technology).

A particle may comprise a plurality of reactive groups, wherein each reactive group comprises a carboxylic acid. A functional group may comprise an amine. A reactive group may be cross-linked to a functional group, for example, using a carbodiimide (e.g., 1-ethyl-3-(3-dimethylaminopropyl)carbodiimide, dicyclohexylcarbodiimide, diisopropylcarbodiimide), optionally using a triazole (e.g., 1-hydroxy-benzotriazole, 1-hydroxy-7-aza-benzotriazole) or an N-hydroxysuccinimidyl ester (e.g., N-hydroxysuccinimide).

A particle may comprise a gold or a gold surface (e.g., overlaying silica). The reactive group or plurality of reactive groups may be gold and the functional group or plurality of functional groups may be thiols (e.g., the functional group of a linker or agent may be a thiol). For example, the agent may comprise a cysteine, e.g., wherein the functional group is a thiol of a cysteine.

A particle may comprise a plurality of reactive groups, wherein each reactive group comprises a maleimide. A functional group may comprise a thiol (e.g., a functional group of a linker or an agent), thereby allowing the functional group to bind a maleimide of the particle. For example, the agent may comprise a cysteine, e.g., wherein the functional group is a thiol of a cysteine.

A particle may comprise a plurality of reactive groups, wherein each reactive group comprises a thiol. A functional group may comprise a maleimide (e.g., a functional group of a linker or an agent), thereby allowing the functional group to bind a thiol of the particle.

A particle may comprise a first linker and a second linker, e.g., wherein the first linker is for linking a first agent to a reactive group and the second linker is for linking a second agent to a reactive group. A particle may comprise a first plurality of linkers and a second plurality of linkers. The first plurality of linkers and/or second plurality of linkers may comprise about 10 to about $10^9$ linkers, such as about $10^2$ to about $10^8$ linkers, about $10^3$ to about $10^7$ linkers, or about $10^4$ to about $10^6$ linkers.

A particle may comprise a first reactive group and a second reactive group, e.g., wherein the first reactive group is for binding a first functional group and the second reactive group is for binding a second functional group. A particle may comprise a first plurality of reactive groups and a second plurality of reactive groups. The first plurality of reactive groups and/or second plurality of reactive groups may comprise about 10 to about $10^9$ reactive groups, such as about $10^2$ to about $10^8$ reactive groups, about $10^3$ to about $10^7$ reactive groups, or about $10^4$ to about $10^6$ reactive groups. A first reactive group (or plurality of reactive groups) may be for linking an agent to the particle, for example, by binding a functional group of either the agent or a linker to the reactive group. A second reactive group (or plurality of reactive groups) may be for linking a second agent to the particle, for example, by binding either the second agent or a functional group of a linker (e.g., second linker) that may be used to link the second agent to the particle.

The first reactive group may be different from the second reactive group, e.g., such that the first reactive group may bind a first functional group and the second reactive group may bind a second functional group that is different from the first functional group. In some embodiments, the first reactive group is related to the second reactive group, e.g., such that the first reactive group and second reactive group bind the same functional group. When the first reactive group and second reactive group bind the same functional group, at least one of the first reactive group and second reactive group may be bound to a protecting group. In this embodiment, the first reactive group may be coupled to a functional group of a first agent or linker for binding the agent, for example, the second reactive group may be deprotected, and then the second reactive group may be coupled to a second agent.

Protecting groups are well known (Greene, T. W. and P. G. M. Wuts, PROTECTIVE GROUPS IN ORGANIC SYNTHESIS, 3rd edition, John Wiley & Sons, New York (1999), hereby incorporated by reference in its entirety) and exemplary groups are summarized below.

Amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl 1-2,2-dibromoethyl carbamate (DB-BOC), 1,1-dimethyl-2,2,2-trichloroethyl carbamate (TCBOC), 1-methyl-1-(4-biphenyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N1N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, hydroxypiperidinyl carbamate, alkyldithio carbamate, benzyl carbamate (Cbz), methoxybenzyl carbamate (Moz), p-nitobenzyl carbamate, bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 2-triphenylphosphonoisopropyl carbamate (Ppoc), 1,1-dimethyl-2-cyanoethyl carbamate, m-chloro-p-acyloxybenzyl carbamate, (dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N-phenylaminothiocarbonyl derivative, t-amyl carbamate, S-benzyl thiocarbamate, cyanobenzyl carbamate, cyclobutyl carbamate, cyclohexyl carbamate, cyclopentyl carbamate, cyclopropylmethyl carbamate, decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, (phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N'-oxide, N-1,1-dimethylthiomethyleneamine, N-benzylideneamine, N-methoxybenzylideneamine, N-diphenylmethyleneamine, N-[(2-pyridyl)mesityl]methyleneamine, N-(N',N-dimethylaminomethylene) amine, N,N-isopropylidenediamine, nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl] amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrob enzenesulfenamide, pentachlorobenzenesulfenamide, 2-nitro-4-methoxybenzenesulfenamide, triphenylmethylsulfenamide, 3-nitropyridinesulfenamide (Npys), toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzyl sulfonamide, trifluoromethylsulfonamide, and phenacylsulfonamide.

Carboxylic acid protecting groups include silyl-, alkyl-, alkenyl-, aryl-, and arylalkyl-protected carboxylic acids.

Silyl protecting groups include trimethylsilyl, triethylsilyl, t-butyldimethylsilyl, t-butyldiphenylsilyl, triisopropylsilyl, and the like.

Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, benzyl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, chlorophenyl, p-methoxyphenyl, 2,4-dinitrophenyl, benzyl, methoxybenzyl, 3,4-dimethoxybenzyl, o-nitrobenzyl, nitrobenzyl, p-halobenzyl, 2,6-dichlorobenzyl, cyanobenzyl, phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (DMIPS), diethylisopropylsilyl (DEIPS), dimethylthexylsilyl, t-butyldimethylsilyl (TBS), t-butyldimethylsilyl (TBDMS), t-butyldiphenylsilyl (TBDPS), tribenzylsilyl, tri-xylylsilyl, triphenylsilyl, diphenylmethylsilyl (DPMS), t-butylmethoxyphenylsilyl (TBMPS), formate, benzoylformate, proprionate, acetate, chloroacetate, dichloroacetate, trichloroacetate, trifluoroacetate, methoxyacetate, triphenylmethoxyacetate, phenoxyacetate, chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate, alkyl allyl carbonate, alkyl-nitrophenyl carbonate, alkyl benzyl carbonate, alkyl methoxybenzyl carbonate, alkyl 3,4-dimethoxy benzyl carbonate, alkyl o-nitrobenzyl carbonate, alkyl nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzene sulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

1,2- or 1,3-diol protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxy benzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(M,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Thiol protecting groups include thioesters, carbonates, sulfonates, allyl thioethers, thioethers, silyl thioethers, alkyl thioethers, arylalkyl thioethers, and alkyloxyalkyl thioethers.

Ester protecting groups include formates, acetates, propionates, pentanoates, crotonates, benzoates, formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxycrotonate, benzoate, p-benylbenzoate, 2,4,6-trimethylbenzoate. Carbonate ester protecting groups include 9-fluorenylmethyl, ethyl, 2,2,2-trichloroethyl, 2-(trimethylsilyl)ethyl, 2-(phenyl sulfonyl)ethyl, vinyl, allyl, and p-nitrobenzyl carbonate. Silyl ester protecting groups include trimethylsilyl, triethylsilyl, t-butyldimethylsilyl, t-butyldiphenylsilyl, triisopropylsilyl ether, and other trialkylsilyl ethers. Alkyl ester protecting groups include methyl, benzyl, p-methoxybenzyl, 3,4-dimethoxybenzyl, trityl, t-butyl, and allyl ether, and derivatives thereof. Arylalkyl ester protecting groups include benzyl, p-methoxybenzyl (PMB), 3,4-dimethoxybenzyl, o-nitrobenzyl, p-nitrobenzyl, p-halobenzyl, 2,6-dichlorobenzyl, p-cyanobenzyl, 2- and 4-picolyl ethers.

Figure 8:
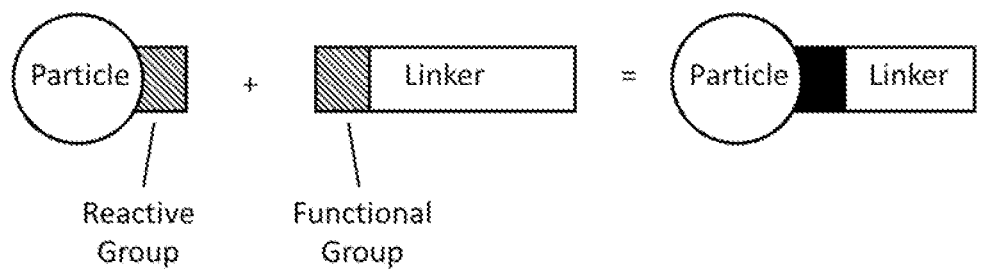
FIG. 8 depicts a particle comprising a reactive group, a linker comprising a functional group, and an agent. Combining the particle and linker may thus form a covalent or non-covalent bond between the reactive group and functional group, depending on the nature of each group. The particle/linker complex may then be combined with an agent to form a covalent or non-covalent bond between the linker and the agent, thereby linking the particle to the agent.
Figure 8:
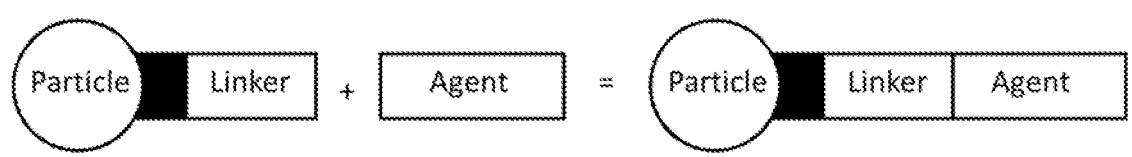

In some aspects, the invention relates to a method of making a particle as described herein, comprising incubating an unloaded particle (e.g., a particle comprising a reactive group) with a linker (e.g., a linker comprising a functional group), thereby forming a bond between the particle (e.g., a reactive group of the particle) and the linker (e.g., the functional group). See FIG. 8. In some embodiments, the method comprises incubating an unloaded particle (e.g., a particle comprising a plurality of reactive groups) with a plurality of linkers (e.g., wherein each linker comprises a functional group), thereby forming bonds between the particle (e.g., a population of reactive groups of the particle) and a population of linkers (e.g., the functional groups of the population of linkers). The method may comprise incubating a linker with an agent of the invention, thereby forming a bond between the linker and agent. In some embodiments, the method comprises incubating a plurality of linkers with a plurality of agents, thereby forming bonds between a population of linkers and a population of agents. In some embodiments, the reactive group, linker, functional group, and/or agent can form a bond with a carboxyl, primary amine, or thiol. In certain preferred embodiments, the reactive group and/or functional group can form a bond with a carboxyl, primary amine, or thiol.

A reactive group and/or functional group may comprise a biotin-binding protein (e.g., avidin, monomeric avidin, streptavidin, monomeric streptavidin, neutravidin, monomeric neutravidin) or biotin. For example, a reactive group may comprise biotin and a functional group may comprise a biotin-binding protein or a reactive group may comprise a biotin-binding protein and a functional group may comprise biotin. A linker may comprise a biotin-binding protein or biotin, e.g., wherein either a reactive group of the particle comprises biotin or a biotin-binding protein, respectively, or an agent comprises biotin or a biotin-binding protein, respectively. An agent may comprise a biotin-binding protein or biotin, e.g., wherein either a reactive group of the particle comprises biotin or a biotin-binding protein, respectively, or a linker comprises biotin or a biotin-binding protein, respectively.

A linker may comprise biotin and a thiol, biotin and an amine, or biotin and a carboxylic acid. For example, the linker may bind to an agent comprising a biotin-binding protein, and the functional group of the linker may be the thiol, amine, or carboxylic acid, i.e., for linking the agent to a particle. Similarly, the linker may bind to a particle comprising a biotin-binding protein (e.g., wherein the functional group of the linker is biotin), and the thiol, amine, or carboxylic acid of the linker may be used to crosslink an agent to the particle.

The reactive group, linker, functional group, and/or agent may comprise an α-haloacyl, alkene, alkyl halide, alkyne, amine, aryl azide, aryl halides, azide, carbodiimide, carboxyl, diene, dienophile, glyoxal, imidoester, isocyanide, maleimide, N-hydroxysuccinimidyl (NETS) ester, phosphine, tetrazine, or thiol, e.g., for bonding the agent to the particle. For example, the particle may comprise an amine-functionalized silica surface wherein the plurality of reactive groups are the amines. The reactive group, linker, functional group, and/or agent may comprise an antibody (or antigen-binding portion thereof), peptide, protein, nucleic acid, or aptamer.

The reactive group, linker, functional group, and/or agent may comprise an azide or alkyne, e.g., for immobilizing an agent via the azide-alkyne Huisgen cycloaddition. Huisgen cycloaddition is the reaction of a dipolarophile with a 1,3-dipolar compound that leads to 5-membered (hetero) cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitrile oxides, azides, and diazoalkanes. Metal catalyzed click chemistry is an extremely efficient variant of the Huisgen 1,3-dipolar cycloaddition reaction between alkyl-aryl)-sulfonyl azides, C—N triple bonds and C—C triple bonds, which is well-suited to the methods disclosed herein. The results of these reactions are 1,2-oxazoles, 1,2,3-triazoles or tetrazoles. For example, 1,2,3-triazoles are formed by a copper catalyzed Huisgen reaction between alkynes and alkyl/aryl azides. Metal-catalyzed Huisgen reactions proceed at ambient temperature, are not sensitive to solvents, i.e., nonpolar, polar, semipolar, and are highly tolerant of functional groups. Non-metal Huisgen reactions (also referred to as strain-promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity of the reaction components as compared to the metal-catalyzed reactions. Examples include DIFO and DIMAC. Reaction of the alkynes and azides is very specific and essentially inert against the chemical environment of biological tissues.

The reactive group, linker, functional group, and/or agent may comprise a thiol or an alkene, e.g., for immobilizing an agent via a thiol-ene reaction alkene (hydrothiolation, i.e., addition of RS—H across a C═C bond). The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene.

The reactive group, linker, functional group, and/or agent may comprise a diene or a dienophile, e.g., for immobilizing an agent via the Diels-Alder reaction. The Diels-Alder reaction combines a diene (a molecule with two alternating double bonds) and a dienophile (an alkene) to make rings and bicyclic compounds.

The reactive group, linker, functional group, and/or agent may comprise an isocyanide or a tetrazine, e.g., for immobilizing an agent via a 4+1 cycloaddition.

The reactive group, linker, functional group, and/or agent may comprise a maleimide or a thiol, e.g., for immobilizing an agent via a maleimide-thiol reaction (see, e.g., U.S. Patent Application Publication No. 2010/0036136, hereby incorporated by reference).

The reactive group, linker, functional group, and/or agent may comprise a phosphine or an azide, e.g., for immobilizing an agent via the Staudinger reaction. The classical Staudinger reaction is a chemical reaction in which the combination of an azide with a phosphine or phosphite produces an aza-ylide intermediate, which upon hydrolysis yields a phosphine oxide and an amine. A Staudinger reaction is a mild method of reducing an azide to an amine; and triphenylphosphine is commonly used as the reducing agent. In a Staudinger ligation, an electrophilic trap (usually a methyl ester) is appropriately placed on a triarylphosphine (usually in ortho to the phosphorus atom) and reacted with the azide, to yield an aza-ylide intermediate, which rearranges in aqueous media to produce a compound with amide group and a phosphine oxide function. The Staudinger ligation is so named because it ligates (attaches/covalently links) the two starting molecules together, whereas in the classical Staudinger reaction, the two products are not covalently linked after hydrolysis.

Functional groups can be joined to agents through varying lengths of spacer arms or bridges, which may be alkyl chains, PEG chains, amino-acid chains, or any other suitable spacers. For example, a linker may comprise a polyethylene glycol (PEG) chain, e.g., which serves as a spacer between the functional group and the agent. A linker may comprise, for example, diethylene glycol, triethylene glycol, tetraethylene glycol, pentaethylene glycol, or hexaethylene glycol. A linker may comprise, for example a first functional group (e.g., $R^1$), a polyethylene glycol spacer (e.g., —[$OCH_2CH_2$]$_n$ O—, wherein n is an integer from 2 to 100, such as 2 to 50, or 2 to 20), and a second functional group (e.g., $R^2$). For example, the linker may be a molecule of formula $R^1[OCH_2CH_2]_nOR^2$ or $R^2[OCH_2CH_2]_nOR^1$. $R^1$ and $R^2$ may each independently be selected from a moiety comprising an α-haloacyl, alkene, alkyl halide, alkyne, amine, aryl azide, aryl halides, azide, carbodiimide, carboxyl, diene, dienophile, glyoxal, imidoester, isocyanide, maleimide, N-hydroxysuccinimidyl (NHS) ester, phosphine, tetrazine, or thiol. $R^1$ may be thiol and $R^2$ may be carboxyl, or $R^2$ may be thiol and $R^1$ may be carboxyl. $R^1$ may be thiol and $R^2$ may be amine, or $R^2$ may be thiol and $R^1$ may be amine. $R^1$ may be carboxyl and $R^2$ may be amine, or $R^2$ may be carboxyl and $R^1$ may be amine.

Reactive groups and functional groups suitable for reacting with primary amines include imidoesters and N-hydroxysuccinimidyl (NHS) esters. Examples of imidoester functional groups include dimethyladipimidate, dimethylpimelimidate, and dimethylsuberimidate. Examples of NHS-ester functional groups include disuccinimidyl glutamate, disuccinimidyl suberate, and bis(sulfosuccinimidyl) suberate. Accessible amine groups present on the N-termini of peptides, polypeptides, and proteins react with NHS-esters to form amides. NHS-ester cross-linking reactions can be conducted in phosphate, bicarbonate/carbonate, HEPES and borate buffers. Other buffers can be used if they do not contain primary amines. The reaction of NHS-esters with primary amines may be conducted at a pH of between about 7 and about 9 and a temperature between about 4° C. and 30° C. for about 30 minutes to about 2 hours. The concentration of NHS-ester functional group may vary from about 0.1 to about 10 mM. NHS-esters are either hydrophilic or hydrophobic. Hydrophilic NHS-esters are reacted in aqueous solutions although DMSO may be included to achieve greater solubility. Hydrophobic NHS-esters are dissolved in a water miscible organic solvent and then added to the aqueous reaction mixture.

Sulfhydryl-reactive functional groups and reactive groups include maleimides, alkyl halides, aryl halides, and a-haloacyls which react with sulfhydryls to form thiol ether bonds and pyridyl disulfides which react with sulfhydryls to produce mixed disulfides. Sulfhydryl groups on peptides, polypeptides, and proteins can be generated by techniques known to those with skill in the art, e.g., by reduction of disulfide bonds or addition by reaction with primary amines using 2-iminothiolane. Examples of maleimide functional groups include succinimidyl 4-{N-maleimido-methyl)cyclohexane-1-carboxylate and m-maleimidobenzoyl-N-hydroxysuccinimide ester. Examples of haloacetal functional groups include N-succinimidyl (4-iodoacetal) aminobenzoate and sulfosuccinimidyl (4-iodoacetal) aminobenzoate. Examples of pyridyl disulfide functional groups include 1,4-di-[3'-2'-pyridyldithio(propionamido)butane] and N-succinimidyl-3-(2-pyridyldithio)-propionate.

Reactive groups and/or functional groups may comprise carboxyl groups for binding to primary amines or hydrazides by using carbodiimides, which result in formation of amide or hydrazone bonds. In this manner, carboxy-termini of peptides, polypeptides, and proteins can be immobilized on a particle. Examples of carbodiimide functional groups and reactive groups include 1-ethyl-3-(3-dimethylaminopropyl)-carbodiimide hydrochloride and N,N'-dicyclohexylcarbodiimide. Arylazide becomes reactive when exposed to ultraviolet radiation to form aryl nitrene. Examples of arylazide functional groups include azidobenzoyl hydrazide and N-5-azido-2 nitrobenzoyloxysuccinimide. Glyoxal functional groups target the guanidyl portion of arginine. An example of a glyoxal functional group is p-azidophenyl glyoxal monohydrate.

Heterobifunctional linkers which possess two or more different functional groups (e.g., a first functional group, a second functional group, and optionally additional functional groups) are suitable for use herein. Examples include linkers that are amine-reactive at one end and sulfhydryl-reactive at the other end such as 4-succinimidyl-oxycarbonyl-a-(2-pyridyldithio)-toluene, N-succinimidyl-3-(2-pyridyldithio)-propionate and the maleimide linkers discussed above. Such linkers can be used to indirectly join a reactive group of the particle with a functional group of the agent.

An agent may be immobilized on a particle by binding to a reactive group. For example, a peptide, polypeptide, or protein may be immobilized by forming a bond between a carboxyl, primary amine, or thiol of the peptide, polypeptide, or protein and a reactive group. Alternatively, an agent may be modified, e.g., with a linker, to form a bond with a reactive group. Various methods for modifying an agent, such as a protein, carbohydrate, or lipid, are known in the art (see, e.g., U.S. Patent Application Publication Nos. 2014/0212425, 2014/0377837, and 2015/0005447, and U.S. Pat. Nos. 4,711,955, 5,047,519, 7,332,355, 9,040716, hereby incorporated by reference).

1,3-Dipolar compounds can be incorporated into proteins, lipids, oligosaccharides, oligonucleotides, and glycans using metabolic machinery, covalent inhibitors, and enzymatic transfers. For example, an azido group, $N_3$, can be applied at the N-terminus of proteins or peptides using azidoacetyl chloride (see, e.g., Haridas, et al., Tetrahedron Letters 48 (2007) 4719-4722). The azido group is a nucleophilic group that will exchange with other nucleophilic groups, e.g., OH, $NH_2$ and halogens (Br, Cl, or I). $NaN_3$ is an azidizing agent which is capable of aziding proteins by simply contacting the proteins with a 10 times molar excess of $NaN_3$. A process for C-terminal azidization is described in Cazalis, et al., Bioconjugate Chem., 15 (2004) 1005-1009. The incubation of cells with peracetylated N-azidoacetylmannosamine provides cell surface glycans with azido sialic acid (see, e.g., Codelli et al., J. Amer. Chem. Soc., 130 (34) 11486-11493 (2008)). Azido-tagged lipids are described in Smith, et al., Bioconjugate Chem., 19 (9), 1855-1863 (2008). PEGylation is a commonly used technique for adding groups to peptides and proteins and is suitable for use herein. For example, PEG may be covalently bound to amino acid residues via a reactive moiety. Reactive moieties (as opposed to reactive groups herein) are those to which an activated PEG molecule may be bound (e.g., a free amino or carboxyl group). For example, N-terminal amino acid residues and lysine residues have a free amino group and C-terminal amino acid residues have a free carboxyl group. Sulfhydryl groups (e.g., as found on cysteine residues) may also be used as a reactive moiety for attaching PEG. In addition, enzyme-assisted methods for introducing activated groups (e.g., hydrazide, aldehyde, and aromatic-amino groups) specifically at the C-terminus of a polypeptide. Accordingly, PEG incorporating 1,3-dipolar compounds may be utilized herein. Those skilled in the art can utilize any known process for coupling a 1,3-dipolar compound into proteins, lipids, oligosaccharides, oligonucleotides and glycans.

A particle may comprise a reactive group comprising an azido group or an alkynyl group and a linker or agent (e.g., a functional group of a linker or agent) may comprise an alkynyl group or azido group, respectively. An alkynyl group may form a covalent bond with an azido group, for example, using a copper-catalyzed alkyne-azide cycloaddition. Methods for preparing particles comprising an azido group or an alkynyl group are known (see, e.g., Xu, Z. et al. J Nanoparticle Research 17:56 (2015)).

Dipolarophile-functionalized proteins, polypeptides, and peptides can be synthesized by linking at the N-terminus with, for example, an alkyne (e.g., 3-butynyl chloroformate). In some embodiments, thiols on cysteines are functionalized with alkyne bearing maleimide. Providing a C-terminal dipolarophile can be accomplished, e.g., by coupling with propargylamine using a linking agent such as N-hydroxysuccinimide/DCC. Terminal alkynes can be installed using metabolic building blocks such as alkynoic acids. Lipids may be functionalized with alkynes. For example, alkyne-modified fatty acids can be generated by reaction of terminal alkynyl-alkyl bromide with trimethyl phosphine to yield a 16 carbon alkynyl-dimethylphosphonate (see, e.g., Raghavan et al., Bioorg. Med. Chem. Lett., 18 (2008) 5982-5986). As above, PEGylation may be used for adding dipolarophile groups to peptides and proteins and is suitable for use herein. Diels-Alder functionalities and thiol-ene functionalities may likewise be attached to proteins, lipids, oligosaccharides, oligonucleotides and glycans.

In certain preferred embodiments, the reactive group comprises a nucleic acid, e.g., for hybridizing with an agent or functional group (e.g., an agent or functional group that comprises a complementary nucleic acid). The term "nucleic acid" refers to DNA or RNA. A nucleic acid may be single stranded or double stranded. A nucleic acid may comprise single stranded regions and/or double stranded regions. A nucleic acid comprises a nucleotide sequence, which is the order of consecutive nucleotides in the nucleic acid, read from 5' to 3'. A nucleic acid may comprise multiple nucleotide sequences. For example, a double stranded nucleic acid comprises two nucleotide sequences that each span the length of the nucleic acid, wherein one nucleotide sequence may be the reverse complement of the other nucleotide sequence. A nucleic acid also comprises nucleotide sequences that are shorter than the length of the nucleic acid. For example, a single stranded nucleic acid that is ten nucleotides long has two nucleotide sequences that are nine nucleotides long. Similarly, a single stranded nucleic acid that is ten nucleotides long has three nucleotide sequences that are eight nucleotides long. The nucleotides of a nucleic acid may be, for example, cytosine (C), guanine (G), adenine (A), thymine (T), and/or uracil (U). The nucleotides may be modified or unmodified. For example, one or more nucleotides may be methylated. A nucleic acid may comprise a nucleotide analog and/or an unnatural base pair. The nucleotides of a nucleic acid may comprise 5-methylcytosine, pseudouridine, dihydrouridine, inosine, xanthosine, and/or 7-methylguanosine.

A particle may comprise a reactive group, wherein the reactive group comprises a nucleic acid; and an agent, wherein the agent is linked to a complementary nucleic acid that can hybridize with the nucleic acid of the reactive group, thereby forming a non-covalent association between the agent and the particle. Similarly, a particle may comprise a reactive group, wherein the reactive group comprises a nucleic acid; and a functional group, wherein the functional group comprises a complementary nucleic acid that can hybridize with the nucleic acid of the reactive group, thereby forming a non-covalent association between the agent and the particle. The nucleic acid may comprise a nucleotide sequence and the complementary nucleic acid may comprise a complementary nucleotide sequence, e.g., wherein the nucleotide sequence has at least 95%, 96%, 97%, 98%, or 99% sequence identity with the reverse complement of the complementary nucleotide sequence. The nucleotide sequence may have 100% sequence identity with the reverse complement of the complementary nucleotide sequence.

Preferably, the melting temperature of the nucleic acid and complementary nucleic acid in physiological fluid (e.g., blood) is greater than body temperature (e.g., the body temperature of a subject, such as a human or mouse). For example, the melting temperature of the nucleic acid and complementary nucleic acid in physiological fluid is preferably greater than 37° C., such as greater than about 38° C., greater than about 39° C., greater than about 40° C., greater than about 41° C., greater than about 42° C., greater than about 43° C., greater than about 44° C., or greater than about 45° C. The melting temperature of the nucleic acid and complementary nucleic acid may be about 37° C. to about 120° C., such as about 38° C. to about 120° C., about 39° C. to about 120° C., about 40° C. to about 120° C., about 41° C. to about 120° C., about 42° C. to about 120° C., about 43° C. to about 120° C., about 44° C. to about 120° C., about 45° C. to about 120° C., about 46° C. to about 120° C., about 47° C. to about 120° C., about 48° C. to about 120° C., about 49° C. to about 120° C., about 50° C. to about 120° C., about 38° C. to about 100° C., about 39° C. to about 100° C., about 40° C. to about 100° C., about 41° C. to about 100° C., about 42° C. to about 100° C., about 43° C. to about 100° C., about 44° C. to about 100° C., about 45° C. to about 100° C., about 46° C. to about 100° C., about 47° C. to about 100° C., about 48° C. to about 100° C., about 49° C. to about 100° C., or about 50° C. to about 100° C.

The length of the nucleic acid of the reactive group, nucleotide sequence of the reactive group, complementary nucleic acid, and complementary nucleotide sequence is preferably greater than 9 nucleotides. The length of the nucleic acid of the reactive group, nucleotide sequence of the reactive group, complementary nucleic acid, and complementary nucleotide sequence may be greater than 10, 11, 12, 13, 14, 15, 16, 17, 18, 19, or 20 nucleotides. The length of the nucleic acid of the reactive group, nucleotide sequence of the reactive group, complementary nucleic acid, and complementary nucleotide sequence may be about 10 nucleotides to about 100 nucleotides, such as about 11 nucleotides to about 80 nucleotides, about 12 nucleotides to about 60 nucleotides, about 13 nucleotides to about 50 nucleotides, about 14 nucleotides to about 40 nucleotides, about 15 nucleotides to about 30 nucleotides, or about 16 nucleotides to about 25 nucleotides. The GC content of the nucleic acid, nucleotide sequence, complementary nucleic acid, and complementary nucleotide sequence may be about 10% to about 100%, such as about 40% to about 100%, about 45% to about 100%, about 50% to about 100%, about 55% to about 100%, about 40% to about 95%, about 45% to about 90%, about 50% to about 85%, or about 55% to about 80%.

XII. Positioning of an Agent on a Particle

In some embodiments, the geometry of the particle is such that the immobilized agent has a reduced, or substantially reduced, ability to interact with a biomolecule on the surface of a cell, such as an immune cell, blood cell, or lymphocyte. An immobilized agent may have less than 50% (e.g., 45, 40, 35, 30, 25, 20, 15, 10, 9, 8, 7, 6, 5, 4, 3, 2, or 1%) of the ability to bind to a biomolecule on a surface of a cell relative to a free, soluble form of the agent. For example, in some embodiments, TNFα or IL-2 immobilized on the surface of a particle described herein has less than 50 (e.g., 45, 40, 35, 30, 25, 20, 15, 10, 9, 8, 7, 6, 5, 4, 3, 2, or 1) % of the ability of free TNFα or IL-2 to bind to a TNFα receptor or IL-2 receptor on the surface of a cell.

In some embodiments, the soluble biomolecule bound to the particle has a reduced, or substantially reduced, ability to interact with its cognate ligand (the second member of the specific binding pair). The biomolecule may be bound to the particle by virtue of the agent. A biomolecule bound to a particle may have less than 50% (e.g., 45, 40, 35, 30, 25, 20, 15, 10, 9, 8, 7, 6, 5, 4, 3, 2, or 1%) of the ability to interact with its cognate ligand relative to the ability of an unbound, biomolecule. For example, a soluble TNFR bound to a particle described herein has less than 50 (e.g., 45, 40, 35, 30, 25, 20, 15, 10, 9, 8, 7, 6, 5, 4, 3, 2, or 1) % of the ability of free, soluble TNFR to interact with free TNFα. In another example, a soluble virion bound to a particle described herein has less than 50 (e.g., 45, 40, 35, 30, 25, 20, 15, 10, 9, 8, 7, 6, 5, 4, 3, 2, or 1) % of the ability of free virion to interact with its cognate cell surface receptor(s) and infect a cell.

In some embodiments, the agent may be immobilized on an inner surface of a particle (e.g., the pores of a porous particle or the inner surface of a tube). In some embodiment, the agent can be immobilized on the outer surface of a particle, but is sterically precluded from interacting with a cell surface by way of one or more protrusions from the particle. In some embodiments, e.g., toroidal particles, the agent is immobilized on the inner surface of the particle such that the agent has a reduced, or substantially reduced, ability to interact with a biomolecule on the surface of a cell and/or the soluble biomolecule bound to the particle by virtue of the agent has a reduced, or substantially reduced, ability to interact with its cognate ligand (the second member of the specific binding pair).

Exemplary particle geometries capable of reducing or substantially reducing the interaction of an agent with a biomolecule on a cell surface, or the interaction between a biomolecule bound to the particle, and its cognate ligand, are set forth in FIGS. 1 to 6 and described herein.

XIII. Clearance Agents and Coatings

In some embodiments, a particle comprises a clearance agent. The clearance agent may facilitate clearance of the particle through a biological pathway, such as by excretion in the urine, degradation, excretion by a hepatobiliary pathway, and/or phagocytosis.

For example, the particle may comprise a reservoir, wherein the reservoir comprises a clearance agent. The reservoir may be a hole or void in the body of a particle, e.g., a void in the body of a porous silicon particle.

For particles comprising pores, the reservoir may be a pore or the reservoir may be larger or smaller than the average pore size. A reservoir may consist of a recess in the body of a particle (e.g., a shallow recess, a concavity, or a void), wherein the width or diameter of the recess is larger than the width or diameter of the average pore size. The width or diameter of a reservoir may be at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 100, 110, 120, 130, 140, 150, 175, 200, 250, 300, 400, or even about 500 times as large as the width or diameter of the average pore size. The width or diameter of the reservoir may be about 2 times to about 10 times the width or diameter of the average pore size, such as about 2 times to about 8 times or about 2 times to about 6 times. The width or diameter of a reservoir may be about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 100, 110, 120, 130, 140, 150, 175, 200, 250, 300, 400, or even about 500 times as large as the width or diameter of the average pore size.

For particles comprising a DNA scaffold, a reservoir may be an interior region of the DNA scaffold. The reservoir (e.g., interior region) may be inaccessible to cells, e.g., the DNA scaffold may be constructed such that the scaffold sterically hinders cells from entering the interior region. In some embodiments, the reservoir (e.g., interior region) is inaccessible to extracellular proteins, e.g., the DNA scaffold may be constructed such that the scaffold sterically hinders extracellular proteins from entering the reservoir. The reservoir (e.g., interior region) may be inaccessible to antibodies. Nevertheless, the DNA scaffold may allow for the reservoir (e.g., interior region) to become accessible to cells and/or extracellular proteins after a predetermined period of time. For example, the DNA scaffold may comprise a biodegradable wall that may degrade after a predetermined period of time (e.g., by hydrolysis), thereby exposing the clearance agent to cells and/or extracellular proteins. The DNA scaffold may comprise a biodegradable latch that may degrade after a predetermined period of time (e.g., by hydrolysis), allowing the DNA scaffold to undergo a conformational change, thereby exposing the clearance agent to cells and/or extracellular proteins (see, e.g., PCT Patent Application Publication No. WO2014/170899, hereby incorporated by reference). Similarly, the DNA scaffold may comprise a reservoir that comprises and opening, as described below.

The reservoir may comprise an opening. The opening may be covered by a cap or member, thereby inhibiting interactions between the clearance agent and cells and/or extracellular proteins (e.g., antibodies). The cap or member may comprise a polymer, such as a biodegradable polymer. The cap or member may degrade after a predetermined period of time (e.g., by hydrolysis), thereby exposing the clearance agent to cells and/or extracellular proteins. The cap or member may degrade (e.g., biodegrade) after exposure to a biological fluid (e.g., blood plasma or extracellular fluid) for about 1 day to about 5 years, such as about 1 day to about 4 years, about 1 day to about 3 years, or about 1 day to about 1 year.

A predetermined period of time may be a period of time that the particle is in a liquid (e.g., an aqueous liquid). The predetermined period of time may be a period of in vivo residence of a particle (e.g., exposure to biological fluids, pH, enzymes, and/or temperatures). The predetermined period of time may be determined, at least in part, by the binding of the particle to a biomolecule. For example, the particle may be configured such that the binding of a biomolecule exposes the clearance agent to cells and/or extracellular proteins (see, e.g., PCT Patent Application Publication No. WO2014/170899, hereby incorporated by reference). The predetermined period of time may be about 1 day to about 5 years, such as about 1 day to about 3 years, or about 1 day to about 1 year.

Exemplary materials suitable for use as caps or membranes, are described in U.S. Pat. No. 7,918,842, which is hereby incorporated by reference. In general, these materials degrade or dissolve either by enzymatic hydrolysis or exposure to water in vivo or in vitro, or by surface or bulk erosion. Representative synthetic, biodegradable polymers include: poly(amides) such as poly(amino acids) and poly (peptides); poly(esters) such as poly(lactic acid), poly(glycolic acid), poly(lactic-co-glycolic acid), and poly(caprolactone); poly(anhydrides); poly(orthoesters); poly (carbonates); and chemical derivatives thereof (substitutions, additions of chemical groups, for example, alkyl, alkylene, hydroxylations, oxidations, and other modifications routinely made by those skilled in the art), copolymers and mixtures thereof. Other polymers that may be used in caps or membranes include: poly(ethers) such as poly(ethylene oxide), poly(ethylene glycol), and poly(tetramethylene oxide); vinyl polymers—poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; poly (siloxanes); and any chemical derivatives thereof (substitutions, additions of chemical groups, for example, alkyl, alkylene, hydroxylations, oxidations, and other modifications routinely made by those skilled in the art), copolymers and mixtures thereof. In certain embodiments, the reservoir cap is formed from one or more cross-linked polymers, such as cross-linked polyvinyl alcohol.

In some embodiments, a particle comprises a coating. In some embodiments, the coating comprises a clearance agent. The coating may mask a clearance agent.

The particle may comprise a first surface and a second surface; the agent may be immobilized on the first surface; and the coating may cover at least a portion of the second surface. The first surface may be an interior surface or an inner surface, e.g., the first surface may be oriented such that the agent has a reduced ability to bind to a molecule on a cell surface. Examples of an interior surface or inner surface include the inner walls of a pore, reservoir, or tube, the inner circumferential surface of a toroid, or the hollow of a concave surface. Other examples of an interior surface or inner surface include the outer surface of a particle, wherein the outer surface is protected from interactions with cells by one or more protrusions. The second surface may be an exterior surface or outer surface, e.g., the second surface may be oriented such that the coating can interact with a cell. In some embodiments, a particle may comprise one or more core subparticles and a plurality of protecting subparticles. The particle may comprise a shield and the shield may comprise the plurality of protecting subparticles. The first surface may be the surface of the one or more core particles and the second surface may be the surface of the protecting subparticles.

A coating may inhibit interactions between particles, e.g., the coating may reduce the propensity of particles to form aggregates. The coating may inhibit interactions between a particle and cells, e.g., by presenting a biologically-inert surface. The coating may inhibit non-specific interactions with extracellular molecules, e.g., non-specific adsorption of biomolecules. A coating may inhibit specific interactions with cells or extracellular molecules, e.g., a coating may disfavor or delay the excretion or phagocytosis of a particle. A coating may target a particle for excretion or phagocytosis. A coating or other feature (e.g., an "excretion-inducing compound") that targets a particle for excretion or phagocytosis may be masked by a coating (e.g., a second coating) that delays the excretion or phagocytosis of the particle, e.g., to promote maintenance of the particles in the bloodstream for a predetermined amount of time.

A coating may comprise a plurality of elongated coating molecules bound at one end to the surface of the particle. A coating may inhibit interactions between a biomolecule bound to a particle and a second member of the specific binding pair that includes the biomolecule. A coating may inhibit interactions between a biomolecule bound to a particle and a cell. An agent may be oriented on a particle relative to a coating such that the agent has a reduced ability to bind to a molecule on the surface of a cell. An agent may be oriented on a particle relative to a coating such that the agent has a reduced ability to bind to a target on the surface of a cell. An agent may be oriented on a particle relative to a coating such that the coating sterically inhibits the agent from binding to a molecule on the surface of a cell. An agent may be oriented on a particle such that the coating sterically inhibits the agent from binding to a target on the surface of a cell. A coating may be oriented on a particle such that the agent of the particle has a reduced ability to bind to a molecule on the surface of a cell. A coating may reduce the ability of the agent of a particle to activate a cell surface receptor protein, relative to the ability of a natural ligand of the cell surface receptor protein.

A particle may comprise a second coating, e.g., wherein the second coating consists of a second plurality of coating molecules. A particle may comprise a second plurality of coating molecules. The second coating and/or second plurality of coating molecules may decrease the clearance of the particle in vivo, e.g., by masking the coating and/or plurality of coating molecules. The second coating and/or second plurality of coating molecules may be biodegradable, e.g., to expose the coating and/or plurality of coating molecules to cells and/or extracellular proteins after a predetermined period of time. The second coating and/or second plurality of coating molecules may comprise a biodegradable polymer, e.g., each molecule of the second plurality of coating molecules may comprise a biodegradable polymer. The second coating and/or second plurality of coating molecules may comprise CD47, which inhibits phagocytosis.

In some embodiments, the particle comprises a first surface (e.g., an interior surface) and a second surface (e.g., an exterior surface or outer surface); the agent is immobilized on the first surface; and the coating covers at least a portion of the second surface. The orientation of the first surface may reduce the ability of the agent to interact with molecules on a cell surface. The orientation of the second surface may permit interactions between the coating and cells, extracellular molecules, and/or different particles. An "interaction" between the coating and cells, extracellular molecules, and/or different particles may be a weak, neutral, or unfavorable interaction, e.g., to disfavor stable binding of the particle to a cell, extracellular molecule, or other particle. Alternatively, an interaction between the coating and either cells and/or extracellular molecules may be a specific or designed interaction, e.g., to favor clearance of the particle through a biological pathway, such as phagocytosis. In certain preferred embodiments, the second surface is substantially free of agent. In certain preferred embodiments, the first surface is substantially free of coating. In certain preferred embodiments, the coating covers substantially all of the second surface.

In some embodiments, the particle comprises a first surface (e.g., an interior surface) and a second surface (e.g., an exterior surface or outer surface); the agent is immobilized on the first surface and the second surface; and the coating covers at least a portion of the second surface. In such embodiments, the coating (and/or a second coating) may inhibit interactions between the agent and molecules on a cell surface. In certain preferred embodiments, the coating covers substantially all of the second surface.

In some embodiments, the particle comprises a first surface (e.g., an interior surface) and a second surface (e.g., an exterior surface or outer surface); the agent is immobilized on the first surface; and the coating covers at least a portion of the first surface and at least a portion of the second surface. In such embodiments, the coating preferably does not affect the ability of the agent to specifically bind to a biomolecule. In certain preferred embodiments, the coating covers substantially all of the second surface.

In some embodiments, the particle comprises a surface; the agent is immobilized on the surface; and the coating covers at least a portion of the surface. In such embodiments, the coating may not affect the ability of the agent to specifically bind to a biomolecule. The coating may allow for some of the agent to specifically bind to a biomolecule and inhibit interactions between some of the agent and biomolecule. The coating may inhibit interactions between the agent and molecules on a cell surface. In certain preferred embodiments, the coating covers substantially all of the surface.

In some embodiments, the particle comprises a coating that covers at least a portion of the second surface and a second coating that covers at least a portion, such as substantially all, of the coating on the second surface. In such embodiments the coating may comprise a clearance agent, such as an "excretion-inducing compound" to target a particle for excretion or phagocytosis. Such a coating may comprise beta-cyclodextrin. The second coating may comprise a material, e.g., a second plurality of coating molecules, to inhibit interaction with cells and/or inhibit non-specific interactions with extracellular molecules, e.g., non-specific adsorption of biomolecules. The second coating may be biodegradable, e.g., to expose the coating on the second surface to cells and/or extracellular proteins after a predetermined period of time. For example, in a particle comprising one or more core subparticles and a plurality of protecting sub-particles, wherein a capture agent is immobilized on the surface on the core subparticle(s) (i.e., the first surface), at least a portion of the surface of the protecting subparticles (i.e., the second surface) comprises a coating, for example a coating comprising either a clearance agent or a coating comprising a material to inhibit interaction with cells and/or to inhibit non-specific interaction with extracellular molecules.

A coating may comprise coating molecules, e.g., a coating may consist of a plurality of coating molecules or a coating may consist of a population of coating molecules. As used herein, the terms "plurality of coating molecules" and "population of coating molecules" each refer to a coating. The term "coating," however, may refer to additional compositions, such as a hydrogel. A coating molecule may be a clearance agent (and thus, a clearance agent may be a coating molecule).

A particle may comprise a plurality of coating molecules. The particle may comprise a surface and a plurality of agents immobilized on the surface, and at least one molecule of the plurality of coating molecules may be bound to the surface. For example, all or substantially all of the molecules of the plurality of coating molecules may be bound to the surface.

The particle may comprise a surface and a second surface, wherein a plurality of agents immobilized on the surface, and at least one molecule of the plurality of coating molecules may be bound to the second surface. For example, all or substantially all of the molecules of the plurality of coating molecules may be bound to the second surface. In some embodiments, some of the molecules of the plurality of coating molecules are bound to the surface and some of the molecules of the plurality of coating molecules are bound to the second surface.

In some embodiments, the coating molecules increase the clearance of the particle in vivo. For example, the coating molecules may comprise a pathogen-associated molecular pattern.

In some embodiments, the particles described herein have a coating comprising an excretion-inducing compound, which facilitates the removal of the particles from the circulation, e.g., via the kidneys, liver/intestines (e.g., via bile), or phagocytosis (e.g., by antigen-presenting cells). A plurality of coating molecules may be a plurality of excretion-inducing compounds. For example, in embodiments in which the particles are toroidal, the inner circumferential surface (e.g., a first surface) may comprise an immobilized agent and the outer surface (e.g., a second surface) may comprise a compound that induces the clearance of the particles, e.g., by the kidneys, liver, or macrophages. In some embodiments, the excretion-inducing compound is programmed. That is, the compound can be covered with a coating that degrades (e.g., through the action of enzymes, hydrolysis, or gradual dissolution) over time (e.g., a predetermined amount of time) eventually exposing the excretion-inducing compound or other feature that increases the rate of clearance. The coating may degrade after exposure to a biological fluid (e.g., blood plasma or extracellular fluid) for about 1 day to about 5 years, such as about 1 day to about 3 years, or about 1 day to about 1 year. Thus, the in vivo residence of a particle may be modified and/or controlled.

A coating may comprise an organic polymer, such as polyethylene glycol (PEG). An organic polymer may be attached to a particle, e.g., attached to a surface of the particle. The organic polymer may include PEG, polylactate, polylactic acids, sugars, lipids, polyglutamic acid, polyglycolic acid (PGA), polylactic acid (PLA), poly(lactic-co-glycolic acid) (PLGA), polyvinyl acetate (PVA), and combinations thereof. In certain embodiments, the particle is covalently conjugated with PEG, which discourages adsorption of serum proteins, facilitates efficient urinary excretion and decreases aggregation of the particle (see, e.g., Burns et al., *Nano Letters,* 9(1):442-448 (2009) and U.S. Patent Application Publication Nos. 2013/0039848 and 2014/0248210, each of which is hereby incorporated by reference).

In one embodiment, the coating comprises at least one hydrophilic moiety, for example, Pluronic® type polymers (a nonionic polyoxyethylene-polyoxypropylene block copolymer with the general formula $HO(C_2H_4O)_a(—C_3H_6O)_b(C_2H_4O)_aH$), a triblock copolymer poly(ethylene glycol-b-(DL-lactic acid-co-glycolic acid)-b-ethylene glycol) (PEG-PLGA-PEG), a diblock copolymer polycaprolactone-PEG (PCL-PEG), poly(vinylidene fluoride)-PEG (PVDF-PEG), poly(lactic acid-co-PEG) (PLA-PEG), poly(methyl methacrylate)-PEG (PMMA-PEG) and so forth. In an embodiment with such a moiety, the hydrophilic moiety is a PEG moiety such as: a [Methoxy(Polyethyleneoxy)Propyl]-Trimethoxysilane (e.g., $CH_3(OC_2H_4)_{6-9}(CH_2)OSi(OCH_3)_3$), a [Methoxy(Polyethyleneoxy)Propyl]-Dimethoxysilane (e.g., $CH_3(OC_2H_4)_{6-9}(CH_2)OSi(OCH_3)_2$), or a [Methoxy(Polyethyleneoxy)Propyl]-Monomethoxysilane (e.g., $CH_3(OC_2H_4)_{6-9}(CH_2)OSi(OCH_3)$). Suitable coatings are described, for example, in U.S. Patent Application Publication No. 2011/0028662 (hereby incorporated by reference).

The coating may include a polyhydroxylated polymer, such as natural polymers or hydroxyl-containing polymers including multiply-hydroxylated polymers, polysaccharides, carbohydrates, polyols, polyvinyl alcohol, poly amino acids such as polyserine, or other polymers such as 2-(hydroxyethyl)methacrylate, or combinations thereof. In some embodiments, the polyhydroxylated polymers are polysaccharides. Polysaccharides include, mannan, pullulan, maltodextrin, starches, cellulose, and cellulose derivatives, gums, xanthan gum, locust bean gum, or pectin, combinations thereof (see, e.g., U.S. Patent Application Publication No. 2013/0337070, hereby incorporated by reference).

In some embodiments, the coating comprises a zwitterionic polymer (see, e.g., U.S. Patent Application Publication Nos. 2014/0235803, 2014/0147387, 2013/0196450, and 2012/0141797; and U.S. Pat. No. 8,574,549, each of which is hereby incorporated by reference).

Other suitable coatings include poly-alpha hydroxy acids (including polyactic acid or polylactide, polyglycolic acid, or polyglycolide), poly-beta hydroxy acids (such as polyhydroxybutyrate or polyhydroxyvalerate), epoxy polymers (including polyethylene oxide (PEO)), polyvinyl alcohols, polyesters, polyorthoesters, polyamidoesters, polyesteramides, polyphosphoesters, and polyphosphoester-urethanes. Examples of degradable polyesters include: poly(hydroxyalkanoates), including poly(lactic acid) or (polylactide, PLA), poly(glycolic acid) or polyglycolide (PGA), poly(3-hydroxybutyrate), poly(4-hydroxybutyrate), poly(3-hydroxyvalerate), and poly(caprolactone), or poly(valerolactone). Examples of polyoxaesters include poly(alkylene oxalates) such as poly(ethylene oxalate)) and polyoxaesters containing amido groups. Other suitable coating materials include polyethers including polyglycols, ether-ester copolymers (copoly(ether-esters)) and polycarbonates. Examples of biodegradable polycarbonates include polyorthocarbonates, polyiminocarbonates, polyalkylcarbonates such as poly(trimethylene carbonate), poly(1,3-dioxan-2-one), poly(p-dioxanone), poly(6,6-dimethyl-1,4-dioxan-2-one), poly(1,4-dioxepan-2-one), and poly(1,5-dioxepan-2-one). Suitable biodegradable coatings can also include polyanhydrides, polyimines (such as poly(ethylene imine) (PEI)), polyamides (including poly-N-(2-hydroxypropyl)-methacrylamide), poly(amino acids) (including a polylysine such as poly-L-lysine, or a polyglutamic acid such as poly-L-glutamic acid), polyphosphazenes (such as poly(phenoxy-co-carboxylatophenoxy phosphazene), polyorganophosphazenes, polycyanoacrylates and polyalkylcyanoacrylates (including polybutylcyanoacrylate), polyisocyanates, and polyvinylpyrrolidones.

The chain length of a polymeric coating molecule may be about 1 to about 100 monomer units, such as about 4 to about 25 units.

A particle may be coated with a naturally occurring polymer, including fibrin, fibrinogen, elastin, casein, collagens, chitosan, extracellular matrix (ECM), carrageenan, chondroitin, pectin, alginate, alginic acid, albumin, dextrin, dextrans, gelatins, mannitol, n-halamine, polysaccharides, poly-1,4-glucans, starch, hydroxyethyl starch (HES), dialdehyde starch, glycogen, amylase, hydroxyethyl amylase, amylopectin, glucoso-glycans, fatty acids (and esters thereof), hyaluronic acid, protamine, polyaspartic acid, polyglutamic acid, D-mannuronic acid, L-guluronic acid, zein and other prolamines, alginic acid, guar gum, and phosphorylcholine, as well as co-polymers and derivatives thereof. The coating may also comprise a modified polysaccharide, such as cellulose, chitin, dextran, starch, hydroxyethyl starch, polygluconate, hyaluronic acid, and elatin, as well as co-polymers and derivative thereof.

A particle may be coated with a hydrogel. The hydrogel can be formed, for example, using a base polymer selected from any suitable polymer, such as poly(hydroxyalkyl (meth)acrylates), polyesters, poly(meth)acrylamides, poly(vinyl pyrrolidone), or polyvinyl alcohol. A cross-linking agent can be one or more of peroxides, sulfur, sulfur dichloride, metal oxides, selenium, tellurium, diamines, diisocyanates, alkyl phenyl disulfides, tetraalkyl thiuram disulfides, 4,4'-dithiomorpholine, p-quinine dioxime and tetrachloro-p-benzoquinone. Also, boronic acid-containing polymers can be incorporated in hydrogels, with optional photopolymerizable groups.

In certain preferred embodiments, the coating comprises a material that is approved for use by the U.S. Food and Drug Administration (FDA). These FDA-approved materials include polyglycolic acid (PGA), polylactic acid (PLA), Polyglactin 910 (comprising a 9:1 ratio of glycolide per lactide unit, and known also as VICRYL™), polyglyconate (comprising a 9:1 ratio of glycolide per trimethylene carbonate unit, and known also as MAXON™), and polydioxanone (PDS).

The attachment of a coating to a particle may be accomplished by a covalent bond or a non-covalent bond, such as by ionic bond, hydrogen bond, hydrophobic bond, coordination, adhesive, or physical absorption or interaction.

Conventional nanoparticle coating methods include dry and wet approaches. Dry methods include: (a) physical vapor deposition (Zhang, Y. et al., Solid State Commun. 115:51 (2000)), (b) plasma treatment (Shi, D. et al., Appl. Phys. Lett. 78:1243 (2001); Vollath, D. et al., J. Nanoparticle Res. 1:235 (1999)), (c) chemical vapor deposition (Takeo, O. et al., J. Mater. Chem. 8:1323 (1998)), and (d) pyrolysis of polymeric or non-polymeric organic materials for in situ precipitation of nanoparticles within a matrix (Sglavo, V. M. et al., J. Mater Sci. 28:6437 (1993)). Wet methods for coating particles include: (a) sol-gel processes and (b) emulsification and solvent evaporation techniques (Cohen, H. et al., Gene Ther. 7:1896 (2000); Hrkach, J. S. et al., Biomaterials 18:27 (1997); Wang, D. et al., J. Control. Rel. 57:9 (1999)). A coating may be applied by electroplating, spray coating, dip coating, sputtering, chemical vapor deposition, or physical vapor deposition. Additionally, methods for coating various nanoparticles with polysaccharides are known in the art (see, e.g., U.S. Pat. No. 8,685,538 and U.S. Patent Application Publication No. 2013/0323182, each of which is hereby incorporated by reference).

In some embodiments, the particles may be adapted to facilitate clearance by renal excretion. Renal clearance for subjects with normal renal function generally requires particles with at least one dimension that is less than 15 nm (see, e.g., Choi, H. S., et al., Nat Biotechnol 25(1):1165 (2007); Longmire, M. et al., Nanomedicine 3(5):703 (2008)). Nevertheless, larger particles may be excreted in the urine. For embodiments in which a particle is too large for renal clearance, the particle may nevertheless be cleared following in vivo degradation to a smaller size.

In some embodiments, the particles may be adapted to facilitate clearance by hepatobiliary excretion. The mononuclear phagocytic system (MPS), which includes the Kupffer cells in the liver, is involved in the liver uptake and subsequent biliary excretion of nanoparticles. Certain size and surface properties of nanoparticles are known to increase uptake by the MPS in the liver (see Choi et al., J. Dispersion Sci. Tech. 24(3/4):475-487 (2003); and Brannon-Peppas et al., J. Drug Delivery Sci. Tech. 14(4):257-264 (2004), each of which is incorporated by reference). For example, increasing the hydrophobicity of a particle is known to increase uptake by the MPS. Thus, one of ordinary skill in the art can select for particles having certain characteristics to modulate biliary excretion. The hepatobiliary system allows for the excretion of particles that are somewhat larger than those that may be excreted through the renal system (e.g., 10 to 20 nm). For embodiments in which a particle is too large for hepatobiliary excretion, the particle may nevertheless be cleared following in vivo degradation to a smaller size. In such embodiments, a coating that facilitates clearance by hepatobiliary excretion may cover a portion of an inner surface of a particle such that the coating becomes exposed following degradation of the particle. The particle may comprise a plurality of coating molecules, e.g., hydrophobic molecules, that cover a portion of a surface. The surface may be exposed following degradation of the particle, allowing for clearance of the degraded particle.

In some embodiments, the particle is adapted to facilitate clearance by phagocytosis. For example, the particle may comprise a clearance agent, wherein the clearance agent comprises a pathogen-associated molecular pattern, e.g., for recognition by macrophages. Pathogen-associated molecular patterns (PAMPs) include unmethylated CpG DNA (bacterial), double-stranded RNA (viral), lipopolysacharride (bacterial), peptidoglycan (bacterial), lipoarabinomannan (bacterial), zymosan (yeast), mycoplasmal lipoproteins such as MALP-2 (bacterial), flagellin (bacterial), poly(inosinic-cytidylic) acid (bacterial), lipoteichoic acid (bacterial), and imidazoquinolines (synthetic). In preferred embodiments, the PAMP clearance agent is masked such that macrophages do not engulf the particle prior to the binding of the particle to one or more targets. For example, a PAMP clearance agent may be masked by any one of the aforementioned coatings (e.g., a polymeric coating, such as a biodegradable polymeric coating). Macrophages can engulf particles as large as 20 μm (see, e.g., Cannon, G. J. and Swanson, J. A., J. Cell Science 101:907-913 (1992); Champion, J. A., et al., Pharm Res 25(8):1815-1821 (2008)). In some embodiments, a clearance agent that facilitates clearance by phagocytosis may cover a portion of an inner surface of a particle such that the clearance agent becomes exposed following degradation of the particle. The particle may comprise a plurality of clearance agents, e.g., PAMPs, that cover a portion of a surface. The surface may be exposed following degradation of the particle, allowing for clearance of the degraded particle. The clearance agent may cover a portion of a surface that overlaps a surface comprising an agent. The clearance agent (e.g., PAMPs) may elicit an immune response against the particle, e.g., following the degradation of a second coating or following the degradation of the particle.

In some embodiments, an immune response directed against a clearance agent (e.g., PAMPs) may outcompete an immune response directed against the agent and/or agent/biomolecule complex, thereby inhibiting or delaying the onset of an immune response directed against the agent and/or agent/biomolecule complex. For example, degradation of a particle may expose both a clearance agent and an agent (and/or agent/biomolecule complex) to leukocytes. A PAMP clearance agent may allow for rapid clearance of the degraded particle by macrophages, thereby delaying an immune response (e.g., B-cell mediated immune response) against the agent and/or agent/biomolecule complex.

A clearance agent may be calreticulin, which induces phagocytosis.

In certain preferred embodiments, the coating molecule comprises a nucleic acid, e.g., for hybridizing with a coating molecule to a particle comprising a DNA scaffold. For example, a particle may comprise a nucleic acid and a coating molecule, wherein the coating molecule comprises a complementary nucleic acid that can hybridize with the nucleic acid, thereby forming a bond between the coating molecule and the particle (i.e., hydrogen bonds). The nucleic acid may comprise a nucleotide sequence and the complementary nucleic acid may comprise a complementary nucleotide sequence, e.g., wherein the nucleotide sequence has at least 95%, 96%, 97%, 98%, or 99% sequence identity with the reverse complement of the complementary nucleotide sequence. The nucleotide sequence may have 100% sequence identity with the reverse complement of the complementary nucleotide sequence.

Preferably, the melting temperature of the nucleic acid and complementary nucleic acid in physiological fluid (e.g., blood) is greater than body temperature (e.g., the body temperature of a subject, such as a human or mouse). For example, the melting temperature of the nucleic acid and complementary nucleic acid in physiological fluid is preferably greater than 37° C., such as greater than about 38° C., greater than about 39° C., greater than about 40° C., greater than about 41° C., greater than about 42° C., greater than about 43° C., greater than about 44° C., or greater than about 45° C. The melting temperature of the nucleic acid and complementary nucleic acid may be about 37° C. to about 120° C., such as about 38° C. to about 120° C., about 39° C. to about 120° C., about 40° C. to about 120° C., about 41° C. to about 120° C., about 42° C. to about 120° C., about 43° C. to about 120° C., about 44° C. to about 120° C., about 45° C. to about 120° C., about 46° C. to about 120° C., about 47° C. to about 120° C., about 48° C. to about 120° C., about 49° C. to about 120° C., about 50° C. to about 120° C., about 38° C. to about 100° C., about 39° C. to about 100° C., about 40° C. to about 100° C., about 41° C. to about 100° C., about 42° C. to about 100° C., about 43° C. to about 100° C., about 44° C. to about 100° C., about 45° C. to about 100° C., about 46° C. to about 100° C., about 47° C. to about 100° C., about 48° C. to about 100° C., about 49° C. to about 100° C., or about 50° C. to about 100° C.

The length of the nucleic acid of the reactive group, nucleotide sequence of the reactive group, complementary nucleic acid, and complementary nucleotide sequence is preferably greater than 9 nucleotides. The length of the nucleic acid of the reactive group, nucleotide sequence of the reactive group, complementary nucleic acid, and complementary nucleotide sequence may be greater than 10, 11, 12, 13, 14, 15, 16, 17, 18, 19, or 20 nucleotides. The length of the nucleic acid of the reactive group, nucleotide sequence of the reactive group, complementary nucleic acid, and complementary nucleotide sequence may be about 10 nucleotides to about 100 nucleotides, such as about 11 nucleotides to about 80 nucleotides, about 12 nucleotides to about 60 nucleotides, about 13 nucleotides to about 50 nucleotides, about 14 nucleotides to about 40 nucleotides, about 15 nucleotides to about 30 nucleotides, or about 16 nucleotides to about 25 nucleotides. The GC content of the nucleic acid, nucleotide sequence, complementary nucleic acid, and complementary nucleotide sequence may be about 10% to about 100%, such as about 40% to about 100%, about 45% to about 100%, about 50% to about 100%, about 55% to about 100%, about 40% to about 95%, about 45% to about 90%, about 50% to about 85%, or about 55% to about 80%.

In some embodiments, a particle may be cleared by an organism in about 1 day to about 5 years, such as about 1 day to about 3 years, or about 1 day to about 1 year.

XIV. Methods of Administration

The disclosure contemplates that compositions described herein (e.g., any of the generally or specifically described particles or plurality of particles described herein) may be administered to cells and tissues in vitro and/or in vivo. Administration in vivo includes administration to an animal model of disease, such as an animal model of cancer, or administration to a subject in need thereof. Suitable cells, tissues, or subjects include animals, such as companion animals, livestock, zoo animals, endangered species, rare animals, non-human primates, and humans. Exemplary companion animals include dogs and cats.

For delivery in vitro, such as to and/or around cells or tissues in culture, compositions may be added to the culture media, such as to contact the microenvironment or contact soluble material in the culture media or to contact the cell or even to penetrate the cell. The desired site of activity influences the delivery mechanism and means for administering the compositions (e.g., particles described herein).

For delivery in vivo, such as to cells or tissues in vivo (including to the microenvironment of cells and tissue) and/or to a subject in need thereof, numerous methods of administration are envisioned. The particular method may be selected based on the particle composition and the particular application and the patient. Various delivery systems are known and can be used to administer agents of the disclosure. Any such methods may be used to administer any of the agents described herein. Methods of introduction can be enteral or parenteral, including but not limited to, intradermal, intramuscular, intraperitoneal, intramyocardial, intravenous, subcutaneous, pulmonary, intranasal, intraocular, epidural, and oral routes. A composition of the disclosure may be administered by any convenient route, for example, by infusion or bolus injection, by absorption through epithelial or mucocutaneous linings (e.g., oral mucosa, rectal and intestinal mucosa, etc.) and may be administered together (either concurrently or consecutively) with other biologically active agents. Administration can be systemic or local.

In certain embodiments, a composition is administered intravenously, such as by bolus inject or infusion. In certain embodiments, a composition is administered orally, subcutaneously, intramuscularly or intraperitoneally.

In certain embodiments, it may be desirable to administer a composition of the disclosure locally to the area in need of treatment (e.g., to the site of a tumor, such as by injection into the tumor).

The liver is a frequent site of metastases. Thus, in certain embodiments, delivery of an composition described herein is directed to the liver. For example, a venous catheter may be placed in the hepatic portal vein to deliver agent of the disclosure to the liver. Other methods of delivery via the hepatic portal vein are also contemplated.

In certain embodiments, compositions of the disclosure are administered by intravenous infusion. In certain embodiments, the a composition is infused over a period of at least 10, at least 15, at least 20, or at least 30 minutes. In other embodiments, the agent is infused over a period of at least 60, 90, or 120 minutes. Regardless of the infusion period, the disclosure contemplates that, in certain embodiments, each infusion is part of an overall treatment plan where agent is administered according to a regular schedule (e.g., weekly, monthly, etc.) for some period of time. However, in other embodiments, a composition is delivered by bolus injection, e.g., as part of an overall treatment plan where agent is administered according to a regular schedule for some period of time.

For any of the foregoing, it is contemplated that compositions of the disclosure (include one agent or a combination of two or more such agents) may be administered in vitro or in vivo via any suitable route or method. Compositions may be administered as part of a therapeutic regimen where a composition is administered one time or multiple times, including according to a particular schedule. Moreover, it is contemplated that the compositions of the disclosure will be formulated as appropriate for the route of administration and particular application. The disclosure contemplates any combination of the foregoing features, as well as combinations with any of the aspects and embodiments of the disclosure described herein.

The foregoing applies to any compositions (e.g., a particle or plurality of particles) of the disclosure, used alone or in combination, and used for any of the methods described herein. The disclosure specifically contemplates any combination of the features of such compositions of the disclosure, compositions, and methods with the features described for the various pharmaceutical compositions and routes of administration described in this section and below.

XV. Pharmaceutical Compositions

In certain embodiments, the subject particle or particles of the present disclosure are formulated with a pharmaceutically acceptable carrier. One or more compositions (e.g., comprising a particle or plurality of particles described herein) can be administered alone or as a component of a pharmaceutical formulation (composition). Any of the compositions of the disclosure generally or specifically described herein may be formulated, as described herein. In certain embodiments, the composition includes two or more particles of the disclosure or a particle of the disclosure formulated with a second therapeutic agent.

A composition of the disclosure may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject particle or particles include, for example, those suitable for oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining one or more particles and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a particle of the disclosure. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral administration (capsules, tablets, pills, dragees, powders, granules, and the like), one or more compositions of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

In certain embodiments, methods of the disclosure include topical administration, either to skin or to mucosal membranes such as those on the cervix and vagina. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The subject agents of the disclosure may be mixed under sterile conditions with a pharmaceutically acceptable carrier, and with any preservatives, buffers, or propellants which may be required. The ointments, pastes, creams and gels may contain, in addition to a subject agent of the disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a subject agent of the disclosure, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more compositions of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more particles in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In a preferred embodiment, the compositions of the present disclosure are formulated in accordance with routine procedures as a pharmaceutical composition adapted for intravenous administration to human beings or animals, such as companion animals. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another embodiment, the compositions (e.g., particle or particles) described herein are formulated for subcutaneous, intraperitoneal, or intramuscular administration to human beings or animals, such as companion animals.

In certain embodiments, the agents and particles of the present disclosure are formulated for local delivery to a tumor, such as for delivery for intratumoral injection.

In certain embodiments, the composition is intended for local administration to the liver via the hepatic portal vein, and the agents and particles may be formulated accordingly.

In certain embodiments, a particular formulation is suitable for use in the context of deliver via more than one route. Thus, for example, a formulation suitable for intravenous infusion may also be suitable for delivery via the hepatic portal vein. However, in other embodiments, a formulation is suitable for use in the context of one route of delivery, but is not suitable for use in the context of a second route of delivery.

The amount of an agent or particle of the disclosure which will be effective in the treatment of a condition, such as cancer, and/or will be effective in neutralizing soluble TNFR and/or will be effective in decreasing the amount or TNF alpha binding activity of soluble TNFR, particularly soluble TNFR present in a tumor microenvironment and, optionally, in plasma and/or will be effective in inhibiting tumor cell proliferation, growth or survival in vitro or in vivo can be determined by standard clinical or laboratory techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. Effective doses for administration to humans or animals may be extrapolated from dose-response curves derived from in vitro or animal model test systems.

In certain embodiments, compositions of the disclosure, including pharmaceutical preparations, are non-pyrogenic. In other words, in certain embodiments, the compositions are substantially pyrogen-free. In one embodiment the formulations of the disclosure are pyrogen-free formulations that are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26(1):223 (2000)). When therapeutic proteins are administered in relatively large dosages and/or over an extended period of time (e.g., such as for the patient's entire life), even small amounts of harmful and dangerous endotoxin could be dangerous. In certain specific embodiments, the endotoxin and pyrogen concentrations in the composition are less than 10 EU/mg, or less than 5 EU/mg, or less than 1 EU/mg, or less than 0.1 EU/mg, or less than 0.01 EU/mg, or less than 0.001 EU/mg.

The foregoing applies to any of the agents of the disclosure, compositions, and methods described herein. The disclosure specifically contemplates any combination of the features of agents of the disclosure described herein, compositions, and methods (alone or in combination) with the features described for the various pharmaceutical compositions and routes of administration described in this section and above.

The disclosure provides numerous general and specific examples of agents and categories of agents suitable for use in the methods of the present disclosure ("agents of the disclosure"). The disclosure contemplates that any such agent or category of agent can be formulated as described herein for administration in vitro or in vivo.

Moreover, in certain embodiments, the disclosure contemplate compositions, including pharmaceutically compositions comprising any agent of the disclosure described herein formulated with one or more pharmaceutically acceptable carrier and/or excipient. Such compositions may be described using any of the functional and/or structural features of an agent of the disclosure provided herein. Any such compositions or pharmaceutical compositions can be used in vitro or in vivo in any of the methods of the disclosure.

Similarly, the disclosure contemplates an isolated or purified agent of the disclosure. An agent of the disclosure described based on any of the functional and/or structural features of an agent described herein may be provided as an isolated agent or a purified agent. Such isolated or purified agents have numerous uses in vitro or in vivo, including use in any of the in vitro or in vivo methods described herein.

XVI. Applications

The compositions (e.g., particles and pharmaceutical compositions thereof) described herein are useful in a variety of diagnostic and therapeutic applications. For example, the particles described herein can be used to treat cancer, detoxify a subject, or treat viral or bacterial infections.

Therapeutic applications include administering one or more of the compositions described herein to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject (see, e.g., U.S. Patent Application Publication No. 2008/0241223; U.S. Pat. Nos. 5,501,856; 5,164,188; 4,863,457; and 3,710,795; EP488401; and EP430539, the disclosures of each of which are incorporated by reference in their entirety). The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount," in an in vivo setting, means a dosage sufficient to treat, inhibit, or alleviate one or more symptoms of the disorder being treated or to otherwise provide a desired pharmacologic and/or physiologic effect, e.g., modulate (e.g., enhance) an immune response to an antigen. The precise dosage will vary according to a variety of factors such as subject-dependent variables e.g., age, immune system health, etc.), the disease, and the treatment being effected.

In some aspects, the invention relates to a method of treating or preventing a disease or condition in a patient by administering a composition comprising nanoparticles as described herein to the patient. In some embodiments, the invention relates to a method of reducing the concentration of a biomolecule in a patient, such as the concentration of the biomolecule in a bodily fluid of the patient (e.g., blood and/or extracellular fluid), by administering a composition comprising nanoparticles as described herein to the patient.

As used herein, a mammal can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the mammal is an infant (e.g., a human infant). In certain preferred embodiments, the subject is a human.

As used herein, a subject mammal "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment.

The term "preventing" is art-recognized, and when used in relation to a condition, is well understood in the art, and includes administration of a composition which reduces the frequency of, or delays the onset of, symptoms of a medical condition in a subject mammal relative to a subject which does not receive the composition.

Suitable human doses of any of the compositions described herein can further be evaluated in, e.g., Phase I dose escalation studies. See, e.g., van Gurp et al., *Am J Transplantation* 8(8):1711-1718 (2008); Hanouska et al., *Clin Cancer Res* 13(2, part 1):523-531 (2007); and Hetherington et al., *Antimicrobial Agents and Chemotherapy* 50(10):3499-3500 (2006).

A method may further comprising measuring the concentration of a biomolecule of interest in a subject (e.g., in the serum of the blood of the subject) prior to administering to the subject a composition comprising a plurality of particles that target the biomolecule. A method may further comprise calculating the number of particles to administer to a subject, e.g., based on the concentration of the biomolecule in the subject (e.g., in the serum of the blood of the subject) and/or the height, weight, and/or age of the subject.

Toxicity and therapeutic efficacy of such compositions can be determined by known pharmaceutical procedures in cell cultures or experimental animals (e.g., animal models of cancer, toxicity, or infection). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibit a high therapeutic index are preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such compositions lies generally within a range of circulating concentrations of the compositions that include the $ED_{50}$ with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Plasma concentrations may be measured, for example, by high performance liquid chromatography (HPLC). In some embodiments, e.g., where local administration is desired, cell culture or animal modeling can be used to determine a dose required to achieve a therapeutically effective concentration within the local site.

In some embodiments of any of the methods described herein, a particle can be administered to a mammal in conjunction with one or more additional therapeutic agents (e.g., therapeutic agents for treating an infection or treating cancer).

In some embodiments, the particle and additional therapeutic agent can be administered to the mammal using different routes of administration. For example, the additional therapeutic agent can be administered subcutaneously or intramuscularly and the particle can be administered intravenously.

In some embodiments, a method of the invention comprises measuring the concentration of a biomolecule in a subject. For example, the method may comprise measuring the concentration of a biomolecule in the blood of a subject. The method may further comprise administering to the subject a composition comprising a plurality of particles that target the biomolecule (i.e., a plurality of particles as described herein, comprising an agent that selectively binds to the biomolecule). The measuring step may allow for the appropriate dosing of the particles. Thus, the measuring step may be performed prior to administering the composition. Nevertheless, the measuring step may be performed after administering the composition, e.g., to assess the efficacy of the composition. The method may further comprise administering to the subject a second or subsequent dose of a composition comprising a plurality of particles, e.g., if warranted in light of the measured concentration of the biomolecule. In this way, the concentration of a biomolecule may be titrated, e.g., by iteratively measuring the concentration of the biomolecule in the subject and administering the composition at varying doses or rates. Similarly, the number of particles administered to the subject may be titrated against the concentration of the biomolecule that is targeted by the particles.

Titrating either the concentration of a biomolecule in a subject or the number of particles administered to the subject may be particularly useful, for example, when the biomolecule contributes to a deleterious local effect (e.g., in a tumor) but has a beneficial systemic effect. Thus, a plurality of particles may be inserted either into or adjacent to a location in a patient to bind the biomolecule in the location, and the systemic concentration of the biomolecule may be monitored to determine whether additional particles may be safely administered to the subject.

Titrating either the concentration of a biomolecule in a subject or the number of particles administered to the subject may also be useful, for example, to maintain a concentration of the biomolecule within a predetermined range. The predetermined range may be a range that is associated with a healthy state, e.g., wherein the subject is overproducing the biomolecule, or the predetermined range may be a therapeutic range. Such titration may be particularly useful in methods of treating diseases caused by the over-secretion of hormones. For example, a particle may comprise an agent that binds to the biomolecule growth hormone, e.g., for use in a method of treating acromegaly or gigantism, and such particles may be titrated to ensure that levels of growth hormone remain in a healthy range. A particle may comprise an agent that binds to the biomolecule thyroxine and/or triiodothyronine, e.g., for use in a method of treating hyperthyroidism, and such particles may be titrated to ensure that levels of thyroxine and/or triiodothyronine remain in a healthy range. A particle may comprise an agent that binds to the biomolecule adrenocorticotropic hormone or cortisol, e.g., for use in a method of treating Cushing's disease, and such particles may be titrated to ensure that levels of adrenocorticotropic hormone and/or cortisol remain in a healthy range. An example of a therapeutic range includes the titration of a blood clotting factor, such as Factor VIII, Factor IX, or Factor XI, to a range that inhibits blood clotting for a period of time. Such a range may be below a normal, healthy concentration, and yet the therapeutic range may be useful, for example, to inhibit thrombosis or ischemia in certain patients.

XVII. Adoptive Cell Transfer Therapy

A method may comprise administering a composition comprising a plurality of particles as described herein to a subject who has received adoptive cell transfer therapy (ACT). A method may comprise administering a composition comprising a plurality of particles as described herein to a subject who might benefit from adoptive cell transfer therapy. The method may further comprise administering adoptive cell transfer therapy to the subject, e.g., before, after, or concurrently with the administration of the composition comprising a plurality of particles.

Adoptive cell transfer therapy may comprise administering a composition comprising lymphocytes to a subject. The lymphocytes may be T lymphocytes (i.e., T cells), such as tumor-infiltrating lymphocytes (TILs). In preferred embodiments, the lymphocytes are T lymphocytes, such as tumor-infiltrating lymphocytes. The composition comprising lymphocytes may be substantially free from cells that are not lymphocytes, e.g., the composition may be substantially free from cells and cell fragments derived from myeloid progenitor cells (e.g., erythrocytes, mast cells, basophils, neutrophils, eosinophils, monocytes, macrophages, megakaryocytes, platelets). The composition comprising lymphocytes may be substantially free from cells that are not T cells, e.g., the composition may be substantially free from natural killer cells, B cells, and/or plasma cells. The composition comprising lymphocytes may comprise cells wherein the cells consist essentially of T cells. The composition comprising lymphocytes may be substantially free from cells that are not tumor-infiltrating lymphocytes. The composition comprising lymphocytes may comprise tumor-infiltrating lymphocytes. The composition comprising lymphocytes may comprise cells wherein the cells consist essentially of tumor-infiltrating lymphocytes.

The composition comprising lymphocytes may comprise recombinant lymphocytes, e.g., wherein the lymphocytes comprise an exogenous nucleic acid. For example, the lymphocytes may comprise a chimeric antigen receptor (CAR). Similarly, the lymphocytes may comprise a gene knockout, e.g., which reduces the risk of a graft-versus-host immune response or a host-versus-graft immune response (e.g., for a non-autologous transplant, such as an allogeneic transplant). In some embodiments, the composition comprising lymphocytes may comprise recombinant T cells, such as recombinant tumor-infiltrating lymphocytes, e.g., the lymphocytes may be recombinant T cells, such as recombinant tumor-infiltrating lymphocytes.

Adoptive cell transfer therapy may comprise an autologous transplant or a non-autologous transplant, such as an allogeneic transplant.

The subject may have received adoptive cell transfer therapy about 1 year prior to administering the composition to the subject, such as about 6 months, about 5 months, about 4 months, about 3 months, about 2 months, about 1 month, about 4 weeks, about 3 weeks, about 2 weeks, about 14 days, about 13 days, about 12 days, about 11 days, about 10 days, about 9 days, about 8 days, about 7 days, about 6 days, about 5 days, about 4 days, about 3 days, about 2 days, or 1 day prior to administering the composition to the subject. The method may comprise administering a composition comprising a plurality of particles to a subject less than about 1 year after administering a composition comprising lymphocytes to the subject, such as less than about 6 months, about 5 months, about 4 months, about 3 months, about 2 months, about 1 month, about 4 weeks, about 3 weeks, about 2 weeks, about 14 days, about 13 days, about 12 days, about 11 days, about 10 days, about 9 days, about 8 days, about 7 days, about 6 days, about 5 days, about 4 days, about 3 days, about 2 days, or 1 day after administering a composition comprising lymphocytes to the subject. The method may comprise administering a composition comprising a plurality of particles to a subject within about 1 year of administering a composition comprising lymphocytes to the subject, such as within about 6 months, about 5 months, about 4 months, about 3 months, about 2 months, about 1 month, about 4 weeks, about 3 weeks, about 2 weeks, about 14 days, about 13 days, about 12 days, about 11 days, about 10 days, about 9 days, about 8 days, about 7 days, about 6 days, about 5 days, about 4 days, about 3 days, about 2 days, or within about 1 day of administering a composition comprising lymphocytes to the subject.

Adoptive cell transfer therapy may be particularly effective in subjects who have a neoplasm, such as cervical cancer, breast cancer, lymphoma, leukemia, chronic lymphocytic leukemia, follicular lymphoma, large-cell lymphoma, lymphoblastic leukemia, myeloid leukemia, multiple myeloma, bile duct cancer, colorectal cancer, neuroblastoma, lung cancer, sarcoma, synovial sarcoma, or melanoma. Nevertheless, adoptive cell transfer therapy may be useful to treat other diseases, such as serious or life-threatening infections (e.g., HIV).

XVIII. Selected Applications Related to Neoplasms

In some embodiments, the particles described herein can be useful for treating a subject with cancer. Exemplary agents useful in the particle compositions described herein, and/or soluble biomolecules which can be scavenged by such particles, are described herein (e.g., Table 2) and known in the art. For example, particles capable of scavenging sTNFR, MMP2, MMP9, sIL-2R, sIL-1 receptor, and the like are useful for treating a cancer and/or for enhancing an immune response to a cancer by relieving immune dis-inhibition.

The immune dis-inhibition approach to immunotherapy is based, in part, on the concept that many cancer patients are generally immunologically competent overall but their immune systems are locally inhibited in the microenvironments of their tumors. If this inhibition of the immune system is relieved by administering a particle of the disclosure, the patient's own immune system can act on the tumor. Thus, in certain embodiments, particles of the disclosure provide an immunotherapy approach without the need for hyper-stimulating the patient's immune system by adding exogenous, active cytokines intended to bind cell surface receptors to provoke an immune response and/or without otherwise hyper-stimulating the patient's immune system.

Without being bound by theory, because the cancer patients are, generally, immunologically competent, the ability of lymphocytes to recognize tumor antigens is generally unaffected by the tumor. Thus, lymphocytes are drawn to the tumor microenvironment as they would be to any aberrant cell cluster, at which point cytokines and cytotoxic factors, such as Tumor Necrosis Factor (TNF, such as TNF alpha, the main cytotoxic "sword" of the immune system) cleave from lymphocytes into the microenvironment. If the cancer cells were instead virally infected cells, the TNF (such as TNF alpha) would engage a TNF receptor (TNFR) on the surface of the infected cell, resulting in rapid destruction by either apoptosis or oxidative stress depending on whether an R1 or R2 type receptor for TNF is engaged. In other words, in the context of a normal immune response that is not being stimulated by the presence of a tumor and/or tumor antigens, TNF deployed by lymphocytes would be available to bind cell surface TNF receptors (R1 and/or R2 receptors) as part of mounting an immune response. Even in the tumor context, the lymphocytes are deployed to the tumor site.

However, many types of cancer cells behave differently than other aberrant cell types, such as virally infected cells, in that they overproduce TNF receptors (both types) and shed them into a cloud around the tumor. Thus, the microenvironment of cancer cells and/or tumors includes amounts of soluble TNF receptors. Without being bound by theory, the soluble TNF receptor concentration in the tumor microenvironment exceed that found in the microenvironment of healthy cells, such as healthy cells of the same tissue type. Additionally or alternatively, the rate and extent of TNF receptor shedding is greater for cancer cells than from healthy cells. Moreover, without being bound by theory, the concentrations of soluble TNF receptor found in the plasma of cancer patients may, in certain embodiments, be higher than in healthy patients.

Regardless of the mechanism, in this model, these shed, soluble TNF receptors bind to the TNF endogenously released by the recruited lymphocytes, neutralizing the endogenous TNF and effectively creating a bubble of immunologic privilege around the tumor, within which the tumor continues to grow and shed additional TNF receptors. In other words, the shed, soluble TNF receptors soak up the TNF alpha endogenously produced by lymphocytes and prevent or inhibit that TNF from binding cell surface TNF receptors on the cancer cells. This decreases or eliminates the TNF available to bind cell surface TNF receptors on the cancer cells. The soluble TNF receptors essentially outcompete for binding to TNF alpha, and thus, decrease the activity of TNF, such as TNF alpha for binding cell surface TNF receptors.

The above scenario can similarly play out in the context of IL-2 and shed, soluble IL-2 receptors.

In some embodiments, the biomolecule is a toxin released by a cancer cell upon apoptosis.

The present disclosure provides pharmacologic approaches that can be deployed systemically or locally to relieve the inhibition of the immune system created by shed receptors in cancer (e.g., immune dis-inhibition). The present disclosure provides methods and compositions for decreasing the amount and/or activity (e.g., neutralizing the activity) of soluble TNF receptors and/or soluble IL-2 receptors (or any other soluble biomolecules that result in immune dis-inhibition) such as in the microenvironment of cancer cells and tumors. Without being bound by theory, decreasing the amount and/or activity of, for example, soluble TNF receptors (e.g., such as in the tumor microenvironment), may be used as part of a method for inhibiting proliferation, growth, or survival of a cell, such as a cancer cell. In certain embodiments, it may be used for inhibiting survival of a cell, such as a cancer cell. Exemplary methods and agents are described herein.

Regulatory T-cells (TREGs) can secrete the same ligands as cancer cells as a way of tamping down the immune response to avoid, e.g., autoimmune disease caused by overactive T-cells or prolonged T-cell function. For instance, CD80/B7-1 and CD86/B7-2 bind to the CTLA-4 receptor on T-cells and inhibit T-cell activity. Rather than blockading the CTLA-4 receptor, the particles described herein can be designed to scavenge CD80/B7-1 and/or CD86/B7-2. Likewise, the particles described herein can be designed to scavenge other immune checkpoint inhibitors, such as PD-L1, e.g., using particles comprising PD-1 receptor. Such particle compositions offer several benefits over other approaches to stimulating the immune system for the treatment of cancer.

The target may be soluble PD-L2, e.g., to inhibit an interaction between soluble PD-L2 and PD1. The agent may be PD1. Inhibition of an interaction between soluble PD-L2 and PD1 may allow for PD1 to bind a membrane-bound version of PD-L2, thereby favoring apoptosis of a cancer cell. The target may be soluble PD1. The agent may be a ligand of PD1, such as PD-L2, soluble PD-L2 or a variant thereof, or an anti-PD1 antibody, such as nivolumab or pembrolizumab. Particles targeting PD1 (i.e., soluble PD1) and ligands thereof may be particularly useful for treating autoimmune disease, in addition to other diseases and conditions.

The target may be soluble CTLA4, e.g., to inhibit an interaction between B7-1 or B7-2 and soluble CTLA4. The agent may be a ligand of CTLA4 such as soluble B7-1, soluble B7-2 or variants thereof, or an anti-CTLA4 antibody, such as ipilimumab or tremelimumab. Inhibition of interaction between B7-1 or B7-2 and soluble CTLA4 may allow for B7-1 or B7-2 to bind to CD28 on T cells, thereby favoring activation of T cells. Particles targeting CTLA4 (i.e., soluble CTLA4) may be particularly useful for treating melanomas and lung cancer, such as non-small cell lung cancer, in addition to other diseases and conditions.

The agent may be a protein that specifically binds adenosine, such as the adenosine-binding portion of an adenosine receptor. The target may be adenosine. Particles targeting adenosine may be particularly useful for treating solid tumors, and such particles may be injected into a solid tumor, e.g., to inhibit adenosine signaling within the tumor microenvironment.

The agent may be osteoprotegerin or a ligand-binding portion thereof, e.g., for selectively binding ligands of osteoprotegerin. Particles targeting ligands of osteoprotegerin may be particularly useful for treating cancer, such as breast cancer, in addition to other diseases and conditions.

In some embodiments, the subject is one who has, is suspected of having, or is at risk for developing a cancer. In some embodiments, the subject is one who has, is suspected of having, or is at risk for developing an autoimmune disease.

As used herein, a subject "at risk for developing" a cancer is a subject having one or more (e.g., two, three, four, five, six, seven, or eight or more) risk factors for developing a cancer. For example, a subject at risk of developing a cancer may have a predisposition to develop a cancer (i.e., a genetic predisposition to develop a cancer such as a mutation in a tumor suppressor gene (e.g., mutation in BRCA1, p53, RB, or APC) or has been exposed to conditions that can result in the condition). Thus, a subject can be one "at risk of developing a cancer when the subject has been exposed to mutagenic or carcinogenic concentrations of certain compounds (e.g., carcinogenic compounds in cigarette smoke such as acrolein, arsenic, benzene, benz[a]anthracene, benzo[a]pyrene, polonium-210 (Radon), urethane, or vinyl chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., glioblastoma such as glioblastoma multiforme), melanoma, thyroid cancer, ovarian cancer, testicular cancer, prostate cancer, cervical cancer, vaginal cancer, or bladder cancer. In certain preferred embodiments, a patient (or subject) has brain cancer, endometrial cancer, prostate cancer, renal cancer, or squamous cell cancer (e.g., squamous cell cancer of the head and neck), each of which are particularly sensitive to extracellular biomolecules that may exacerbate the disease.

Similarly, a subject at risk for developing an infection is one having one or more risk factors that increase the likelihood of exposure to a pathogenic microorganism.

A subject "suspected of having" a cancer or an infection is one having one or more symptoms of the cancer or infection. It should be understood that subjects at risk for developing, or suspected of having, a cancer or an infection does not include all subjects within the species of interest.

In some embodiments, the methods include determining whether the subject has a cancer.

XIX. Selected Applications Related to Inflammatory and Autoimmune Disorders

In some embodiments, the particles described herein can be used for treating an inflammatory disorder and/or an autoimmune disorder. Exemplary agents useful in the particle compositions described herein, and/or soluble biomolecules which can be scavenged by such particles, are described herein (e.g., Table 2) and known in the art. For example, particles capable of scavenging cytokines (e.g., TNFα or interleukins, such as IL-2, IL-6, or IL-1) or chemokines (e.g., CXCL8 or CXCL1) can be useful for treating a variety of autoimmune and/or inflammatory disorders.

The agent may be soluble CD28 or a ligand-binding portion thereof, e.g., for selectively binding ligands of CD28, such as soluble B7 (e.g., soluble B7-1 or soluble B7-2). The agent may be galiximab. The target may be a ligand of CD28, such as soluble B7. Particles targeting ligands of CD28 may be particularly useful for preventing or treating lupus, such as systemic lupus erythematosus, in addition to other diseases and conditions.

The agent may be an anti-B7-H4 antibody, e.g., for selectively binding soluble B7-H4. The target may be soluble B7-H4. Particles targeting soluble B7-H4 may be particularly useful for treating arthritis, such as rheumatoid arthritis and juvenile idiopathic arthritis, in addition to other diseases and conditions.

The agent may be soluble CD278 (inducible co-stimulator; "ICOS") or a ligand-binding portion thereof, e.g., for selectively binding ligands of CD278, such as ICOSL (inducible co-stimulator ligand; CD275). The target may be a ligand of CD278, such as ICOSL. Particles targeting ligands of CD278 may be particularly useful for preventing or treating lupus, such as systemic lupus erythematosus, in addition to other diseases and conditions.

The agent may be an anti-CD275 antibody, e.g., for selectively binding CD275 (inducible co-stimulator ligand; "ICOSL"). The target may be CD275. Particles targeting CD275 may be particularly useful for preventing or treating lupus, such as systemic lupus erythematosus, in addition to other diseases and conditions.

The agent may be an anti-CD40L antibody, such as dapirolizumab, ruplizumab, or toralizumab, e.g., for selectively binding CD40L (CD40 Ligand; CD154). The target may be CD40L. Particles targeting CD40L may be particularly useful for preventing or treating lupus, such as systemic lupus erythematosus, arthritis, such as rheumatoid arthritis, collagen-induced arthritis, and juvenile idiopathic arthritis, and Sjogren's syndrome, in addition to other diseases and conditions.

The agent may be soluble CD134 (OX40) or a ligand-binding portion thereof, e.g., for selectively binding ligands of CD134, such as CD252 (OX40 ligand; "OX40L"). The target may be a ligand of CD134, such as CD252. Particles targeting ligands of CD134 may be particularly useful for preventing or treating lupus, such as lupus nephritis, symptoms thereof, such as glomerulonephritis, and systemic sclerosis, in addition to other diseases and conditions.

The agent may be 4-1BB (CD137) or a ligand-binding portion thereof, e.g., for selectively binding ligands of 4-1BB, such as soluble 4-1BB ligand (soluble 4-1BBL). The target may be a ligand of 4-1BB, such as soluble 4-1BB ligand. Particles targeting ligands of 4-1BB may be particularly useful for preventing or treating lupus, such as systemic lupus erythematosus, and arthritis, such as rheumatoid arthritis, in addition to other diseases and conditions.

The agent may be 4-1BB ligand, e.g., for selectively binding soluble 4-1BB (soluble CD137). The agent may be an anti-4-1BB antibody, such as urelumab. The target may be soluble 4-1BB. Particles targeting soluble 4-1BB may be particularly useful for preventing or treating arthritis, such as rheumatoid arthritis, in addition to other diseases and conditions, including cancer. In some embodiments, the inflammatory disorder can be, e.g., acute disseminated encephalomyelitis; Addison's disease; Ankylosing spondylitis; Antiphospholipid antibody syndrome; Autoimmune hemolytic anemia; Autoimmune hepatitis; Autoimmune inner ear disease; Bullous pemphigoid; Chagas disease; Chronic obstructive pulmonary disease; Coeliac disease; Dermatomyositis; Diabetes mellitus type 1; Diabetes mellitus type 2; Endometriosis; Goodpasture's syndrome; Graves' disease; Guillain-Barre syndrome; Hashimoto's disease; Idiopathic thrombocytopenic purpura; Interstitial cystitis; Systemic lupus erythematosus (SLE); Metabolic syndrome, Multiple sclerosis; Myasthenia gravis; Myocarditis, Narcolepsy; Obesity; Pemphigus Vulgaris; Pernicious anaemia; Polymyositis; Primary biliary cirrhosis; Rheumatoid arthritis; Schizophrenia; Scleroderma; Sjogren's syndrome; Vasculitis; Vitiligo; Wegener's granulomatosis; Allergic rhinitis; Prostate cancer; Non-small cell lung carcinoma; Ovarian cancer; Breast cancer; Melanoma; Gastric cancer; Colorectal cancer; Brain cancer; Metastatic bone disorder; Pancreatic cancer; a Lymphoma; Nasal polyps; Gastrointestinal cancer; Ulcerative colitis; Crohn's disorder; Collagenous colitis; Lymphocytic colitis; Ischaemic colitis; Diversion colitis; Behcet's syndrome; Infective colitis; Indeterminate colitis; Inflammatory liver disorder, Endotoxin shock, Rheumatoid spondylitis, Ankylosing spondylitis, Gouty arthritis, Polymyalgia rheumatica, Alzheimer's disorder, Parkinson's disorder, Epilepsy, AIDS dementia, Asthma, Adult respiratory distress syndrome, Bronchitis, Cystic fibrosis, Acute leukocyte-mediated lung injury, Distal proctitis, Wegener's granulomatosis, Fibromyalgia, Bronchitis, Cystic fibrosis, Uveitis, Conjunctivitis, Psoriasis, Eczema, Dermatitis, Smooth muscle proliferation disorders, Meningitis, Shingles, Encephalitis, Nephritis, Tuberculosis, Retinitis, Atopic dermatitis, Pancreatitis, Periodontal gingivitis, Coagulative Necrosis, Liquefactive Necrosis, Fibrinoid Necrosis, Hyperacute transplant rejection, Acute transplant rejection, Chronic transplant rejection, Acute graft-versus-host disease, Chronic graft-versus-host disease, or combinations of any of the foregoing. In some embodiments, the autoimmune or inflammatory disorder can be, e.g., colitis, multiple sclerosis, arthritis, rheumatoid arthritis, osteoarthritis, juvenile arthritis, psoriatic arthritis, acute pancreatitis, chronic pancreatitis, diabetes, insulin-dependent diabetes mellitus (IDDM or type I diabetes), insulitis, inflammatory bowel disease, Crohn's disease, ulcerative colitis, autoimmune hemolytic syndromes, autoimmune hepatitis, autoimmune neuropathy, autoimmune ovarian failure, autoimmune orchitis, autoimmune thrombocytopenia, reactive arthritis, ankylosing spondylitis, silicone implant associated autoimmune disease, Sjogren's syndrome, systemic lupus erythematosus (SLE), vasculitis syndromes (e.g., giant cell arteritis, Behcet's disease, and Wegener's granulomatosis), vitiligo, secondary hematologic manifestation of autoimmune diseases (e.g., anemias), drug-induced autoimmunity, Hashimoto's thyroiditis, hypophysitis, idiopathic thrombocytic pupura, metal-induced autoimmunity, myasthenia gravis, pemphigus, autoimmune deafness (e.g., Meniere's disease), Goodpasture's syndrome, Graves' disease, HIV-related autoimmune syndromes, and/or Gullain-Barre disease.

In some embodiments, the autoimmune or inflammatory disorder is a hypersensitivity reaction. As used herein, "hypersensitivity" refers to an undesirable immune system response. Hypersensitivity is divided into four categories. Type I hypersensitivity includes allergies (e.g., Atopy, Anaphylaxis, or Asthma). Type II hypersensitivity is cytotoxic/antibody mediated (e.g., Autoimmune hemolytic anemia, Thrombocytopenia, Erythroblastosis fetalis, or Goodpasture's syndrome). Type III is immune complex diseases (e.g., Serum sickness, Arthus reaction, or SLE). Type IV is delayed-type hypersensitivity (DTH), Cell-mediated immune memory response, and antibody-independent (e.g., Contact dermatitis, Tuberculin skin test, or Chronic transplant rejection). As used herein, "allergy" means a disorder characterized by excessive activation of mast cells and basophils by IgE. In certain instances, the excessive activation of mast cells and basophils by IgE results (either partially or fully) in an inflammatory response. In certain instances, the inflammatory response is local. In certain instances, the inflammatory response results in the narrowing of airways (i.e., bronchoconstriction). In certain instances, the inflammatory response results in inflammation of the nose (i.e., rhinitis). In certain instances, the inflammatory response is systemic (i.e., anaphylaxis).

In some embodiments, the methods include determining whether the subject has an autoimmune disease.

XX. Selected Applications Related to Pathogens and Toxins

In some embodiments, the particles described herein can be designed to bind to microorganisms (e.g., viruses or bacteria) or components of microorganisms, such as endotoxin. Accordingly, the particles described herein can be useful to treat, e.g., an infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. In addition, bacterial, fungal and other pathogenic infections are included, such as *Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis*, Group B *Streptococcus* sp., *Microplasma hominis, Hemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobacillus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever), and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain 0157:H7, *Vibrio cholerae, Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L. mexicana*), and *Plasmodium*.

The target may be a viral protein. The viral protein may be from arbovirus, adenovirus, alphavirus, arenaviruses, astrovirus, BK virus, bunyaviruses, calicivirus, cercopithecine herpes virus 1, Colorado tick fever virus, coronavirus, Coxsackie virus, Crimean-Congo hemorrhagic fever virus, cytomegalovirus, Dengue virus, ebola virus, echinovirus, echovirus, enterovirus, Epstein-Barr virus, flavivirus, foot-and-mouth disease virus, hantavirus, hepatitis A, hepatitis B, hepatitis C, herpes simplex virus I, herpes simplex virus II, human herpes virus, human immunodeficiency virus type I (HIV-I), human immunodeficiency virus type II (HIV-II), human papillomavirus, human T-cell leukemia virus type I, human T-cell leukemia virus type II, influenza, Japanese encephalitis, JC virus, Junin virus, lentivirus, Machupo virus, Marburg virus, measles virus, mumps virus, naples virus, norovirus, Norwalk virus, orbiviruses, orthomyxovirus, papillomavirus, papovavirus, parainfluenza virus, paramyxovirus, parvovirus, picornaviridae, poliovirus, polyomavirus, poxvirus, rabies virus, reovirus, respiratory syncytial virus, rhinovirus, rotavirus, rubella virus, sapovirus, smallpox, togaviruses, Toscana virus, varicella zoster virus, West Nile virus, or Yellow Fever virus. The viral protein may be, for example, a viral capsid protein or a viral envelope protein.

The target may be a bacterial protein or a component of a bacterial cell wall. For example, the bacterial protein or cell wall component may be from *Actinomyces israelii, Bacillus anthracis, Bacillus cereus, Bacteroides fragilis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni,*

*Chlamydia pneumoniae, Chlamydia trachomatis, Chlamydophila psittaci, Clostridium botulinum, Clostridium difficile, Clostridium perfringens, Clostridium tetani, Corynebacterium diptheriae, Ehrlichia canis, Ehrlichia chaffeensis, Enterococcus faecalis, Enterococcus faecium, Escherichia coli, Francisella tularensis, Haemophilus influenzae, Haemophilus vaginalis, Helicobacter pylori, Klebsiella pneumoniae, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Nocardia asteroides, Rickettsia rickettsii, Salmonella typhi, Salmonella typhimurium, Shigella sonnei, Shigella dysenteriae, Staphylococcus aureus, Staphylococcus epidermidis, Staphylococcus saprophyticus, Streptococcus agalactiae, Streptococcus pneumoniae, Streptococcus pyogenes, Streptococcus viridans, Treponema pallidum, Ureaplasma urealyticum, Vibrio cholerae, Yersinia pestis, Yersinia enterocolitica,* or *Yersinia pseudotuberculosis.*

The target may be a yeast or fungal protein or a component of a yeast or fungal cell wall. For example, the yeast or fungal protein or cell wall component may be from *Apophysomyces variabilis, Aspergillus clavatus, Aspergillus flavus, Aspergillus fumigatus, Basidiobolus ranarum, Candida albicans, Candida glabrata, Candida guilliermondii, Candida krusei, Candida lusitaniae, Candida parapsilosis, Candida tropicalis, Candida stellatoidea, Candida viswanathii, Conidiobolus coronatus, Conidiobolus incongruous, Cryptococcus albidus, Cryptococcus gattii, Cryptococcus laurentii, Cryptococcus neoformans, Encephalitozoon intestinalis, Enterocytozoon bieneusi, Exophiala jeanselmei, Fonsecaea compacta, Fonsecaea pedrosoi, Geotrichum candidum, Histoplasma capsulatum, Lichtheimia corymbifera, Mucor indicus, Paracoccidioides brasiliensis, Phialophora verrucosa, Pneumocystis carinii, Pneumocystis jirovecii, Pseudallescheria boydii, Rhinosporidium seeberi, Rhodotorula mucilaginosa, Stachybotrys chartarum, Syncephalastrum racemosum,* or *Rhizopus oryzae.*

The target may be a protozoan protein. The protozoan protein may be from *Cryptosporidium, Giardia intestinalis, Giardia lamblia, Leishmania aethiopica, Leishmania braziliensis, Leishmania donovani, Leishmania infantum, Leishmania major, Leishmania mexicana, Leishmania tropica, Plasmodium coatneyi, Plasmodium falciparum, Plasmodium garnhami, Plasmodium inui, Plasmodium odocoilei, Trichomonas gallinae, Trichomonas vaginalis, Tritrichomonas foetus, Trypanosoma brucei, Trypanosoma cruzi, Trypanosoma equiperdum, Trypanosoma evansi, Trypanosoma lewisi, Trypanosoma pestanai, Trypanosoma suis,* or *Trypanosoma vivax,*

The target may be a toxin, such as a bacterial toxin, a plant toxin, or a zootoxin. The toxin may be, for example, melittin, brevetoxin, tetrodotoxin, chlorotoxin, tetanus toxin, bungarotoxin, *Clostridium botulinum* toxin, ricin, epsilon toxin of *Clostridium perfringens, Staphylococcus* enterotoxin B, or endotoxin.

The target may be a bacterial cell-surface lipopolysaccharide, lipopolysaccharide-binding protein, lipoteichoic acid, a bacterial lipoprotein, a bacterial peptidoglycan, lipoarabinomannan, a bacterial flagella protein (e.g., flagellin), profilin, HSP70, zymosan, double-stranded RNA, bacterial ribosomal RNA, or DNA comprising unmethylated CpG. treating or preventing an infection caused by a pathogen, comprising administering to a subject a composition comprising a plurality of particles as described herein. In some embodiments, the particle comprises an agent that specifically binds to a biomolecule of a pathogen, or a biomolecule produced by the pathogen. In some embodiments, the particle comprises an agent that specifically binds to a biomolecule of the subject (e.g., a biomolecule produced by the subject), such as a cytokine or peroxiredoxin (e.g., peroxiredoxin 1 or peroxiredoxin 2). For example, a method may comprise administering to a subject a composition comprising a plurality of particles that selectively bind TNFα, interleukin 1, interleukin 6, interleukin 8, interleukin 12, interferon gamma, macrophage migration inhibitory factor, GM-CSF, and/or a blood clotting factor, e.g., to treat or prevent sepsis associated with an infection caused by a pathogen. In some embodiments, the method is a method of treating or preventing sepsis, e.g., comprising administering to a subject a composition comprising a plurality of particles as described herein.

The target may be paracetamol (acetaminophen). The agent may be an antibody that specifically binds paracetamol, or an antigen-binding portion thereof. Particles that target paracetamol may be particularly useful for treating or preventing paracetamol toxicity.

XXI. Selected Applications Related to Diet and Metabolism

In some embodiments, the particles described herein can be used to treat obesity, an eating disorder, reduce body mass, promote healthy eating, or reduce the appetite of a subject. For example, in some embodiments, particles comprising agents (e.g., antibodies or soluble forms of the ghrelin receptor (GHSR)) that bind to ghrelin can be administered to a subject (e.g., an overweight or obese subject) to reduce the subject's appetite, treat obesity or an obesity-related disorder, or a metabolic disorder.

As used herein, a metabolic disorder can be any disorder associated with metabolism, and examples include but are not limited to, obesity, central obesity, insulin resistance, glucose intolerance, abnormal glycogen metabolism, type II diabetes, hyperlipidemia, hypoalbuminemia, hypertriglyceridemia, metabolic syndrome, syndrome X, a fatty liver, fatty liver disease, polycystic ovarian syndrome, and *acanthosis nigricans.*

"Obesity" refers to a condition in which the body weight of a mammal exceeds medically recommended limits by at least about 20%, based upon age and skeletal size. "Obesity" is characterized by fat cell hypertrophy and hyperplasia. "Obesity" may be characterized by the presence of one or more obesity-related phenotypes, including, for example, increased body mass (as measured, for example, by body mass index, or "BMI"), altered anthropometry, basal metabolic rates, or total energy expenditure, chronic disruption of the energy balance, increased Fat Mass as determined, for example, by DEXA (Dexa Fat Mass percent), altered maximum oxygen use ($VO_2$), high fat oxidation, high relative resting rate, glucose resistance, hyperlipidemia, insulin resistance, and hyperglycemia. See also, for example, Hopkinson et al., *Am J Clin Nutr* 65(2):432-8 (1997) and Butte et al., *Am J Clin Nutr* 69(2):299-307 (1999). "Overweight" individuals are generally having a body mass index (BMI) between 25 and 30. "Obese" individuals or individuals suffering from "obesity" are generally individuals having a BMI of 30 or greater. Obesity may or may not be associated with insulin resistance.

An "obesity-related disease" or "obesity related disorder" or "obesity related condition," which are all used interchangeably, refers to a disease, disorder, or condition, which is associated with, related to, and/or directly or indirectly caused by obesity. The "obesity-related diseases," or the "obesity-related disorders" or the "obesity related conditions" include but are not limited to, coronary artery disease/ cardiovascular disease, hypertension, cerebrovascular disease, stroke, peripheral vascular disease, insulin resistance, glucose intolerance, diabetes mellitus, hyperglycemia, hyperlipidemia, dyslipidemia, hypercholesteremia, hypertriglyceridemia, hyperinsulinemia, atherosclerosis, cellular proliferation and endothelial dysfunction, diabetic dyslipidemia, HIV-related lipodystrophy, peripheral vessel disease, cholesterol gallstones, cancer, menstrual abnormalities, infertility, polycystic ovaries, osteoarthritis, sleep apnea, metabolic syndrome (Syndrome X), type II diabetes, diabetic complications including diabetic neuropathy, nephropathy, retinopathy, cataracts, heart failure, inflammation, thrombosis, congestive heart failure, and any other cardiovascular disease related to obesity or an overweight condition and/or obesity related asthma, airway, and pulmonary disorders.

In yet another aspect, the disclosure features a method for increasing muscle mass or muscle strength in a subject in need thereof, which method comprises administering to the subject one or more of the compositions described herein in an amount sufficient to increase muscle mass or muscle strength in the subject. For example, particles comprising an agent (e.g., an antibody or soluble activin receptor) that binds to myostatin can be administered to a subject to increase muscle mass.

In some embodiments, the subject is one having a muscle disorder (e.g., a muscle wasting disorder).

A muscle wasting disorder, as used herein, encompasses disorders or conditions in which muscle wasting is one of the primary symptoms, such as muscular dystrophy, spinal cord injury, neurodegenerative diseases, anorexia, sarcopenia, cachexia, muscular atrophy due to immobilization, prolonged bed rest, or weightlessness, and the like, as well as disorders in which an abnormally high fat-to-muscle ratio is implicated in a disease or pre-disease state, e.g., Type II diabetes or Syndrome X.

Atrophy of skeletal muscle occurs in muscles of adult animals as a result of lack of use, aging, starvation, and as a consequence of a variety of diseases, disorders, and conditions such as sepsis, muscular dystrophy, AIDS, aging, and cancer. The loss of muscle is generally characterized by decreases in protein content, force production, fatigue resistance, and muscle fiber diameter. These decreases can be attributed to both a decrease in protein synthesis and an increase in protein degradation. Muscle wasting and related conditions to which the compositions and methods of the invention are directed include any condition in which enhanced muscle growth, or diminishment of muscle wasting, produces a therapeutically or otherwise desirable result. Conditions include muscular dystrophy, sarcopenia, cachexia, diabetes mellitus, and the improvement of muscle mass where such improvement is ethical and desirable, e.g., in food animals.

One class of muscle wasting disorders, as mentioned above, is the muscular dystrophies. These are a heterogeneous group of neuromuscular disorders, which include the most common type, Duchenne muscular dystrophy (DMD), multiple types of limb girdle MD (LGMD) and other congenital MDs (CMD). Progressive muscle damage and muscle loss, tissue inflammation and replacement of healthy muscle with fibrous and fatty tissues result in muscle wasting in muscular dystrophy. Extreme muscle loss is one of the most prominent signs of the disease, and leads to complications and symptoms, including death.

Sarcopenia is the age-related loss of muscle mass, strength and function. It begins in the fourth decade of life and accelerates after the age of approximately 75 years. Many factors, including physical inactivity, motor-unit remodeling, decreased hormone levels, and decreased protein synthesis, may all contribute to sarcopenia. With the exception of physical inactivity, all of these may be subject to genetic control where gene modulation may be useful. For example, the rate of muscle protein synthesis and protein breakdown affects sarcopenia. The balance of protein synthesis and breakdown determines the protein content in the body. Research has consistently reported that muscle protein synthesis rates are lower in older adults when compared to younger adults. A decrease in muscle protein catabolism, effected by, e.g., gene modulation, could result in slowing or reversal of the loss of muscle mass.

XXII. Selected Applications Related to Aging and Neurodegenerative Disorders

In some embodiments, compositions described herein are useful for promoting healthy aging in subject. For example, particles comprising an agent (e.g., an antibody or soluble form of a receptor) capable of binding to any one of TGFβ1, CCL11, MCP-1/CCL2, beta-2 microglobulin, GDF-8/myostatin, or haptoglobin can be used to promote healthy aging in a subject, extend the lifespan of a subject, prevent or delay the onset of an age-related disorder in a subject, or treat a subject suffering from an age-related disorder. In some embodiments, particles comprising an agent that binds to TGFβ1 can be used to enhance/promote neurogenesis and/or muscle regeneration in a subject, e.g., an elderly subject. In some embodiments, the age-related disorder is a cardiovascular disease. In some embodiments, the age-related disorder is a bone loss disorder. In some embodiments, the age-related disorder is a neuromuscular disorder. In some embodiments, the age-related disorder is a neurodegenerative disorder or a cognitive disorder. In some embodiments, the age-related disorder is a metabolic disorder. In some embodiments, the age-related disorder is sarcopenia, osteoarthritis, chronic fatigue syndrome, Alzheimer's disease, senile dementia, mild cognitive impairment due to aging, schizophrenia, Parkinson's disease, Huntington's disease, Pick's disease, Creutzfeldt-Jakob disease, stroke, CNS cerebral senility, age-related cognitive decline, pre-diabetes, diabetes, obesity, osteoporosis, coronary artery disease, cerebrovascular disease, heart attack, stroke, peripheral arterial disease, aortic valve disease, stroke, Lewy body disease, amyotrophic lateral sclerosis (ALS), mild cognitive impairment, pre-dementia, dementia, progressive subcortical gliosis, progressive supranuclear palsy, thalamic degeneration syndrome, hereditary aphasia, myoclonus epilepsy, macular degeneration, or cataracts.

The biomolecule may be alpha-synuclein, tau, amyloid precursor protein, or amyloid β. For example, a method may comprise administering a composition comprising a plurality of particles to a subject with Alzheimer's disease, and the particles may comprise an agent that specifically binds amyloid β (e.g., soluble amyloid β and/or amyloid β aggregates). The biomolecule may be Aβ40 or Aβ42. The agent may comprise aducanumab, bapineuzumab, crenezumab, gantenerumab, ponezumab, solanezumab, or an antigen-binding portion of any one of the foregoing. Similarly, a method may comprise administering a composition comprising a plurality of particles to a subject with Alzheimer's disease, and the particles may comprise an agent that specifically binds tau.

The biomolecule may be TDP-43 or FUS. The biomolecule may be a prion. The biomolecule may be PrP$^{Sc}$, a soluble PrP protein, or a PrP aggregate.

XXIII. Selected Diagnostic Applications

The particles described herein are also useful as diagnostic agents, or in conjunction with diagnostic tool or apparatus. For example, the particles described herein can be coupled to a detection device that monitors the concentration of a given soluble ligand of interest. For example, a nano channel in a detection device lined with an agent (e.g., a first member of a binding pair) can detect (e.g., in a blood sample) or monitor (e.g., as an implanted device in a subject) the concentration of a soluble biomolecule (e.g., the second member of a binding pair). Such a detector can be useful, e.g., for determining the effectiveness of the particles described herein (at scavenging the soluble biomolecule) or determine/adjust the appropriate dosage of a particle composition (e.g., increasing a dose or dose frequency to more effectively scavenge a soluble biomolecule).

In some embodiments, the particles described herein and the detection devices are integrated and function as a "microgland" or "nanogland" (see, e.g., Sabek et al., *Lab Chip* 13(18):3675-3688 (2013)). The nanogland features, e.g., a nano-channel diagnostic capable of providing a precise, quantitative measure of the concentration of a soluble biomolecule in a biological fluid of the subject in which the nanogland is implanted. Also featured in the nanogland is a means (e.g., nano-syringe) that would release particles capable of scavenging the biomolecule, e.g., when the concentration of the biomolecule in the biological fluid reaches a set threshold concentration. Given that many thousands of nano-channels can be deployed in a fingernail-sized implantable biochip, microglands or nanoglands can be designed to monitor many different soluble biomolecules and release multiple types of therapeutic particles.

XXIV. Selected In Vitro Applications

In some aspects, the invention relates to a method for removing a biomolecule from a composition, comprising contacting the composition with a particle as described herein. Such methods are particularly useful for scientific research. For example, it is relatively easy to add a biomolecule to a solution, however it is somewhat more challenging to remove a specific biomolecule from a solution.

Current techniques for removing a biomolecule from solution include, for example, binding the biomolecule to a particle, such as a sepharose bead, and then physically separating the bead from the solution. The particles described herein may sequester a biomolecule in a composition, thereby inhibiting interactions with other components of the composition (e.g., cells), without the need to physically separate the particles from the composition.

A particle may comprise a fluorophore. A particle may be magnetic or paramagnetic or a particle may comprise a magnetic or paramagnetic subparticle or component that allows the particle to be attracted to a magnetic field.

A method may comprise contacting a composition with a particle as described herein, wherein the composition is a cell culture. For example, the cell culture may be a bacterial cell culture or a tissue culture. Such methods may be useful, for example, to remove a secreted protein from the cell culture or to remove a contaminant from the cell culture.

A method may comprise contacting a composition with a particle as described herein, wherein the composition is a cell lysate. The cell lysate may be a prokaryotic or eukaryotic cell lysate. Such methods may be useful, for example, to inhibit the activity of a target biomolecule.

The above methods may be particularly useful for assessing the function of a biomolecule of interest in a particular system. For example, the biomolecule may be introduced to a system (e.g., tissue culture) to assess the effect of the biomolecule on the system (e.g., cell proliferation or cell death), and the biomolecule may be depleted from a similar system using a particle as described herein to assess the effect of the absence of the biomolecule on the system.

In some aspects, the invention relates to a method for expanding or differentiating a population of cells, comprising contacting a composition comprising the population of cells with a plurality of particles as described herein. The plurality of particles may scavenge one or more molecules that favor an alternate differentiation pathway that competes with a desired differentiation pathway. Thus, the method may favor the differentiation of the population of cells into a desired cell type relative to an alternate cell type. The method may further comprise contacting the composition with a cytokine (e.g., as described herein). The method may further comprise contacting the composition with one or more of a chemokine, interleukin, growth factor, wnt-family protein, tumor necrosis factor, and/or hormone (e.g., as described herein).

The population of cells may comprise stem cells. The population of cells may comprise somatic stem cells or embryonic stem cells. The population of cells may comprise induced stem cells, such as induced pluripotent stem cells. The population of cells may comprise progenitor cells, precursor cells, blast cells, unipotent cells, multipotent stem cells, pluripotent stem cells, and/or intermediate progenitor cells. The population of cells may comprise meiocytes. The population of cells may comprise hematopoietic stem cells, mammary stem cells, intestinal stem cells, mesenchymal stem cells, endothelial stem cells, neural stem cells, olfactory adult stem cells, neural crest stem cells, or testicular cells. The population of cells may comprise satellite cells, oligodendrocytes progenitor cells, thymocytes, angioblasts, bone marrow stromal cells, pancreatic progenitor cells, endothelial progenitor cells, or melanoblasts. The population of cells may comprise multipotential hematopoietic stem cells, common myeloid progenitor cells, myeloblasts, monoblasts, promonocytes, monocytes, common lymphoid progenitor cells, lymphoblasts, prolymphocytes, and/or small lymphocytes.

In some embodiments, the invention relates to a method for differentiating a cell, comprising contacting a composition comprising the cell with a plurality of particles as described herein. The plurality of particles may scavenge one or more molecules that favor an alternate differentiation pathway that competes with a desired differentiation pathway. Thus, the method may favor the differentiation of the cell into a desired cell type relative to an alternate cell type. The method may further comprise contacting the composition with a cytokine (e.g., as described herein). The method may further comprise contacting the composition with one or more of a chemokine, interleukin, growth factor, wnt-family protein, and/or tumor necrosis factor (e.g., as described herein).

The cell may be a stem cell. The cell may be a somatic stem cell or an embryonic stem cell. The cell may be an induced stem cell, such as an induced pluripotent stem cell. The cell may be a progenitor cell, precursor cell, blast cell, unipotent cell, multipotent stem cell, pluripotent stem cell, and/or intermediate progenitor cell. The cell may be a meiocyte. The cell may be a hematopoietic stem cell, mammary stem cell, intestinal stem cell, mesenchymal stem cell, endothelial stem cell, neural stem cell, olfactory adult stem cell, neural crest stem cell, or testicular cell. The cell may be a satellite cell, oligodendrocyte progenitor cell, thymocyte, angioblast, bone marrow stromal cell, pancreatic progenitor cell, endothelial progenitor cell, or melanoblast.

The cell may be a multipotential hematopoietic stem cell, common myeloid progenitor cell, myeloblast, monoblast, promonocyte, monocyte, common lymphoid progenitor cell, lymphoblast, prolymphocyte, and/or small lymphocyte.

XXV. Kits for Administering the Agent

In certain embodiments, the disclosure also provides a pharmaceutical package or kit comprising one or more containers filled with at least one composition (e.g., particle or particles) of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In certain embodiments, the kit includes additional materials to facilitate delivery of the subject agents. For example, the kit may include one or more of a catheter, tubing, infusion bag, syringe, and the like. In certain embodiments, a composition (e.g., comprising particles as described herein) is packaged in a lyophilized form, and the kit includes at least two containers: a container comprising the lyophilized composition and a container comprising a suitable amount of water, buffer, or other liquid suitable for reconstituting the lyophilized material.

XXVI. Kits for Coupling an Agent to a Particle

In some aspects, the invention relates to a kit for making a scavenging particle. The kit may comprise a plurality of particles. The kit may comprise instructions for coupling the reactive groups of a particle to a plurality of agents to prepare the scavenging particle. The kit may comprise instructions for functionalizing the reactive groups of a particle to prepare the scavenging particle. The kit may further comprise a plurality of linkers. Each linker of the plurality of linkers may comprise a first functional group capable of selectively reacting with an agent bearing a predetermined moiety capable of reacting with the first functional group. Each linker of the plurality of linkers may comprise a second functional group capable of selectively reacting with the reactive groups of the particles. In some embodiments, the kit does not comprise linkers, e.g., when the reactive groups of the particle can selectively react with the agent, thereby coupling the agent to the particle. The kit may further comprise a plurality of agents, each agent bearing the predetermined moiety. A predetermined moiety may be a primary amine, guanidinium, thiol, or carboxyl group, e.g., for an agent that comprises a peptide or protein. In some embodiments, the kit does not comprise an agent, e.g., for creating a custom scavenging particle.

In some embodiments, the kit comprises a second plurality of linkers, e.g., wherein each linker of the second plurality of linkers comprises a third functional group capable of selectively reacting with an agent bearing a second predetermined moiety capable of reacting with the third functional group. For example, the first functional group may be capable of reacting with a predetermined moiety of a protein, and the third functional group may be capable of reacting with a predetermined moiety of a nucleic acid, such that the particle may be loaded with a protein and/or nucleic acid by utilizing different linkers.

XXVII. Methods for Making a Scavenging Particle

In some aspects, the invention relates to a method for making a scavenging particle. The method may comprise reacting a particle with a plurality of agents. Each agent of the plurality of agents may comprise a functional group or predetermined moiety capable of selectively reacting with a reactive group of the plurality of reactive groups. Each reactive group may be oriented on the particle such that, after the agent is coupled to the particle, the agent has a reduced ability to bind to a molecule on the surface of a cell (e.g., a eukaryotic cell, such as a diploid cell, such as a human diploid cell, such as an immune cell or a cancer cell).

The method may further comprise reacting the plurality of agents with a plurality of linkers, e.g., prior to reacting the particle with the plurality of agents. For example, each linker of the plurality of linkers may comprise a first functional group capable of selectively reacting with an agent bearing a predetermined moiety capable of reacting with the first functional group. Each linker of the plurality of linkers may comprise a second functional group capable of selectively reacting with the reactive groups of the particles. Thus, the agent may be functionalized to add a functional group that can selectively react with a reactive group of the particle. Each linker may comprise a protecting group, e.g., which protects the second functional group. The method may further comprise deprotecting the linker, e.g., after reacting the plurality of agents with the plurality of linkers.

The method may further comprise reacting the particle with a plurality of linkers, e.g., prior to reacting the particle with the plurality of agents. For example, each linker of the plurality of linkers may comprise a second functional group capable of selectively reacting with a reactive group. Each linker of the plurality of linkers may comprise a first functional group capable of selectively reacting with an agent bearing a predetermined moiety capable of reacting with the first functional group. Thus, the particle may be functionalized to selectively react with a predetermined moiety of the agent. Each linker may comprise a protecting group, e.g., which protects the first functional group. The method may further comprise deprotecting the linker, e.g., after reacting the particle with the plurality of linkers.

Methods of preparing a scavenging particle may result in particles comprising agent that cannot bind to a biomolecule, e.g., if the binding region of the agent couples to a reactive group and/or a linker. A population of agents may nevertheless be accessible to specifically bind to the biomolecule. In some embodiments, each agent of the plurality of agents can specifically bind to the biomolecule. In some embodiments, each agent of the particle can specifically bind to the biomolecule.

Methods of preparing a scavenging particle may result in particles comprising agent that can interact with cells, such as cancer cells or immune cells. A population of agents may nevertheless display a reduced ability to bind to a molecule on the surface of a cell (e.g., a diploid human cell, cancer cell, and/or immune cell). In some embodiments, each agent of a plurality of agents displays a reduced ability to bind to a molecule on the surface of a cell (e.g., a diploid human cell, cancer cell, and/or immune cell), e.g., relative to agent immobilized on the outside surface of a particle. In some embodiments, each agent of a particle displays a reduced ability to bind to a molecule on the surface of a cell (e.g., a diploid human cell, cancer cell, and/or immune cell), e.g., relative to agent immobilized on the outside surface of a particle.

XXVIII. Methods for Assembling a Scavenging Particle from Subparticles

In some aspects, the invention relates to a method of assembling a particle from subparticles. For example, the particle may be one of the particles described herein.

In some embodiments, heterobifunctional linkers are used to join subparticles together, for example, to join a core subparticle to another subparticle. In some embodiments, linkers that do not join subparticles to particles may provide additional functionality, such as inhibiting protein adsorption or inhibiting or facilitating recognition and clearance by immune cells. In the following examples, a linker molecule with a first functional group at a first end, such as —$NH_2$, and a second functional group, such as —COOH at a second end, is referred to as '$NH_2$-linker-COOH'. The linker molecules may be selected from the linker molecules described herein for linking an agent to a particle, for example in section XI 'Immobilizing an agent on a particle'. In some embodiments, a subparticle, e.g. a core subparticle, is porous, such as a porous silicon particle or a porous silica particle as described herein, and a plurality of further subparticles are joined to the porous subparticle by means of linkers.

According to some embodiments, a scavenging particle may be prepared by a layer-by-layer method, comprising providing a core subparticle, binding an agent to the surface of the core particle, then binding protecting or 'shield' subparticles, also referred to herein as bumper or stud particles, to the surface of the core particle.

According to some embodiments, the scavenging particle is prepared with all of the bumper or stud particles in place, and the agent is added subsequently.

In some embodiments, the present disclosure provides a method of assembling a particle as disclosed herein, comprising: providing a first (e.g., a core) subparticle having a surface, wherein a plurality of first reactive groups are coupled to the surface; providing one or more second (e.g., protecting) subparticles each having a surface, wherein one or more second reactive groups are coupled to the surface, and wherein the second reactive groups are capable of forming a bond with the first reactive groups; and combining the core subparticle with the one or more protecting subparticles under conditions that form a bond between the first reactive groups and the second reactive groups.

In further embodiments, the first subparticle further comprises a plurality of a third reactive group, thus presenting two different types of reactive groups to the environment, as described for instance in Section XI, 'Immobilizing an Agent on a Particle'. In preferred embodiments, the third reactive group represents an orthogonal linkage chemistry to that used by the first and second reactive groups. Thus, for example, the first and second reactive groups may be amines, and the third reactive group may be a biotin-binding protein such as streptavidin. According to these embodiments, the plurality of the first reactive group may be used to bind the first subparticle to the second subparticle, and the plurality of the third reactive group may be used to bind a capture agent to the first subparticle. These two steps—binding of the capture agent and binding of the second subparticle—may be performed in any order.

In some embodiments, a plurality of the second subparticle is provided, such that when the first subparticle and the plurality of second subparticles is reacted with one another, the resulting particle comprises the first subparticle (e.g., a core subparticle) and a plurality of second subparticles (e.g., a plurality of protecting or shield subparticles).

In some embodiments, a core or shield subparticle is a silica particle, a particle comprising a silica surface, such as a silicon particle having an oxidized surface, or a particle having a non-silica core and a silica outer layer.

In some embodiments, a core or shield subparticle comprises porous silicon or porous silica. In some embodiments, the particle is a porous silicon particle. In some such embodiments, the subparticle comprises a silica surface, such as having an oxidized surface. In some embodiments, the subparticle is a porous silica particle. In some embodiments, the subparticle comprises a porous silicon or silica outer layer and one or more materials other than silicon or silica within the interior of the subparticle, such as within the pores or within the non-pore material of the subparticle.

In some embodiments a subparticle, e.g. a protecting subparticle, comprises a polymer, such as a biodegradable polymer. Suitable polymers may be those as described herein, such as polyethylene glycol (PEG), polylactate, polylactic acids, sugars, lipids, polyglutamic acid, polyglycolic acid (PGA), polylactic acid (PLA), poly(lactic-co-glycolic acid) (PLGA), polyvinyl acetate (PVA), and combinations thereof. In a preferred embodiment, a plurality of subparticles comprise PLGA. For suitable polymer types for use in forming the subparticles, see e.g. Makadia and Siegel, *Polymers* 2011, 3, 1377-1397.

In some embodiments a polymer layer may be provided on the surface of a particle formed from a different material, e.g., attached to a surface of the particle.

In some embodiments a component of the polymer may comprise the second reactive group. A reactive group may be provided as part of a monomer forming the polymer. A component of the polymer comprising a reactive group may be chemically linked to other components of the polymer, such as crosslinked to them. A subparticle may be formed from a copolymer comprising a first monomer type and a second monomer type, the second monomer type comprising a reactive group. In a preferred embodiment a subparticle comprises a copolymer comprising a PLGA derivative comprising a reactive group, such as PLGA-COOH. The reactive group so provided may act as the second reactive group in assembly of a particle.

In some embodiments a subparticle comprising a polymer comprises a coating on the surface of the subparticle, the coating comprising a plurality of coating moieties bonded to the polymer. In some embodiments the coating moieties form part of a monomer forming part of the polymer, the monomer being selected such that after polymerization, on or after formation of the subparticle, a coating moiety is present at the surface of the polymeric subparticle.

In a preferred embodiment a subparticle comprises a copolymer comprising PLGA and PEG. The PEG moiety may be chemically bonded to the PLGA molecule. See e.g. Cheng et al. Formulation of Functionalized PLGA-PEG Nanoparticles for In Vivo Targeted Drug Delivery, Biomaterials. 2007 February; 28(5): 869-876.

The length and conformation of the PLGA and/or PEG moieties may be selected from linear or branched chains, short- or long chain moieties. The PEG moiety may be selected to have a molecular weight in the region 1 kDa to 40 kDa, such as 2 kDa to 20 kDa, such as 5 kDa to 20 kDa. Without being bound by theory, in PEG/PLGA-PEG copolymers, when solubilized in aqueous solution, PEG moieties are found at the surface of the particle, where they may act to inhibit interaction with cells, such as macrophages, as known in the art.

In some embodiments, the PEG moiety may comprise a reactive group, such as —COOH, or a reactive group described elsewhere herein. In a preferred embodiment a subparticle comprises a block copolymer comprising a monomer comprising PLGA-PEG bonded to a reactive group. Such a polymer may be formed from reaction of PLGA-COOH with a heterobifunctional molecule such as $NH_2$-PEG-COOH. In this embodiment, according to the method of fabrication, the subparticle comprises the reactive group presented at the external surface of the particle—see e.g. Cheng et al., op cit. The reactive group may be different from —COOH. For example, in some preferred embodiments the reactive group is a thiol, as can be formed for example from the reaction of PLGA-COOH with NH$_2$-PEG-SH to form PLGA-PEG-SH, which may be incorporated into the subparticle.

The reactive group may function as the second reactive group in the above-described assembly of a particle, and may be selected to bond with a first reactive group provided on the surface of a subparticle, such as a core subparticle, as described herein.

In this way, the subparticle comprises a plurality of coating moieties bonded to the polymer, and the coating moieties comprise the second reactive group. Another reactive group may also be provided at the end of a linear polymer, such as PEG, forming part of the coating.

In some embodiments, the first and second reactive groups are selected from an aldehyde, an alkene, an alkyl halide, an alkyne, an amine, an alkoxyamine, an aryl azide, an aryl halide, a hydrazide, an azide, a carbodiimide, a carboxylic acid or a derivative thereof, a diene, a dienophile, a glyoxal, a haloacyl, an imidoester, an isocyanate, a maleimide, an N-hydroxysuccinimidyl ester, a glyoxal, a phosphine, a tetrazine, a thiol, a nucleic acid, a biotin, a biotin-binding protein, or a member of an antibody-antigen pair, such that, as described above, they are capable of forming a bond with each other.

According to some embodiments, the first and second reactive groups are an amine and a carboxylic acid or a derivative thereof, a carbodiimide, and are capable of forming an amide with each other. According to some embodiments, the first and second reactive groups are an imidoester and an amine, and are capable of reacting with each other to form an amidine. According to some embodiments, the first and second reactive groups are a maleimide or a haloacetyl and a thiol, and are capable of reacting with each other to form a thioether. According to some embodiments, the first and second reactive groups are both a thiol, and are capable of reacting with each other to form a disulfide. According to some embodiments, the first and second reactive groups are a hydrazide and an aldehyde, and are capable of reacting with each other to form a hydrazone. According to some embodiments, the first and second reactive groups are an alkoxyamine and an aldehyde, and are capable of reacting with each other to form an oxime. According to some embodiments, the first and second reactive groups are an aryl azide and an alkene or diene, and are capable of reacting with each other to form a bond. According to some embodiments, the first and second reactive groups are an azide and an alkyne, and are capable of reacting with each other to form a triazine. According to some embodiments, the first and second reactive groups are an azide and a phosphine, and are capable of reacting with each other to form a bond according to the Staudinger reaction. According to some embodiments, the first and second reactive groups are a tetrazine and an isocyanate or diene, and are capable of reacting with each other to form a bond. According to some embodiments, the first and second reactive groups are an aryl halide or an alkyl halide and an alkyne, and are capable of reacting with each other to form a bond. According to some embodiments, the first and second reactive groups are a diene and a dienophile, and are capable of reacting with each other to form a bond. According to some embodiments, the first and second reactive groups are both nucleic acids, and are capable of reacting with each other to form a duplex nucleic acid. According to some embodiments, the first and second reactive groups are a biotin and a biotin-binding protein, and are capable of reacting with each other to form a complex. According to some embodiments, the first and second reactive groups are an antibody and an antigen, and are capable of reacting with each other to form a complex.

In some embodiments, the first and second reactive groups are selected from an amine, such as a primary amine, a carboxyl, a gold surface on a subparticle, a thiol, a biotin, a maleimide, or a biotin-binding protein, such as streptavidin. In some embodiments, the first reactive group is an amine and the second reactive group is a carboxyl. In some embodiments, the first reactive group is a carboxyl and the second reactive group is an amine. In some embodiments, both the first and second reactive groups are amines. In some embodiments, the first reactive group is a gold surface and the second reactive group is a thiol. In some embodiments, the first reactive group is a thiol and the second reactive group is a gold surface. In some embodiments, the first reactive group is a thiol and the second reactive group is a maleimide. In some embodiments, the first reactive group is a maleimide and the second reactive group is a thiol. In some embodiments, the first reactive group is a biotin, and the second reactive group is a biotin-binding protein. In some embodiments, the first reactive group is a biotin-binding protein, and the second reactive group is a biotin.

In some embodiments, a carboxylic acid derivative suitable for use as a reactive group is an activated carboxylic acid, e.g., a derivative of a carboxylic acid that is more susceptible to nucleophilic attack than a free carboxyl group. In some embodiments, an activated carboxylic acid may be selected from an acid anhydride, an acid chloride, a thioester, an NHS ester, an imidoester, an acid azide, or a haloaryl ester.

In some embodiments, the particles resulting from these methods comprise a core subparticle and a plurality of protecting subparticles. The particles may additionally comprise an agent as described herein, or reactive groups capable of binding to an agent as described herein. According to some embodiments, the core subparticle is coupled to the protecting subparticles by a first linking moiety comprising a first coupling group, i.e., a moiety formed by the reaction or interaction of first and second reactive groups as detailed above, such as an amide, a triazole, or a nucleic acid duplex. According to some embodiments, the particle comprises an agent as described herein, and the agent is coupled to the core particle by a second linking moiety comprising a second coupling group (e.g., a group formed by the reaction or interaction of reactive groups orthogonal to the reactive groups that form the first coupling group).

According to some embodiments, the first and second coupling groups are independently selected from an amide, an amidine, an oxime, a triazole, a disulfide, a thioether, a succinimide, an isoxazole, a pyridazine, a urea, a hydrazone, an oxime, a secondary amine, a complex between a protein and a substrate, a complex between an antibody and an antigen, a gold-sulfur bond, or a duplex nucleic acid. In some embodiments, the first and second coupling groups are the same. In some embodiments, the first and second coupling groups are different.

In some embodiments, the length of the first linking moiety disposed between the core subparticle and the first coupling group, and the length of the second linking moiety disposed between the core subparticle and the second coupling group are similar or identical. In other embodiments, the portion of the first linking moiety disposed between the core subparticle and the first coupling group, and the portion of the second linking moiety disposed between the core subparticle and the second coupling group are different. By varying the lengths of different linkers, one can achieve differential positioning of the linked moieties. For example, for a core subparticles with two types of linking moieties attached via linkers of similar lengths, protecting subparticles with can be attached using long linkers and agents with short linkers, ensuring that the agents are disposed within the "shield" of the protecting subparticles. Similarly, using longer linkers to attach protecting subparticles reduces the density and increases the flexibility/malleability of the overall complex, while using shorter linkers to attach protecting subparticles results in complexes that are more rigid and dense.

In some embodiments, the first or second linking moiety further comprises a spacer, such as an alkyl chain, a PEG chain, or an amino-acid chain. The spacer in the first linking moiety may be disposed between the core subparticle and the coupling group, or between the coupling group and the protecting subparticle. The spacer in the second linking moiety may be disposed between the core subparticle and the coupling group, or between the coupling group and the agent. As discussed above, the length of the spacers may be varied to orient different components of the particle complex in different spatial relationships, and/or to vary the density/rigidity of the complex.

In some embodiments, one or both of the reactive groups are attached to the surfaces of their respective particles via a linker. For instance, a heterobifunctional linker may be used. The linker molecules may be selected from the linker molecules described herein for linking an agent to a particle, for example in section XI 'Immobilizing an agent on a particle'.

Methods of preparing the subparticles for use in assembling a particle are described herein. Additionally, many strategies for functionalizing nanoparticles are known in the art and are described, for instance, in Xu et al., 'Water-soluble PEGylated silicon nanoparticles and their assembly into swellable nanoparticle aggregates', J Nanopart Res (2015) 17:56; Yu et al. 'Targeting Strategies for Multifunctional Nanoparticles in Cancer Imaging and Therapy', Theranostics 2012, 2(1) Jokerst et al. Nanoparticle PEGylation for imaging and therapy, Nanomedicine (Lond). 2011 June; 6(4): 715-728; Godin et al. Tailoring the degradation kinetics of mesoporous silicon structures through PEGylation, J Biomed Mater Res A. 2010 Sep. 15; 94(4): 1236-1243; and Sanz et al., Effect of PEG biofunctional spacers and TAT peptide on dsRNA loading on gold nanoparticles, J Nanopart Res (2012) 14:917, the contents of each of which are incorporated by reference as if fully set forth herein.

In some embodiments, a subparticle comprising a plurality of reactive groups may be prepared by reacting a linker comprising the reactive group and a surface-reactive group with the subparticle. Advantageously, the linker is heterobifunctional, i.e., the reactive group is different from the surface-reactive group. This may avoid, or reduce, a tendency for the subparticles to aggregate while being functionalized.

In some embodiments, a subparticle comprises a plurality of carboxylated linker molecules, such that a plurality of carboxylated linker molecules, -linker-COOH, is attached to the surface of the subparticle and presented to the environment. In some embodiments, such a subparticle is created by first providing a subparticle comprising a silica surface comprising a plurality of amine groups. A plurality of heterobifunctional $NH_2$-linker-COOH molecules may then be attached via their amine groups to the amine groups on the surface of the subparticle using Solulink™ chemistry. By this reaction, a subparticle displaying a plurality of carboxyl groups is formed.

In some embodiments, a subparticle comprising a plurality of carboxylated linker molecules is created by first providing a subparticle comprising a carboxylated surface. A plurality of $NH_2$-linker-COOH heterobifunctional molecules may then be bonded to the —COOH groups using amide chemistry, such as EDC or EDC/NHS chemistry. By this reaction, a subparticle displaying a plurality of carboxyl groups is formed.

In some embodiments, a subparticle comprising a plurality of carboxylated linker molecules is created by first providing a subparticle comprising a gold surface, for example gold particles or a gold surface coating over a core comprising a different material. The gold surface may be continuous or discontinuous. Thiolated linker-COOH molecules, HS-linker-COOH may then be bonded to the gold surface by thiol linkage chemistry. In some embodiments, HS-linker-COOH bonds spontaneously to the gold surface. By this reaction, a subparticle displaying a plurality of carboxyl groups is formed.

In some embodiments, a subparticle comprises a plurality of aminated linker molecules, such that a plurality of aminated linker molecules, -linker-$NH_2$, is attached to the surface of the subparticle and presented to the environment. Such subparticles may be prepared analogously to the carboxylated subparticles described above.

In some embodiments, a subparticle comprises a plurality of thiolated linker molecules, such that a plurality of thiolated linker molecules, -linker-SH, is attached to the surface of the subparticle and presented to the environment. In some embodiments, such a subparticle may be formed by providing a subparticle comprising a silica surface comprising a plurality of amine groups, and reacting the plurality of amine groups with a plurality of COOH-linker-SH molecules using amide linkage chemistry. By this reaction, a subparticle displaying a plurality of thiol groups is formed. Alternatively, a subparticle may be provided that comprises a surface having a plurality of —COOH groups, and $NH_2$-linker-SH molecules may be bound via their —$NH_2$ groups to the —COOH groups using amide linkage chemistry.

In some embodiments, a subparticle comprises a gold surface, such as a gold layer overlaying a silica particle. The layer may be continuous or discontinuous. In such embodiments the gold on the surface forms a 'reactive group', in that each area of gold is able to bind to a functional group, e.g., a thiol group, on the capture agent, a linker, or a coating molecule. In preferred embodiments, the first subparticle is a core subparticle comprising porous silicon, and comprises a decoration of gold nanoparticles immobilized on the surface of the porous silicon. The gold nanoparticles may be formed on the surface of the porous silicon, for example by precipitation.

In some embodiments, a subparticle comprises a plurality of immobilized biotin-binding proteins, such as streptavidin.

In some embodiments, a subparticle comprises a plurality of biotinylated linker molecules, such that a plurality of thiolated linker molecules, -linker-SH, is attached to the surface of the subparticle and presented to the environment. In some embodiments, heterobifunctional linker molecules may be used to achieve such a coating, such as HS-linker-biotin for subparticles having a gold surface, or COOH-linker-biotin for subparticles having an aminated surface, or $NH_2$-linker-biotin for subparticles having a carboxylated surface.

In some embodiments, a subparticle comprises a plurality of capture agent moieties, such that the capture agent is attached to the surface of the subparticle and presented to the environment. In some embodiments, such a subparticle may be formed by providing a subparticle comprising a surface having a plurality of carboxyl groups, and capture agents having a free amine group may be bound to the carboxyl groups using amide linkage chemistry. For example, the capture agent may be TNF or a TNF homotrimer, which comprises free amines.

In some embodiments, a subparticle comprising a plurality of capture agent moieties may be prepared by providing a subparticle comprising a surface having a plurality of amino groups, and capture agents having a free amine group may be bound to the amine groups using Solulink chemistry. For example, the capture agent may be TNF or a TNF homotrimer, which comprises free amines.

In some embodiments, a subparticle comprising a plurality of capture agent moieties may be prepared by providing a subparticle comprising a surface having a plurality of maleimide groups, and capture agents having a free thiol group may be bound to the amine groups using maleimide chemistry. For example, the capture agent may be TNF (e.g., a reduced TNF homotrimer), which comprises free cysteine residues.

In some embodiments, a subparticle may be functionalized with capture agent moieties by click chemistry, biotin-streptavidin linkages, or through thiol functionality on the subparticle (for example, by providing a capture agent that is linked to a maleimide group).

In some embodiments, a subparticle comprises a mixed coating comprising a first plurality of linker molecules and a second plurality of coating molecules, as described herein in section XIII 'Clearance and coatings'.

The various subparticles described above may be combined into particles of the invention in various configurations. It will be apparent to those of skill based on the present disclosure that a first type of subparticle could act as a core subparticle, while a second type of subparticle capable of coupling with the first type of subparticle could act as a protecting subparticle.

In preferred embodiments, a protecting subparticle (such as the second subparticle in the methods described herein) comprises a first plurality of linker molecules and a second plurality of coating molecules comprising a polymer such as PEG or PLGA. The coating molecules may provide a biological function, for instance they may inhibit clearance by macrophages and/or act to achieve an extended time in circulation.

Once the desired subparticles have been prepared, they may be reacted together to form a particle by chemistry suited to the reactive groups they display.

In some embodiments, the first subparticle comprises a plurality of aminated linker molecules and the plurality of second subparticles comprises a plurality of carboxylated linker molecules, and the two may be reacted to form amide linkages, e.g., by using EDC or EDC/NHS chemistry.

In some embodiments, the first subparticle comprises a plurality of carboxylated linker molecules and the plurality of second subparticles comprises a plurality of aminated linker molecules, and the two may be reacted to form amide linkages, e.g., by using EDC or EDC/NHS chemistry.

In some embodiments, the first subparticle comprises a gold surface, and the plurality of second subparticles comprises a plurality of thiolated linker molecules. Then the plurality of second subparticles may be bonded to the first subparticle by thiol linkages. In some embodiments, the thiolated linker molecules on the plurality of second subparticles spontaneously bonds to the gold surface of the first subparticle.

In some embodiments, the first subparticle comprises a plurality of immobilized biotin-binding proteins (e.g., avidin) and the plurality of second subparticles comprises a plurality of biotinylated linked molecules. Then, the plurality of second subparticles will bind to the first subparticle by the association of biotin with the biotin-binding protein.

In some embodiments, the reaction between the first subparticle and the plurality of second subparticles leaves unreacted reactive groups on the particle surfaces. The size of the subparticles will influence the area between them and hence the number of unreacted amine groups. Typically, larger subparticles will leave larger unreacted areas, and hence a larger number of unreacted reactive groups, between them. In these embodiments, further molecules may be attached to the unreacted reactive groups on the subparticles. For example, a plurality of coating molecules may be attached, for example to inhibit protein adsorption. Coating molecules may comprise a polymer, such as PEG to provide a coating, such as a methoxy-PEG layer. In some embodiments, when the unreacted groups are carboxyl groups, $NH_2$-PEG-OMe molecules may be linked to the carboxyl groups. In some embodiments, when the unreacted groups are thiol groups, maleimide chemistry may be used to passivate the thiol groups. For example, maleimide-PEG-OMe molecules may be linked to the thiol groups. In some embodiments, when the subparticle comprises unreacted gold surface area, thiol chemistry may be used to passivate gold surface. For example, HS-PEG-OMe molecules may be linked to the gold surface.

In some embodiments, the unreacted reactive groups may be used to immobilize capture agent on the surface of a subparticle. When the unreacted reactive groups are amine groups, for example, amine groups on the capture agent may be bonded to the unreacted amine groups on the surface of the subparticle, for example using Solulink™ chemistry, or carboxyl groups on the capture agent may be bonded to the unreacted amine groups on the surface of the subparticle. When the unreacted reactive groups are carboxyl groups, the amine groups on the capture agent may be bonded to the unreacted carboxyl groups by amide chemistry. When the unreacted reactive groups are thiol groups, the capture agent may be bonded to the unreacted thiol groups by maleimide chemistry. When the subparticle comprises unreacted gold surface, the capture agent may be bonded to the gold surface by thiol chemistry. For example, capture agents comprising cysteine residues may be directly bonded to gold on the surface. Such bonding is known to occur, for example, for capture agents rich in cysteine residues, such as the TNF and TNFR family of ligands and receptors, such as TNFalpha and TNFR1/2.

In some embodiments, the differing identities of the first and second reactive groups are used to ensure that the second reactive groups (on the plurality of second subparticles) is passivated and the first reactive groups (on the first subparticle) are bound to capture agents. Thus, in the finished subparticle, the capture agents are present only on the surface of the first subparticle, where they are protected from being accessed by receptor molecules on cell surfaces.

In variants of the above embodiments a linker may be provided on the surface of the first subparticle, on the surfaces of the plurality of second subparticles, or on both. Conversely, the reactive groups on the first and second subparticles may be attached to a linker, or directly to the surface of the subparticle, so long as at least the first or second subparticle comprises a linker attaching the reactive group to the subparticle. Thus, a first linker may be provided on the surface of the particle and a second linker on the surface of the subparticles. A linker may comprise a reactive group to bond to a functional group on the subparticle surface, or on a second linker. The linker may be selected to provide an optimal separation between the subparticles and the surface of the particle. Examples of linkers are described herein.

In some embodiments, the heterobifunctional linkers are selected to provide a coating on the subparticles that may, for example, inhibit protein adsorption or macrophage interaction. For example, the linkers may comprise a polymer such as PEG, as known in the art and described herein, such as heterobifunctional PEG molecules. Similarly, heterobifunctional PEG molecules may be used as linkers to join a plurality of second subparticles to a first subparticle comprising a gold surface in a method as described for thiolated linkers above. Thiolated PEG molecules may be bonded to the subparticles with the thiol groups facing outwards, which may then be bonded to the gold surface. A further layer of molecules may be bonded to remaining, non-attached thiols, such as maleimide-PEG-OMe molecules.

In some embodiments, capture agents may be bonded to the surface of the first subparticle directly, by means of bonding (e.g., covalent bond, coordinative bond, inclusion complex, etc.) between a reactive group on the surface and a functional group on the capture agent, or by means of a linker as described herein, the linker having a functional group to react with the reactive group on the surface, the functional group being for example an amine to react with an amine on the surface by means of Solulink chemistry; a carboxyl group, to react with an amine group on the surface by means of amide linkage chemistry; an amine group, to react with a carboxyl group on the surface by means of amide linkage chemistry; a thiol group to react with gold or a maleimide group on the surface of the particle; or a maleimide group to react with a thiol group on the surface of the particle.

In some embodiments, the coverage of a surface with a coating, such as of PEG-containing molecules, is controlled such that the moieties at the end of the molecule tend to be presented towards the surface of the coating. For example, PEG-containing molecules may be provided at a density on the surface such that the molecules have a tendency to form a linear, 'brush-like' arrangement on the surface, e.g., at a density above that at which the PEG molecules tend to form a folded 'mushroom' arrangement on the surface. Techniques for forming such coatings are known in the art.

These examples provide methods for assembling a particle, complete with a core particle and shield/protecting subparticles, the subparticles having a coating. In preferred embodiments as described above, the capture agent may be added to functionalise the particle as the last step. In some embodiments the assembled particles comprising subparticles are stable in suspension, and may have the capture agent immobilised onto them when the particles are needed for use. In some embodiments, more than one type of capture agent may be added, to form particles to scavenge a single, or more than one, target. Such a particle may be called a 'programmable particle', in the sense that a user may program the particle to capture a selected target by bonding the corresponding capture agent to the particle.

Further exemplary embodiments are provided below.

In some embodiments, a first subparticle is provided with plurality of amine groups on its surface. A plurality of second subparticles is provided, each comprising a coating comprising a plurality of linker-COOH molecules attached to their surface, such that the —COOH group faces outwards. The plurality of second subparticles is bonded to the particle by reacting the —COOH group on the plurality of second subparticles with the amine groups on the first subparticle, to form amide linkages, e.g., using EDC or EDC/NHS chemistry. This process will leave unreacted amine groups on the surface of the first particle, and unreacted carboxyl groups on the surface of the plurality of second subparticles. Further molecules may then be attached to the unreacted —COOH groups on the plurality of second subparticles. For example, a plurality of coating molecules may be attached, for example to inhibit protein adsorption, by means of amide linkage chemistry such as EDC/NHS chemistry. Coating molecules may comprise a polymer, such as PEG to provide a coating, such as a methoxy-PEG layer, formed from linkage of $NH_2$-PEG-OMe molecules to the carboxyl groups. Capture agent may be immobilized on the surface of the first subparticle by means of bonding amine groups on the capture agent to the amine groups on the surface, for example using Solulink™ chemistry. The coating molecules may be attached before the capture agent, or the capture agent may be attached before the coating molecules.

In some embodiments, a first subparticle is provided with a surface comprising gold, such as a gold layer overlying a silica particle. The layer may be continuous or discontinuous. A plurality of second subparticles is provided, each comprising a coating comprising a plurality of thiolated linker molecules, linker-SH, attached to their surface, such that the thiol groups face outwards. The plurality of second subparticles is then bonded to the first subparticle by means of bonding the thiol group on the linker coating to the gold on the surface of the particle, to form thiol linkages. This process will leave unreacted gold on the surface of the first subparticle, and unreacted thiol groups on the plurality of second subparticles. Further molecules may be attached to the unreacted thiol groups on the plurality of second subparticles. For example, a plurality of coating molecules may be attached, for example to inhibit protein adsorption, by means of maleimide/thiol linkage chemistry to a maleimide-containing passivating molecule to form a thioether bond. Coating molecules may provide a PEG coating, such as maleimide-PEG-OMe molecules. Capture agent may be immobilized on the unreacted area of the gold surface of the particle, for example by means of bonding between cysteine groups on the capture agent to the gold on the surface. Such bonding is known in the art for capture agents rich in cysteine residues, such as the TNF and TNFR family of ligands and receptors, such as TNFalpha and TNFR1/2. The coating molecules may be attached before the capture agent, or the capture agent may be attached before the coating molecules.

In some embodiments, a first subparticle is provided with a surface comprising immobilized biotin-binding proteins, such as streptavidin. A plurality of second subparticles is provided, each comprising a coating comprising a plurality of linker-biotin molecules, such that the biotin groups face outwards. The plurality of second subparticles is then bonded to the first subparticles by bonding the biotin groups on the plurality of second subparticles to the biotin-binding proteins on the surface of the first subparticle. This process will leave unreacted streptavidin on the particle surface in the spaces between the subparticles. Capture agent may be immobilized on the surface of the first subparticle by bonding biotinylated capture agent to the remaining streptavidin. Remaining unreacted biotin groups on the subparticles may be passivated by reacting them with streptavidin, or streptavidin-coupled passivating molecules. This may be done before or after the capture agent is added. The coating molecules may be attached before the capture agent, or the capture agent may be attached before the coating molecules.

In some embodiments, a first subparticle is provided with a plurality of amine groups on its surface. A plurality of second subparticles is provided, each comprising a coating comprising a plurality of PEG-COOH molecules attached to their surface, such that the carboxyl groups face outwards. The plurality of second subparticles is then bonded to the first subparticle by reacting the carboxyl groups on the second subparticles with the amine groups on the surface of the particle, to form amide linkages, e.g., by using EDC or EDC/NHS chemistry. This process will leave unreacted amine groups on the surface of the first subparticle and unreacted carboxyl groups on the surface of the second subparticle. Further molecules may be attached to the unreacted carboxyl groups on the subparticles. For example, a plurality of coating molecules may be attached, such as $NH_2$-PEG-OMe molecules to inhibit protein adsorption, by means of amide linkage chemistry such as EDC/NHS chemistry. Capture agent may be immobilized on the surface of the first subparticle by means of bonding amine groups on the capture agent to the amine groups on the surface, for example using Solulink™ chemistry. The coating molecules may be attached before the capture agent, or the capture agent may be attached before the coating molecules.

In some embodiments, a first subparticle is provided with a plurality of capture agents comprising amine group on its surface, such that the capture agents face outwards. A plurality of second subparticles is provided, each comprising a coating comprising a plurality of PEG-COOH molecules attached to their surface, such that the carboxyl groups face outwards. The plurality of second subparticles is then bonded to the first subparticle by reacting the carboxyl groups on the second subparticles with the amine groups on the surface of the particle, to form amide linkages, e.g., by using EDC or EDC/NHS chemistry. This process will leave unreacted amine groups on the capture agents bound to the first subparticle and unreacted carboxyl groups on the surface of the second subparticle. The unreacted amine groups on the capture agents bound to the first subparticle may be left unreacted. Further molecules may be attached to the unreacted carboxyl groups on the subparticles. For example, a plurality of coating molecules may be attached, such as $NH_2$-PEG-OMe molecules to inhibit protein adsorption, by means of amide linkage chemistry such as EDC/NHS chemistry.

In some embodiments a first subparticle and a second subparticle may be linked by a linker comprising a complex between an antibody and an antigen for the antibody. The first subparticle, e.g. a core subparticle, may comprise a surface and a plurality of a first antibody immobilised on the surface. Then the second subparticle, e.g. a protecting subparticle, may comprise a surface and an antigen for the antibody immobilised on its surface. The second subparticle may then be bound to the first subparticle by the antibody-antigen complex. In some embodiments, the antibody bound to the first subparticle may also serve as a capture agent for the target. In these embodiments, the antigen bound to the second subparticle may be the target or a fragment or variant thereof. For instance, if the target is TNFR, the antibody bound to the first subparticle may be anti-TNFR and the antigen bound to the second subparticle may be TNFR or a fragment or variant thereof that is still capable of binding to the anti-TNFR antibody bound to the first subparticle. In some embodiments, the antibody does not serve as a capture agent for the target, and capture agent may be provided on the particle either in the form of a different antibody, or as elsewhere described herein. In either case, the second subparticle (such as a plurality of protecting subparticles) may then be bound to the surface of the first subparticle (e.g. the core subparticle) by the antibody-antigen complex. If the antibody is also intended to serve as a capture agent, steric effects between the protecting subparticles will cause unbound antibodies to remain on the surface of the core subparticle, which antibodies are then free to capture the target.

In some embodiments the assembled particle comprises a plurality of PEG-containing moieties bound to residual unbound antigen on the protecting subparticles. PEG may be bound to the antigen on the protecting subparticles by methods described herein. For example, PEG moieties may be conjugated to the antibody, or to another ligand (e.g., another antibody, or a binding protein) for the target. In this way, off-target effects of the particle may be avoided.

In some embodiments the core particle has a surface; a plurality of a first antibody bound to the surface; and a plurality of a second antibody bound to the surface. The first antibody may serve as the capture agent, and the second antibody may serve to bind the protecting subparticle. The protecting subparticle may then comprise an antigen for the second antibody immobilized on its surface. The protecting subparticle may then be bound to the core subparticle by a complex of the second antibody and the antigen bound to the surface of the protecting subparticle. In some such embodiments, the antigen bound to the surface of the protecting subparticle is a ligand in a binding pair, such as avidin/biotin. Then residual unbound antigen may form an anchor point for the attachment of PEG moieties to the protecting subparticle. For example, if the antigen bound to the surfaces of the protecting subparticles is biotin, PEG moieties conjugated to avidin may be bound to the surfaces of the protecting subparticles by an avidin/biotin complex.

Figure 9:
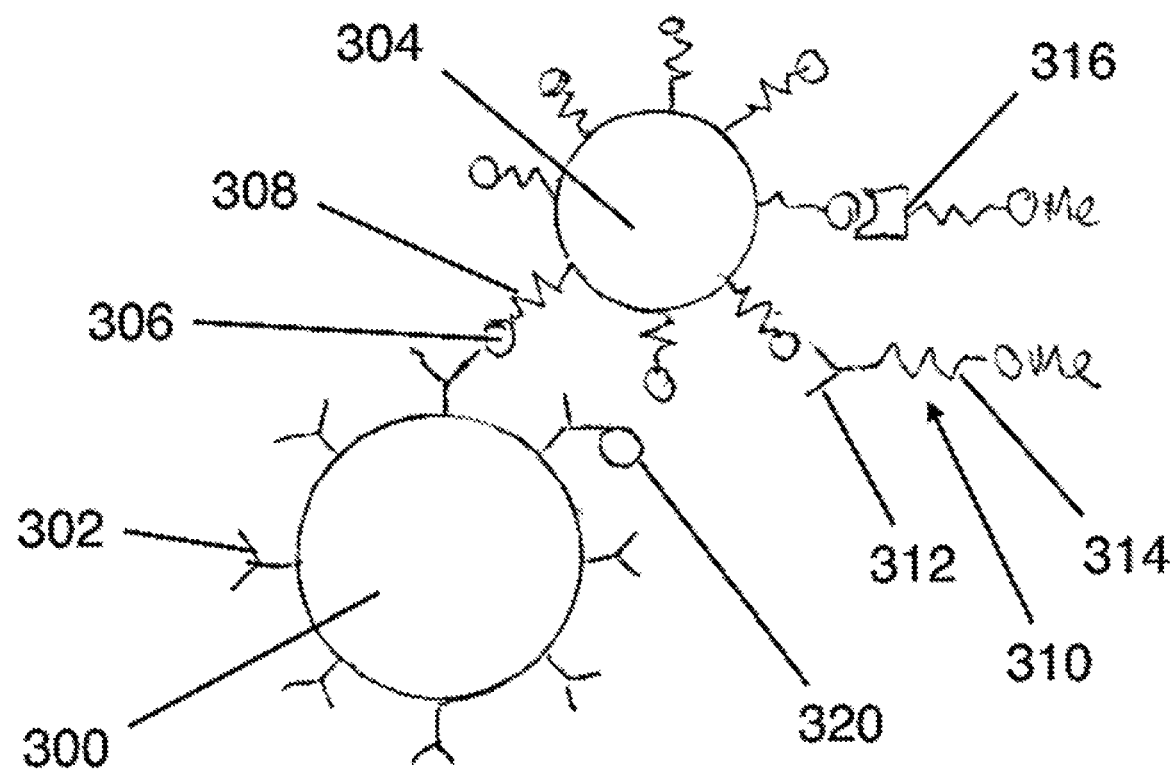
FIG. 9 depicts a particle comprising subparticles, assembled by antibody-antigen coupling.
Figure 10:
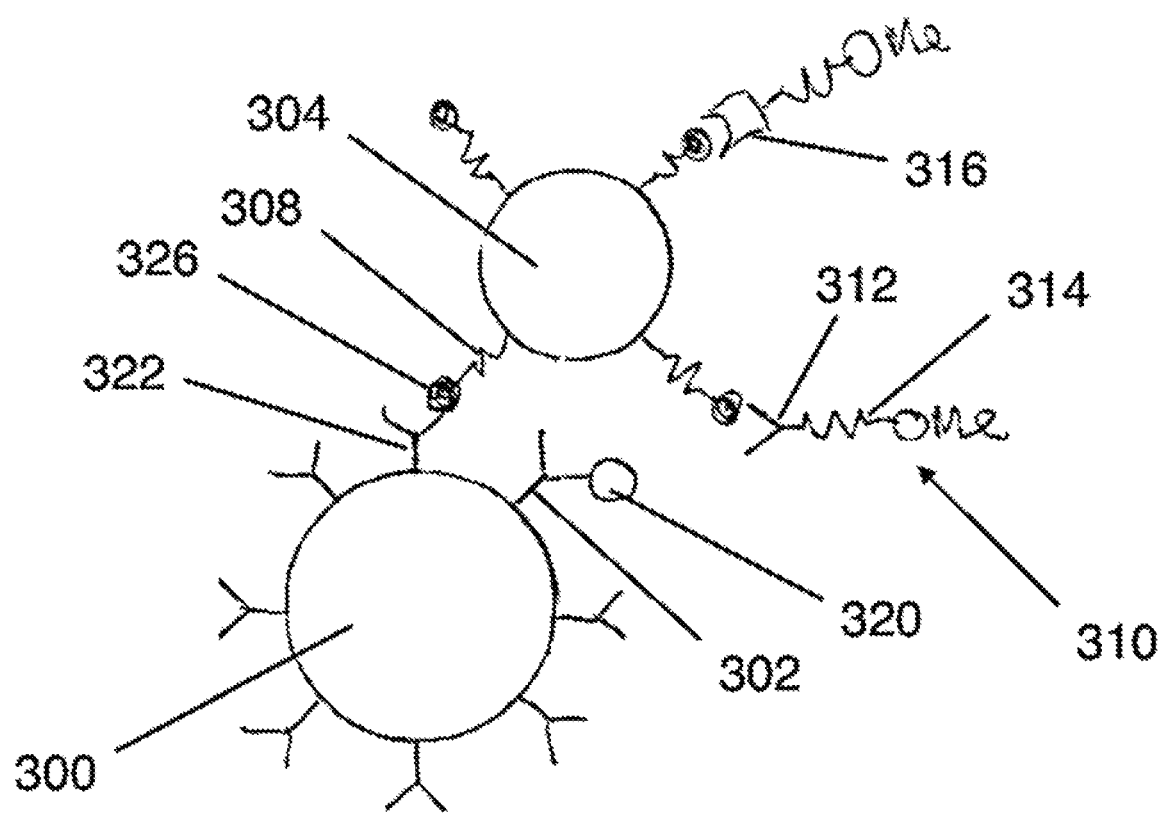
FIG. 10 depicts a further particle comprising subparticles, assembled by antibody-antigen coupling.
Figure 11:
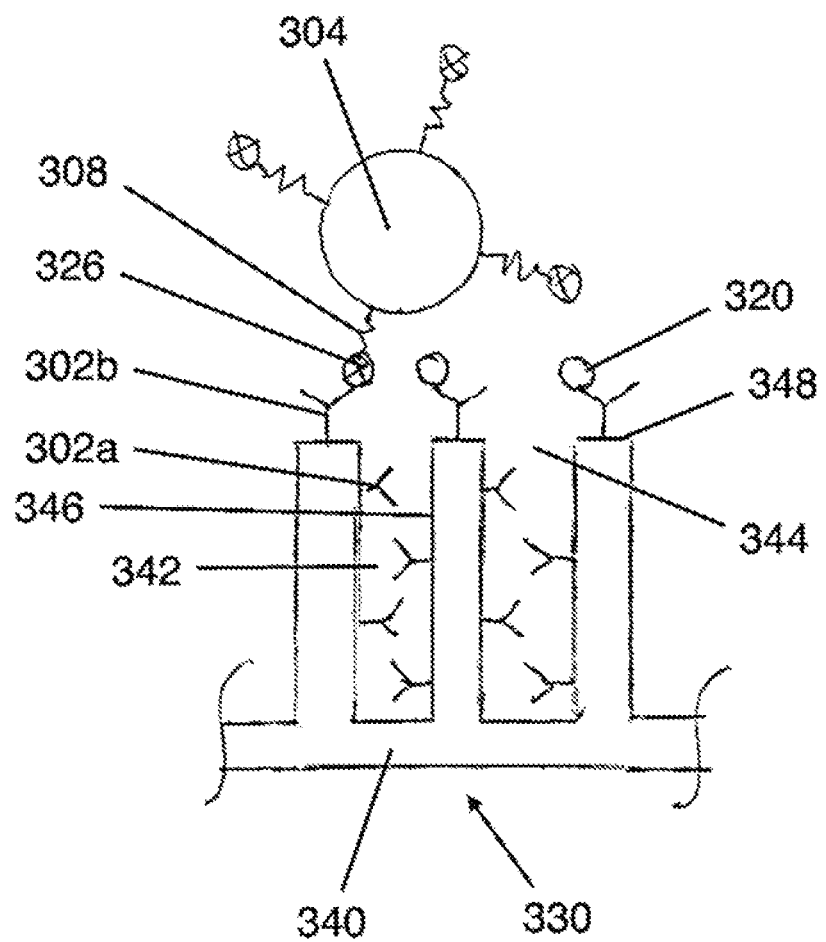
FIG. 11 depicts a particle comprising a porous core subparticle assembled by antibody-antigen coupling.

In some embodiments the core subparticle is porous and comprises an inner surface inside the pores and an outer surface, and an antibody disposed on the inner and outer surfaces. The antibody may serve as a capture agent. The protecting subparticle may then comprise an antigen for the antibody immobilized on its surface and is configured, such as dimensioned, to be excluded from at least a plurality of the pores. For example, the protecting subparticle may have a cross-sectional dimension larger than the maximum cross sectional dimension of a plurality, such as greater than 50%, greater than 60%, greater than 70%, greater than 80%, or greater than 90% of pores. A particle assembled from such subparticle comprises one or more protecting subparticles bound to the core subparticle by an antibody-antigen complex, such that the protecting subparticle is bound to the antibody only outside the pores. Antibodies disposed within the pores of the core subparticle will remain free to capture the target.

In some embodiments, an antibody and/or antigen may be bound to a subparticle by linkers, as described herein.

In an embodiment, the first, or capture agent antibody, is an anti-TNFR antibody and the antigen may be TNFR or an epitope thereof.

In some embodiments, an antigen linked to a surface of a protecting subparticle may be a second antibody which is a target for the first antibody disposed on or linked to the surface of a core subparticle, such that the first antibody binds the second antibody. In some such embodiments the first antibody may be a capture agent for the target biomolecule, for example the first antibody being adapted to bind either the target biomolecule or the second antibody.

Examples of antibody-antigen linked particles are shown in FIGS. 9 to 11, in which a core subparticle is shown, coupled to a single protecting subparticle, which is representative of a plurality of subparticles and is not drawn to scale. In some embodiments, the particle comprises a plurality of core subparticles coupled to a plurality of protecting subparticles as depicted in the figures.

Referring to FIG. 9, a core subparticle 300 comprises a plurality of a first antibody 302, which is the capture agent, immobilised on its surface, optionally on a linker. A protecting or shield subparticle 304 comprises a plurality of an antigen 306 for the antibody 302, immobilized on its surface by means of an optional linker 308. Antibody 302 that is not bound to antigen 306 on the protecting subparticle is free to bind soluble target biomolecule 320, while being inhibited by the protecting subparticle from interacting with the same biomolecule when on the surface of a cell. In some embodiments the antigen 306 may be the target biomolecule, or a fragment or variant thereof. Residual antigen 306 on the protecting subparticle may be bound by coating molecules 310, for example comprising a coating moiety bound to further antibody 312 to the antigen 306 or a binding partner 316 for the antigen 306. The antibody 312 may be the same as the agent antibody 302 or may be different. The binding partner 316 for the antigen 306 may, for example, be a member of a biotin/streptavidin pair. The coating moiety is selected for example to inhibit clearance from the circulation, such as a methoxy-PEG moiety 314. In some embodiments subparticle 304 comprises a mixed coating of linker-antigen 308, 306 and a PEG coating, both being immobilised on the surface of particle 304.

Referring to FIG. 10, core subparticle 300 comprises a plurality of a first antibody 302, which is the capture agent, and a plurality of a second antibody 322, distinct from the first, which is a binding, or coupling, antibody for the protecting subparticles. Protecting subparticle 304 comprises a plurality of antigen 326 reactive with the coupling antibody, attached to its surface by means of an optional linker 308. The capture agent antibody is free to scavenge soluble target biomolecules 320 while being inhibited by the protecting subparticle from interacting with a cell. Residual antigen 326 may be bound to a methoxy-PEG moiety 314 by means of antibody 312 or binding partner 316 as above.

Referring to FIG. 11, the core subparticle 330 is porous and comprises a body material 340 and one or more pores 342, each having an opening 344 and an inner surface 346 inside the pores and an outer surface 348, and an antibody 302 disposed on the inner surface, shown as 302a and on the outer surface, shown as 302b. The antibody 302a, b may serve as a capture agent. The protecting subparticle 304 comprises an antigen 326 for the antibody 302b immobilized on its surface and is dimensioned to be excluded from the pores, so preventing antibody 302a on the inner surface from being bound by the antigen 326, thus leaving antibody 302a free to scavenge target 320. Also, unbound antibody 302b on surface 348 is free to scavenge target 320, being inhibited by the protecting subparticle from contacting a cell surface. Residual antigen 326 may be bound by a coating molecule as in FIGS. 9 and 10.

In preferred embodiments, the above methods provide a composite particle comprising a silica core subparticle and silica or polymeric protecting subparticles, so allowing clearance by macrophages as known for single silica particles and, as necessary, biodegradation of the polymeric particles, as is known for example for polymers such as PLGA. Without being bound by theory, the composite particle may be taken up by a macrophage and may enter the phagosome, where the linker chemistry will break down to release the component subparticles. The separated component subparticles will then follow the same clearance pathway as single silica or polymer particles taken up individually by the macrophage. Embodiments comprising silica components or silica and polymer components may be advantageous over embodiments having protecting subparticles comprising gold, or a gold shell, as they will be readily cleared from the body while the gold subparticles may tend to accumulate.

The foregoing applies to any of the compositions and methods described herein. The disclosure specifically contemplates any combination of the features of such compositions and methods (alone or in combination) with the features described for the various kits described in this section.

Unless otherwise defined, all technical and scientific terms used herein have the same meaning as commonly understood by one of ordinary skill in the art to which this disclosure pertains. Preferred methods and materials are described herein, although methods and materials similar or equivalent to those described herein can also be used in the practice or testing of the presently disclosed methods and compositions. All publications, patent applications, patents, and other references mentioned herein are incorporated by reference in their entirety.

The disclosure contemplates all combinations of any of the foregoing aspects and embodiments, as well as combinations with any of the embodiments set forth in the detailed description and examples. These and other aspects of the present disclosure will be further appreciated upon consideration of the following Examples, which are intended to illustrate certain particular embodiments of the disclosure but are not intended to limit its scope, as defined by the claims.

EXEMPLIFICATION

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Example 1—Method for Treating a Cancer

A human patient is identified by a medical practitioner as having a cancer (e.g., lung, colon, breast, brain, liver, pancreatic, skin, or hematological cancer) that shed soluble TNFR or soluble IL-2R. The patient is administered a composition comprising particles (described herein) that bind to and sequester soluble TNFR or IL-2R in an amount effective to treat the cancer. Optionally, the patient is given "maintenance doses" of the composition to maintain inhibition of the effects of soluble TNFR or IL-2R and thereby continue to enhance immune surveillance against the cancer in the patient.

Example 2—Method for Detoxifying a Human

A human patient is presents with symptoms of toxicity associated with botulinum toxin. The patient is administered a composition comprising particles (described herein) that bind to and sequester soluble botulinum toxin in an amount effective to ameliorate one or more symptoms associated with the toxicity.

Example 3—Method for Treating a Viral Infection

A human patient is identified by a medical practitioner as having an HIV-1 infection. The patient is administered a composition comprising particles (described herein) that bind to and sequester soluble HIV-1 virions in an amount effective to reduce titers of the virus in the patient's circulation. The patient is given "maintenance doses" of the composition to maintain reduction of HIV-1 virion titers and thereby suppress the infection in the patient, as well as reduce the likelihood of transmission of the virus to another.

Example 4—Method for Manufacturing Silicon Particles

Porous silicon disks are manufactured with sizes of 1000 nm by 400 nm and 1000 nm by 800 nm with variable pore sizes. The size and morphology of the disks, as well as pore diameters, are characterized by scanning electron microscopy. Gold nanoparticles (Au) are deposited in the pores of the porous silicon disks. Tumor necrosis factors (TNFs) are conjugated to the surfaces of the gold nanoparticles through dative covalent bonds. The ligand density and TNF-Au binding stabilities are assessed.

Example 5—Method for Manufacturing Polymer Particles

Poly(lactide-co-glycolide) (PLGA) particles are fabricated by emulsion. The size and morphology of the PLGA particles are characterized by scanning electron microscopy, atomic force microscopy, and transmission electron microscopy. The particles are coated with quaternary ammonium beta-cyclodextrin, for macrophage recruitment (i.e., phagocytosis). The coating is verified by atomic force microscopy and transmission electron microscopy. Coating density and uniformity is characterized by transmission electron microscopy and dynamic light scattering.

The beta-cyclodextrin-coated PLGA particles are incubated with macrophages, and phagocytosis is monitored by fluorescence microscopy and by flow cytometry.

The beta-cyclodextrin-coated PLGA particles are coated with a blend of polyethylene glycol (PEG) and thiol moieties to allow for prevention of opsonization and evasion of macrophage uptake, as well as binding to other particles. The uniformity and density of the PEG and thiol coatings are characterized by atomic force microscopy. Coating stabilities are characterized by incubating the particles in media for various periods of time. Evasion and uptake of the particles are monitored at various time points by incubating the particles with macrophages, as described above.

The PLGA particles are coated with tumor necrosis factor (TNF), and the particles are combined by disulfide bonds to form a "sponge," comprising TNF on the interior surface of the sponge. The exterior surface (i.e., outer surface) of the sponge is optionally blocked with particles that do not comprise TNF to prevent interactions between the TNF of the sponge and cells.

Example 6—Pharmacokinetics of Polymer-Based Particles

The sponge of Example 5 (i.e., a composition comprising "sponges" of Example 5, such as $10^3$ to $10^{12}$ sponges) is administered either intravenously or intratumorally into mouse models of primary and metastatic cancer as well as healthy controls. The toxicity of the sponge is determined by identifying $LD_{50}$'s for each route of administration. The half-life of the sponge is determined by monitoring plasma concentrations of the sponge by LC/MS and ICP for each route of administration. The biodistribution of the sponge is determined by taking biopsies of the mice and analyzing tissue for the sponge and its components by LC/MS, ICP, and confocal microscopy.

Example 7—Efficacy of Polymer-Based Particles

The sponge of Example 5 (i.e., a composition comprising "sponges" of Example 5, such as $10^3$ to $10^{12}$ sponges) is administered to mice comprising MDA-MB-231 or 4T1 xenografts. The MDA-MB-231 model is used to assess reductions in tumor size and growth, and the 4T1 model is used to assess inhibition of metastasis. The sponge is administered intratumorally to MDA-MB-231 mice once a week for 6 weeks, and body weight and tumor sizes are monitored periodically. The sponge is administered intravenously to 4T1 mice once a week for 6 weeks, and the number of metastases are monitored.

Example 8—Pharmacokinetics and Efficacy of Silicon/Gold-Based Particles

The experiments of Examples 6 and 7 are repeated with the porous silicon particles of Example 5.

Example 9—Method for Manufacturing DNA Particles

A DNA nanotube will be assembled using protocols similar to those described in Douglas et al. (Nature 459 (7245):414-8 (2009), hereby incorporated by reference in its entirety). The nanotubes will include five internal biotins. DNA strands that are not incorporated into nanotubes will be removed using a 300 kDa MWCO filter unit. The nanotubes will be characterized by atomic force microscopy.

Biotin-labeled TNFα will be mixed with streptavidin tetramer in a 3:1 ratio to produce TNFα modules with three human TNFα bound to one streptavidin molecule, at a concentration of about 300 nM. The TNFα modules will then be incubated with the DNA nanotubes to produce nanotubes comprising the TNFα modules. The nanotubes will be purified using a 300 kDa MWCO filter unit and characterized by atomic force microscopy.

A TNFα assay will be used to confirm the TNFα modules are attached to the nanotubes and to generate solutions of nanotubes comprising TNFα at 5 nM, 10 nM, 15 nM, 25 nM, 35 nM, and 50 nM concentrations (Abcam Catalogue #ab181421).

The ability of the TNFα nanotubes to bind soluble TNF-receptor will be assessed using an ELISA assay (Abcam Catalogue #ab100642). Briefly, the nanotubes will be added at various concentrations to different wells of a 96-well plate coated with an anti-soluble TNF receptor antibody. Soluble TNF receptor will be added to the wells, the plate will be incubated for a period of time, and then the nanotubes will be washed from the wells along with soluble TNF that is bound to the nanotubes. A biotinylated anti-soluble TNF receptor antibody will be added to the wells, the wells will be washed to remove unbound antibody, horseradish peroxidase-conjugated streptavidin will be added to the wells, the wells will be washed to remove unbound horseradish peroxidase, and 3,3',5,5'-tetramethylbenzidine (TMB) will be added to the wells. The amount of TNF-receptor bound to the anti-TNF receptor antibodies of the wells will be quantified by monitoring TMB at 450 nm and/or production of 3,3',5,5'-tetramethylbenzidine diimine from TMB at 650 nm. Wells that receive higher concentrations of nanotubes will display higher absorbance at 450 nm and lower absorbance at 650, corresponding to less soluble TNF-receptor bound to the wells, and thus, less peroxidase activity.

Example 10—Method for Manufacturing Porous Silicon-Polymer Particles

Porous silicon disks are manufactured with sizes of 1000 nm by 400 nm or 1000 nm by 800 nm, and with variable pore sizes. Fabrication is described for example in U.S. Pat. No. 8,920,625, which is fully incorporated by reference herein. The pores may be substantially uniform or may have a size distribution. The size and morphology of the disks, as well as pore diameters, are characterized by scanning electron microscopy. Gold nanoparticles (Au) are deposited on the surfaces of the porous silicon disks, including on the external surfaces of the disks. Briefly, fresh porous silicon particles are suspended in water with a surfactant. Tetrachloroauric acid solution is added into the porous silicon particle solution under sonication to a selected final concentration, and sonicated for a further 20 min. Metallic gold is reduced in contact with the silicon surface to form nanoparticles of order 5 nm diameter on the silicon surface. Typically gold is loaded onto porous silicon disks 1000 nm×400 nm at around 2 ug Au per 0.05 bn particles.

The polymer particles of example 5 are brought into contact with the gold-coated porous silicon disks and the thiol groups are allowed to react with the gold on the external surfaces of the disks to bond the polymer particles to the disks to form composite polymer-Au-pSi particles. The polymer particles are preferably sized so as not to enter the pores, or not to enter at least a proportion of the pores, of the porous silicon disks, so as to leave the pores open for scavenging by capture agent within the pores. Evasion and uptake of the assembled particles are monitored at various time points by incubating the particles with macrophages.

The composite particles are then brought into contact with an agent, such as tumor necrosis factor (TNF), which bonds to remaining gold areas in the pores of the disks by reaction of cysteine residues with the gold surface. In some embodiments gold will remain on the outer surface of the disks that has not reacted with PLGA-PEG-SH particles, and TNF may bond to this gold also. However, the TNF on the outer surfaces is sterically hindered by the protecting subparticles from contacting a cell surface.

Example 11—Method for Manufacturing Particles Assembled from PLGA-PEG Copolymer and Porous Silicon Subparticles Porous silicon disks are manufactured with sizes of 1000 nm by 400 nm or 1000 nm by 800 nm, and with variable pore sizes. Fabrication is described for example in U.S. Pat. No. 8,920,625 The pores may be substantially uniform or may have a size distribution. The size and morphology of the disks, as well as pore diameters, are characterized by scanning electron microscopy. Gold nanoparticles (Au) are deposited on the surfaces of the porous silicon disks, including on the external surfaces of the disks.

Poly(lactide-co-glycolide) (PLGA)—PEG-SH copolymer particles are fabricated by emulsion. Fabrication of similar particles is described for example in Kamaly et al, PNAS 110(16), 6506-6511, 2013, for particles comprising PLGA-PEG-COOH. Briefly, 10-30% PLGA-PEG-COOH (2 KDa-10 KDa PEG component) was mixed with 90%-70% PLGA-COOH (Viscosity: 0.15-0.25), dissolved in dichloromethane, sonicated in 4% PVA solution, and added dropwise to water followed by stirring. Nanoparticles are then collected by centrifugation and washed. Alternatively, PLGA-PEG-SH copolymer (instead of PLGA-PEG-COOH copolymer) particles are fabricated similarly, for example comprising 10%-30% PLGA-PEG-SH and 90%-70% PLGA-SH, such as comprising 10% PLGA-PEG-SH and 90% PLGA-SH.

The size and morphology of the PLGA-PEG-COOH (or PLGA-PEG-SH) particles particles are characterized by scanning electron microscopy, atomic force microscopy, and transmission electron microscopy. The presence of PEG-COOH moieties at the surface of the particles is confirmed by $^{1}$H-NMR. Size and uniformity of the particles is characterized by dynamic light scattering and transmission electron microscopy. The presence of PEG-SH moieties at the surface of PLGA-PEG-SH particles is confirmed by standard assays such as zeta potential, atomic force microscopy and transmission electron microscopy. Size and uniformity of the particles is characterized by transmission electron microscopy and dynamic light scattering.

The PLGA-PEG-COOH (or PLGA-PEG-SH) particles are incubated with macrophages, and phagocytosis is monitored by fluorescence microscopy and by flow cytometry. The uniformity and density of the coating is characterized by atomic force microscopy. Coating stability is characterized by incubating the particles in media for various periods of time.

To bind PLGA-PEG-SH particles to gold-coated porous silicon disks, PLGA-PEG-SH particles are brought into contact with gold-porous silicon disks and the thiol allowed to react with the gold on the external surfaces of the disks to bond the PLGA-PEG-SH particles to the disks to form composite PLGA-PEG-Au-pSi particles. A similar fabrication process is described for example in Mi et al., Adv. Healthc. Mater. 5(8): 936-946, 2016 and in US Patent Application Publication No. US2017/056327, for PLGA-PEG-COOH particles bonded using amide linkage chemistry directly onto porous silicon disks having an APTES (aminopropyltriethoxysilane) coating. To bind PLGA-PEG-COOH particles on gold-coated porous silicon particles, amine-PEG-SH linkers, typically with a 5 kDa PEG component, are first coated on gold-porous silicon particles and —COOH groups on the PLGA-PEG-COOH particles are then coupled to the amine groups by standard amide chemistry.

In this way a plurality of shield or protecting subparticles is provided on the external surface of the disks. The PLGA particles are preferably sized so as not to enter the pores of the porous silicon disks, so as to leave the pores open for scavenging by capture agent within the pores. In some embodiments, remaining free thiol groups will be quenched or blocked as is known in the art. Evasion and uptake of the assembled particles are monitored at various time points by incubating the particles with macrophages.

The composite particles are then brought into contact with an agent, such as tumor necrosis factor (TNF), which bonds to remaining gold areas in the pores of the disks by reaction of cysteine residues with the gold surface. In some embodiments gold will remain on the outer surface of the disks that has not reacted with PLGA-PEG-SH particles, and TNF may bond to this gold also. However, the TNF on the outer surfaces is sterically hindered by the protecting subparticles from contacting a cell surface. Remaining areas of unreacted gold surface may be blocked to inhibit non-specific binding of species to the gold, by reacting a thiolated PEG moiety, such as a thiolated methoxy PEG (i.e. SH-PEG-OMe), with the gold. The size of the PEG moiety is selected to inhibit non-specific binding while not inhibiting significantly capture of target species by the agent. The PEG portion of the SH-PEG-OMe or COOH-PEG-OMe molecule may be selected such that the molecule may have a molecular weight in the range 500 Da to 50 kDa, such as in the range 1 kDa to 20 kDa, or in the range 2 kDa to 10 kDa. A molecular weight of 5 kDa has been found to be effective to inhibit non-specific binding while not inhibiting capture of the target species by the agent.

Figure 12:
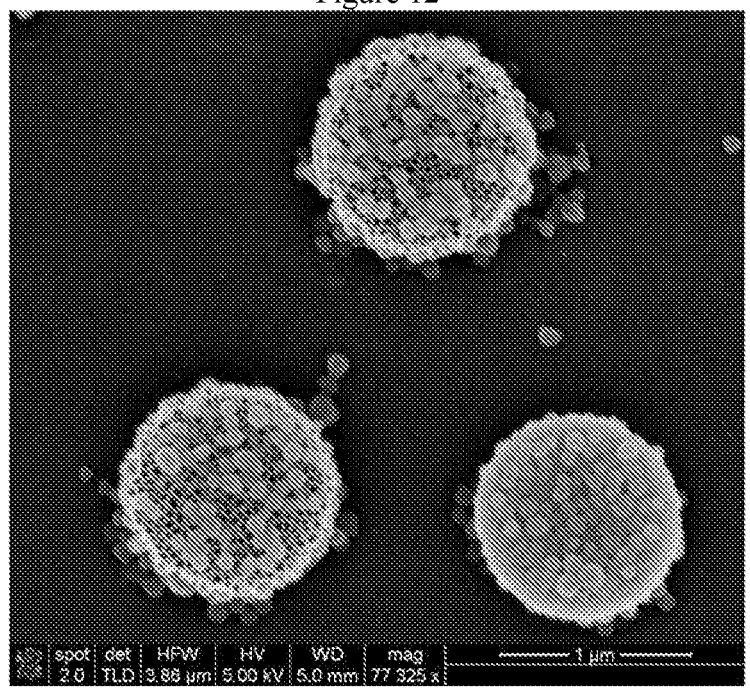
FIG. 12 shows a pSi disk with PLGA-10% PEG NP shielding showing front and rear sides.
Figure 13:
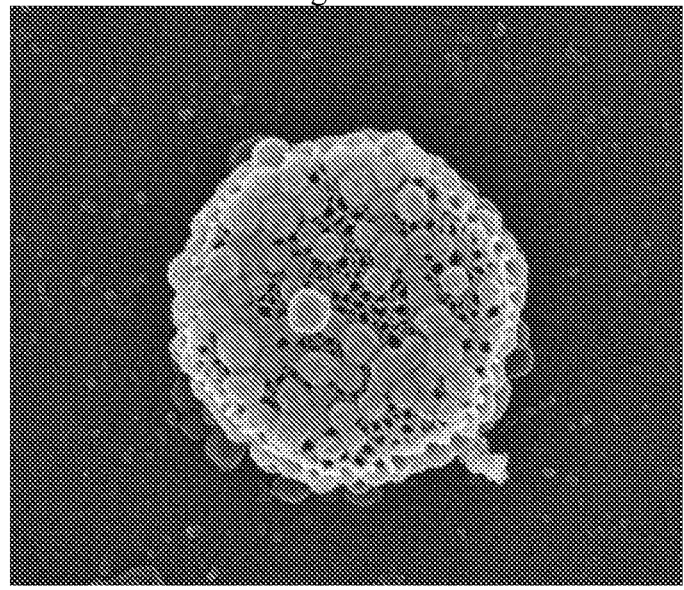
FIG. 13 shows a pSi disk with PLGA-30% PEG NP shielding.
Figure 14:
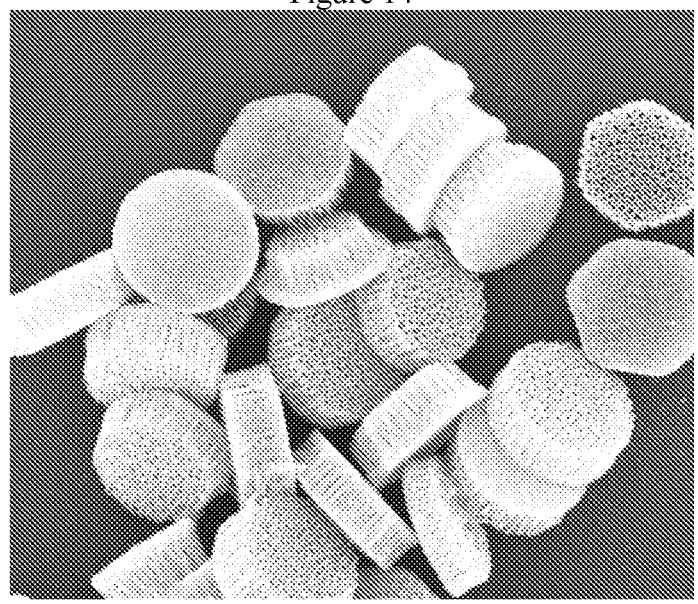
FIG. 14 shows a pSi disk with 10 kDa PEG shielding.

Particles fabricated according to this example are shown in FIGS. 12 and 13. In FIG. 12 the protecting subparticles were formed from 10% PLGA-PEG(2 kDa)-COOH plus 90% PLGA-COOH, and in FIG. 13 the protecting subparticles were formed from 30% PLGA-PEG(2 kDa)-COOH plus 70% PLGA-COOH. Particles formed from 20% PLGA-PEG(2 kDa)-COOH and 80% PLGA-COOH were also successfully coupled to porous silicon disks. It was found that the particles comprising a higher PLGA-PEG-COOH component had higher solubility in the aqueous solution in which the coupling of the PLGA-PEG subparticles to the porous silicon took place, and so subparticles formed using 10% PLGA-PEG-COOH were chosen for in-vitro tests.

Example 12 Agents Other than TNF

Particles that scavenge targets other than sTNFR may be made using similar methods. For example, the capture agent may be a TNFR, which will immobilize on gold by means of cysteine residues in a similar manner to TNF. The capture agent may be linked to the gold within the pores using a linker as described herein, such as a SH-linker-reactive group linker, and the agent may be immobilized on the gold by reaction between the reactive group, such as —COOH or —NH$_2$, and a functional group on the agent. The capture agent may be any agent described herein. In some embodiments the capture agent is linked to the surface of the porous silicon within the pores, for example an APTES modified porous silicon surface, using a linker as described herein, such as a COOH-linker-reactive group linker, wherein the —COOH group is reacted with the aminated surface of the porous silicon as known in the art and described for example in Mi et al. Adv. Healthc. Mater. 5(8): 936-946, 2016. In such embodiments the porous silicon disk may not comprise gold. The agent may be immobilized on the APTES-linker modified porous silicon surface by reaction between the reactive group on the linker, such as maleimide, —COOH or —NH$_2$, and a functional group on the agent. Such an agent may comprise an antibody or fragment thereof, or other capture agents as described herein.

Example 13 Method for Manufacturing Particles Comprising Porous Silicon and PEG Shielding Porous silicon disks are manufactured with sizes of 1000 nm by 400 nm or 1000 nm by 800 nm, and with variable pore sizes, as described for example 11. Gold nanoparticles (Au) are deposited on the surfaces of the porous silicon disks, including on the external surfaces of the disks.

PEG-SH coating molecules are coupled to the gold nanoparticles by incubation of the PEG-SH with the porous silicon disks comprising gold nanoparticles in aqueous solution, at a selected concentration of PEG-SH and for a selected reaction time. For a given concentration of PEG-SH and of particle in the solution, the reaction time may be selected to control the coverage of the PEG-SH on gold. The reaction between PEG-SH and gold is sufficiently slow that coverage may be conveniently controlled by means of the reaction time, typically in the range 5 to 60 minutes.

In some embodiments, the silicon disks may comprise an APTES coating to provide an aminated surface instead of comprising gold nanoparticles, and PEG-COOH may be coupled to the surface of the porous silicon disk by means of amide bonding chemistry as described herein.

The PEG-SH or PEG-COOH molecules may comprise a methoxy group, such as SH-PEG-OMe or COOH-PEG-OMe, which is known to inhibit uptake particles by macrophages. In this way, the PEG coating comprising functionalized PEG molecules may achieve both of: inhibiting interactions of the agent with a target biomolecule when on a cell surface, such as a cell surface receptor, and inhibiting clearance of the particle by macrophages.

An agent is then bound to the gold by contacting the particle with agent in a coupling solution. The agent may bind to the gold at remaining portions of the gold surface that have not been covered by PEG-SH. By controlling the time for which the PEG-SH is reacted with the gold, the remaining area of gold available for binding of the agent may be controlled. The amount of agent that is coupled may be controlled by selecting the concentration of agent in the coupling solution and/or the time for which the agent is reacted with the PEG-coated porous silicon disks. The amount of agent coupled to the disks may be measured for example by measuring the amount of agent remaining in the coupling solution after the coupling reaction.

The PEG portion of the PEG-SH or PEG-COOH molecule may be selected such that the molecule may have a molecular weight in the range 500 Da to 50 kDa, such as in the range 2 kDa to 20 kDa, or in the range 5 kDa to 20 kDa. In some embodiments the molecule has a molecular weight of 5 kDa, 10 kDa or 20 kDa. In some embodiments the molecular weight is selected to achieve shielding of an agent coupled to the external surface of the porous silicon disk from interaction with a biomolecule on the surface of a cell, i.e. so as to inhibit binding of the agent to the biomolecule or activation of the biomolecule by the agent in the case that the biomolecule is a cell surface receptor.

It has been found that 10 kDa and 20 kDa PEG-SH molecules are effective to inhibit such binding and/or activation.

In an example fabrication sequence, the gold-coated porous silicon disks are first reacted with 10 kDa SH-PEG-OMe for a shielding PEG coupling time, then reacted with an agent at a selected concentration in the coupling solution for an agent coupling time. The agent coupling time may be selected such that the agent coupling reaction goes to completion within that time. The shielding PEG coupling time and the agent concentration in the coupling solution may be selected independently to control the coverage of the gold surface with the PEG and the agent, and may be chosen to be in a ratio to control the ratio of the PEG and agent on the gold surface. Typical coupling conditions are given below for coupling to human TNF capture agent. Following coupling of both shielding PEG and the agent, remaining gold surface may be blocked by reacting the particles with blocking PEG for a blocking PEG reaction time, which may be selected to be sufficient to saturate the remaining gold surface with blocking PEG.

To add a shielding PEG, 30 million gold coated pSi particles were incubated with 50 ug/ml 10 kDa PEG-SH (NanoCS) in 100 uL PBS (pH 7.2) solution for 15 min, and then the PEGylated particles were collected and washed by centrifugation.

To add a capture agent, human TNF, 30 million 10 kDa PEG-coated pSi particles from the above step were mixed into 100 μL 50 ug/mL Human TNF (RD Systems) in PBS (pH 7.2) solution with shaking for 30 min at room temperature, then the TNF-coupled particles were washed by centrifugation.

To add a blocking PEG, TNF-loaded 10 kDa PEG-coated particles from the above steps were mixed with 5 mg/mL 5 k PEG-SH (NanoCS) in 100 uL PBS (pH 7.2) for 15 min, then the completed particles were collected and washed by centrifugation.

Example 14 Testing of the Function of Particles Described Herein

The ligand density and TNF-Au binding stabilities are assessed. The scavenging action of the particles is tested at a physiologically relevant concentration of sTNFR1/2, and shielding of any surface TNF that may be present by the protecting subparticles or the protecting PEG shielding may be tested by contacting the particles with a cell line that undergoes apoptosis when contacted with TNF.

Example 15 PLGA-PEG NP-Shielded Porous Silicon Particles

Figure 15:
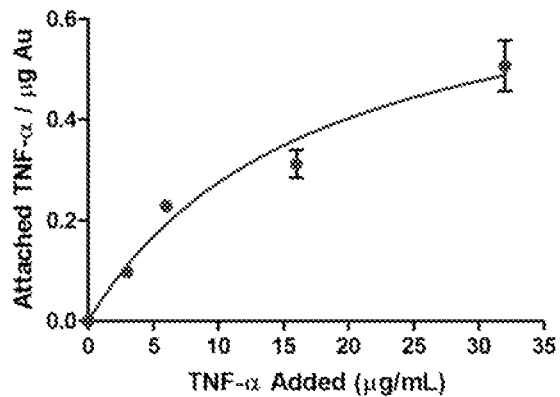
FIG. 15 shows a quantitation of human TNF on PLGA-PEG-nanoparticle-shielded pSi disks

The amount of human TNF agent coupled to the porous silicon particles comprising PLGA-PEG protecting particles according to the procedure described above is shown in FIG. 15. Porous silicon particles with 2 μg are incubated in TNF coupling solution at a range of concentrations and the remaining TNF in the solution is measured by ELISA. The amount of TNF per microgram of Au on the particles is plotted against the concentration of TNF in the coupling solution. The ability to couple TNF to the particles shows that the gold has accessible binding sites for TNF following coupling of the PLGA-PEG particles to the gold. The concentration of TNF on the particles is around 50% of that achieved for mouse TNF on PEG-shielded particles (see below).

Capture of human sTNFR1/2 from serum is tested as follows. 0.1 ug human sTNFR1 or sTNFR2 (RD systems) is mixed with 50 ml bovine serum (2 ng/ml) and particles are incubated in the sTNFR1/2+serum test solution. At time intervals, the particles are spun down, a 1 ml sample is taken and the sTNFR1/2 level in the sample is tested by ELISA. A curve of capture percentage of the initial concentration of sTNFR1/2 is plotted as a function of time to show the time course and final value of the capture percentage. Capture of sTNFR1 and sTNFR2 from the same solution is tested by using a solution containing 2 ng/ml sTNFR1 and up to 10 ng/ml sTNFR2 in serum and analyzing the samples for sTNFR1 and sTNFR2. A typical physiological level of sTNFR1 in healthy humans is in the range 0.5-2 ng/ml, and of sTNFr2 in the range 1-3 ng/ml; in disease such as cancer, the level in serum may be in the range 1.5-3 ng/ml for sTNFR1 and 3-5 ng/ml for sTNFR2 (see e.g. Lentz and Kumar, Therapeutic Apheresis and Dialysis 2008, 12(6) 491-499), so capture from these starting concentrations reflects capture from physiologically relevant levels.

Figure 16:
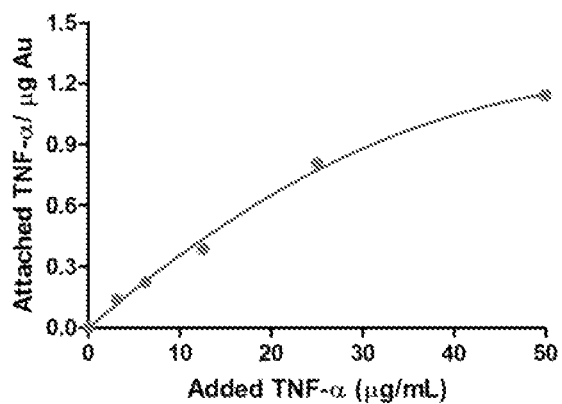
FIG. 16 shows a quantitation of mouse TNF on 10 kDa methoxy-PEG-shielded pSi disks

Example 16 TNF Coupling and Capture Performance of PEG-Shielded Porous Silicon Particles TNF (RD systems recombinant mouse TNF cat. Ref. 410-mt) was coupled to 10 kDa PEG-shielded gold-coated porous silicon particles. 100 μl of coupling solution comprising varied mouse TNF concentrations in PBS was added to batches of particles pre-coupled with 10 kDa methoxy-PEG-SH, each batch containing 2 μg of Au (0.03 billion particles). The mixture was shaken for 15 min at room temperature. The TNF-α conjugated particles were collected by centrifugation. The TNF concentrations remaining in the supernatant were measured by ELISA. The TNF on the particle was calculated through the differential between the initial TNF concentration in the solution and that detected in the supernatant. The amount of TNF coupled to the particles is shown in FIG. 16 as a function of the concentration of TNF in the loading solution.

Figure 17:
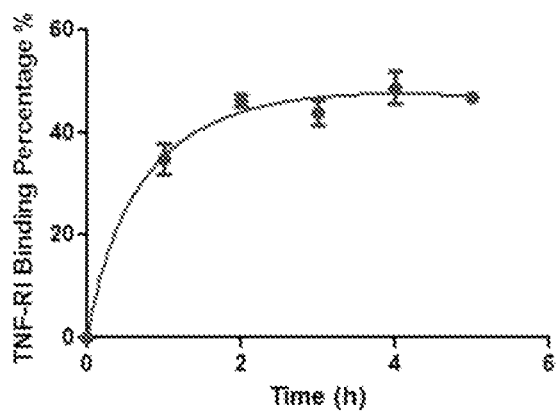
FIG. 17 shows the capture of mouse sTNFR1 from bovine serum with initial 2 ng/ml mouse sTNFR1

To test capture performance, TNF coupling to 10 kDa PEG-shielded porous silicon particles was carried out in 25 μg/ml TNF coupling solution. TNF was coupled to 3 million particles, which bound about 0.15 μg TNF. Capture of sTNFR1 was tested from bovine serum containing 4 ng total (2 ng/ml) mouse sTNFR1 (RD Systems mouse sTNFR1 protein cat no. 425-R1-050). Typical levels of sTNFR1 in healthy mice and in humans are each in the range 0.5-2 ng/ml, so this concentration represents physiological levels of sTNFR1. 15 ng of TNF on 0.3 million particles was added to the serum. At each time point, 1, 2, 3, 4 and 5 h, the test volume was centrifuged, 10 μl samples were taken from the supernatant and the sTNFR1 concentration was measured by ELISA. FIG. 17 shows the time course of capture as a percentage of the initial sTNFR1 concentration. 15 ng TNF on 0.3 million particles captured around 45% of the 4 ng initial sTNFR1 within 2 h. That is, 15 ng TNF on particles captured 1.8 ng of sTNFR1. An interpretation of this result is that for an expected trimeric configuration of the TNF coupled to the gold surface, with molecular weight 52.5 kDa, and expected monomeric form of sTNFR1 in solution at this low concentration, of molecular weight 21 kDa, the mean occupancy of each TNF trimer is 0.3, i.e. around 1 in 3 of the trimeric TNF capture agents captures a sTNFR1 molecule in this experiment. FIG. 17 shows that capture of a target by an agent on the surface of the particle is achieved, and efficient, in the presence of the 10 kDa PEG shielding molecules.

Example 17 Shielding of Capture Agent by PLGA-PEG Particles and by PEG-Coating

To test the effectiveness of shielding of a capture agent on porous silicon disks by coupling of PLGA-PEG protecting subparticles, or PEG coating molecules forming a shield, to the disks, each of these two particle types with a TNF capture agent was incubated with TNF-sensitive L929 mouse fibroblast cells, which express TNFR1 receptors on their cell membrane and which undergo apoptosis when TNF binds the receptor in the presence of actinomycin D. L929 cells are used as a standard test for potency of TNF (see Matthews, N. and M. L. Neale (1987) in Lymphokines and Interferons, A Practical Approach. Clemens, M. J. et al. (eds): IRL Press. 221). The test comprised culturing L929 cells in the presence of an excess of the particles, such that each cell would be in contact with multiple particles, and observing the growth of the cells in culture over time. In such an assay, continued growth in culture indicates that the TNF is shielded from binding to sTNFR1 on the cell surface. The experiments were done using an 'Incucyte' automated cell culture instrument with automated cell confluence imaging.

Figure 18A:
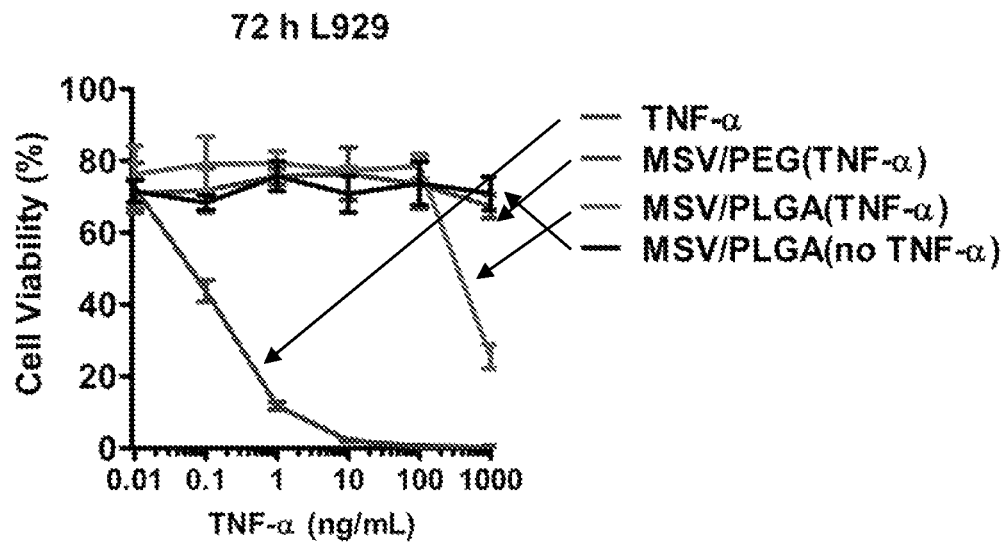
FIG. 18A shows the viability of mouse fibroblast cells at various effective TNF-α concentrations, either in solution or on a shielded particle.
Figure 18B:
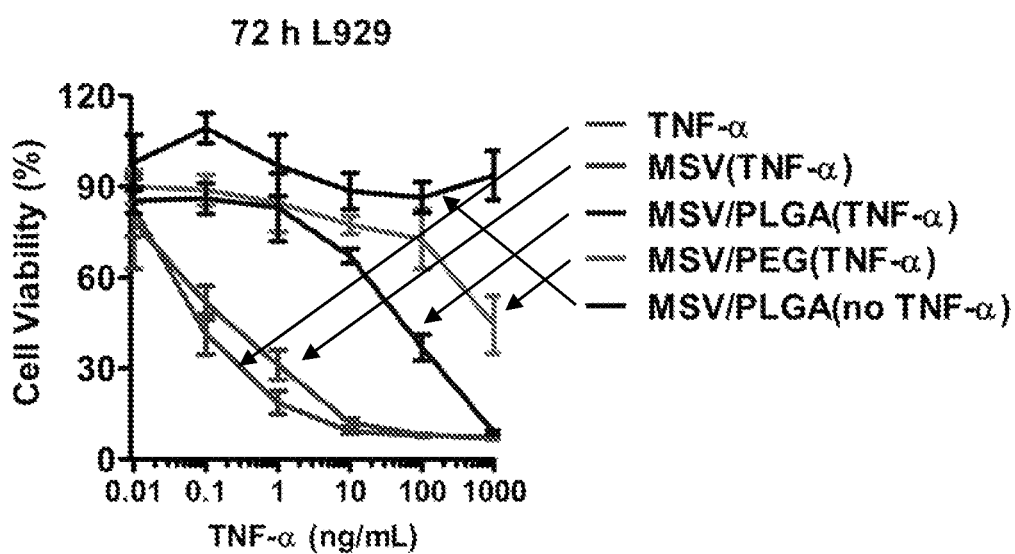
FIG. 18B shows the viability of mouse fibroblast cells at various effective TNF-α concentrations, either in solution or on a shielded particle.

Results are shown in FIGS. 18a and 18b. The experimental groups indicated on the figure legends were as follows ('MSV' means 'multi-stage vector', i.e. the porous silicon disk): (1) Free TNF; (2) MSV(TNF): TNF-loaded porous silicon disk without shielding; (3) MSV/PLGA(TNF): PLGA-PEG NP-shielded porous silicon disk; (4) MSV/PEG (TNF): 10 kDa methoxy-PEG-shielded porous silicon disk; (5) MSV/PLGA(no TNF): PLGA-shielded porous silicon disk without TNF capture agent. Results are shown as percent viability after 72 hr culture, plotted against concentration of TNF (either free or on particles) in contact with the cell culture. Percent viability is measured as the ratio of the cell coverage in the treatment well to the cell coverage in a control well containing only culture medium.

Free TNF shows high toxicity; in FIG. 18b, TNF on MSV (i.e. porous silicon disks) without shielding shows similar toxicity to free TNF; MSV without TNF and with PLGA-PEG protecting subparticles show no toxicity; and both MSV/PLGA (i.e. porous silicon disks shielded with PLGA-PEG protecting subparticles) and MSV/PEG (i.e. porous silicon disks shielded with 10 kDa methoxy-PEG) show no toxicity at least up to 10 ng/ml TNF—a level at which the non-shielded particles cause 100% toxicity. This demonstrates the effectiveness of both types of shielding.

Example 18 Particles Comprising Anti-sTNFR2 Antibody Capture Agent to Scavenge sTNFR2

Porous silicon disks with deposited gold nanoparticles on their surface, pretreated with 10 kDa shielding PEG as described above, had thiolated streptavidin coupled to the gold and biotinylated anti-mouse sTNFR2 antibody (Biolegend, cat. no. 113403) was then coupled to the immobilised streptavidin to load the antibody onto the particle. 100 million particles were incubated with 500 µL thiolated streptavidin (1 mg/mL) in PBS (pH=7.2) for 15 min under shaking. After centrifugation and washing 3 times, 200 µL 10K PEG-thiol (10 µg/mL) was used to coat the surface of the particles for 15 min. Particles were collected by centrifugation after 3 times wash with PBS buffer, then, under shaking, the resulting particles were reacted with 500 µL antibody (50 µg/mL) in PBS buffer (pH=7.2) for 30 min and then washed 3× with PBS buffer by centrifugation. The particles were then used for capture tests.

Figure 19:
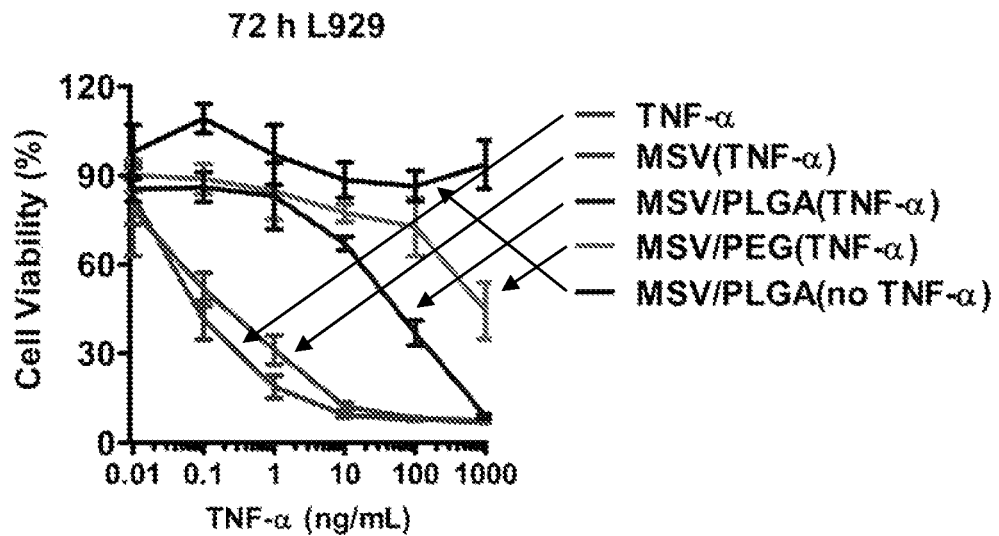
FIG. 19 shows a time course of sTNFR capture by PEG-shielded and unshielded particles.
Figure 20:
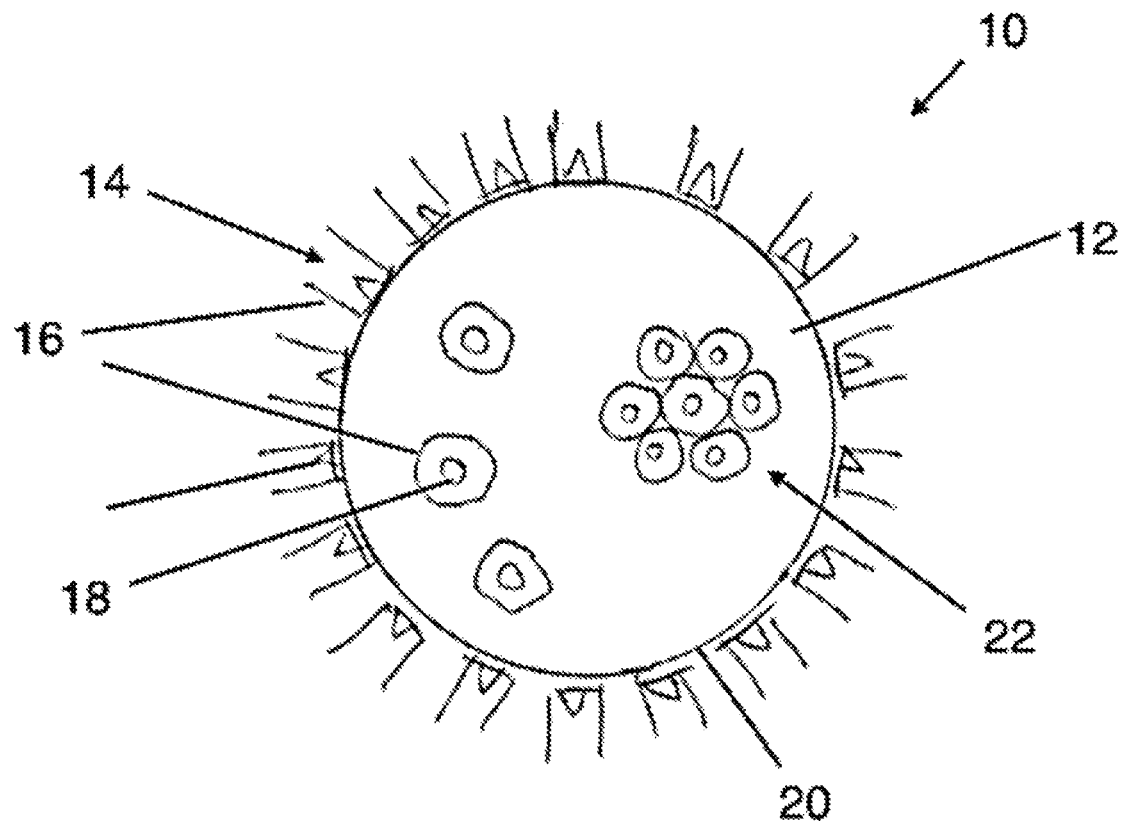
FIG. 20 depicts an exemplary arrangement of a core particle bound to a plurality of cup-shaped active subparticles.

A first batch of particles did not have blocking PEG added to the gold surface; a second batch of the particles had 5 kDa blocking SH-PEG-OMe coupled to the remaining gold surface after coupling of the shielding PEG and capture antibody. To test capture of endogenous mouse sTNFR2 from mouse serum, 50 million anti-sTNFR2 antibody-coupled porous silicon particles were mixed with 1.4 ml of mouse serum. The concentration of endogenous sTNFR2 in the serum was measured by ELISA (RD systems) and found to be 4.0 ng/ml. At each time point (0.5, 1, 2, 4, 6 h) the sample was spun, 100 ul samples were taken from the supernatant, the particles were resuspended, and the sTNFR2 in the sample was measured by ELISA. FIG. 19 shows that by 0.5 h, around 80% of the sTNFR2 had been captured. A typical concentration of sTNFR2 in healthy humans is 2-5 ng/ml, and in mice is typically 4-10 ng/ml, showing that the particles are able to capture sTNFR2 from serum at physiologically relevant concentrations. The blocking PEG coating did not decrease the capture efficacy and so is a practically usable means to reduce non-specific binding. This demonstrates the principle of using a capture agent other than TNF in the particles of the invention.

The example demonstrates that, in further embodiments, antibody capture agents other than anti-sTNFR2 antibodies, and capture agents other than antibodies, may be coupled to the streptavidin-loaded particles by conjugating the capture agent with biotin. It will be understood that streptavidin analogs may be used also to conjugate biotinylated capture agents, and that further coupling pairs, such as protein coupling pairs or nucleic acid coupling pairs, may be used to couple capture agents to the particle surface. In further embodiments, streptavidin or other avidin analogs that bind biotin, or other members of a coupling pair, may be coupled to the surface of the porous silicon disk by chemistry other than gold-thiol chemistry, such as using amide linkage chemistry to an APTES-coated surface.

What is claimed is:

1. A scavenging construct comprising:
   a first particle;
   a second particle coupled to the first particle;
   a capture environment;
   a first region of protected surface; and
   a first agent immobilized on the first region of protected surface, wherein the first agent can bind a first molecule on the surface of an exosome; and further wherein:
   the capture environment is a volume between the surface of the first particle and the second particle;
   the capture environment has a characteristic dimension from 30 nm to 1 µm; and
   the first region of protected surface is a surface of the first particle adjacent to the capture environment.

2. The scavenging construct of claim 1, wherein the first particle or second particle comprises metal, alumina, silica, glass, silicon, or a polymer.

3. The scavenging construct of claim 1, wherein the first particle or second particle comprises a DNA scaffold, wherein the DNA scaffold optionally comprises a three-dimensional shape having an opening.

4. The scavenging construct of claim 1, wherein the capture environment has a characteristic dimension from 30 nm to 120 nm.

5. The scavenging construct of claim 1, wherein the first molecule on the surface of the exosome is selected from a receptor, a ligand for a receptor, a cytokine, a chemokine, and an immune checkpoint protein.

6. The scavenging construct of claim 1, wherein the first molecule on the surface of the exosome is selected from CD9, CD63, CD81, CD82, TNFR1, TNFR2, PD-L1, PD-L2, TGFbeta1, CCL11, MCP-1/CCL2, beta-2 microglobulin, GDF-8/myostatin, haptoglobin, Fas-L, TRAIL, MICA, MICB, a Matrix metalloprotease, and CEACAM1.

7. The scavenging construct of claim 1, wherein the first agent is disposed on the first region of protected surface such that it has a reduced ability to interact with a molecule on the surface of a cell.

8. A scavenging construct comprising:
   a first particle;
   a capture environment;
   a first region of protected surface;
   a first agent immobilized on the first region of protected surface, wherein the first agent can bind a first molecule on the surface of an exosome;
   a second region of protected surface; and
   a second agent immobilized on the second region of protected surface, wherein:

the second agent can bind a second molecule on the surface of the exosome, and wherein the first agent is different from the second agent.

9. The scavenging construct of claim 8, wherein the second molecule on the surface of the exosome is selected from CD9, CD63, CD81, CD82.

10. The scavenging construct of claim 8, wherein the first region of protected surface is adjacent to the second region of protected surface.

11. The scavenging construct of claim 8, wherein the first region of protected surface is oriented with respect to the second region of protected surface at an angle.

12. The scavenging construct of claim 11, wherein the angle is in the range from 0° to 90°.

13. A scavenging construct comprising:
   a first particle;
   a second particle coupled to the first particle;
   a capture environment;
   a first region of protected surface; and
   a reactive group immobilized on the first region of protected surface; wherein:
   the reactive group can selectively react with a first agent comprising a first predetermined functional group; and
   the first agent, when coupled to the reactive group can bind a first molecule on the surface of an exosome; and further wherein:
   the capture environment is a volume between the surface of the first particle and the second particle;
   the capture environment has a characteristic dimension from 30 nm to 1 μm; and
   the first region of protected surface is a surface of the first particle adjacent to the capture environment.

14. A method of inhibiting the activity of a biomolecule in a subject, comprising administering a scavenging construct of claim 1 to a subject in need thereof.

15. The scavenging construct of claim 3, wherein the DNA scaffold comprises a three-dimensional shape having an opening selected from a single ended tube or cup, an open box, blind pore, recess, concavity, or void.

* * * * *